(12) United States Patent
Lipp et al.

(10) Patent No.: US 9,061,352 B2
(45) Date of Patent: *Jun. 23, 2015

(54) DRY POWDER FORMULATIONS AND METHODS FOR TREATING PULMONARY DISEASES

(75) Inventors: Michael M. Lipp, Framingham, MA (US); Jean C. Sung, Cambridge, MA (US)

(73) Assignee: Pulmatrix, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/817,963

(22) PCT Filed: Aug. 26, 2011

(86) PCT No.: PCT/US2011/049435
§ 371 (c)(1),
(2), (4) Date: May 2, 2013

(87) PCT Pub. No.: WO2012/030664
PCT Pub. Date: Mar. 8, 2012

(65) Prior Publication Data
US 2013/0213398 A1     Aug. 22, 2013

Related U.S. Application Data

(60) Provisional application No. 61/431,242, filed on Jan. 10, 2011, provisional application No. 61/387,925, filed on Sep. 29, 2010, provisional application No. 61/378,146, filed on Aug. 30, 2010.

(51) Int. Cl.
| | | |
|---|---|---|
| *A61K 33/06* | (2006.01) | |
| *B22F 5/10* | (2006.01) | |
| *B22F 3/11* | (2006.01) | |
| *C22C 21/00* | (2006.01) | |
| *A61K 47/02* | (2006.01) | |
| *A61M 15/00* | (2006.01) | |

(52) U.S. Cl.
CPC .............. *B22F 5/10* (2013.01); *B22F 3/1125* (2013.01); *C22C 21/00* (2013.01); *A61K 47/02* (2013.01); *A61M 15/00* (2013.01)

(58) Field of Classification Search
CPC ...... A61K 33/06; A61K 33/14; A61K 9/0075
See application file for complete search history.

(56) References Cited

U.S. PATENT DOCUMENTS

| | | |
|---|---|---|
| 4,233,405 A | 11/1980 | Neubeck |
| 4,637,815 A | 1/1987 | Lemole |
| 4,828,844 A | 5/1989 | Rontgen-Odenthal et al. |
| 5,175,152 A | 12/1992 | Singh |
| 5,230,884 A | 7/1993 | Evans et al. |
| 5,466,680 A | 11/1995 | Rudy |
| 5,571,535 A | 11/1996 | Flowers et al. |
| 5,612,053 A | 3/1997 | Baichwal et al. |
| 5,633,003 A | 5/1997 | Cantor |
| 5,654,007 A | 8/1997 | Johnson et al. |
| 5,709,202 A | 1/1998 | Lloyd et al. |
| 5,785,049 A | 7/1998 | Smith et al. |
| 5,817,028 A | 10/1998 | Anderson |
| 5,855,913 A | 1/1999 | Hanes et al. |
| 5,883,084 A | 3/1999 | Peterson et al. |
| 5,898,037 A | 4/1999 | Marx |
| 5,981,559 A | 11/1999 | Nagaoka et al. |
| 5,985,309 A | 11/1999 | Edwards et al. |
| 6,083,922 A | 7/2000 | Montgomery |
| 6,165,463 A | 12/2000 | Platz et al. |
| RE37,053 E | 2/2001 | Hanes et al. |
| 6,214,536 B1 | 4/2001 | Boucher |
| 6,254,854 B1 | 7/2001 | Edwards et al. |
| 6,447,752 B2 | 9/2002 | Edwards et al. |
| 6,451,352 B1 | 9/2002 | Yvin et al. |
| 6,475,523 B1 | 11/2002 | Staniforth |
| 6,572,849 B2 | 6/2003 | Shahinian, Jr. |
| 6,582,728 B1 | 6/2003 | Platz et al. |
| 6,635,283 B2 | 10/2003 | Edwards et al. |
| 6,732,732 B2 | 5/2004 | Edwards et al. |
| 6,749,835 B1 | 6/2004 | Lipp et al. |
| 6,830,764 B2 | 12/2004 | Inui et al. |
| 7,008,644 B2 | 3/2006 | Batycky et al. |
| 7,112,572 B2 | 9/2006 | Deadman et al. |
| 7,182,961 B2 | 2/2007 | Batycky et al. |
| 7,192,919 B2 | 3/2007 | Tzannis et al. |
| 7,306,787 B2 | 12/2007 | Tarara et al. |
| 7,384,649 B2 | 6/2008 | Batycky et al. |
| 7,556,798 B2 | 7/2009 | Edwards et al. |

(Continued)

FOREIGN PATENT DOCUMENTS

| | | |
|---|---|---|
| CN | 1240349 | 1/2000 |
| CN | 1446877 | 10/2003 |

(Continued)

OTHER PUBLICATIONS

Problemy Tuberkuleza, 58(1):40-41 (1980).
International Search Report dated Feb. 9, 2012 from corresponding PCT Application No. PCT/US2011/049435.
Jagdeep et al., "Cospray-Dried Unfractionated Heparin With L-Leucine as a Dry Powder Inhaler Mucolytic for Cystic Fibrosis Therapy," Journal of Pharmaceutical Sciences, 97:4857-4868 (2008).
Adi, et al., "Agglomerate strength and dispersion of pharmaceutical powders," Journal of Aerosol Science, 42:285-294, 2011.

(Continued)

*Primary Examiner* — Sean Basquill
*Assistant Examiner* — Andrew S Rosenthal
(74) *Attorney, Agent, or Firm* — McDermott Will & Emery LLP

(57) ABSTRACT

The present invention is directed toward respirable dry particles for delivery of divalent metal cation salts and/or monovalent cation salts to the respiratory tract and methods for treating a subject having a respiratory disease and/or infection.

8 Claims, 73 Drawing Sheets

(56) References Cited

U.S. PATENT DOCUMENTS

| | | | |
|---|---|---|---|
| 7,575,761 B2 | 8/2009 | Bennett et al. | |
| 7,838,532 B2 | 11/2010 | Surber et al. | |
| 7,879,358 B2 | 2/2011 | Jackson et al. | |
| 8,187,637 B2 | 5/2012 | Edwards et al. | |
| 2001/0008632 A1 | 7/2001 | Freund et al. | |
| 2001/0038858 A1 | 11/2001 | Roser et al. | |
| 2002/0177562 A1 | 11/2002 | Weickert et al. | |
| 2003/0138403 A1 | 7/2003 | Drustrup | |
| 2003/0186894 A1 | 10/2003 | Kuo et al. | |
| 2003/0232019 A1 | 12/2003 | Basu et al. | |
| 2004/0009128 A1 | 1/2004 | Rabinowitz et al. | |
| 2004/0047810 A1* | 3/2004 | Staniforth et al. | 424/46 |
| 2004/0105821 A1 | 6/2004 | Bernstein et al. | |
| 2005/0004020 A1 | 1/2005 | Yu et al. | |
| 2005/0054682 A1 | 3/2005 | Phillips | |
| 2005/0211244 A1 | 9/2005 | Nilsson et al. | |
| 2005/0220720 A1 | 10/2005 | Edwards et al. | |
| 2005/0255049 A1 | 11/2005 | Slowey et al. | |
| 2005/0276845 A1 | 12/2005 | Roser et al. | |
| 2005/0281740 A1 | 12/2005 | Gong et al. | |
| 2006/0073173 A1 | 4/2006 | Banach et al. | |
| 2006/0142208 A1 | 6/2006 | Boucher | |
| 2006/0147520 A1 | 7/2006 | Ruegg | |
| 2006/0276483 A1 | 12/2006 | Surber et al. | |
| 2007/0053844 A1 | 3/2007 | Watanabe et al. | |
| 2007/0092535 A1 | 4/2007 | Watts | |
| 2007/0202051 A1 | 8/2007 | Schuschnig | |
| 2007/0270502 A1 | 11/2007 | Edwards et al. | |
| 2007/0275091 A1 | 11/2007 | King et al. | |
| 2007/0292454 A1 | 12/2007 | Bell et al. | |
| 2008/0038207 A1 | 2/2008 | Edwards et al. | |
| 2008/0063722 A1 | 3/2008 | Ward et al. | |
| 2008/0152764 A1 | 6/2008 | Kremer et al. | |
| 2008/0190424 A1 | 8/2008 | Lucking et al. | |
| 2009/0208999 A1 | 8/2009 | Groenendaal et al. | |
| 2009/0232744 A1* | 9/2009 | Keller et al. | 424/45 |
| 2010/0159007 A1 | 6/2010 | Staniforth | |
| 2010/0285142 A1 | 11/2010 | Staniforth et al. | |
| 2011/0192397 A1 | 8/2011 | Saskar et al. | |
| 2011/0236492 A1 | 9/2011 | Morton | |
| 2012/0070417 A1 | 3/2012 | Batycky | |
| 2012/0107414 A1 | 5/2012 | Lipp | |
| 2013/0004542 A1 | 1/2013 | Martyn | |

FOREIGN PATENT DOCUMENTS

| | | |
|---|---|---|
| CN | 101237853 | 3/2007 |
| CN | 101106975 | 1/2008 |
| EP | 0367723 | 5/1990 |
| EP | 0652011 | 5/1995 |
| EP | 0681833 | 11/1995 |
| EP | 1466610 | 10/2004 |
| JP | 05123398 | 5/1993 |
| JP | 2004-503482 | 2/2004 |
| JP | 2004-532217 | 10/2004 |
| NZ | 328476 | 5/1999 |
| NZ | 305168 | 8/1999 |
| NZ | 530123 | 1/2007 |
| WO | 9206695 | 4/1992 |
| WO | 9612470 | 5/1996 |
| WO | 96/31221 | 10/1996 |
| WO | 9736574 | 10/1997 |
| WO | 9744013 | 11/1997 |
| WO | 98/16205 | 4/1998 |
| WO | 9951096 | 10/1999 |
| WO | 9964014 | 12/1999 |
| WO | 0013677 | 3/2000 |
| WO | 0066206 | 11/2000 |
| WO | 01/13892 | 3/2001 |
| WO | WO01/13892 | 3/2001 |
| WO | 0185136 | 11/2001 |
| WO | 0185137 | 11/2001 |
| WO | 01/95874 | 12/2001 |
| WO | 0195874 | 12/2001 |
| WO | 0209574 | 2/2002 |
| WO | 02/083079 | 10/2002 |
| WO | 02083079 | 10/2002 |
| WO | 03/043585 | 5/2003 |
| WO | 03035028 | 5/2003 |
| WO | 03103632 | 12/2003 |
| WO | 2004/002551 | 1/2004 |
| WO | 2004096204 | 11/2004 |
| WO | 2005004852 | 1/2005 |
| WO | 2005041921 | 5/2005 |
| WO | 2005041922 | 5/2005 |
| WO | 2005092289 | 10/2005 |
| WO | 2006102438 | 9/2006 |
| WO | 2008025560 | 6/2008 |
| WO | 2010/111641 | 9/2010 |
| WO | 2010/111644 | 9/2010 |
| WO | 2010011650 | 9/2010 |
| WO | 2010111640 | 9/2010 |
| WO | 2010111641 | 9/2010 |
| WO | 2010111644 | 9/2010 |
| WO | WO2010/111650 | 9/2010 |
| WO | WO2010/111680 | 9/2010 |
| WO | 2011048379 | 4/2011 |
| WO | 2012-030645 | 3/2012 |
| WO | 2012/030645 | 3/2012 |
| WO | 2012/030664 | 3/2012 |
| WO | 2012030647 | 3/2012 |
| WO | 2012030664 | 3/2012 |

OTHER PUBLICATIONS

ADJEi and Garren, "Pulmonary delivery of peptide drugs: effect of partical size on bioavailability of leuprolide acetate in healthy male volunteers", J.Pharm. Res., 7:565-569 (1990).

Aldrich Catalog pp. 1502, 1998-1999.

Anderson, et al., "Effect of cystic fibrosis on inhaled aerosol boluses" Am. Rev. Respir. Dis., 140: 1317-1324 (1989).

Bergeron, et al., "Controlling droplet deposition with polymer additives" Nature. 405:772-775 (2000).

Boren, "The development of a molecular model of lung" Arch Intern Med 126(3):491-495 (1970).

Broadhead, et al., The Spray Drying of Pharmaceuticals, Drug Development and Industrial Pharmacy, 18 (11&12):1169-1206, 1992.

Bromberg and Klibanov, "Transport of proteins dissolved in organic solvents across biomimetic membranes", Proc. Natl. Acad. Sci. USA, 92(5):1262-6 (1995).

Bucca, C. and G. Rolla, "Nebulised magnesium in asthma: the right solution for an old remedy?" The Lancet, 361:2095-2096 (2003).

Burg, et al., "Cellular Response to Hyperosmotic Stresses," Am. Physiological Soc., 87:1441-1474 (2007).

Cataldo, et al., "Induced sputum: comparison between isotonic and hypertonic saline solution inhalation in patients with asthma" Chest, 120(6):1815-21 (2001).

Chan, H., "Spray Dried Powders and Powder Blends of Recombinant Human Deoxyribonuclease (rhDNase) for Aerosol Delivery," Pharmaceutical Research, 14(4): 431-437, 1997.

Jaffari, et al., "Rapid characterisation of the inherent dispersibility of respirable powders using dry dispersion laser diffraction," International Journal of Pharmaceuticals, 447:124-131, 2013.

Chiou, et al., "A novel production method for inhalable cyclosporine A powders by confined liquid impinging jet precipitation," Journal of Aerosol Science, 39:500-509, 2008.

Choi, et al., "Inhalation delivery of proteins from ethanol suspensions" Proc. Natl. Acad. Sci. 98:11103-11107 (2001).

Clarke, et al, "Resistance to two-phase-gas-liquid flow in airways" J. Appl. Physiol.29(4):464-471 (1970).

Copp, et al., "Hypertonic Shock Inhibits Growth Factor Receptor Signaling, Induces Caspase-3 Activation, and Causes Reversible Fragmentation of the Mitocholdrial Network," Am. J. Physiol, 288:C403-C415 (2005).

Costello, B., et al., "Use of the Du Nouy Ring with a Rotational Rheometer to Measure Interfacial Rheology Properties", Annual Transactions of the Nordic Rheology Society. 2006, 14.

Crowder, et al., "2001: An Odyssey in Inhaler Formulation and Design," Pharmaceutical Technology, 99-113, Jul. 2001.

(56) References Cited

OTHER PUBLICATIONS

Davis, et al., "Charged Polymers Modulate Retrovirus Transduction via Membrane Charge Neutralization and Virus Aggregation", Biophys J,86:1234-1242 (2004).
Dawson, et al., "Enhanced viscoelasticity of human cystic fibrotic sputum correlates with increasing microheterogeneity in particle transport", J. of Biol. Chem., 278(50):50393-50401 (2003).
Denn, M.M., "Viscoelasticity", In Process Fluid Mechanics, Prentice-Hall, Englewood Cliffs, New Jersey, pp. 358-373 (1980).
Edwards, et al., "Inhaling to mitigate exhaled bioaerosols," PNAS (2004), vol. 101, pp. 17383-17388.
Edwards, "The macrotransport of aerosol particles in the lung: aerosol deposition phenomena" J. Aerosol Sci., 26:293-317 (1995).
Edwards, et al., "Novel Inhalents for Control and Protection Against Airborne Infections," Respiratory Drug Delivery, 2006, pp. 41-48.
Eng PA, et al., "Short-term efficacy of ultrasonically nebulized hypertonic saline in cystic fibrosis," Pediatr. Pulmonol., 21:77-83 (1996).
"European Search Report from corresponding EP Appl. No. 11177874 dated Nov. 21, 2011".
Evrensel, et al., "Viscous airflow through a rigid tube with compliant lining: A simple model for the air-mucus interaction in pulmonary pathways", J.Biomech. Eng., 115:262-267 (1993).
Feng, et al., "Improved clearability of cystic fibrosis sputum with dextran treatment in vitro," Am. J. Respir. Crit. Care Med., 157(3):710-714 (1998).
Ferguson, et al., "Transmission intensity and impact of control policies on the foot and mouth epidemic in Great Britain", Nature, 414(6861):329 (2001).
Fiegel et al., "Airborne Infectious Disease and the Suppression of Pulmonary Bioaerolsols," DDT, Jan. 2006, 11 (1/2), pp. 51-57.
French, et al., "The influence of formulation on emission, deaggregation and deposition of dry powders for inhalation", J. Aerosol Sci., 27:769-783 (1996).
Friedmen, et al. "A Randomized, Prospective, Double-Blind Study on the Efficacy of Dead Sea Salt Nasal Irrigations," The Laryngoscope, 2006, pp. 878-882, 116.
Fuge, et al., "The geochemistry of iodine—a review", Environmental Geochemistry and Health, 8(2):31-54 (1986).
Gad-El-Hak, et al., "On the interaction of compliant coatings with boundary layer flows", J. Fluid Mech., 140:257-280 (1984).
Ganderton, "The generation of respirable clouds from coarse powder aggregates", Biopharmaceutical Sciences,3:101-105 (1992).
Geller, et al., "Development of a DPI Tobramycin Formulation using Pulmosphere Technology," J. of Aerosol Medicine and Pulmonary Drug Delivery, 24:175-182, 2011.
Ghoroi, et al., "A novel production method for inhalable cyclosporine A powders by confined liquid impinging jet precipitation," 85:11-24, 2013.
Goldberg, et al., "Mechanism of enhancement of microbial cell hydrophobicity by cationic polymers", J. Bacteriology, 172:5650-5654 (1990).
Gonda, "Aerosols for delivery of therapeutic and diagnostic agents to the respiratory tract", Critical Reviews in Therapeutic Drug Carrier Systems, 6:273-313 (1990).
Guo-Zhong Tao, et al., "Hyposmotic Stress Induces Cell Growth Arrest via Proteasome Activation and Cyclin/Cyclin-Dependent Kinase Degradation," J. Biological Chemistry, 277(22): 19295-19303 (2002).
Hardy, et al. "Sensitivity of aerosol bolus behavior to methacholine-induced bronchoconstriction", Chest, 114 (2):404-10 (1998).
Hatch, G.E., "Comparative Biochemistry of Airway Lining Fluid," In: Parent, R.A., Ed., Treatise on Pulmonary Toxicology, vol. 1: Comparative Biology of the Normal Lung, CRC Press, Boca Raton, Florida (1992).
Hawley's Condensed Chemical Dictionary, 14th edition John Wiley & Sons, 2001, pp. 161 and 977.
Heyder J., et al., "Deposition of particles in the human respiratory tract in the size range 0.005-15μm" J. Aerosol Sci., 17:811-825 (1986).
Hirschman, et al., "Inhibition of human immunodeficiency virus type 1 replication by nonionic block polymer surfactants" J. Med. Virol. 42(3):249-54 (1994).
Hsu, et al., "Role of Viscoelasticity in Tube Model of Airway Reopening. I. Nonnewtonian Sols.", J. Appl Physiol. 76 (6):2481-2489 (1994).
Im, et al., "In vivo determination of surface tension in the horse trachea and in vitro model studies", Respir. Physiol., 109:81-93 (1997).
Iwasaki, et al., "Exacerbation of influenzavirus pneumonia by intranasal administration of surfactant in a mouse model" Arch. Viral., 144:675-685 (1999).
Kaye, et al., "Simultaneously Manufactured Nano-In-Micro(SIMANIM) Particles for Dry-Powder Modified-ReleaseDelivery of Antibodies," Pharmaceutics, Preformulations and Drug Delivery, 98:11:4055-4068, 2009.
Kilpatrick, et al., "Calcium Chloride and Adrenaline as Bronchial Dilators Compared by Sequential Analysis," British Medical Journal (1954), pp. 1388-1391.
King, "Rheology of cystic fibrosis sputum after in vitro treatment with hypertonic saline alone and in combination with recombinant human deoxyribonuclease I" Am. J. Respir. Crit. Care Med., 156(1):173-7 (1997).
King and Tarsitamo, "The effect of structured and unstructured preoperative teaching: a replication", Nurs. Res., 31(6):324-9 (1982).
King, et al., "The role of mucus gel viscosity, spinnability, and adhesive properties in clearance by simulated cough", Biorheology, 26:737-745 (1989).
King, M., et al., "Mucomodulator Therapy in Cystic Fibrosis: Balancing Mucus Clearability Against the Spread of Airborne Pathogens," Pediatric Pulmonolgy, 2004, pp. 77-79, Supp. 26.
Kirkness, et al., "Decreased surface tension of upper airway mucosal lining liquid increases upper airway patency in anaesthetised rabbits", J. Physiol., 547(Pt 2):603-11(2003).
Kurashima, et al., "A pilot study of surfactant inhalation for the treatment of asthmatic attack" Arerugi, 40(2):160-3 (1991).
Lipp, et al., "Solving medical problems with chemical engineering", Chemtech, 42-57 (Mar. 1997).
Macosko, C.W., "Linear Viscoelasticity", in Rheology. Principles, Measurements, and Applications, Wiley-VCH, New York, pp. 109-133 (1994).
Mai, X.-M, et al., "Hypertonic saline challenge tests in the diagnosis of bronchial hyperresponsiveness and asthma in children," Pediatric Allergy & Immunology, Oct. 2002, 13(5), pp. 361-267.
Makker, et al., "Relation of hypertonic saline responsiveness of the airways to exercise induced asthma symptom severity and to histamine or methacholine reactivity," Thorax, 1993, 48, pp. 142-147.
Marriott, et al., "Changes in the Gel Properties of Tracheal Mucus Induced bu Divalent Cations," Biorheology, 1979, pp. 331-337, vol. 16.
The Merck Index, 12th edition, Merck &Co., Inc., Whitehouse Station, NJ, p. 1089. 1996, pp. 177 & 1614-1615.
Merck Manual Home Edition, "Asthma: Lung and Airway Disorders," accessed at www.merck.com/mmhe/print/sec04/ch044a/html accessed on May 5, 2010.
Merck Manual Home Edition, "Chronic Obstructive Pulmonary Disease," accessed at www.merck.com/mmhe/print/sec04/ch045a/html accessed on Mar. 21, 2010.
Merck Manual Home Edition, "Acute Respiratory Distress Syndrome (ARDS)," accessed on Nov. 17, 2011 at www.merckmanuals.com/home/lung_and_airway_disorders/respiratory_filure_and_acute_respiratory_distress_syndrome/acute_respiratory_distress_syndrome_ards.html#v727948.
The Online Merck Manual Medical Second Home Edition article, entitled, "Influenza"—accessed on Feb. 22, 2010 at www.merck.com/mmhe/print/sec17/ch198/ch198d.html.
Miller, M.J., "Assessing the use of Pharmacokinetic Models in Risk Assessments on Inhaled Toxicants", School of Public Health Sciences, Environmental Health, and Toxicology (1992). 6 parts.
Modler, "Calcium as an Adjuvant for Spray-Drying Acid Whey," Journal of Dairy Science, 61:294-299, 1978.

(56) References Cited

OTHER PUBLICATIONS

Morrison, F.A., "Introduction, How Much Do I Need to Learn about Rheology?" In Understanding Rheology, Oxford University Press, New York, pp. 1-11 (2001).

Mouro, D., et al. "Enhancement of Xcelodose Capsule-Filling Capabilities Using Roller Compaction," Pharmaceutical Technology, Feb. 2006.

Nanaumi, et al., "Properties of mixed monolayers of DPCC and viscoelasticity-giving substances", Colloids & Surfaces B: Bioinformatics, 17:167-174 (2000).

Nannini, L.J., et al., "Magnesium Sulfate as a Vehicle for Nebulized Salbutamol in Acute Asthma", Am. J. Med., 108:193-197 (2000).

Oneda, et al., "The Effect of Formulation Variables on the Dissolution and Physical Properties of Spray-Dried Microspheres Containing Organic Salts," Powder Technology, 130:377-384, 2003.

Takebayashi, et al., "Role of tachykinins in airway responses to ozone in rats" J Appl Physiol 85:442-450 (1998).

Papineni and Rosenthal, "The size distribution of droplets in the exhaled breath of healthy human subjects", J. Aerosol Med., 10(2):105-116 (1997).

Patton and Platz, "Pulmonary delivery of peptides and proteins for systemic action", Adv. Drug Del. Rev., 8:179-196 (1992).

Paul, Fundamental Immunology, Raven Press, New York, pp. 699-716, 1984.

Perry's Chemical Engineers' Handbook, 7th ed., 1997, pp. 2-10, 2-11, 2-120, 2-121.

Piret, et al., "Sodium lauryl sulfate, a microbicide effective against enveloped and nonenveloped viruses" Curr. Drug Targets. 3(1):17-30 (2002).

Rabbini, et al., "The Influence of formulation components on the aerosolisation properties of spray dried powders," J. of Controlled Release, 110:130-140, 2005.

Raynal, et al., "Calcium-dependent Protein Interactions in MUC5B Provide Reversible Cross-links in Salivary Mucus," The Journal of Biological Chemistry, Aug. 2003, pp. 28703-28710, vol. 278 (31).

Riedler, J., et al. "Inhaled hypertonic saline increases sputum expectoration in cystic fibrosis," J. Pediatr Child Health, 32:48-50 (1996).

Robinson, M., et al., "Effect of hypertonic saline amiloride, and cough on mucociliary clearance in patients with cystic fibrosis," Am J. Respir. Crit. Care Med., 153:1503-1509 (1996).

Robinson, M., et al., "Effect of increasing doses of hypertonic saline on mucociliary clearance in patients with cystic fibrosis," Thorax, 52:900-903 (1997).

Robinson, M., et al., The effect of inhaled mannitol on bronchial mucus clearance in cystic fibrosis patients: a pilot study, Eur. Respir. J., 14:678-685 (1999).

Rosenblum, E. E. ("fish." Grolier Multimedia Encyclopedia, 2006, Grolier Online, accessed Nov. 21, 2006 (gme.grolier.com/cgi-bin/article?assetid=0106750-0).

Rote Liste Service, "Rote Liste 2002" (2002), Editor Cantor Verlag, Frankfurt/Main, XP002416908, par. [72087], par. [28005].

Rudt and Muller, "In vitro Phagocytosis Assay of Nano- and Microparticles by chemiluminescence. I. Effect of Analytical Parameters, Particle Size and Particle Concentration", J. Controlled Release, 22:263-272 (1992).

Sanders, et al., "Cystic fibrosis sputum: a barrier to the transport of nanospheres", Am J Respir Crit Care Med., 162:1905-1911 (2000).

Sarrell, et al., "Nebulized 3% Hypertonic Saline Solution Treatment in Ambulatory Children with Viral Bronchiolitis Decreases Symptoms," Chest, 2002, 122, pp. 2015-2020.

Schelling G., et al., Biophyiscal Journal, 66:134-140 (1994).

Schurch, et al., "Surfactant displaces particles toward the epithelium in airways and alveoli", Respir Physiol., 80:17-32 (1990).

Serrano, P., et al., "New Data on Pharmacological Properties and Indications of Magnesium," In New Perspectives in Magnesium Research, Springher-Verglag, London, pp. 127-139 (2007).

Seville, et al., "Spray-Dried Powders for Pulmonary Drug Delivery," Crit. Rev. in Therapeutic Drug Carrier Systems, 24(4), 307-360, 2007.

Shigeta, et al. "Synergistic Anti-Influenza Virua A (H1N1) Activities of PM-523 (Polyoxometalate) and Ribavarin In Vitro and In Vivo," Antimicrobial Agents & Chemotherapy, 1997, 41, pp. 1423-1427.

Suara, et al., "Effect of Zinc Salts on Respiratory Syncytial Virus Replication," Antimicrobial Agents and Chemotherapy, Mar. 2004, pp. 783-790, vol. 48 (3).

Tabata and Ikada, "Macrophage phagocytosis of biodegradable microspheres composed of L-lactic acid/glycolic acid homo- and copolymers", J. Biomed. Mater. Res., 22:837-858 (1988).

Tansey, "The challenges in the development of metered dose inhalation aerosols using ozone-friendly propellants" Spray Technol, Market. 4:26-29 (1994).

Tibby, et al., "Exogenous surfactant supplementation in infants with respiratory syncytial virus bronciolitis" Am J Respir Crit Care Med., 162(4 Pt 1):1251 (2000).

Timsina, et al., Drug Delivery to the respiratory tract using dry powder inhalers Int. J. Pharm., 101:1-13 (1995).

Tsurumi et al., "Effect of high salt treatment on influenza B viral protein synthesis in MDCK cells," Microbiology and immunology, 1983, 27(6), pp. 519-529 (Full document).

A.D.A.M. Healthcare: Ulcerative Colitis: Inflammatory bowel Disease: retrieved from the internet: [http://adam.about.com/reports/000069_1.htm] [Jun. 20, 2006].

Vehring, "Pharmaceutical Particle Engineering via Spray Drying" Pharma. Res., vol. 25, No. 5, May 2008.

Vinnikov, et al., "Aerosol Inhalations of Calcium Chloride in Combination Therapy of Pulmonary Tuberculosis," Kazanskii Meditsinskii Zhurnal (1962), vol. 4, pp. 7-9 (translation included).

Visser, "Van der Waals and other cohesive forces affecting powder fluidization", Powder Technology, 58:1-10 (1989).

Vollenbroich, et al., "Mechanism of inactivation of enveloped viruses by the biosurfactin from *Bacillus subtilis*" Biologicals, 25(3):289-97 (1997).

Wade, C.E., "Hypertonic saline resuscitation in sepsis," Critical Care, Oct. 2002, 6(5), 397-398.

Wark, Rab, McDonald V. Nebulized hypertonic saline for cystic fibrosis (Cochrane Review). In: The Cochrane Library. Oxford, UK: Update Software, 2005.

Watanabe et al., "Why Inhaling Salt Water Changes What We Exhale," Journal of Colloid and Interface Science, 2007, 307, pp. 71-78.

Watanabe, et al., "Immunogenicity and protective efficacy of replication-incompetent influenza virus-like particles" Journal of Virology 76(2):767-773 (2002).

Wikipedia, "Hypertonic" Wikipedia, 2006, accessed Nov. 21, 2006 (en.wikipedia.org/wiki/Hypertonic).

Williams, "Portal to the interior: viral pathogenesis and natural compounds that restore mucosal immunity and modulate inflammation", Alternative Medicine Review, 8(4):395-409 (2003).

Zanen and Lamm, "The optimal particle size for parasymathicolytic aerosols in mild asthmatics", J. Int. J. Pharm., 114:111-115 (1995).

Zasadzinski, et al., "The physics and physiology of lung surfactants", Current Opinion in Colloid & Interface Science, 6:506-513 (2001).

Zayas, et al., "A new paradigm in respiratory hygiene: modulating respiratory secretions to contain cough bioaerosol without affecting mucus clearance," BMC Pulm. Med., 11 (2007). I had marked it pink but no date.

Edwards, et al., "Novel Inhalants for Control and Protection Against Airborne Infections," RDD 2006 Meeting, Abstract, (Apr. 23, 2006).

Sung, et al., "iSPERSE™: Formulation and In Vitro Characterization of a Novel Dry Powder Drug Delivery Technology," RDD Europe 2011 Meeting, Abstract, (May 3, 2011).

Sung, et al., "iSPERSE™: Formulation and In Vitro Characterization of a Novel Dry Powder Drug Delivery Technology," RDD Europe 2011 Meeting, Poster, (May 3, 2011).

Arold, et al., "Efficacy of Fluticasone and Salmeterol in a Novel Dry Powder Delivery Platform," ATS 2011 Meeting, Abstract #C22 (May 15, 2011).

Arold, et al., "A Novel Inhaled Dry Powder Delivery Platform; Efficacy of Fluticasone and Salmeterol during Allergic Asthma," ISAM 2011 Meeting, Poster (Apr. 6, 2011).

(56) References Cited

OTHER PUBLICATIONS

Hava, et al., "Inhaled Cationic Salts Inhibit Infection of Multiple Viral Pathogens and Prevent Influenza Infection In Vivo," ATS 2011 Meeting, Abstract #C60 (May 16, 2011).

Sung, "A Novel Platform for DP Inhalation Drugs," 2011 Manufacturing Chemist J article Nov. 7, 2011, accessed online on Jan. 11, 2013.

Arold, et al., "iSPERSE: A Novel Inhaled Dry Powder Delivery Platform for the Delivery of Large Molecule Drugs to the Lung for Local and Systemic Treatments," ATS 2012 Meeting, Abstract (May 18, 2012).

Sung, et al., "Pulmonary Delivery of Combination Drug Products via a Novel Dry Powder Delivery Technology," US-Japan Drug Delivery Symposium 2011, Abstract (Dec. 16, 2011).

Hava, et al., "Reduced Neutrophilic Airway Inflammation by Inhalation of Dry Powder Calcium Salts in a Mouse Model of Sub-Chronic Tobacco Smoke Exposure," ATS 2012 Meeting, Abstract (May 18, 2012).

Manzanedo, et al., "Formulation Characterization of a Novel Levofloxacin Pulmonary Dry Powder Drug Delivery Technology," RDD 2012 Meeting, Abstract (May 13, 2012).

Wright, et al., "Inhaled Calcium Salts Reduce Expression of Inflammatory Mediators Associated with Tobacco Smoke Exposure to Reduce Airway Inflammation," ERS 2012 Meeting, Poster (Sep. 1, 2012).

Lawlor, et al., "Development of iSPERSE™ Based Platform for the Delivery of Macromolecules via Dry Powder Formulations," RDD 2012 Meeting, Abstract (May 13, 2012).

Wright, et al., "Cationic Salt Dry Powders Inhibit Inflammatory Responses in a Rhinovirus-induced Exacerbation Mouse Model of Allergic Airway Inflammation," ATS 2012 Meeting, Abstract (May 18, 2012).

Manzanedo, et al., "Novel Respiratory Dry Powder Drug Delivery Technology for High Drug Load LABA/LAMA," AAPS 2012 Meeting, Abstract (May 12, 2012).

Sung, "A Next-Generation Inhaled Dry Powder Delivery Platform," Drug Development & Delivery, Jul./Aug. 2012, journal article.

Sung, "New Formulation Expands Potential for Pulmonary and Systemic Therapies," Pharmaceutical Formulation & Quality (PFQ), Dec. 2011/Jan. 2012, Journal Article, accessed online Jan. 11, 2013.

Lawlor, "A High Load Macromolecule Delivery Platform for Pulmonary Dry Powder Drug Delivery," AAPS 2012 Meeting, Poster (May 21, 2012).

DeHaan, et al., "Inhaled Calcium Based Dry Powder Enhances Whole Lung Mucociliary Clearance in Sheep," ATS 2011 Meeting, Abstract (May 15, 2011).

Kenyon, et al., "Late-breaking Abstract: Inhaled Calcium Salts Reduce Tobacco Smoke Induced Airway Inflammation and Improve Lung Pathology," ERS 2011 Meeting, Abstract (Sep. 27, 2011).

Nair, et al., "Inhaled Cationic Airway Lining Modulator (iCALM) attenuates allergen-induced eosinophilic bronchitis," ATS 2012 Meeting, Abstract (May 18, 2012).

Hava, et al., "Inhaled Cationic Airway Lining Modulator (iCALM) Therapy, a Novel Aerosol Treatment for Respiratory Infections Reduces Clinical Symptoms and Transmission of Influenza A Infection," ATS 2010 Meeting, Abstract #A6846 (May 14, 2010).

Hava, et al., "Inhaled Calcium Salts Reduce Acute Airway Inflammation Associated with Tobacco Smoke Exposure," ATS 2011 Meeting, Abstract #713 (May 16, 2011).

Wright, et al., "Inhaled Calcium Based Dry Powder Inhibits Rhinovirus-induced Inflammation and Exacerbation in a Mouse Model of Allergic Airway Inflammation," ERS 2011 Meeting, Abstract (Sep. 24, 2011).

* cited by examiner

FIG. 1A

Feedstock Formulations I, II, III, & XIV
Table of Properties

| Formulation | Lot | Spray Dryer | Solids conc (g/L) | Liquid feed static mixing | Inlet temp (°C) | Outlet temp (°C) | Atomizer gas (kg/hr) | Process gas (kg/hr) | Liquid feed (mL/min) | Product collection | Yield (%) |
|---|---|---|---|---|---|---|---|---|---|---|---|
| I (Citrate) Leucine: CaCl2: Na3Cit 10.0: 35.1: 54.9 | I-A | Niro | 10 | Yes | 282 | 98 | 14.5 Air press (mm) | 85 Aspirator | 70 | Cartridge filter | 75% |
|  | I-B | Büchi | 5 | No | 220 | 108 | 40 | 90% | 6.7 | Cyclone (high performance) | 83% |
|  | I-C | Büchi | 5 | No | 220 | 95 | 40 | 90% | 7 | Cyclone (high performance) | 81% |
| II (Lactate) Leucine: CaLact: NaCl 10.0: 58.6: 31.4 | II-A | Niro | 10 | Yes | 282 | 98 | 14.5 Air press (mm) | 85 Aspirator | 70 | Cartridge filter | 63% |
|  | II-B | Büchi | 5 | No | 220 | 91-109 | 40 | 90% | 5.2 | Cyclone (high performance) | 73% |
|  | II-C | Büchi | 5 | No | 220 | 100 | 40 | 90% | 6 | Cyclone (high performance) | 69% |
| III (Sulfate) Leucine: CaCl2: Na2SO4 10.0: 39.6: 50.4 | III-A | Niro | 10 | Yes | 282 | 98 | 14.5 Air press (mm) | 85 Aspirator | 70 | Cartridge filter | 74% |
|  | III-B | Büchi | 5 | No | 220 | 83 | 30 | 80% | 9.3 | Cyclone (high performance) | 73% |
|  | III-C | Büchi | 5 | No | 220 | 92 | 40 | 90% | 7 | Cyclone (high performance) | 76% |
| Placebo Leucine 100 | Placebo-A | Niro | 15 | Yes | 282 | 98 | 14.5 Air press (mm) | 85 Aspirator | 70 | Cartridge filter | 63% |
|  | Placebo-B | Büchi | 5 | No | 220 | 82 | 40 | 90% | 7 | Cyclone (high performance) | 66% |

FIG. 1A (Continued)

| IV (Lactate with maltodextrin) Maltodextrin: CaLact: NaCl 10.0: 58.6: 31.4 | | | | | | | Air press (mm) | Aspirator | | | |
|---|---|---|---|---|---|---|---|---|---|---|---|
| XIV-A | Büchi | 5 | No | 220 | 90-98 | 40 | 90% | 5.2 | Cyclone (high performance) | 72% |
| XIV-B | Büchi | 5 | No | 220 | 100 | 40 | 90% | 5.2 | Cyclone (high performance) | 77% |
| XIV-C | Büchi | 5 | No | 220 | 100-106 | 40 | 90% | 5.6 | Cyclone (high performance) | 78% |

FIG. 1B

Feedstock Formulations I, II, III, & XIV
Table of Properties (Cont.)    HPLC

| Formulation | Lot | Ca²⁺ Content (%) | | | Na⁺ Content (%) | Density | | Karl Fischer Water content (%) | |
|---|---|---|---|---|---|---|---|---|---|
| | | Theoretical | Ave | StDev | Theoretical | Tap density (g/cc) Ave | Bulk density (g/cc) Ave | Ave | StDev |
| I (Citrate) Leucine: CaCl2: Na3Cit 10.0: 35.1: 54.9 | I-A | 12.7 | 12.5 | 0.1 | 14.7 | 0.34 | 0.19 | | |
| | I-B | | | | | | | | |
| | I-C | | | | | | | | |
| II (Lactate) Leucine: CaLact: NaCl 10.0: 58.6: 31.4 | II-A | 10.8 | 11.3 | 0.1 | 12.3 | 0.72 | 0.31 | 6.6% | |
| | II-B | | | | | | | | |
| | II-C | | | | | | | | |
| III (Sulfate) Leucine: CaCl2: Na2SO4 10.0: 39.6: 50.4 | III-A | 14.3 | 13.6 | 0.2 | 16.4 | 0.39 | 0.18 | | |
| | III-B | | | | | | | | |
| | III-C | | | | | | | | |
| Placebo Leucine 100 | Placebo-A | 0.0 | 0.0 | 0.0 | 0.0 | 0.04 | 0.034 | | |
| | Placebo-B | | | | | | | | |

FIG. 1B (Continued)

| IV (Lactate with maltodextrin) Maltodextrin:CaLact:NaCl 10.0:58.6:31.4 | | | | | | | | |
|---|---|---|---|---|---|---|---|---|
| XIV-A | 14.3 | | | 16.4 | 0.75 | 0.43 | 6.0% | |
| XIV-B | 14.3 | | | 16.4 | | | 6.7% | 0.43 |
| XIV-C | 14.3 | 10.74 | 0.02 | 16.4 | | | 2.8% | 0.02 |

FIG. 1C

Feedstock Formulations I, II, III, & IV
Table of Properties (cont.)   ACI-2, Gravimetric

| Formulation | Lot | FPF_TD <3.4 um | | FPF_TD <5.6 um | | % Mass collected | |
|---|---|---|---|---|---|---|---|
| | | Ave | StDev | Ave | StDev | Ave | StDev |
| I (Citrate) Leucine: CaCl2: Na3Cit 10.0: 35.1: 54.9 | I-A | 45.7% | 0.9% | 61.6% | 1.3% | 66.3% | 1.3% |
| | I-B | 33.3% | | 49.2% | | 61.2% | |
| | I-C | 52.1% | | 64.8% | | 67.7% | |
| II (Lactate) Leucine: CaLact: NaCl 10.0: 58.6: 31.4 | II-A | 43.4% | 1.4% | 63.5% | 1.8% | 69.7% | 1.8% |
| | II-B | 35.5% | | 55.4% | | 61.1% | |
| | II-C | 34.7% | | 56.5% | | 65.1% | |
| II (Sulfate) Leucine: CaCl2: Na2SO4 10.0: 39.6: 50.4 | III-A | 60.1% | 2.8% | 82.7% | 3.2% | 88.6% | 3.3% |
| | III-B | 47.4% | | 62.0% | | 72.3% | |
| | III-C | 53.2% | | 69.0% | | 74.4% | |
| Placebo Leucine 100 | Placebo-A | 28.8% | 2.3% | 52.9% | 3.2% | 65.1% | 3.4% |
| | Placebo-B | 52.6% | | 74.4% | | 80.9% | |
| IV (Lactate with maltodextrin) Maltodextrin: CaLact: NaCl 10.0: 58.6: 31.4 | XIV-A | 47.5% | 7.2% | 71.3% | 4.9% | 77.6% | 2.3% |
| | XIV-B | 44.8% | 1.2% | 66.6% | 0.7% | 73.2% | 0.2% |
| | XIV-C | 47.7% | 0.5% | 68.2% | 0.6% | 72.0% | 0.8% |

FIG. 1D

Feedstock Formulations I, II, III, & IV
Table of Properties (cont.)   ACI-8, Gravimetric

| Formulation | Lot | MMAD (um) Ave | MMAD (um) StDev | GSD Ave | GSD StDev | FPF_TD Ave | FPF_TD StDev | FPF_TD <5.6um (%) Ave | FPF_TD <5.6um (%) StDev | FPF_TD <5.0um (%) Ave | FPF_TD <5.0um (%) StDev | Grav. Recov. | FPF_RD <5.0um (%) Ave | FPF_RD <5.0um (%) StDev |
|---|---|---|---|---|---|---|---|---|---|---|---|---|---|---|
| I (Citrate) Leucine: CaCl2: Na3Cit 10.0: 35.1: 54.9 | I-A | 2.72 | 0.06 | 2.09 | 0.01 | 41.7% | 1.6% | 56.2% | 1.6% | 53.9% | 1.8% | 65.0% | 82.9% | 1.2% |
| | I-B | | | | | | | | | | | | | |
| | I-C | | | | |

FIG. 1E

Feedstock Formulations I, II, III, & IV
Table of Properties (cont.) ACI-8, Chemical

| Formulation | Lot | MMAD (um) | | GSD | | FPF_TD <5.0um (%) | | Anal. | FPF_RD <5.0um (%) | |
|---|---|---|---|---|---|---|---|---|---|---|
| | | Ave | StDev | Ave | StDev | Ave | StDev | Recov. | Ave | StDev |
| I (Citrate) *Leucine: CaCl2: Na3Cit 10.0: 35.1: 54.9* | I-A | 3.37 | 0.02 | 2.76 | 0.02 | 51.9% | 2.0% | 79.5% | 65.3% | 1.2% |
| | I-B | | | | | | | | | |
| | I-C | | | | | | | | | |
| III(Lactate) *Leucine: CaLact: NaCl 10.0: 58.6: 31.4* | II-A | 3.57 | 0.13 | 2.61 | 0.05 | 53.1% | 1.9% | 84.2% | 63.1% | 1.8% |
| | II-B | | | | | | | | | |
| | II-C | | | | | | | | | |
| II (Sulfate) *Leucine: CaCl2: Na2SO4 10.0: 39.6: 50.4* | III-A | 2.79 | 0.14 | 3.33 | 0.19 | 54.9% | 2.7% | 72.4% | 75.9% | 1.6% |
| | III-B | | | | | | | | | |
| | III-C | | | | | | | | | |

FIG. 1F
Feedstock Formulations I, II, III, & XI
Table of Properties (cont.)

| Formulation | Lot | Spraytec Dv50 (um) | | GSD | | V < 5.0um (%) | | HELOS/RODOS Bar | x50/dg (um) | | GSD | | 1/4 bar | 0.5/4 bar |
|---|---|---|---|---|---|---|---|---|---|---|---|---|---|---|
| | | Ave | StDev | Ave | StDev | Ave | StDev | | Ave | StDev | Ave | StDev | | |
| I (Citrate) Leucine: CaCl2: Na3Cit 10.0: 35.1: 54.9 | I-A | 3.07 | 0.29 | 3.19 | 0.28 | 69.80 | 4.74 | 0.5 bar | 2.62 | 0.04 | 1.93 | 0.02 | 1.17 | 1.19 |
| | | | | | | | | 1.0 bar | 2.57 | 0.04 | 1.88 | 0.03 | | |
| | | | | | | | | 2.0 bar | 2.49 | 0.03 | 1.84 | 0.00 | | |
| | | | | | | | | 4.0 bar | 2.20 | 0.03 | 1.82 | 0.04 | | |
| | I-B | 6.97 | | 3.29 | | 40.46 | | 1.0 bar | 2.88 | | 2.11 | | 1.21 | |
| | I-C | 3.02 | | 3.71 | | 72.91 | | | | | | | | |
| III (Lactate) Leucine: CaLact: NaCl 10.0: 58.6: 31.4 | II-A | 1.78 | 0.23 | 3.57 | 0.18 | 83.13 | 1.39 | 0.5 bar | 1.57 | 0.02 | 2.51 | 0.02 | 1.08 | 1.12 |
| | | | | | | | | 1.0 bar | 1.51 | 0.02 | 2.51 | 0.02 | | |
| | | | | | | | | 2.0 bar | 1.47 | 0.02 | 2.53 | 0.01 | | |
| | | | | | | | | 4.0 bar | 1.40 | 0.03 | 2.51 | 0.03 | | |
| | II-B | 2.85 | | 3.16 | | 69.51 | | 1.0 bar | 2.04 | | 2.17 | | 1.09 | |
| | II-C | 1.86 | | 3.61 | | 85.33 | | | | | | | | |
| II (Sulfate) Leucine: CaCl2: Na2SO4 10.0: 39.6: 50.4 | III-A | 3.05 | 0.10 | 3.73 | 0.18 | 67.62 | 0.94 | 0.5 bar | 2.59 | 0.14 | 2.32 | 0.40 | 1.42 | 1.47 |
| | | | | | | | | 1.0 bar | 2.50 | 0.10 | 2.24 | 0.36 | | |
| | | | | | | | | 2.0 bar | 2.17 | 0.07 | 2.08 | 0.17 | | |
| | | | | | | | | 4.0 bar | 1.76 | 0.06 | 1.86 | 0.08 | | |
| | III-B | 4.61 | | 3.27 | | | | 1.0 bar | 3.26 | | 2.13 | | 1.02 | |
| | III-C | 2.93 | | 3.23 | | 68.12 | | | | | | | | |

FIG. 1F (Continued)

| | | | | | | | | | | | | | |
|---|---|---|---|---|---|---|---|---|---|---|---|---|---|
| Placebo Leucine 100 | Placebo-A | 21.77 | 3.66 | 3.25 | 0.05 | 12.07 | 1.60 | 0.5 bar | 7.68 | 0.34 | 2.09 | 0.07 | 1.37 | 1.62 |
| | | | | | | | | 1.0 bar | 6.47 | 0.17 | 2.07 | 0.05 | | |
| | | | | | | | | 2.0 bar | 5.69 | 0.11 | 2.09 | 0.04 | | |
| | | | | | | | | 4.0 bar | 4.74 | 0.20 | 2.10 | 0.03 | | |
| | Placebo-B | 7.52 | | 3.41 | | 37.21 | | | | | | | | |
| IV (Lactate with maltodextrin) Maltodextrin: CaLact: NaCl 10.0: 58.6: 31.4 | XIV-A | 1.59 | 0.25 | 2.90 | 0.11 | 87.16 | 1.23 | 0.5 bar | 1.45 | | 1.88 | | 1.00 | 1.04 |
| | | | | | | | | 1.0 bar | 1.40 | 0.01 | 1.87 | 0.01 | | |
| | | | | | | | | 2.0 bar | 1.42 | 0.02 | 1.88 | 0.01 | | |
| | | | | | | | | 4.0 bar | 1.39 | 0.01 | 1.87 | 0.01 | | |
| | XIV-B | 1.60 | 0.25 | 2.29 | 0.15 | 90.18 | 4.81 | 0.5 bar | 1.31 | | 1.85 | | 1.02 | 1.04 |
| | | | | | | | | 1.0 bar | 1.28 | | 1.84 | | | |
| | | | | | | | | 2.0 bar | 1.28 | | 1.84 | | | |
| | | | | | | | | 4.0 bar | 1.26 | | 1.83 | | | |
| | XIV-C | 1.69 | 0.07 | 2.69 | 0.22 | 88.88 | 0.75 | 0.5 bar | 1.30 | | 1.84 | | 0.98 | 1.02 |
| | | | | | | | | 1.0 bar | 1.24 | | 1.81 | | | |
| | | | | | | | | 2.0 bar | 1.25 | | 1.82 | | | |
| | | | | | | | | 4.0 bar | 1.27 | | 1.83 | | | |

Scanning electron Microscopy (SEM) images of representative sample of Formulation I Scanning electron Microscopy (SEM) images of representative sample of Formulation III Scanning electron Microscopy (SEM) images of representative sample of Formulation II Scanning electron Microscopy (SEM) images of representative sample of Formulation IV FIG. 6A
Feedstock Formulations 1-9
Table of Properties

| Formulation | Counterion | Excipient | Formulation | Ratio | Ca2+ % | Na % | Ca:Na Ratio | x50(μm) @ 1 bar | GSD @ 1 bar | 1/4 bar |
|---|---|---|---|---|---|---|---|---|---|---|
| 1 (III-B) | Lactate | 10% Leucine | leu:CaLact:NaCl | 10: 58.6: 31.4 | 10.8% | 12.3% | 1:2 | 2.04 | 2.17 | 1.09 |
| 2 | Lactate | 50% Leucine | leu:CaLact:NaCl | 50: 48.4: 1.6 | 8.9% | 0.6% | 8:1 | | | |
| 3 | Lactate | 10% Leucine | leu:CaLact:NaCl | 10: 66.6: 23.4 | 12.2% | 9.2% | 1:1.3 | 3.39 | 2.25 | 0.95 |
| 4(I-B) | Citrate | 10% Leucine | leu:CaCl2:Na3Cit | 10: 35.1: 54.9 | 12.7% | 14.7% | 1:2 | 2.88 | 2.11 | 1.21 |
| 5 | Citrate | 67% Leucine | leu:CaCl2:Na3Cit | 67.1: 30: 2.9 | 10.8% | 0.8% | 8:1 | | | |
| 6 | Citrate | None | CaCl2:Na3Cit | 39:61 | 16.3% | 0.4% | 1:2 | | | |
| 7 (II-B) | Sulfate | 10% Leucine | leu:CaCl2:Na2SO4 | 10: 39.6: 50.4 | 14.3% | 8.2% | 1:2 | 3.26 | 2.13 | 1.02 |
| 8 | Sulfate | 68% Leucine | leu:CaCl2:Na2SO4 | 67.6: 30: 2.4 | 10.8% | 0.4% | 8:1 | | | |
| 9 | Sulfate | None | CaCl2:Na2SO4 | 44:56 | 15.9% | 9.1% | 1:2 | | | |

| Formulation | Spraytec dV50 (μm) | Spraytec GSD | water % |
|---|---|---|---|
| 1 (III-B) | 2.85 | 3.16 | 6.58% |
| 2 | 6.14 | 2.71 | |
| 3 | 4.82 | 3.10 | 5.21% |
| 4(I-B) | 6.97 | 3.29 | |
| 5 | 8.39 | 3.08 | |
| 6 | 6.38 | 3.41 | 7.21% |
| 7 (II-B) | 4.61 | 3.27 | |
| 8 | 21.23 | 3.01 | |
| 9 | 8.20 | 3.55 | 6.53% |

FIG. 6B

Feedstock Formulations 1-9
Table of Properties

| Formulation | Powder weight μm | Emitted Dose % | FPF_TD <3.4 um % | FPF_TD <5.6 um % | % Mass collected | yield % | Tapped density (g/cc) |
|---|---|---|---|---|---|---|---|
| 1 (I+B) | 25.86 | 100.00% | 35.55% | 55.42% | 61.12% | 73.26% | 0.89 |
| 2 | 15.10 | 98.86% | 24.93% | 48.92% | 62.69% | 34.06% | 0.46 |
| 3 | 30.03 | 99.85% | 18.00% | 37.52% | 58.12% | 85.11% | 0.74 |
| 4(I-B) | 25.84 | 99.45% | 33.25% | 49.17% | 61.16% | 82.72% | 0.26 |
| 5 | 25.16 | 99.68% | 11.47% | 27.47% | 47.73% | n/a | 0.42 |
| 6 | 25.34 | 100.00% | 9.47% | 20.19% | 36.09% | 83.53% | 0.32 |
| 7 (II-B) | 23.15 | 99.38% | 47.37% | 62.00% | 72.27% | 72.57% | 0.42 |
| 8 | 25.10 | 98.05% | 13.15% | 25.24% | 47.68% | n/a | 0.22 |
| 9 | 25.32 | 100.00% | 8.62% | 19.42% | 38.54% | 54.91% | 0.49 |

FIG. 7

1. Salt aerosol
2. Bacteria/Virus

MUCUS — 1800μm

Collection buffer

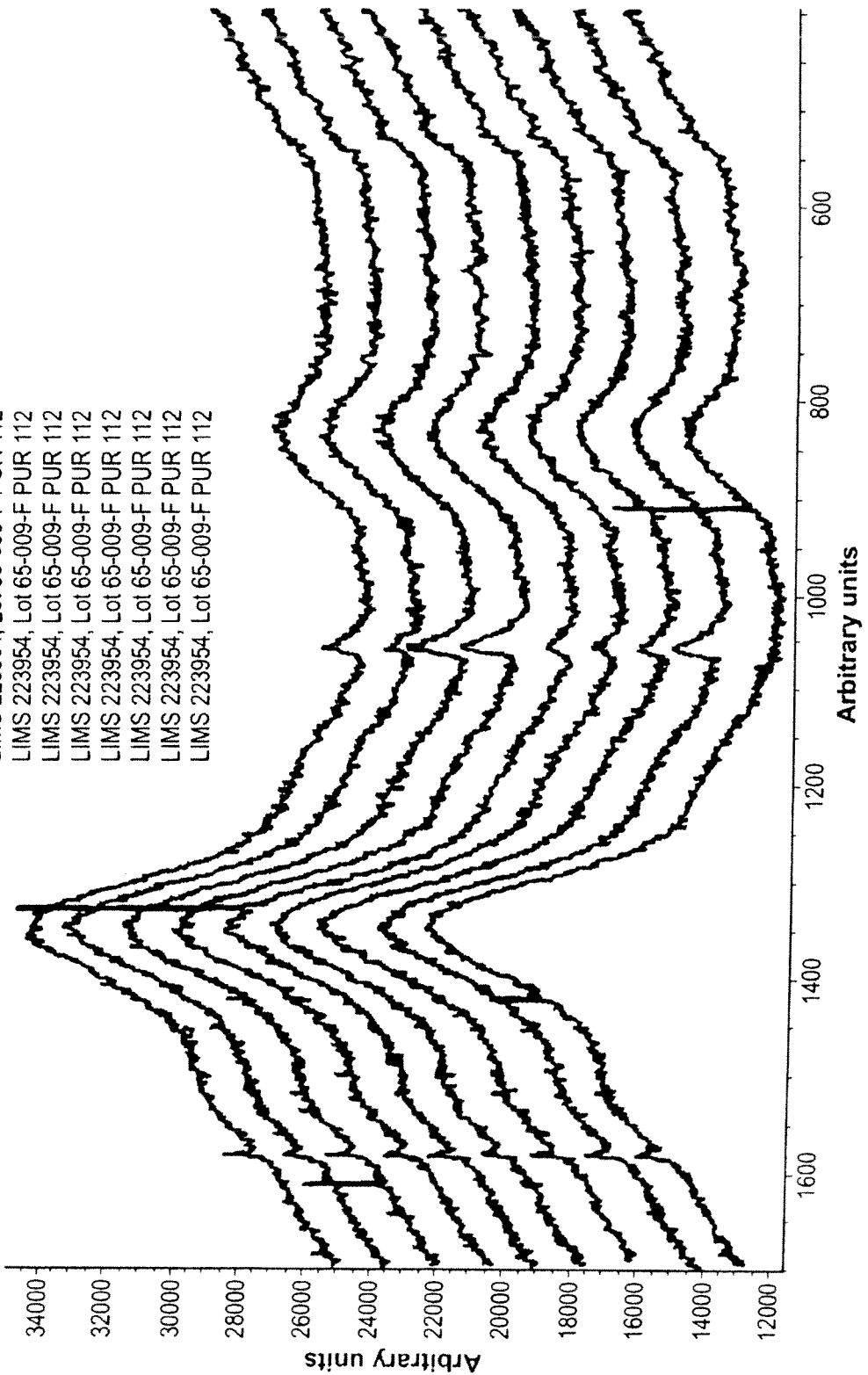

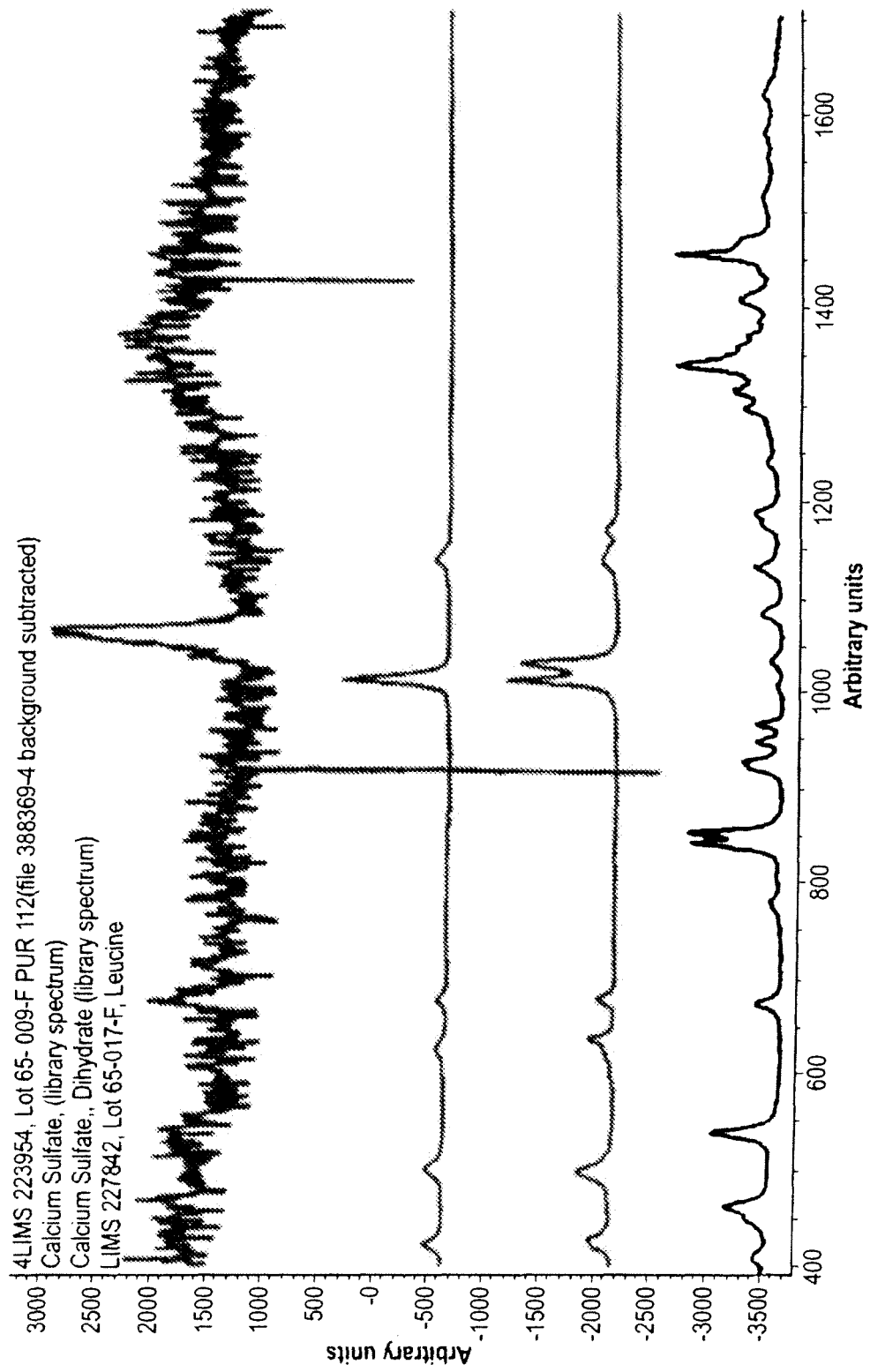

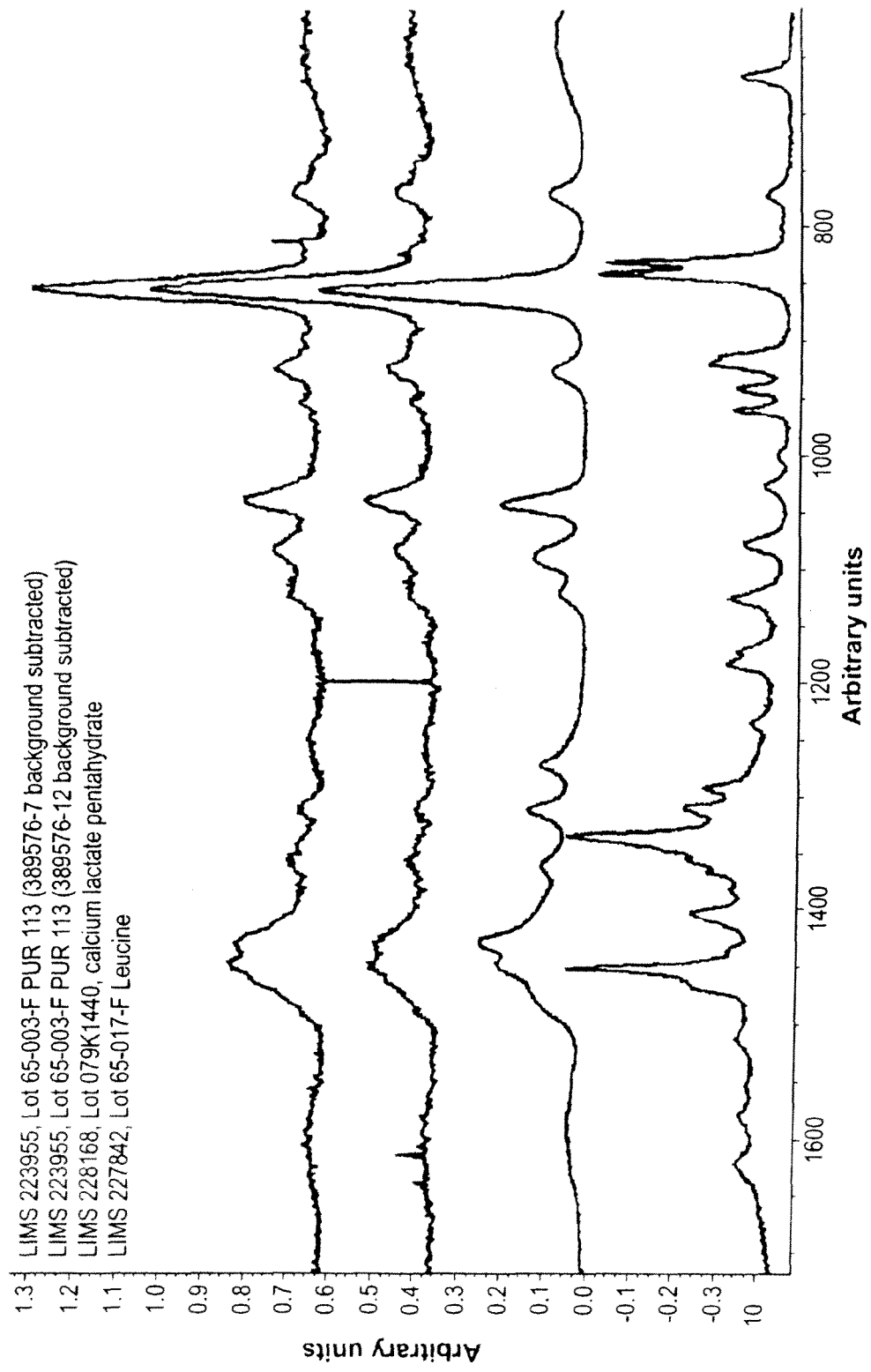

FIG. 37

| Powder formulations | | | Table 27 | | | |
|---|---|---|---|---|---|---|
| Formulation # | Formulation composition | | | | | |
| | Excipient | Excipient (wt %) | Calcium salt | Calcium salt (wt %) | Sodium salt | Sodium salt (wt %) |
| 1 | Leucine | 50.0 | Calcium chloride | 29.5 | Sodium chloride | 20.5 |
| 2 | Leucine | 50.0 | Calcium acetate | 33.8 | Sodium chloride | 16.2 |
| 3 | Leucine | 50.0 | Calcium lactate | 37.0 | Sodium chloride | 13.0 |
| 4 | Leucine | 50.0 | Calcium chloride | 22.0 | Sodium sulfate | 28.0 |
| 5 | Leucine | 50.0 | Calcium chloride | 19.5 | Sodium citrate | 30.5 |
| 6 | Leucine | 10.0 | Calcium lactate | 66.6 | Sodium chloride | 23.4 |
| 7 | Leucine | 10.0 | Calcium chloride | 39.6 | Sodium sulfate | 50.4 |
| 8 | Leucine | 10.0 | Calcium chloride | 35.1 | Sodium citrate | 54.9 |
| 9 | n.a. | n.a. | Calcium lactate | 74.0 | Sodium chloride | 26.0 |
| 10 | n.a. | n.a. | Calcium chloride | 44.0 | Sodium sulfate | 56.0 |
| 11 | n.a. | n.a. | Calcium chloride | 39.0 | Sodium citrate | 61.0 |
| 12 | Leucine | 10.0 | Calcium lactate | 58.6 | Sodium chloride | 31.4 |
| 13 | Maltodextrin | 10.0 | Calcium lactate | 58.6 | Sodium chloride | 31.4 |
| 14 | Mannitol | 10.0 | Calcium lactate | 58.6 | Sodium chloride | 31.4 |
| 15 | Lactose | 10.0 | Calcium lactate | 58.6 | Sodium chloride | 31.4 |
| 16 | Half leucine and half maltodextrin (wt basis) | 10.0 | Calcium lactate | 58.6 | Sodium chloride | 31.4 |
| 17 | Half leucine and half maltodextrin (wt basis) | 20.0 | Calcium lactate | 52.1 | Sodium chloride | 27.9 |
| 18 | Leucine | 20.0 | Calcium lactate | 52.1 | Sodium chloride | 27.9 |
| 19 | Leucine | 12.0 | Calcium lactate | 57.3 | Sodium chloride | 30.7 |
| 20 | Leucine | 8.0 | Calcium lactate | 59.9 | Sodium chloride | 32.1 | n.a. not applicable

DRY POWDER FORMULATIONS AND METHODS FOR TREATING PULMONARY DISEASES

RELATED APPLICATIONS

This application is the U.S. National Stage of International Application No. PCT/US2011/049435, filed Aug. 26, 2011, published in English, and claims the benefit of U.S. Patent Application No. 61/431,242 filed on Jan. 10, 2011, the benefit of 61/387,925, filed on Sep. 29, 2010, and the benefit of U.S. Patent Application No. 61/378,146 filed on Aug. 30, 2010, the entire teachings of these applications are incorporated herein by reference.

GOVERNMENT SUPPORT

This invention was made with government support under W911NF-10-1-0382 awarded by the Defense Advanced Research Projects Agency. The government has certain rights in the invention.

BACKGROUND OF THE INVENTION

Pulmonary delivery of therapeutic agents can offer several advantages over other modes of delivery. These advantages include rapid onset, the convenience of patient self-administration, the potential for reduced drug side-effects, ease of delivery by inhalation, the elimination of needles, and the like. Inhalation therapy is capable of providing a drug delivery system that is easy to use in an inpatient or outpatient setting, results in very rapid onset of drug action, and produces minimal side effects.

Metered dose inhalers (MDIs) are used to deliver therapeutic agents to the respiratory tract. MDIs are generally suitable for administering therapeutic agents that can be formulated as solid respirable dry particles in a volatile liquid under pressure. Opening of a valve releases the suspension at relatively high velocity. The liquid then volatilizes, leaving behind a fast-moving aerosol of dry particles that contain the therapeutic agent. MDIs are reliable for drug delivery to the upper and middle airways but are limited because they typically deliver only low doses per actuation. However, it is the bronchioles and alveoli that are often the site of manifestation of pulmonary diseases such as asthma and infections.

Liquid aerosol delivery is one of the oldest forms of pulmonary drug delivery. Typically, liquid aerosols are created by an air jet nebulizer, which releases compressed air from a small orifice at high velocity, resulting in low pressure at the exit region due to the Bernoulli effect. See, e.g., U.S. Pat. No. 5,511,726. The low pressure is used to draw the fluid to be aerosolized out of a second tube. This fluid breaks into small droplets as it accelerates in the air stream. Disadvantages of this standard nebulizer design include relatively large primary liquid aerosol droplet size often requiring impaction of the primary droplet onto a baffle to generate secondary splash droplets of respirable sizes, lack of liquid aerosol droplet size uniformity, significant recirculation of the hulk drug solution, and low densities of small respirable liquid aerosol droplets in the inhaled air.

Ultrasonic nebulizers use flat or concave piezoelectric disks submerged below a liquid reservoir to resonate the surface of the liquid reservoir, forming a liquid cone which sheds aerosol particles from its surface (U.S. 2006/0249144 and U.S. Pat. No. 5,551,416). Since no airflow is required in the aerosolization process, high aerosol concentrations can be achieved, however the piezoelectric components are relatively expensive to produce and are inefficient at aerosolizing suspensions, requiring active drug to be dissolved at low concentrations in water or saline solutions. Newer liquid aerosol technologies involve generating smaller and more uniform liquid respirable dry particles by passing the liquid to be aerosolized through micron-sized holes. See, e.g., U.S. Pat. No. 6,131,570; U.S. Pat. No. 5,724,957; and U.S. Pat. No. 6,098,620. Disadvantages of this technique include relatively expensive piezoelectric and fine mesh components as well as fouling of the holes from residual salts and from solid suspensions.

Dry powder inhalation has historically relied on lactose blending to allow for the dosing of particles that are small enough to be inhaled, but aren't dispersible enough on their own. This process is known to be inefficient and to not work for some drugs. Several groups have tried to improve on these shortcomings by developing dry powder inhaler (DPI) formulations that are respirable and dispersible and thus do not require lactose blending. Dry powder formulations for inhalation therapy are described in U.S. Pat. No. 5,993,805 to Sutton et al.; U.S. Pat. No. 69,216,527 to Platz et al.; WO 0000176 to Robinson et al.; WO 9916419 to Tarara et al.; WO 0000215 to Bot et al; U.S. Pat. No. 5,855,913 to Hanes et al.; and U.S. Pat. Nos. 6,136,295 and 5,874,064 to Edwards et al.

Broad clinical application of dry powder inhalation delivery has been limited by difficulties in generating dry powders of appropriate particle size, particle density, and dispersibility, in keeping the dry powder stored in a dry state, and in developing a convenient, hand-held device that effectively disperses the respirable dry particles to be inhaled in air. Another limiting factor for long-term storage of dry powders has been the challenge of maintaining stable physicochemical properties with the passage of time. In addition, the particle size of dry powders for inhalation delivery is inherently limited by the fact that smaller respirable dry particles are harder to disperse in air. Dry powder formulations, while offering advantages over cumbersome liquid dosage forms and propellant-driven formulations, are prone to aggregation and low flowability which considerably diminish dispersibility and the efficiency of dry powder-based inhalation therapies. For example, interparticular Van der Waals interactions and capillary condensation effects are known to contribute to aggregation of dry particles. Hickey, A. et al., "Factors Influencing the Dispersion of Dry Powders as Aerosols", Pharmaceutical Technology, August, 1994.

To overcome interparticle adhesive forces, Batycky et al. in U.S. Pat. No. 7,182,961 teach production of so called "aerodynamically light respirable particles," which have a volume median geometric diameter (VMGD) of greater than 5 microns ($\mu m$) as measured using a laser diffraction instrument such as HELOS (manufactured by Sympatec, Princeton, N.J.). See Batycky et al., column 7, lines 42-65. Another approach to improve dispersibility of respirable particles of average particle size of less than 10 $\mu m$, involves the addition of a water soluble polypeptide or addition of suitable excipients (including amino acid excipients such as leucine) in an amount of 50% to 99.9% by weight of the total composition. Eljamal et al., U.S. Pat. No. 6,582,729, column 4, lines 12-19 and column 5, line 55 to column 6, line 31. However, this approach reduces the amount of active agent that can be delivered using a fixed amount of powder. Therefore, an increased amount of dry powder is required to achieve the intended therapeutic results, for example, multiple inhalations and/or frequent administration may be required. Still other approaches involve the use of devices that apply mechanical forces, such as pressure from compressed gasses, to the small particles to disrupt interparticular adhesion during or just prior to administration. See, e.g., U.S. Pat. No. 7,601,336 to Lewis et al., U.S. Pat. No. 6,737,044 to Dickinson et al., U.S. Pat. No. 6,546,928 to Ashurst et al., or U.S. Pat. Applications 20090208582 to Johnston et al.

A further limitation that is shared by each of the above methods is that the aerosols produced typically include substantial quantities of inert carriers, solvents, emulsifiers, propellants, and other non-drug material. In general, the large quantities of non-drug material are required for effective formation of respirable dry particles small enough for alveolar delivery (e.g. less than 5 microns and preferably less than 3 microns). However, these amounts of non-drug material also serve to reduce the purity and amount of active drug substance that can be delivered. Thus, these methods remain substantially incapable of introducing large active drug dosages accurately to a patient for systemic delivery.

Therefore, there remains a need for the formation of small particle size aerosols that are highly dispersible. Furthermore, there is a need for creating powders that are dense in mass and in drug, in order to maximize the quantity of drug within a given delivery container. In addition, methods that produce aerosols comprising greater quantities of drug and lesser quantities of non-drug material are needed. Finally, a method that allows a patient to administer a unit dosage rapidly with one or two, small volume breaths is needed.

SUMMARY OF THE INVENTION

The invention relates to respirable dry powders comprised of dry particles that contain one or more divalent metal cations, such as calcium ($Ca^{2+}$), as an active ingredient or inactive ingredient, and to dry powders that contain the respirable particles. Preferably, the respirable dry particles are small, dense and highly dispersible, as described in detail herein.

In one aspect, the respirable dry powder comprises respirable dry particles comprising a divalent metal cation salt, a monovalent metal cation salt, one or more additional therapeutic agents, and optionally an excipient, wherein the ratio of divalent metal cation to monovalent metal cation is from about 8:1 (mole:mole) to about 2:1 (mole:mole), about 4:1 (mole:mole) to about 2:1 (mole:mole), or 3.9:1 (mole:mole) to about 2:1 (mole:mole). As shown herein, respirable dry particles that contain calcium ions and sodium ions with these ranges provide superior efficacy. Accordingly, these types of formulations can provide the therapeutic benefits of the divalent metal cation, and of the additional therapeutic agent. Preferably the divalent metal cation salt is a calcium salt such as calcium lactate, calcium sulfate, calcium carbonate, calcium citrate and combinations thereof. Preferable the monovalent metal cation salt is a lithium salt, a potassium salt or a sodium salt. In some embodiments the monovalent metal cation salt is a sodium salt selected from the group consisting of sodium chloride, sodium citrate, sodium lactate, sodium sulfate and combinations thereof. When present, the excipient can be present from about 1% (w/w) to about 40% (w/w). Preferred excipients are selected from the group consisting of sugars, polysaccharides, sugar alcohols, amino acids, and any combination thereof. In particular embodiments, the excipient is selected from leucine, maltodextrin, mannitol and any combination thereof. The additional therapeutic agent comprises from about 0.01% (w/w) to about 90% (w/w) of the respirable dry particles. Suitable additional therapeutic agents are described herein, and preferred agents are independently selected from the group consisting of LABAs, short-acting beta agonists, corticosteroids, LAMAs, antibiotics, DNAse, sodium channel blockers and combinations thereof. The respirable dry particles have a volume median geometric diameter (VMGD) of about 10 microns or less; a dispersibility ratio (1/4 bar) of 2.0 or less as measured by laser diffraction (RODOS/HELOS system); a Fine Particle Fraction (FPF) of less than 5.6 microns of at least 45%, a Fine Particle Fraction (FPF) of less than 3.4 microns of at least 30%, a mass median aerodynamic diameter (MMAD) of about 7 microns or less, a tap density greater than 0.45 g/cc and/or a heat of solution between about −10 kcal/mol and 10 kcal/mol.

In another aspect, the respirable dry powder comprises respirable dry particles which comprise a calcium salt and a sodium salt, wherein the ratio of $Ca^{2+}$ to $Na^+$ is from about 8:1 (mole:mole) to about 2:1 (mole:mole), 4:1 (mole:mole) to about 2:1 (mole:mole), or 3.9:1 (mole:mole) to about 2:1 (mole:mole). As shown herein, respirable dry particles that contain calcium ions and sodium ions with these ranges provide superior efficacy in certain disease models. The calcium salt can be selected from the group consisting of calcium lactate, calcium sulfate, calcium carbonate, calcium citrate and combinations thereof. The sodium salt can be selected from the group consisting of sodium chloride, sodium citrate, sodium lactate, sodium sulfate and combinations thereof. If desired, the respirable dry powder of this aspect can further comprise an excipient, which is preferably 1% (w/w) to 40% (w/w) of the dry powder. Preferred excipients are selected from the group consisting of sugars, polysaccharides, sugar alcohols, amino acids, and any combination thereof. In some embodiments, the excipient is selected from leucine, maltodextrin, mannitol and any combination thereof. The dry powder of this aspect can further comprise an additional therapeutic agent, such as LABAs, short-acting beta agonists, corticosteroids, LAMAs, antibiotics, DNAse, sodium channel blockers, and combinations thereof. The respirable dry particles have a volume median geometric diameter (VMGD) of about 10 microns or less; a dispersibility ratio (1/4 bar) of 2.0 or less as measured by laser diffraction (RODOS/HELOS system); a Fine Particle Fraction (FPF) of less than 5.6 microns of at least 45%, a Fine Particle Fraction (FPF) of less than 3.4 microns of at least 30%, a mass median aerodynamic diameter (MMAD) of about 7 microns or less, a tap density greater than 0.45 g/cc and/or a heat of solution between about −10 kcal/mol and 10 kcal/mol. Preferably, the calcium cation is present in at least about 5% by weight of the respirable dry powder.

In another aspect, the respirable dry powder comprises respirable dry particles which comprise a divalent metal cation salt, one or more therapeutic agents, and optionally an excipient, wherein the respirable dry particles have a volume median geometric diameter (VMGD) of 10 microns or less, a dispersibility ratio (1/4 bar) of 2.0 or less as measured by laser diffraction (RODOS/HELOS system), and a tap density of about 0.4 g/cc to about 1.2 g/cc. In some embodiments, the respirable dry particles have a tap density of about 0.5 g/cc to about 1.2 g/cc. In some embodiments, the divalent metal cation salt does not have a biological activity selected from the group consisting of anti-bacterial activity, anti-viral activity, anti-inflammatory activity and combinations thereof. Preferred divalent metal cation salts for the dry powders of this aspect are magnesium salts, such as of magnesium lactate and magnesium sulfate. In particular embodiments, the respirable dry particles comprise a) about 20% (w/w) to about 90% (w/w) magnesium salt, and about 0.01% (w/w) to about 20% (w/w) therapeutic agent; b) about 20% (w/w) to about 80% (w/w) magnesium salt, and about 20% (w/w) to about 60% (w/w) therapeutic agent; or c) about 5% (w/w) to about 40% (w/w) magnesium salt, and about 60% (w/w) to about 95% (w/w) therapeutic agent; and wherein all components of the respirable dry particles amount to 100 weight %. Preferably, the respirable dry particles comprise 3% (w/w) or greater magnesium ion. The respirable dry powder may contain about 0.01% (w/w) to about 80% (w/w) excipient. Preferred excipients are selected from the group consisting of sugars, polysaccharides, sugar alcohols, amino acids, and any combination thereof. In some embodiments, the excipient is selected from leucine, maltodextrin, mannitol and any combination thereof. The dry powder of this aspect can further comprise an additional therapeutic agent, such as LABAs, short-acting beta agonists, corticosteroids, LAMAs, antibiotics, DNAse, sodium channel blockers, and combinations thereof. The respirable dry particles have a volume median geometric diameter (VMGD) of about 10 microns or less; a dispersibility ratio (1/4 bar) of 2.0 or less as measured by laser diffraction (RODOS/HELOS system); a Fine Particle Fraction (FPF) of less than 5.6 microns of at least 45%, a Fine Particle Fraction (FPF) of less than 3.4 microns of at least 30%, a mass median aerodynamic diameter (MMAD) of about 7 microns or less, a tap density greater than 0.45 g/cc and/or a heat of solution between about −10 kcal/mol and 10 kcal/mol. Preferably, the divalent metal cation is present in at least about 5% by weight of the respirable dry powder.

The invention also relates to a respirable dry powder or dry particle, as described herein, for use in therapy (e.g., treatment, prophylaxis, or diagnosis). The invention also relates to the use of a respirable dry particle or dry powder, as described herein, for use in treatment, prevention or reducing contagion as described herein, and in the manufacture of a medicament for the treatment, prophylaxis or diagnosis of a respiratory disease and/or infection as described herein.

The invention also relates to a method of reducing inflammation comprising administering to the respiratory tract of a patient in need thereof an effective amount of a respirable dry powder, as described herein. The inflammation can be associated with asthma, chronic obstructive pulmonary disorder (COPD) or cystic fibrosis (CF).

The invention also relates to a method of treating a respiratory disease comprising administering to the respiratory tract of a patient in need thereof an effective amount of a respirable dry powder, as described herein.

The invention also relates to methods for treating a respiratory disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of the respirable dry particles or dry powder. The invention also relates to methods for the treatment or prevention of acute exacerbations of chronic pulmonary diseases, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of the respirable dry particles or dry powder.

BRIEF DESCRIPTION OF THE DRAWINGS

FIGS. 1A-1F is a table that shows properties for dry powders prepared from feedstock Formulations I, II, III and IV described in Examples 1-3 and 14. FIG. 1A includes spray drying parameters used for spray drying the powders. FIG. 1B shows the HPLC results for percent calcium ion content of the powders, density results including tap and bulk densities, and Karl Fischer results for percent water content in the powders. FIG. 1C shows fine particle fraction (FPF) data and percent mass of powders collected using a two-stage (ACI-2) Andersen Cascade Impactor. FIG. 1D shows fine particle fraction (FPF) data and percent mass of powders collected using an eight-stage (ACI-8) Andersen Cascade Impactor. FIG. 1E shows data for mass median aerodynamic diameter (MMAD) and FPF (based on total dose and recovered dose). FIG. 1F shows data for volume median geometric diameter (DV50), geometric standard deviation (GSD) and FPF less than 5.0 microns (FPF<5.0 μm) as measured by Spraytec instrument and geometric or volume particle size distribution (which is also referred to as VMGD, x50/dg or x50), GSD and 1/4 bar and 0.5/4 bar information as measured by HELOS with RODOS attachment instrument.

FIGS. 6A-6B is a table that shows properties for dry powders prepared by feedstock Formulations 1-9. Formulation 1 in FIG. 6 corresponds to Formulation III-B in Example 2. Formulation 4 in FIG. 6 corresponds to Formulation I-B in Example 1. Formulation 7 in FIG. 6 corresponds to Formulation II-B in Example 3. Abbreviations in the table heading are described elsewhere in the specification. In FIG. 6, all powders were made using a Büchi spray dryer.

FIG. 7 is a schematic of the pass-through model.

FIG. 11A shows the changes in body temperature of ferrets treated with a calcium citrate powder compared to the control animals. FIG. 11B shows the changes in body temperature of ferrets treated with a calcium sulfate powder compared to the control animals. FIG. 11C shows the changes in body temperature of ferrets treated with a calcium lactate powder compared to the control animals. FIG. 11D shows the change in body temperature from baseline for each animal using area under the curve for the duration of the study (d0-d10). Data depict the mean±SEM for each group (p=0.09 for the leucine control and lactate group by Student t-test).

FIGS. 27A-H are RAMAN spectra. FIG. 27A shows RAMAN spectra for six particles from the Formulation I sample, and are shown overlaid. FIG. 27B shows spectrum 389575-6 is background subtracted and overlaid with the Raman spectra of calcium citrate tetrahydrate, sodium citrate, and leucine. FIG. 27C shows RAMAN spectra for eight particles from the Formulation II sample, and are shown overlaid. FIG. 27D shows spectrum 388369-4 is background subtracted and overlaid with Raman spectra of calcium sulfate, calcium sulfate dihydrate, sodium sulfate anhydrous, and leucine. FIG. 27E shows RAMAN spectra for twelve particles from the Formulation III sample, and are shown overlaid. FIG. 27F shows spectra 389576-7 and 389576-12 are background subtracted and overlaid with the Raman spectra of calcium lactate pentahydrate, and leucine. FIG. 27G shows RAMAN spectra for twelve particles from the Formulation IV sample, and are shown overlaid. FIG. 27H, spectrum 389577-9 is background subtracted and overlaid with the Raman spectra of calcium lactate pentahydrate.

FIG. 31B is a graph showing change in volume particle size of formulations Formulation I (calcium citrate), Formulation II (calcium sulfate) and Formulation III (calcium lactate) during in-use stability testing at extreme conditions. The graph compares change in median volume particle size versus time elapsed in the chamber at extreme temperature and humidity conditions (30° C., 75% RH). The values in the legend indicate the true value at time zero. The plots show fluctuation as a function of change as compared to time zero.

lactose, (ii) mannitol) or (iii) maltodextrin as excipients. FIG. 31C compares changes in FPF (total dose)<5.6 microns (%) versus time elapsed in the chamber for the second set of powders at extreme temperature and humidity conditions (30° C., 75% RH). The values in the legend indicate the true value at time zero. The plots show fluctuation as a function of change as compared to time zero.

FIG. 37 is a table showing the compositions of exemplary dry powder formulations.

FIG. 42 is a graph showing the results of a study of bacterial pneumonia in a mouse model using Formulations III, IV and V. The data show that Formulation III inhibits bacterial pneumonia more effectively than Formulation IV and Formulation V.

FIGS. 43A-43B are graphs showing the efficacy of Formulation III, Formulation IV and Formulation V in a mouse OVA model of allergic asthma. The results show that Formulation III decreases total (FIG. 43A) and eosinophil (FIG. 43B) cell counts more effectively than Formulation IV and Formulation V.

FIG. 44 is a graph showing the dispersibility of Formulations III, VI, VII and VIII. The emitted dose of the formulations is shown as a function of inhaled energy. The data indicate that all the powders are well-dispersed, with Formulations III, VI and VIII showing a higher dispersibility than Formulation VII.

FIGS. 45A and 45B are graphs illustrating the solid state properties of Formulation VII and Formulation VIII. FIG. 45A shows a high resolution XRPD pattern of both Formulation VII and Formulation VIII which indicates that the powders consists of crystalline leucine and amorphous calcium lactate and sodium chloride. FIG. 45B shows the mDSC graphs of both formulations which indicate the glass transition temperatures of the Formulation VII (91° C.) and Formulation VIII (107° C.).

FIGS. 46A and 46B are graphs showing the results of a study of bacterial pneumonia in a mouse model using dry powders having various molar ion ratios of calcium to sodium, but a fixed dose of calcium. The data indicate that all the dry powders are effective in inhibiting bacterial pneumonia.

FIGS. 47A-47B are graphs showing results of an in vivo influenza study in ferrets. The graphs show the efficacy of Formulation III and Formulation VI on body temperature (FIG. 47A) and body weight (FIG. 47B) ten days following infection. The data indicate that both Formulation III and Formulation VI are effective in treating ferret flu.

FIGS. 48A-48B are graphs showing the efficacy of dry powders having various molar ion ratios of calcium to sodium, but a fixed dose of calcium in an OVA mouse model of allergic asthma. The data show that all formulations decrease total cell (FIG. 48A) and eosinophils cell (FIG. 48B) counts and that dry powders with higher molar ratios of calcium to sodium are more effective.

FIGS. 49A-49D are graphs showing the efficacy of Formulation III and Formulation VII on inflammation induced in a TS model of COPD. The data indicate that both Formulation III and Formulation VII significantly decreases inflammatory cells associated with COPD and that a once-daily dose (QD) of Formulation III is as effective as a twice daily dose (BID).

FIG. 50A and FIG. 506B. A significant reduction in KC and MIP2, two key neutrophil chemokines, was seen when TS Mice were treated Q.D. with Formulations III and VII.

FIG. 51A. A significant reduction in neutrophil inflammation, as represented by cell counts, was seen at the lowest dose tested, when TS Mice were treated B.I.D. with Formulation VIII.

FIG. 51B. A significant reduction in neutrophil inflammation, as represented by cell counts, was seen when OVA sensitized mice were treated with Formation VIII and then infected with rhinovirus.

FIG. 52. No significant increase in airway resistance was observed when mice were treated with Formulation VIII and then challenged with methacholine chloride (MCh) as compared to when the sham treatment group was challenged with MCh.

FIG. 53 is a graph showing a decrease in airway resistance was observed when mice were treated with Formulation XI and 48-A and then challenged with methacholine chloride (MCh) as compared to when the sham (Placebo-B) treatment group was challenged with MCh.

FIG. 54 is a graph showing a decrease in airway resistance was observed when mice were treated with Formulation XIV and 48-B and then challenged with methacholine chloride (MCh) as compared to when the sham (Placebo-B) treatment group was challenged with MCh.

Figure 55A:
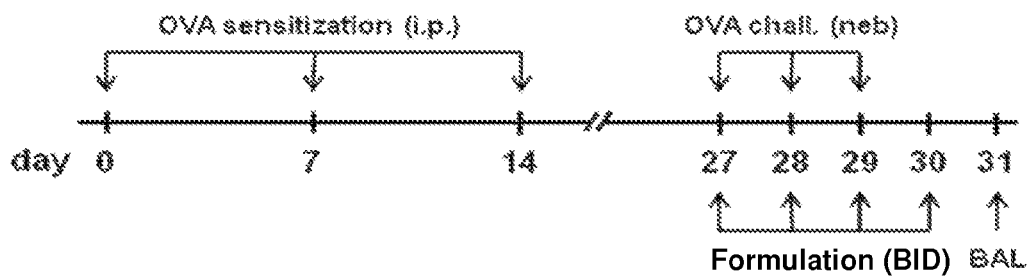

FIG. 55A is a schematic showing mice sensitized and challenged to OVA.

Figure 55B:
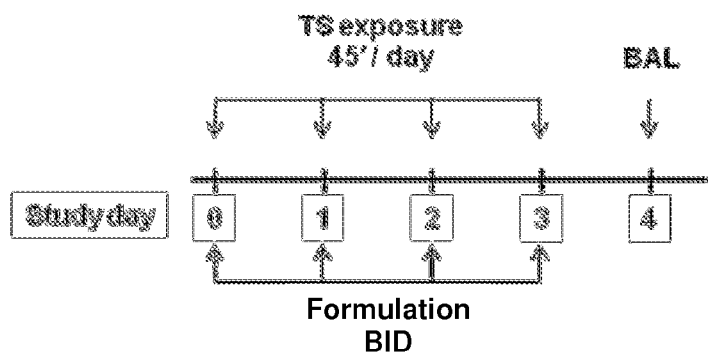

FIG. 55B is a schematic showing a 4-day TS exposure model.

Figure 55C:
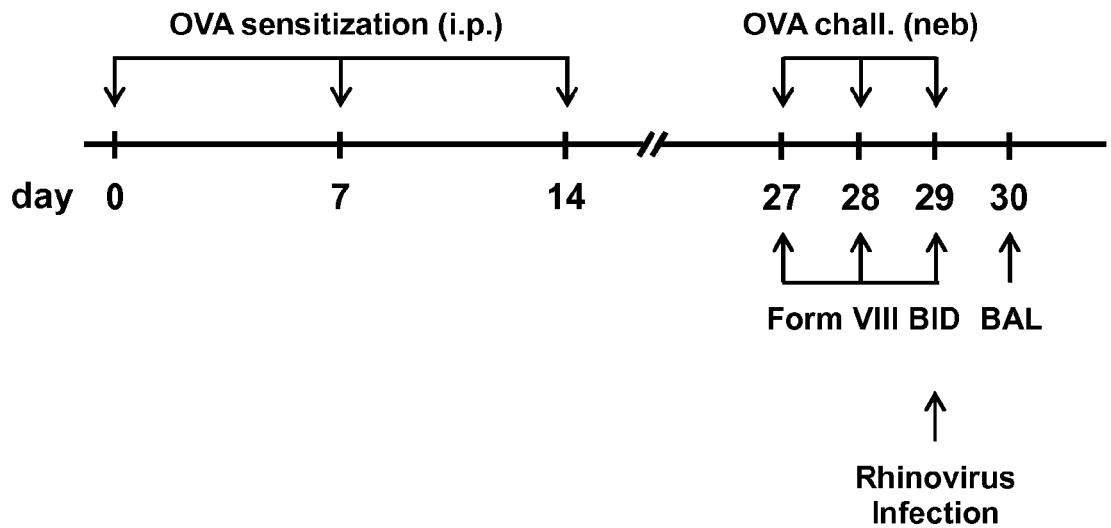

FIG. 55C is a schematic showing the rhinovirus infection model.

Figure 55D:
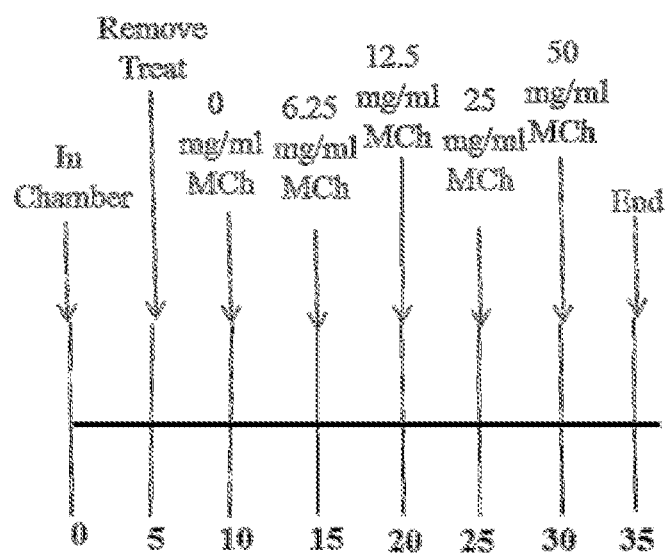

FIG. 55D is a schematic showing the experimental procedure used in Example 45.

DETAILED DESCRIPTION OF THE INVENTION

This invention relates, in part, to respirable dry powders that deliver one or more divalent metal cations, such as calcium, as an active ingredient, and to divalent metal cation-containing (e.g., calcium-containing) respirable dry particles contained within the powders. The invention also relates to respirable dry particles that contain one or more monovalent cations (such as Na$^+$) and to dry powders that contain the respirable particles.

In one aspect, the respirable dry powders and dry particles of the invention may be divalent metal cation (e.g., calcium) dense respirable particles that are small and dispersible. For example, the dry particles can contain a high percentage of divalent metal cation salt (i.e., be dense in divalent metal cation salt) and/or contain divalent metal cation salts that dissociate to release two or more moles of divalent metal cation per mole of salt.

The respirable dry powders and dry particles may contain a high percentage of a divalent metal cation salt (e.g. a calcium salt) that dissociates to release one mole of divalent metal cation per mole of salt or that contains a high molecular weight anion and therefore dissociates to produce a relatively small mass of divalent cation. Accordingly, in some aspects, the respirable dry powders and dry particles of the invention may be divalent metal cation salt (e.g., calcium salt) dense and are small and dispersible.

In another aspect, the respirable dry powders and dry particles are mass dense (e.g. have a tap density or envelope density of greater than about 0.4 g/cc, or at least about 0.45 g/cc, 0.5 g/cc, 0.6 g/cc, 0.7 g/cc or 0.8 g/cc), small, and dispersible.

The respirable dry particles may be large or small, e.g., the dry powder has a geometric diameter (VMGD) between 0.5 microns and 30 microns. Optionally, the MMAD of the dry powder may be between 0.5 and 10 microns, more preferably between 1 and 5 microns. When they are small, the particles optionally have a tap density between 0.4 g/cc and 1.2 g/cc, or between 0.55 g/cc and 1.0 g/cc. When they are large, the particles can have a geometric diameter (VMGD) between 5 microns and 30 microns (more preferably between 10 microns and 30 microns), and optionally, have a tap density between 0.01 g/cc and 0.4 g/cc, or between 0.05 g/cc and 0.25 g/cc.

Respirable dry powders that contain small particles and that are dispersible in air, and preferably dense (e.g., dense in active ingredient) are a departure from the conventional wisdom. It is well known that the propensity for particles to aggregate or agglomerate increases as particle size decreases. See, e.g., Hickey, A. et al., "Factors Influencing the Dispersion of Dry Powders as Aerosols", Pharmaceutical Technology, August, 1994.

As described herein, the invention provides respirable dry powders that contain respirable particles that are small and dispersible in air without additional energy sources beyond the subject's inhalation. Thus, the respirable dry powders and respirable dry particles can be used therapeutically, without including large amounts of non-active components (e.g., excipients) in the particles or powders, or by using devices that apply mechanical forces to disrupt aggregated or agglomerated particles during or just prior to administration. For example, devices such as passive dry powder inhalers may be used to deliver the dry powder or dry particles.

The respirable dry powders and respirable particles of the invention are also generally, dense in active ingredient(s), i.e., divalent metal cations (e.g., calcium containing salt(s)). For example, as described herein, when an excipient is included in the respirable dry powder or particles, the excipient is a minor component (e.g., about 50% or less, by weight, preferably about 20% or less by weight, about 12% or less by weight, about 10% or less by weight, about 8% or less by weight or less by weight). However, in some embodiments, an excipient can be present in higher amounts. Thus, in one aspect, the respirable particles are not only small and highly dispersible, but can contain a large amount of divalent metal cation, for example, calcium ($Ca^{2+}$). Accordingly, a smaller amount of powder will need to be administered in order to deliver the desired dose of divalent metal cation (e.g., calcium). For example, the desired dose of calcium may be delivered with one or two inhalations from a capsule-type or blister-type inhaler.

Respirable dry powder and dry particles that are small, dispersible and dense (e.g., divalent cation dense, divalent cation salt dense, and/or mass dense) provide advantages for therapeutic uses. For example, a desired therapeutically effective dose of divalent metal cation (e.g. calcium) can be delivered when a subject inhales a small volume of dry powder.

DEFINITIONS

The term "dry powder" as used herein refers to a composition that contains finely dispersed respirable dry particles that are capable of being dispersed in an inhalation device and subsequently inhaled by a subject. Such dry powder or dry particle may contain up to about 25%, up to about 20% or up to about 15% water or other solvent, or be substantially free of water or other solvent, or be anhydrous.

The term "dry particles" as used herein refers to respirable particles that may contain up to about 25%, up to about 20%, or up to about 15% water or other solvent, or be substantially free of water or other solvent, or be anhydrous.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

The term "small" as used herein to describe respirable dry particles refers to particles that have a volume median geometric diameter (VMGD) of about 10 microns or less, preferably about 5 microns or less.

As used herein, the terms "administration" or "administering" of respirable dry particles refers to introducing respirable dry particles to the respiratory tract of a subject.

As used herein, the term "respiratory tract" includes the upper respiratory tract (e.g., nasal passages, nasal cavity, throat, pharynx), respiratory airways (e.g., larynx, tranchea, bronchi, bronchioles) and lungs (e.g., respiratory bronchioles, alveolar ducts, alveolar sacs, alveoli).

The term "dispersible" is a term of art that describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by HELOS/RODOS. These quotients are referred to herein as "1/4 bar," and "0.5/4 bar," respectively, and dispersibility correlates with a low quotient. For example, 1/4 bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a 1/4 bar or 0.5/4 bar ratio that is close to 1.0. Highly dispersible powders have a low tendency to agglomerate, aggregate or clump together and/or, if agglomerated, aggregated or clumped together, are easily dispersed or dc-agglomerated as they emit from an inhaler and are breathed in by the subject. Dispersibility can also be assessed by measuring the size emitted from an inhaler as a function of flowrate. As the flow rate through the inhaler decreases, the amount of energy in the airflow available to be transferred to the powder to disperse it decreases. A highly dispersible powder will have its size distribution as characterized aerodynamically by its mass median aerodynamic diameter (MMAD) or geometrically by its VMGD, not substantially increase over a range of flow rates typical of inhalation by humans, such as about 15 to 60 LPM.

The terms "FPF (<5.6)," "FPF (<5.6 microns)," and "fine particle fraction of less than 5.6 microns" as used herein, refer to the fraction of a sample of dry particles that have an aerodynamic diameter of less than 5.6 microns. For example, FPF (<5.6) can be determined by dividing the mass of respirable dry particles deposited on the stage one and on the collection filter of a two-stage collapsed Andersen Cascade Impactor (ACI) by the mass of respirable dry particles weighed into a capsule for delivery to the instrument. This parameter may also be identified as "FPF_TD (<5.6)," where TD means total dose. A similar measurement can be conducted using an eight-stage ACI. The eight-stage ACI cutoffs are different at the standard 60 L/min flowrate, but the FPF_TD (<5.6) can be extrapolated from the eight-stage complete data set. The eight-stage ACI result can also be calculated by the USP method of using the dose collected in the ACI instead of what was in the capsule to determine FPF.

The terms "FPF (<3.4)," "FPF (<3.4 microns)," and "fine particle fraction of less than 3.4 microns" as used herein, refer to the fraction of a mass of respirable dry particles that have an aerodynamic diameter of less than 3.4 microns. For example, FPF (<3.4) can be determined by dividing the mass of respirable dry particles deposited on the collection filter of a two-stage collapsed ACI by the total mass of respirable dry particles weighed into a capsule for delivery to the instrument. This parameter may also be identified as "FPF_TD (<3.4)," where TD means total dose. A similar measurement can be conducted using an eight-stage ACI. The eight-stage ACI result can also be calculated by the USP method of using the dose collected in the ACI instead of what was in the capsule to determine FPF.

The terms "FPF (<5.0)," "FPF (<5.0 microns)," and "fine particle fraction of less than 5.0 microns" as used herein, refer to the fraction of a mass of respirable dry particles that have an aerodynamic diameter of less than 5.0 microns. For example, FPF (<5.0) can be determined by using an eight-stage ACI at the standard 60 L/min flowrate by extrapolating from the eight-stage complete data set. This parameter may also be identified as "FPF_TD (<5.0)," where TD means total dose. When used in conjunction with a geometric size distribution such as those given by a Malvern Spraytec, Malvern Mastersizer or Sympatec Helos particle sizer, "FPF (<5.0)" refers to the fraction of a mass of respirable dry particles that have a geometric diameter of less than 5.0 micrometers.

The terms "FPD (<4.4)", "FPD<4.4 µm", "FPD (<4.4 microns)" and "fine particle dose of less than 4.4 microns" as used herein, refer to the mass of respirable dry powder particles that have an aerodynamic diameter of less than 4.4 micrometers. For example, FPD<4.4 µm can be determined by using an eight-stage ACI at the standard 60 L/min flowrate and summing the mass deposited on the filter, and stages 6, 5, 4, 3, and 2 for a single dose of powder actuated into the ACI.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopia convention, Rockville, Md., 13$^{th}$ Revision, 222-225, 2007. This method utilizes an in vitro device set up to mimic patient dosing.

The term "capsule emitted powder mass" or "CEPM" as used herein, refers to the amount of dry powder formulation emitted from a capsule or dose unit container during an inhalation maneuver. CEPM is measured gravimetrically, typically by weighing a capsule before and after the inhalation maneuver to determine the mass of powder formulation removed. CEPM can be expressed either as the mass of powder removed, in milligrams, or as a percentage of the initial filled powder mass in the capsule prior to the inhalation maneuver.

The term "effective amount," as used herein, refers to the amount of agent needed to achieve the desired effect, such as an amount that is sufficient to increase surface and/or bulk viscoelasticy of the respiratory tract mucus (e.g., airway lining fluid), increase gelation of the respiratory tract mucus (e.g., at the surface and/or bulk gelation), increase surface tension of the respiratory tract mucus, increasing elasticity of the respiratory tract mucus (e.g., surface elasticity and/or bulk elasticity), increase surface viscosity of the respiratory tract mucus (e.g., surface viscosity and/or bulk viscosity), reduce the amount of exhaled particles, reduce pathogen (e.g., bacteria, virus) uptake or pathogen burden, reduce symptoms (e.g., fever, coughing, sneezing, nasal discharge, diarrhea and the like), reduce occurrence of infection, reduce viral replication, or improve or prevent deterioration of respiratory function (e.g., improve forced expiratory volume in 1 second FEV1 and/or forced expiratory volume in 1 second FEV1 as a proportion of forced vital capacity FEV1/FVC) or stimulate innate immunity of airway epithelium. The actual effective amount for a particular use can vary according to the particular dry powder or dry particle, the mode of administration, and the age, weight, general health of the subject, and severity of the symptoms or condition being treated. Suitable amounts of dry powders and dry particles to be administered, and dosage schedules, for a particular patient can be determined by a clinician of ordinary skill based on these and other considerations.

The term "pharmaceutically acceptable excipient" as used herein means that the excipient can be taken into the lungs with no significant adverse toxicological effects on the lungs. Such excipients are generally regarded as safe (GRAS) by the U.S. Food and Drug Administration.

All references to salts herein include anhydrous forms and all hydrated forms of the salt.

Dry Powders and Dry Particles

The invention relates to respirable dry powders and dry particles that contain one or more divalent metal cations, such as beryllium ($Be^{2+}$), magnesium, ($Mg^{2+}$), calcium ($Ca^{2+}$), strontium ($Sr^{2+}$), barium ($Ba^{2+}$), radium ($Ra^{2+}$), or iron (ferrous ion, $Fe^{2+}$), as an active ingredient. The active divalent metal cation (e.g., calcium) is generally present in the dry powders and dry particles in the form of a salt, which can be crystalline or amorphous. The dry powders and dry particles can optionally include additional salts (e.g. monovalent salts, such as sodium salts, potassium salts, and lithium salts.), therapeutically active agents or pharmaceutically acceptable excipients.

In some aspects, the respirable dry powder and dry particles contain one or more salts of a group IIA element (i.e., one or more beryllium salts, magnesium salts, calcium salts, barium salts, radium salts or any combination of the forgoing). In more particular aspects, the respirable dry powder and dry particles contain one or more calcium salts, magnesium salts or any combination of the forgoing. In particular embodiments, the respirable dry powder and dry particles contain one or more calcium salts. In other particular embodiments, respirable dry powder and dry particles contain one or more magnesium salts.

Suitable beryllium salts include, for example, beryllium phosphate, beryllium acetate, beryllium tartrate, beryllium citrate, beryllium gluconate, beryllium maleate, beryllium succinate, sodium beryllium malate, beryllium alpha brom camphor sulfonate, beryllium acetylacetonate, beryllium formate or any combination thereof.

Suitable magnesium salts include, for example, magnesium fluoride, magnesium chloride, magnesium bromide, magnesium iodide, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or any combination thereof.

Suitable calcium salts include, for example, calcium chloride, calcium sulfate, calcium lactate, calcium citrate, calcium carbonate, calcium acetate, calcium phosphate, calcium alginate, calcium stearate, calcium sorbate, calcium gluconate and the like.

Suitable strontium salts include, for example, strontium chloride, strontium phosphate, strontium sulfate, strontium carbonate, strontium oxide, strontium nitrate, strontium acetate, strontium tartrate, strontium citrate, strontium gluconate, strontium maleate, strontium succinate, strontium malate, strontium aspartate in either L and/or D-form, strontium fumarate, strontium glutamate in either L- and/or D-form, strontium glutarate, strontium lactate, strontium L-threonate, strontium malonate, strontium ranelate (organic metal chelate), strontium ascorbate, strontium butyrate, strontium clodronate, strontium ibandronate, strontium salicylate, strontium acetyl salicylate or any combination thereof.

Suitable barium salts include, for example, barium hydroxide, barium fluoride, barium chloride, barium bromide, barium iodide, barium sulfate, barium sulfide (S), barium carbonate, barium peroxide, barium oxide, barium nitrate, barium acetate, barium tartrate, barium citrate, barium gluconate, barium maleate, barium succinate, barium malate, barium glutamate, barium oxalate, barium malonate, barium naphthenate, barium acetylacetonate, barium formate, barium benzoate, barium p-t-butylbenzoate, barium adipate, barium pimelate, barium suberate, barium azelate, barium sebacate, barium phthalate, barium isophthalate, barium terephthalate, barium anthranilate, barium mandelate, barium salicylate, barium titanate or any combination thereof.

Suitable radium salts include, for example, radium fluoride, radium chloride, radium bromide, radium iodide, radium oxide, radium nitride or any combination thereof.

Suitable iron (ferrous) salts include, for example, ferrous sulfate, ferrous oxides, ferrous acetate, ferrous citrate, ferrous ammonium citrate, ferrous ferrous gluconate, ferrous oxalate, ferrous fumarate, ferrous maleate, ferrous malate, ferrous lactate, ferrous ascorbate, ferrous erythrobate, ferrous glycerate, ferrous pyruvate or any combination thereof.

In one aspect, the dry particles of the invention are small, and preferably divalent metal cation (e.g., calcium) dense, and are dispersible. In another aspect of the invention, the dry particles are small, dense in divalent metal cation salt (e.g. contain at least about 30% or at least about 40% (w/w) divalent metal cation salt), and are dispersible. In a further aspect of the invention, the dry particles are small, dense in mass (e.g. tap density, envelope density), and are dispersible. In this last aspect, the particles can be dense in divalent metal cation salt (e.g. calcium, magnesium), or can have low loading of metal cation salt in the formulation.

Generally, the dry particles of the invention have a VMGD as measured by HELOS/RODOS at 1.0 bar of about 10 μm or less (e.g., about 0.1 μm to about 10 μm). Preferably, the dry particles of the invention have an VMGD of about 9 μm or less (e.g., about 0.1 μm to about 9 μm), about 8 μm or less (e.g., about 0.1 μm to about 8 μm), about 7 μm or less (e.g., about 0.1 μm to about 7 μm), about 6 μm or less (e.g., about 0.1 μm to about 6 μm), about 5 μm or less (e.g., less than 5 μm, about 0.1 μm to about 5 μm), about 4 μm or less (e.g., 0.1 μm to about 4 μm), about 3 μm or less (e.g., 0.1 μm to about 3 μm), about 2 μm or less (e.g., 0.1 μm to about 2 μm), about 1 μm or less (e.g., 0.1 μm to about 1 μm), about 1 μm to about 6 μm, about 1 μm to about 5 μm, about 1 μm to about 4 μm, about 1 μm to about 3 μm, or about 1 μm to about 2 μm as measured by HELOS/RODOS at 1.0 bar.

In another aspect, the dry particles of the invention are large, and preferably calcium dense, and are dispersible. In another aspect of the invention, the respirable particles are large, dispersible, and have a relatively low loading of the divalent cation and divalent cation salt, e.g. divalent cation salt is 50% or less (w/w). Generally, the dry particles of the invention have a VMGD as measured by HELOS/RODOS at 1.0 bar of about 30 μm or less (e.g., about 5 μm to about 30 μm). Preferably, the dry particles of the invention have an VMGD of about 25 μm or less (e.g., about 5 μm to about 25 μm), about 20 μm or less (e.g., about 5 μm to about 20 μm), about 15 μm or less (e.g., about 5 μm to about 15 μm), about 12 μm or less (e.g., about 5 μm to about 12 μm), about 10 μm or less (e.g., about 5 μm to about 10 μm), or about 8 μm or less (e.g., 6 μm to about 8 μm) as measured by HELOS/RODOS at 1.0 bar.

In addition, whether the particles are small or large, the dry particles of the invention are dispersible, and have 1/4 bar and/or 0.5/4 bar of about 2.2 or less (e.g., about 1.0 to about 2.2) or about 2.0 or less (e.g., about 1.0 to about 2.0). Preferably, the dry particles of the invention have 1/4 bar and/or 0.5/4 bar of about 1.9 or less (e.g., about 1.0 to about 1.9), about 1.8 or less (e.g., about 1.0 to about 1.8), about 1.7 or less (e.g., about 1.0 to about 1.7), about 1.6 or less (e.g., about 1.0 to about 1.6), about 1.5 or less (e.g., about 1.0 to about 1.5), about 1.4 or less (e.g., about 1.0 to about 1.4), about 1.3 or less (e.g., less than 1.3, about 1.0 to about 1.3), about 1.2 or less (e.g., 1.0 to about 1.2), about 1.1 or less (e.g., 1.0 to about 1.1 μm) or the dry particles of the invention have 1/4 bar of about 1.0.

Alternatively or in addition, the respirable dry particles of the invention can have an MMAD of about 10 microns or less, such as an MMAD of about 0.5 micron to about 10 microns. Preferably, the dry particles of the invention have an MMAD of about 5 microns or less (e.g. about 0.5 micron to about 5 microns, preferably about 1 micron to about 5 microns), about 4 microns or less (e.g., about 1 micron to about 4 microns), about 3.8 microns or less (e.g. about 1 micron to about 3.8 microns), about 3.5 microns or less (e.g. about 1 micron to about 3.5 microns), about 3.2 microns or less (e.g. about 1 micron to about 3.2 microns), about 3 microns or less (e.g. about 1 micron to about 3.0 microns), about 2.8 microns or less (e.g. about 1 micron to about 2.8 microns), about 2.2 microns or less (e.g. about 1 micron to about 2.2 microns), about 2.0 microns or less (e.g. about 1 micron to about 2.0 microns) or about 1.8 microns or less (e.g. about 1 micron to about 1.8 microns).

Alternatively or in addition, the respirable dry powders and dry particles of the invention can have an FPF of less than about 5.6 microns (FPF<5.6 μm) of at least about 20%, at least about 30%, at least about 40%, preferably at least about 45%, at least about 50%, at least about 55%, at least about 60%, at least about 65%, or at least about 70%.

Alternatively or in addition, the dry powders and dry particles of the invention have a FPF of less than 5.0 microns (FPF_TD<5.0 pin) of at least about 20%, at least about 30%, at least about 45%, preferably at least about 40%, at least about 45%, at least about 50%, at least about 60%, at least about 65% or at least about 70%. Alternatively or in addition, the dry powders and dry particles of the invention have a FPF of less than 5.0 microns of the emitted dose (FPF_ED<5.0 μm) of at least about 45%, preferably at least about 50%, at least about 60%, at least about 65%, at least about 70%, at least about 75%, at least about 80%, or at least about 85%. Alternatively or in addition, the dry powders and dry particles of the invention can have an FPF of less than about 3.4 microns (FPF<3.4 μm) of at least about 20%, preferably at least about 25%, at least about 30%, at least about 35%, at least about 40%, at least about 45%, at least about 50%, or at least about 55%.

Alternatively or in addition, the respirable dry powders and dry particles of the invention have a tap density of about 0.1 $g/cm^3$ to about 1.0 $g/cm^3$. For example, the small and dispersible dry particles have a tap density of about 0.1 $g/cm^3$ to about 0.9 $g/cm^3$, about 0.2 $g/cm^3$ to about 0.9 $g/cm^3$, about 0.2 $g/cm^3$ to about 0.9 $g/cm^3$, about 0.3 $g/cm^3$ to about 0.9 $g/cm^3$, about 0.4 $g/cm^3$ to about 0.9 $g/cm^3$, about 0.5 $g/cm^3$ to about 0.9 $g/cm^3$, or about 0.5 $g/cm^3$ to about 0.8 $g/cm^3$, greater than about 0.4 g/cc, greater than about 0.5 g/cc, greater than about 0.6 g/cc, greater than about 0.7 g/cc, about 0.1 $g/cm^3$ to about 0.8 $g/cm^3$, about 0.1 $g/cm^3$ to about 0.7 $g/cm^3$, about 0.1 $g/cm^3$ to about 0.6 $g/cm^3$, about 0.1 $g/cm^3$ to about 0.5 $g/cm^3$, about 0.1 $g/cm^3$ to about 0.4 $g/cm^3$, about 0.1 $g/cm^3$ to about 0.3 $g/cm^3$, less than 0.3 $g/cm^3$. In a preferred embodiment, tap density is greater than about 0.4 g/cc. In another preferred embodiment, tap density is greater than about 0.5 g/cc. Alternatively, tap density is less than about 0.4 g/cc.

Alternatively or in addition, the respirable dry powders and dry particles of the invention can have a water or solvent content of less than about 25%, less than about 20%, less than about 15% by weight of the respirable dry particle. For example, the respirable dry particles of the invention can have a water or solvent content of less than about 25%, less than about 20%, less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The respirable dry particles of the invention can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5%, or about 5%.

As described herein, some respirable dry particles of the invention contain one or more divalent metal cations (e.g., calcium ($Ca^{2+}$)) as an active ingredient which is generally present in the form of a salt (e.g., crystalline and/or amorphous). Suitable calcium salts that can be present in the respirable dry particles of the invention include, for example, calcium chloride, calcium sulfate, calcium lactate, calcium citrate, calcium carbonate, calcium acetate, calcium phosphate, calcium alginate, calcium stearate, calcium sorbate, calcium gluconate and the like. In certain preferred aspects, the dry powder or dry particles of the invention do not contain calcium phosphate, calcium carbonate, calcium alginate, calcium sterate or calcium gluconate. In another preferred aspect, the dry powder or dry particles of the invention include calcium citrate, calcium lactate, calcium chloride, calcium sulfate, or any combination of these salts. In another preferred aspect, the dry powder or dry particles include calcium citrate, calcium lactate, or any combination of these salts. In another preferred aspect, the dry powder or dry particles include calcium carbonate. In a further aspect, the dry powder or dry particles include calcium citrate, calcium lactate, calcium sulfate, calcium carbonate, or any combination of these salts. A preferred calcium salt is calcium lactate. In a certain preferred aspect, the dry powder or dry particles of the invention do not contain calcium chloride. If desired, the respirable dry particles of the invention contain a divalent metal cation salt (e.g., a calcium salt) and further contain one or more additional salts, such as one or more non-toxic salts of the elements sodium, potassium, magnesium, calcium, aluminum, silicon, scandium, titanium, vanadium, chromium, cobalt, nickel, copper, manganese, zinc, tin, silver and the like. Preferably, the dry particles contain at least one calcium salt and at least one monovalent cation salt (e.g., a sodium salt).

Suitable sodium salts that can be present in the respirable dry particles of the invention include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, sodium phosphate, sodium bisulfite, sodium borate, sodium gluconate, sodium metasilicate and the like. In a preferred aspect, the dry powders and dry particles include sodium chloride, sodium citrate, sodium lactate, sodium sulfate, or any combination of these salts.

Suitable lithium salts include, for example, lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate or and combination thereof.

Suitable potassium salts include, for example, potassium chloride, potassium bromide, potassium iodide, potassium bicarbonate, potassium nitrite, potassium persulfate, potassium sulfite, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium sodium tartrate and any combination thereof.

In another aspect of the invention, the respirable dry powders or respirable dry particles are suitable for use as carrier particles for delivering a therapeutic agent. In these aspects, the respirable dry powders contain respirable dry particles that contain one or more divalent metal cations that 1) does not on its own have a pharmacological effect (e.g., magnesium ($Mg^{2+}$), 2) or is present in an amount that does not produce therapeutic efficacy (e.g., a sub-therapeutic amount such as a low % of divalent metal cation salt (e.g., less than about 20%, 15%, 10%, 5% or 3% (w/w)). Preferably, the pharmacological effect is a biological activity selected from anti-bacterial activity, anti-viral activity, anti-inflammatory activity and combinations thereof. Whether a divalent metal cation, on its own, has such a pharmacological effect can be easily evaluated using the in vivo models disclosed and exemplified herein. For example, as used herein, a divalent metal cation does not have anti-bacterial activity when it results in less than 50% reduction in colony forming units recovered from the lung in the mouse model of bacterial pneumonia disclosed in Example 26. As used herein, a divalent metal cation does not have anti-viral activity when it results in less than 50% reduction in nasal wash viral titer in the ferret model of influenza infection disclosed in Example 11. As used herein, a divalent metal cation does not have anti-inflammatory activity when it results in less than 15% reduction in neutrophils recovered from the lung in the tobacco smoke mouse model of COPD disclosed in Example 30. The models and tests are run substantially as described herein, but substituting the divalent metal cation to be tested for the formulation in the examples. These models can also be used to assess therapeutic efficacy of divalent metal cations, such as calcium cations. For example, low calcium loading in a dry powder may not produce therapeutic efficacy because the quantity of such a dry powder needed to deliver an effective dose of calcium ion cannot reasonably be administered to a subject by inhalation. Accordingly, such powders contain calcium ion in an amount that does not produce therapeutic efficacy.

Suitable magnesium salts that can be present in this type of respirable dry particles of the invention include, for example, magnesium fluoride, magnesium chloride, magnesium bromide, magnesium iodide, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or any combination thereof. In a preferred aspect, the dry powder or dry particles include magnesium sulfate, magnesium lactate, magnesium chloride, magnesium citrate, and magnesium carbonate. Preferred magnesium salts are magnesium sulfate and magnesium lactate.

Preferred divalent metal salts (e.g., calcium salts) have one or preferably two or more of the following characteristics: (i) can be processed into a respirable dry particle, (ii) possess sufficient physicochemical stability in dry powder form to facilitate the production of a powder that is dispersible and physically stable over a range of conditions, including upon exposure to elevated humidity, (iii) undergo rapid dissolution upon deposition in the lungs, for example, half of the mass of the cation of the divalent metal can dissolved in less than 30 minutes, less than 15 minutes, less than 5 minutes, less than 2 minutes, less than 1 minute, or less than 30 seconds, and (iv) do not possess properties that can result in poor tolerability or adverse events, such as a significant exothermic or endothermic heat of solution ($\Delta H$) for example, a $\Delta H$ lower than of about −10 kcal/mol or greater than about 10 kcal/mol. Rather, a preferred $\Delta H$ is between about −9 kcal/mol and about 9 kcal/mol, between about −8 kcal/mol and about 8 kcal/mol, between about −7 kcal/mol and about 7 kcal/mol, between about −6 kcal/mol and about 6 kcal/mol, between about −5 kcal/mol and about 5 kcal/mol, between about −4 kcal/mol and about 4 kcal/mol, between about −3 kcal/mol and about 3 kcal/mol, between about −2 kcal/mol and about 2 kcal/mol, between about −1 kcal/mol and about 1 kcal/mol, or about 0 kcal/mol.

Suitable divalent metal cation salts (e.g., calcium salts) can have desired solubility characteristics. In general, highly or moderately soluble divalent metal cation salts (e.g., calcium salts) are preferred. For example, suitable divalent metal cation salts (e.g., calcium salts) that are contained in the respirable dry particles and dry powders can have a solubility in distilled water at room temperature (20-30° C.) and 1 bar of at least about 0.4 g/L, at least about 0.85 g/L, at least about 0.90 g/L, at least about 0.95 g/L, at least about 1.0 g/L, at least about 2.0 g/L, at least about 5.0 g/L, at least about 6.0 g/L, at least about 10.0 g/L, at least about 20 g/L, at least about 50 g/L, at least about 90 g/L, at least about 120 g/L, at least about 500 g/L, at least about 700 g/L or at least about 1000 g/L. Preferably, the divalent metal cation salt has a solubility greater than about 0.90 g/L, greater than about 2.0 g/L, or greater than about 90 g/L. Suitable divalent metal cation salts include calcium salts and magnesium salts.

Dry particles and dry powders of the invention can be prepared, if desired, that contain divalent metal cation salts (e.g., calcium salts) that are not highly soluble in water. As described herein, such dry particles and dry powders can be prepared using a feed stock of a different, more soluble salt, and permitting anion exchange to produce the desired divalent metal cation salts (e.g., calcium salt) prior to or concurrently with spray drying. Alternatively, a suspension may also be fed to the spray dryer to make respirable dry powders and respirable dry particles.

Dry powder and particles of the invention may contain a high percentage of active ingredient (e.g., divalent metal cation (e.g., calcium)) in the composition, and be divalent metal cation dense. The dry particles may contain 3% or more, 5% or more, 10% or more, 15% or more, 20% ore more, 25% or more, 30% or more, 35% or more, 40% or more, 50% or more, 60% or more, 70% or more, 75% or more, 80% or more, 85% or more. 90% or more, or 95% or more active ingredient.

It is advantageous when the divalent metal cation salt (e.g., calcium salt) dissociates to provide two or more moles of divalent metal cation (e.g., $Ca^{2+}$) per mole of salt. Such salts can be used to produce respirable dry powders and dry particles that are dense in divalent metal cation (e.g., calcium). For example, one mole of calcium citrate provides three moles of $Ca^{2+}$ upon dissolution. It is also generally preferred that the divalent metal cation salt (e.g., calcium salt) is a salt with a low molecular weight and/or contain low molecular weight anions. Low molecular weight divalent metal cation salts, such as calcium salts that contain calcium ions and low molecular weight anions, are divalent cation dense (e.g., $Ca^{2+}$) dense relative to high molecular salts and salts that contain high molecular weight anions. It is generally preferred that the divalent metal cation salt (e.g., calcium salt) has a molecular weight of less than about 1000 g/mol, less than about 950 g/mol, less than about 900 g/mol, less than about 850 g/mol, less than about 800 g/mol, less than about 750 g/mol, less than about 700 g/mol, less than about 650 g/mol, less than about 600 g/mol, less than about 550 g/mol, less than about 510 g/mol, less than about 500 g/mol, less than about 450 g/mol, less than about 400 g/mol, less than about 350 g/mol, less than about 300 g/mol, less than about 250 g/mol, less than about 200 g/mol, less than about 150 g/mol, less than about 125 g/mol, or less than about 100 g/mol. In addition or alternatively, it is generally preferred that the divalent metal cation (e.g., calcium ion) contributes a substantial portion of the weight to the overall weight of the divalent metal cation salt. It is generally preferred that the divalent metal cation (e.g., calcium ion) contribute at least 10% of the weight of the overall salt, at least 16%, at least 20%, at least 24.5%, at least 26%, at least 31%, at least 35%, or at least 38% of the weight of the overall divalent metal cation salt (e.g., calcium salt).

Alternatively or in addition, the respirable dry particles of the invention can include a suitable divalent metal cation salt (e.g., calcium salt) that provides divalent metal cation ($Ca^{2+}$), wherein the weight ratio of divalent metal cation (e.g., calcium ion) to the overall weight of said salt is between about 0.1 to about 0.5. For example, the weight ratio of divalent metal cation (e.g, calcium ion) to the overall weight of said salt is between about 0.15 to about 0.5, between about 0.18 to about 0.5, between about 0.2 to about 5, between about 0.25 to about 0.5, between about 0.27 to about 0.5, between about 0.3 to about 5, between about 0.35 to about 0.5, between about 0.37 to about 0.5, or between about 0.4 to about 0.5.

Alternatively or in addition, the respirable dry particles of the invention can contain a divalent metal cation salt (e.g., calcium salt) which provides divalent cation (e.g., $Ca^{2+}$) in an amount of at least about 5% by weight of the respirable dry particles. For example, the respirable dry particles of the invention can include a divalent metal cation salt (e.g., calcium salt) which provides divalent cation (e.g., $Ca^{2+}$) in an amount of at least about 7% by weight, at least about 10% by weight, at least about 11% by weight, at least about 12% by weight, at least about 13% by weight, at least about 14% by weight, at least about 15% by weight, at least about 17% by weight, at least about 20% by weight, at least about 25% by weight, at least about 30% by weight, at least about 35% by weight, at least about 40% by weight, at least about 45% by weight, at least about 50% by weight, at least about 55% by weight, at least about 60% by weight, at least about 65% by weight or at least about 70% by weight of the respirable dry particles.

Alternatively or in addition, the respirable dry particles of the invention can contain a divalent metal cation salt which provides divalent metal cation (e.g., $Ca^{2+}$, $Be^{2+}$, $Mg^{2+}$, $Sr^{2+}$, $Ba^{2+}$, $Fe^{2+}$) in an amount of at least about 5% by weight of the respirable dry particles and also contain a monovalent salt (e.g, sodium salt, lithium salt, potassium salt) which provides monovalent cation (e.g, $Na^+$, $Li^+$, $K^+$) in an amount of at least about 3% by weight of the respirable dry particles. For example, the respirable dry particles of the invention can include a divalent metal cation salt (e.g., calcium salt) which provides divalent cation (e.g., $Ca^{2+}$) in an amount of at least about 7% by weight, at least about 10% by weight, at least about 11% by weight, at least about 12% by weight, at least about 13% by weight, at least about 14% by weight, at least about 15% by weight, at least about 17% by weight, at least about 20% by weight, at least about 25% by weight, at least about 30% by weight, at least about 35% by weight, at least about 40% by weight, at least about 45% by weight, at least about 50% by weight, at least about 55% by weight, at least about 60% by weight, at least about 65% by weight or at least about 70% by weight of the respirable dry particles; and further contain a monovalent salt sodium salt which provides monovalent anion ($Na^+$) in an amount of at least about 3%, at least about 4%, at least about 5%, at least about 6%, at least about 7%, at least about 8%, at least about 9%, at least about 10%, at least about 11%, at least about 12%, at least about 14%, at least about 16%, at least about 18%, at least about 20%, at least about 22%, at least about 25%, at least about 27%, at least about 29%, at least about 32%, at least about 35%, at least about 40%, at least about 45%, at least about 50% or at least about 55% by weight of the respirable dry particles.

Alternatively or in addition, the respirable dry particles of the invention contain a divalent metal cation salt and a monovalent cation salt, where the divalent cation, as a component of one or more salts, is present in an amount of at least 5% by weight of dry particle, and the weight ratio of divalent cation to monovalent cation is about 50:1 (i.e., about 50 to about 1) to about 0.1:1 (i.e., about 0.1 to about 1). The weight ratio of divalent metal cation to monovalent cation, is based on the amount of divalent metal cation and monovalent cation that are contained in the divalent metal cation salt and monovalent salts, respectively, that are contained in the dry particle. In particular examples, the weight ratio of divalent metal cation to monovalent cation is about 0.2:1, about 0.3:1, about 0.4:1, about 0.5:1, about 0.6:1, about 0.7:1, about 0.8:1, about 0.86:1, about 0.92:1, about 1:1; about 1.3:1, about 2:1, about 5:1, about 10:1, about 15:1, about 20:1, about 25:1, about 30:1, about 35:1, about 40:1, about 45:1, or about 50:1, about 20:1 to about 0.1:1, about 15:1 to about 0.1:1, about 10:1 to about 0.1:1, or about 5:1 to about 0.1:1.

Alternatively or in addition, the respirable dry particles of the invention can contain a divalent metal cation salt and a monovalent cation salt, in which the divalent metal cation salt and the monovalent cation salt contain chloride, lactate, citrate or sulfate as the counter ion, and the ratio of divalent metal cation (e.g., $Ca^{2+}$, $Be^{2+}$, $Mg^{2+}$, $Sr^{2+}$, $Ba^{2+}$, $Fe^{2+}$) to monovalent cation (e.g, $Na^+$, $Li^+$, $K^+$) mole:mole is about 50:1 (i.e., about 50 to about 1) to about 0.1:1 (i.e., about 0.1 to about 1). The mole ratio of divalent metal cation to monovalent cation, is based on the amount of divalent metal cation and monovalent cation that are contained in the divalent metal cation salt and monovalent cation salt, respectively, that are contained in the dry particle. Preferably, divalent metal cation, as a component of one or more divalent metal cation salts, is present in an amount of at least 5% by weight of the respirable dry particle. In particular examples, divalent metal cation and monovalent cation are present in the respirable dry particles in a mole ratio of about 8.0:1, about 7.5:1, about 7.0:1, about 6.5:1, about 6.0:1, about 5.5:1, about 5.0:1, about 4.5:1, about 4.0:1, about 3.5:1, about 3.0:1, about 2.5:1, about 2.0:1, about 1.5:1, about 1.0:1, about 0.77:1, about 0.65:1, about 0.55:1, about 0.45:1, about 0.35:1, about 0.25:1, or about 0.2:1, about 8.0:1 to about 0.55:1, about 7.0:1 to about 0.55:1, about 6.0:1 to about 0.55:1, about 5.0:1 to about 0.55:1, about 4.0:1 to about 0.55:1, about 3.0:1 to about 0.55:1, about 2.0:1 to about 0.55:1, or about 1.0:1 to about 0.55:1.

Preferably, the ratio of divalent metal cation (e.g., $Ca^{2+}$, $Be^{2+}$, $Mg^{2+}$, $Sr^{2+}$, $Ba^{2+}$, $Fe^{2+}$) to monovalent cation (e.g, $Na^+$, $Li^+$, $K^+$) mole:mole is about 16.0:1.0 to about 1.0:1.0, about 16.0:1.0 to about 2.0:1.0, about 8.0:1.0 to about 1.0:1.0, about 4.0:1.0 to about 1.0:1.0, about 4:0:1.0 to about 2.0:1.0. More preferably, the divalent metal cation and monovalent cation are present in the respirable dry particles in a mole ratio of about 8.0:1.0 to about 2.0:1.0 or about 4.0:1.0 to about 2.0:1.0. Most preferably, the divalent metal cation is $Ca^{2+}$ and the monovalent cation is $Na^+$.

Preferred respirable dry particles contain at least one calcium salt selected from the group consisting of calcium lactate, calcium citrate, calcium sulfate, and calcium chloride, and also contain sodium chloride.

Calcium citrate, calcium sulfate and calcium lactate possess sufficient aqueous solubility to allow for their processing into respirable dry powders via spray-drying and to facilitate their dissolution upon deposition in the lungs, yet possess a low enough hygroscopicity to allow for the production of dry powders with high calcium salt loads that are relatively physically stable upon exposure to normal and elevated humidity. Calcium citrate, calcium sulfate and calcium lactate also have a significantly lower heat of solution than calcium chloride, which is beneficial for administration to the respiratory tract, and citrate, sulfate and lactate ions are safe and acceptable for inclusion in pharmaceutical compositions.

Accordingly, in addition to any combination of the features and properties described herein, the respirable dry particles of the invention can contain one or more salts in a total amount of at least about 51% by weight of the respirable dry particles; wherein each of the one or more salts independently consists of a cation selected from the group consisting of calcium and sodium and an anion selected from the group consisting of lactate ($C_3H_5O_3^-$), chloride (CE) citrate ($C_6H_5O_7^{3-}$) and sulfate ($SO_4^{2-}$), with the proviso that at least one of the salts is a calcium salt. For example, the respirable dry particles of the invention can include one or more of the salts in a total amount of at least about 55%, at least about 60%, at least about 65%, at least about 70%, at least about 75%, at least about 80%, at least about 85%, at least about 90%, at least about 91%, at least about 92%, or at least about 95% by weight of the respirable dry particles.

Alternatively or in addition, the respirable dry particles of the invention can contain a calcium salt and a sodium salt, where the calcium cation, as a component of one or more calcium salts, is present in an amount of at least 5% by weight of the dry particle, and the weight ratio of calcium ion to sodium ion is about 50:1 (i.e., about 50 to about 1) to about 0.1:1 (i.e., about 0.1 to about 1). The weight ratio of calcium ion to sodium ion, is based on the amount of calcium ion and sodium ion that are contained in the calcium salt and sodium salts, respectively, that are contained in the dry particle. In particular examples, the weight ratio of calcium ion to sodium ion is about 0.2:1, about 0.3:1, about 0.4:1, about 0.5:1, about 0.6:1, about 0.7:1, about 0.8:1, about 0.86:1, about 0.92:1, about 1:1; about 1.3:1, about 2:1, about 5:1, about 10:1, about 15:1, about 20:1, about 25:1, about 30:1, about 35:1, about 40:1, about 45:1, or about 50:1, about 20:1 to about 0.1:1, about 15:1 to about 0.1:1, about 10:1 to about 0.1:1, or about 5:1 to about 0.1:1.

Alternatively or in addition, the respirable dry particles of the invention can contain a calcium salt and a sodium salt, in which the calcium salt and the sodium salt contain chloride, lactate, citrate or sulfate as the counter ion, and the ratio of calcium to sodium mole:mole is about 50:1 (i.e., about 50 to about 1) to about 0.1:1 (i.e., about 0.1 to about 1). The mole ratio of calcium to sodium, is based on the amount of calcium and sodium that are contained in the calcium salt and sodium salt, respectively, that are contained in the dry particle. Preferably, calcium, as a component of one or more calcium salts, is present in an amount of at least 5% by weight of the respirable dry particle. In particular examples, calcium and sodium are present in the respirable dry particles in a mole ratio of about 8.0:1, about 7.5:1, about 7.0:1, about 6.5:1, about 6.0:1, about 5.5:1, about 5.0:1, about 4.5:1, about 4.0:1, about 3.5:1, about 3.0:1, about 2.5:1, about 2.0:1, about 1.5:1, about 1.0:1, about 0.77:1, about 0.65:1, about 0.55:1, about 0.45:1, about 0.35:1, about 0.25:1, or about 0.2:1, about 8.0:1 to about 0.55:1, about 7.0:1 to about 0.55:1, about 6.0:1 to about 0.55:1, about 5.0:1 to about 0.55:1, about 4.0:1 to about 0.55:1, about 3.0:1 to about 0.55:1, about 2.0:1 to about 0.55:1, or about 1.0:1 to about 0.55:1.

If desired, the respirable dry particles described herein can include a physiologically or pharmaceutically acceptable carrier or excipient. For example, a pharmaceutically-acceptable excipient includes any of the standard carbohydrate, sugar alcohol, and amino acid carriers that are known in the art to be useful excipients for inhalation therapy, either alone or in any desired combination. These excipients are generally relatively free-flowing particulates, do not thicken or polymerize upon contact with water, are toxicologically innocuous when inhaled as a dispersed powder and do not significantly interact with the active agent in a manner that adversely affects the desired physiological action of the salts of the invention. Carbohydrate excipients that are useful in this regard include the mono- and polysaccharides. Representative monosaccharides include carbohydrate excipients such as dextrose (anhydrous and the monohydrate; also referred to as glucose and glucose monohydrate), galactose, mannitol, D-mannose, sorbose and the like. Representative disaccharides include lactose, maltose, sucrose, trehalose and the like. Representative trisaccharides include raffinose and the like. Other carbohydrate excipients include maltodextrin and cyclodextrins, such as 2-hydroxypropyl-beta-cyclodextrin can be used as desired. Representative sugar alcohols include mannitol, sorbitol and the like.

Suitable amino acid excipients include any of the naturally occurring amino acids that form a powder under standard pharmaceutical processing techniques and include the non-polar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cystine, glycine, glutamine, serine, threonine, and tyrosine. Representative examples of polar, positively charged amino acids include arginine, histidine and lysine. Representative examples of negatively charged amino acids include aspartic acid and glutamic acid. These amino acids are generally available from commercial sources that provide pharmaceutical-grade products such as the Aldrich Chemical Company, Inc., Milwaukee, Wis. or Sigma Chemical Company, St. Louis, Mo.

Preferred amino acid excipients, such as the hydrophobic amino acid leucine, can be present in the dry particles of the invention in an amount of about 74% or less by weight of respirable dry particles. For example, the respirable dry particles of the invention can contain the amino acid leucine in an amount of about 5% to about 30% by weight, about 10% to about 20% by weight, about 5% to about 20% by weight, about 50% or less by weight, about 45% or less by weight, about 40% or less by weight, about 35% or less by weight, about 30% or less by weight, about 25% or less by weight, about 20% or less by weight, about 18% or less by weight, about 16% or less by weight, about 15% or less by weight, about 14% or less by weight, about 13% or less by weight, about 12% or less by weight, about 11% or less by weight, about 10% or less by weight, about 9% or less by weight, about 8% or less by weight, about 7% or less by weight, about 6% or less by weight, about 5% or less by weight, about 4% or less by weight, about 3% or less by weight, about 2% or less by weight, or about 1% or less by weight.

Preferred carbohydrate excipients, such as maltodextrin and mannitol, can be present in the dry particles of the invention in an amount of about 74% or less by weight of respirable dry particles. For example, the respirable dry particles of the invention can contain maltodextrin in an amount of about 50% or less by weight, about 45% or less by weight, about 40% or less by weight, about 35% or less by weight, about 30% or less by weight, about 25% or less by weight, about 20% or less by weight, about 18% or less by weight, about 16% or less by weight, about 15% or less by weight, about 14% or less by weight, about 13% or less by weight, about 12% or less by weight, about 11% or less by weight, about 10% or less by weight, about 9% or less by weight, about 8% or less by weight, about 7% or less by weight, about 6% or less by weight, about 5% or less by weight, about 4% or less by weight, about 3% or less by weight, about 2% or less by weight, or about 1% or less by weight. In some preferred aspects, the dry particles contain an excipient selected from leucine, maltodextrin, mannitol and any combination thereof. In particular embodiments, the excipient is leucine, maltodextrin, or mannitol.

In particular embodiments, the respirable dry particles of the invention can contain (a) a calcium salt selected from calcium lactate, calcium citrate or calcium sulfate in an amount of at least about 30%, at least about 40%, at least about 45% by weight, or at least about 50% by weight of dry particle; and (b) a sodium salt, such as sodium chloride, in an amount of at least about 25% or at least about 30% by weight of dry particle, and have any of the properties or features described herein. If desired, an excipient, such as leucine, maltodextrin, mannitol or any combination thereof, can be present an amount of about 74% or less or about 50% or less or about 20% or less by weight of the dry particle. For example, the respirable dry particles of the invention can include (a) a calcium salt in an amount of about 30% to about 65%, about 40% to about 65%, or about 45% to about 65% by weight of dry particle; (b) a sodium salt, such as sodium chloride, in an amount of about 25% to about 60%, or about 30% to about 60% by weight of dry particle; (c) an excipient, such as leucine, maltodextrin, mannitol or any combination thereof, in an amount of about 20% or less by weight of dry particle, or more preferably about 10% or less by weight of dry particle, and (d) have any of the properties or features, such as 1/4 bar, 0.5/4 bar, VMGD, MMAD, FPF described herein.

In other embodiments, the respirable dry particles of the invention can contain (a) a calcium salt selected from calcium lactate, calcium citrate or calcium sulfate in an amount of at least about 30%, at least about 40%, at least about 45% by weight, or at least about 50% by weight of dry particle; and (b) a sodium salt, such as sodium chloride, in an amount between about 2% and about 20%, or between about 3.5% and about 10% by weight of dry particle, and have any of the properties or features described herein. If desired, an excipient, such as leucine, maltodextrin, mannitol or any combination thereof, or the like, can be present in an amount of about 74% or less or about 50% or less or about 20% or less by weight of the dry particle. For example, the respirable dry particles of the invention can include (a) a calcium salt in an amount of about 30% to about 65%, about 40% to about 65%, or about 45% to about 65% by weight of dry particle; (b) a sodium salt, such as sodium chloride, in an amount between about 2% and about 20%, or between about 3.5% and about 10% by weight of dry particle; (c) an excipient, such as leucine, maltodextrin, mannitol or any combination thereof, in an amount of about 20% or less by weight of dry particle, or more preferably about 10% or less by weight of dry particle, and (d) have any of the properties or features, such as 1/4 bar, 0.5/4 bar, VMGD, MMAD, FPF described herein.

In some aspects, the respirable dry particles comprise a divalent metal ion salt and a monovalent salt and are characterized by the crystalline and amorphous content of the particles. For example, the respirable dry particles can comprise a mixture of amorphous and crystalline content, such as an amorphous divalent metal ion salt-rich phase and a crystalline monovalent salt or excipient phase. Respirable dry particles of this type provide several advantages. For example as described herein, the crystalline phase (e.g. crystalline sodium chloride and/or crystalline leucine) can contribute to the stability of the dry particle in the dry state and to the dispersibility characteristics, whereas the amorphous phase (e.g., amorphous calcium salt) can facilitate rapid water uptake and dissolution of the particle upon deposition in the respiratory tract. It is particularly advantageous when salts with relatively high aqueous solubilities (such as sodium chloride) that are present in the dry particles are in a crystalline state and when salts with relatively low aqueous solubilities (such as calcium citrate) are present in the dry particles in an amorphous state.

The amorphous phase is also characterized by a high glass transition temperature ($T_g$), such as a $T_g$ of at least 90° C., at least 100° C., at least 110° C., at least 120° C., at least 125° C., at least 130° C., at least 135° C., at least 140° C., between 120° C. and 200° C., between 125° C. and 200° C., between 130° C. and 200° C., between 120° C. and 190° C., between 125° C. and 190° C., between 130° C. and 190° C., between 120° C. and 180° C., between 125° C. and 180° C., or between 130° C. and 180° C.

In some embodiments, the respirable dry particles contain divalent metal cation salt-rich amorphous phase and a monovalent salt crystalline phase and the ratio of amorphous phase to crystalline phase (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain divalent metal cation salt-rich amorphous phase and a monovalent salt crystalline phase and the ratio of amorphous phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain divalent metal cation salt-rich amorphous phase and a monovalent salt crystalline phase and the ratio of crystalline phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5.

In some embodiments, the respirable dry particles comprise a calcium salt, such as calcium citrate, calcium sulfate, calcium lactate, calcium chloride or any combination thereof, and a sodium salt, such as sodium chloride, sodium citrate, sodium sulfate, sodium lactate, or any combination thereof, wherein the respirable dry particle contains a calcium salt-rich amorphous phase, and a crystalline sodium salt phase. In particular embodiments, the calcium salt-rich amorphous phase includes calcium citrate and at least some calcium chloride, calcium lactate and at least some calcium chloride, or calcium sulfate and at least some calcium chloride. In some embodiments, the respirable dry particles contain calcium salt-rich amorphous phase and a sodium salt crystalline phase and the ratio of amorphous phase to crystalline phase (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain calcium salt-rich amorphous phase and a sodium salt crystalline phase and the ratio of amorphous phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain calcium salt-rich amorphous phase and a sodium salt crystalline phase and the ratio of crystalline phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5.

Preferably, the respirable dry particles have a 1/4 bar or 0.5/4 bar of 2 or less, as described herein. For example, a 1/4 bar or 0.5/4 bar of 1.9 or less, 1.8 or less, 1.7 or less, 1.6 or less, 1.5 or less, 1.4 or less, 1.3 or less, 1.2 or less, 1.1 or less or about 1.0. Alternatively or in addition, the respirable dry particles have an MMAD of about 5 microns or less. Alternatively or in addition, the respirable dry particles can have a VMGD between about 0.5 microns and about 5 microns, or a VMGD between about 5 microns and about 20 microns. Alternatively or in addition, the respirable dry particles can have a heat of solution that not is greater than about −10 kcal/mol (e.g., between −10 kcal/mol and 10 kcal/mol).

As described herein, the respirable dry particles can further comprise an excipient, such as leucine, maltodextrin or mannitol. The excipient can be crystalline or amorphous or present in a combination of these forms. In some embodiments, the excipient is amorphous or predominately amorphous. In some embodiments, the respirable dry particles are substantially crystalline.

As described herein, surface RAMAN mapping spectra of respirable dry powders that contained an excipient (i.e., leucine, maltodextrin) indicate that the excipients were not concentrated at the surface of the particles, and that the excipients are either evenly distributed throughout the particle or not exposed to the surface of the particle. Leucine excipients, in particular, have been reported to improve dispersibility when concentrated on the surface of particles. See, e.g., US2003/0186894. Accordingly, it does not appear that leucine is acting as a dispersion enhancer in this way. Thus, in the respirable dry particles of the invention that contain an excipient (e.g., leucine), the excipient can be distributed within the particle but not on the particle surface, or distributed throughout the particle (e.g., homogenously distributed). For example, in some particular embodiments, a respirable dry particle of the invention does not produce a characteristic peak indicative of the presence of an excipient (e.g., leucine) under RAMAN spectroscopy. In more particular embodiments, a dry respirable powder that contains leucine does not produce a characteristic leucine peak (e.g., at 1340 cm$^{-1}$) under RAMAN spectroscopy.

As described herein, some powders of the invention have poor flow properties. Yet, surprisingly, these powders are highly dispersible. This is surprising because flow properties and dispersibility are both known to be negatively affected by particle agglomeration or aggregation. Thus, it was unexpected that particles that have poor flow characteristics would be highly dispersible.

In addition to any of the features and properties described herein, in any combination, the respirable dry particles can have poor flow properties yet have good dispersibility. For example, the respirable dry particles can have a Hausner Ratio that is greater than 1.35 (e.g, 1.4 or greater, 1.5 or greater, 1.6 or greater, 1.7 or greater, 1.8 or greater, 1.9 or greater, 2.0 or greater) and also have a 1/4 bar or 0.5/4 bar that is 2 or less, 1.9 or less, 1.8 or less, 1.7 or less, 1.6 or less, 1.5 or less, 1.4 or less, 1.3 or less, 1.2 or less, 1.1 or less or about 1.0.

In addition to any of the features and properties described herein, in any combination, the respirable dry particles can have a heat of solution that is not highly exothermic. Preferably, the heat of solution is determined using the ionic liquid of a simulated lung fluid (e.g. as described in Moss, O. R. 1979. Simulants of lung interstitial fluid. Health Phys. 36, 447-448; or in Sun, G. 2001. Oxidative interactions of synthetic lung epithelial lining fluid with metal-containing particulate matter. Am J Physiol Lung Cell Mol Physiol. 281, L807-L815) at pH 7.4 and 37° C. in an isothermal calorimeter. For example, the respirable dry particles can have a heat of solution that is less exothermic than the heat of solution of calcium chloride dihydrate, e.g., have a heat of solution that is greater than about −10 kcal/mol, greater than about −9 kcal/mol, greater than about −8 kcal/mol, greater than about −7 kcal/mol, greater than about −6 kcal/mol, greater than about −5 kcal/mol, greater than about −4 kcal/mol, greater than about −3 kcal/mol, greater than about −2 kcal/mol, greater than about −1 kcal/mol or about −10 kcal/mol to about 10 kcal/mol. The respirable dry particles can have a heat of solution of about −8 kcal/mol to about 8 kcal/mol, about −6 kcal/mol to about 6 kcal/mol, or about −4 kcal/mol to about 4 kcal/mol.

If desired, the salt formulation can include one or more additional agents, such as mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF). The additional agent can be blended with a dry powder of the salt formulation or co-spray dried as desired.

In some embodiments, the salt formulation can contain an agent that disrupts and/or disperse biofilms. Suitable examples of agents to promote disruption and/or dispersion of biofilms include specific amino acid stereoisomers, e.g. D-leucine, D-methionine, D-tyrosine, D-tryptophan, and the like. (Kolodkin-Gal, I., D. Romero, et al. "D-amino acids trigger biofilm disassembly." Science 328(5978): 627-629.)

For example, all or a portion of the leucine in the dry powders described herein which contain leucine can be D-leucine.

Examples of suitable mucoactive or mucolytic agents include MUC5AC and MUC5B mucins, DNA-ase, N-acetyl-cysteine (NAC), cysteine, nacystelyn, dornase alfa, gelsolin, heparin, heparin sulfate, P2Y2 agonists (e.g. UTP, INS365), nedocromil sodium, hypertonic saline, and mannitol.

Suitable surfactants include L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, and alkylated sugars.

If desired, the salt formulation can contain an antibiotic. The antibiotic can be suitable for treating any desired bacterial infection, and salt formulations that contain an antibiotic can be used to reduce the spread of infection, either within a patient or from patient to patient. For example, salt formulations for treating bacterial pneumonia or VAT, can further comprise an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), tuberculosis-*mycobacterium* antibiotics and the like.

If desired, the salt formulation can contain an agent for treating infections with mycobacteria, such as *Mycobacterium tuberculosis*. Suitable agents for treating infections with mycobacteria (e.g., *M. tuberculosis*) include an aminoglycoside (e.g. capreomycin, kanamycin, streptomycin), a fluoroquinolone (e.g. ciprofloxacin, levofloxacin, moxifloxacin), isozianid and isozianid analogs (e.g. ethionamide), aminosalicylate, cycloserine, diarylquinoline, ethambutol, pyrazinamide, protionamide, rifampin, and the like.

If desired, the salt formulation can contain a suitable antiviral agent, such as oseltamivir, zanamavir, amantidine, rimantadine, ribavirin, gancyclovir, valgancyclovir, Foscavir, Cytogam® (Cytomegalovirus Immune Globulin), pleconaril, rupintrivir, palivizumab, motavizumab, cytarabine, docosanol, denotivir, cidofovir, and acyclovir. The salt formulation can contain a suitable anti-influenza agent, such as zanamivir, oseltamivir, amantadine, or rimantadine.

Suitable antihistamines include clemastine, asalastine, loratadine, fexofenadine and the like.

Suitable cough suppressants include benzonatate, benproperine, clobutinal, diphenhydramine, dextromethorphan, dibunate, fedrilate, glaucine, oxalamine, piperidione, opiods such as codeine and the like.

Suitable brochodilators include short-acting beta$_2$ agonists, long-acting beta$_2$ agonists (LABA), long-acting muscarinic anagonists (LAMA), combinations of LABAs and LAMAs, methylxanthines, short-acting anticholinergic agents (may also be referred to as short acting anti-muscarinic), long-acting bronchodilators and the like.

Suitable short-acting beta$_2$ agonists include albuterol, epinephrine, pirbuterol, levalbuterol, metaproteronol, maxair, and the like.

Examples of albuterol sulfate formulations (also called salbutamol) include Inspiryl (AstraZeneca Plc), Salbutamol SANDOZ (Sanofi-Aventis), Asmasal clickhalcr (Vectura Group Plc.), Ventolin® (GlaxoSmithKline Plc), Salbutamol GLAND (GlaxoSmithKline Plc), Airomir® (Teva Pharmaceutical Industries Ltd.), ProAir IIFA (Teva Pharmaceutical Industries Ltd.), Salamol (Teva Pharmaceutical Industries Ltd.), Ipramol (Teva Pharmaceutical Industries Ltd), Albuterol sulfate TEVA (Teva Pharmaceutical Industries Ltd), and the like. Examples of epinephrine include Epinephine Mist KING (King Pharmaceuticals, Inc.), and the like. Examples of pirbuterol as pirbuterol acetate include Maxair® (Teva Pharmaceutical Industries Ltd.), and the like. Examples of levalbuterol include Xopenex® (Sepracor), and the like. Examples of metaproteronol formulations as metaproteronol sulfate include Alupent® (Boehringer Ingelheim GmbH), and the like.

Suitable LABAs include salmeterol, formoterol and isomers (e.g. arformoterol), clenbuterol, tulobuterol, vilanterol (Revolair™), indacaterol, carmoterol, isoproterenol, procaterol, bambuterol, milveterol, olodaterol and the like.

Examples of salmeterol formulations include salmeterol xinafoate as Serevent® (GlaxoSmithKline Plc), salmeterol as Inaspir (Laboratorios Almirall, S.A.), Advair® HFA (GlaxoSmithKline PLC), Advair Diskus® (GlaxoSmithKline PLC, Theravance Inc), Plusvent (Laboratorios Almirall, S.A.), VR315 (Novartis, Vectura Group PLC) and the like. Examples of formoterol and isomers (e.g., arformoterol) include Foster (Chiesi Farmaceutici S.p.A), Atimos (Chiesi Farmaceutici S.p.A, Nycomed Intemaional Management), Flutiform® (Abbott Laboratories, SkyePharma PLC), MFF258 (Novartis AG), Formoterol clickhaler (Vectura Group PLC), Formoterol HFA (SkyePharma PLC), Oxis® (Astrazeneca PLC), Oxis pMDI (Astrazeneca), Foradil® Aerolizer (Novartis, Schering-Plough Corp, Merck), Foradil® Certihaler (Novartis, SkyePharma PLC), Symbicort® (AstraZeneca), VR632 (Novartis AG, Sandoz International GmbH), MFF258 (Merck & Co Inc, Novartis AG), Alvesco® Combo (Nycomed International Management GmbH, Sanofi-Aventis, Sepracor Inc), Mometasone furoate (Schering-Plough Corp), and the like. Examples of clenbuterol include Ventipulmin® (Boehringer Ingelheim), and the like. Examples of tulobuterol include Hokunalin Tape (Abbott Japan Co., Ltd., Maruho Co., Ltd.), and the like. Examples of vilanterol include Revolair™ (GlaxoSmithKline PLC), GSK64244 (GlaxoSmithKline PLC), and the like. Examples of indacaterol include QAB149 (Novartis AG, SkyePharma PLC), QMF149 (Merck & Co Inc) and the like. Examples of carmoterol include CHF4226 (Chiese Farmaceutici S.p.A., Mitsubishi Tanabe Pharma Corporation), CHF5188 (Chiesi Farmaceutici S.p.A), and the like. Examples of isoproterenol sulfate include Aludrin (Boehringer Ingelheim GmbH) and the like. Examples of procaterol include Meptin clickhaler (Vectura Group PLC), and the like. Examples of bambuterol include Bambec (AstraZeneca PLC), and the like. Examples of milveterol include GSK159797C (GlaxoSmithKline PLC), TD3327 (Theravance Inc), and the like. Examples of olodaterol include BI1744CL (Boehringer Ingelheim GmbH) and the like.

Examples of LAMAs include tiotroprium (Spiriva), trospium chloride, glycopyrrolate, aclidinium, ipratropium and the like.

Examples of tiotroprium formulations include Spiriva® (Boehringer-Ingleheim, Pfizer), and the like. Examples of glycopyrrolate include Robinul® (Wyeth-Ayerst), Robinul® Forte (Wyeth-Ayerst), NVA237 (Novartis), and the like. Examples of aclidinium include Eklira® (Forest Labaoratories, Almirall), and the like.

Examples of combinations of LABAs and LAMAs include indacaterol with glycopyrrolate, formoterol with glycopyrrolate, indacaterol with tiotropium, olodaterol and tiotropium, vilanterol with a LAMA, and the like.

Examples of combinations of indacaterol with glycopyrrolate include QVA149A (Novartis), and the like. Examples of combinations of formoterol with glycopyrrolate include PT003 (Pearl Therapeutics) and the like. Examples of combinations of olodaterol with tiotropium include BI1744 with Spirva (Boehringer Ingelheim) and the like. Examples of combinations of vilanterol with a LAMA include GSK573719 with GSK642444 (GlaxoSmithKline PLC), and the like.

Examples of methylxanthine include aminophylline, ephedrine, theophylline, oxtriphylline, and the like.

Examples of aminophylline formulations include Aminophylline BOEHRINGER (Boehringer Ingelheim GmbH) and the like. Examples of ephedrine include Bronkaid® (Bayer AG), Broncholate (Sanofi-Aventis), Primatene® (Wyeth), Tedral SA®, Marax (Pfizer Inc) and the like. Examples of theophylline include Euphyllin (Nycomed International Management GmbH), Theo-dur (Pfizer Inc, Teva Pharmaceutical Industries Ltd) and the like. Examples of oxtriphylline include Choledyl SA (Pfizer Inc) and the like.

Examples of short-acting anticholinergic agents include ipratropium bromide, and oxitropium bromide.

Examples of ipratropium bromide formulations include Atrovent®/Apovent/Inpratropio (Boehringer Ingelheim GmbH), Ipramol (Teva Pharmaceutical Industries Ltd) and the like. Examples of oxitropium bromide include Oxivent (Boehringer Ingelheim GmbH), and the like.

Suitable anti-inflammatory agents include leukotriene inhibitors, phosphodiesterase 4 (PDE4) inhibitors, other anti-inflammatory agents, and the like.

Suitable leukotriene inhibitors include montelukast (cystinyl leukotriene inhibitors), masilukast, zafirleukast (leukotriene D4 and E4 receptor inhibitors), pranlukast, zileuton (5-lipoxygenase inhibitors), and the like.

Examples of montelukast formulations (cystinyl leukotriene inhibitor) include Singulair® (Merck & Co Inc), Loratadine, montelukast sodium SCHERING (Schering-Plough Corp), MK0476C (Merck & Co Inc), and the like. Examples of masilukast include MCC847 (AstraZeneca PLC), and the like. Examples of zafirlukast (leukotriene D4 and E4 receptor inhibitor) include Accolate® (AstraZeneca PLC), and the like. Examples of pranlukast include Azlaire (Schering-Plough Corp). Examples of zileuton (5-LO) include Zyflo® (Abbott Laboratories), Zyflo CR® (Abbott Laboratories, SkyePharma PLC), Zileuton ABBOTT LABS (Abbott Laboratories), and the like. Suitable PDE4 inhibitors include cilomilast, roflumilast, oglemilast, tofimilast, and the like.

Examples of cilomilast formulations include Ariflo (GlaxoSmithKline PLC), and the like. Examples of roflumilast include Daxas® (Nycomed International Management GmbH, Pfizer Inc), APTA2217 (Mitsubishi Tanabe Pharma Corporation), and the like. Examples of oglemilast include GRC3886 (Forest Laboratories Inc), and the like. Examples of tofimilast include Tofimilast PFIZER INC (Pfizer Inc), and the like.

Other anti-inflammatory agents include omalizumab (anti-IgE immunoglobulin Daiichi Sankyo Company, Limited), Zolair (anti-IgE immunoglobulin, Genentech Inc, Novartis AG, Roche Holding Ltd), Solfa (LTD4 antagonist and phosphodiesterase inhibitor, Takeda Pharmaceutical Company Limited), IL-13 and IL-13 receptor inhibitors (such as AMG-317, MILR1444A, CAT-354, QAX576, IMA-638, Anrukinzumab, IMA-026, MK-6105, DOM-0910, and the like), IL-4 and IL-4 receptor inhibitors (such as Pitrakinra, AER-003, AIR-645, APG-201, DOM-0919, and the like), IL-1 inhibitors such as canakinumab, CRTh2 receptor antagonists such as AZD1981 (CRTh2 receptor antagonist, AstraZeneca), neutrophil elastase inhibitor such as AZD9668 (neutrophil elastase inhibitor, from AstraZeneca), GW856553X Losmapimod (P38 kinase inhibitor, GlaxoSmithKline PLC), Arofylline LAB ALMIRALL (PDE-4 inhibitor, Laboratorios Almirall, S.A.), ABT761 (5-LO inhibitor, Abbott Laboratories), Zyflo® (5-LO inhibitor, Abbott Laboratories), BT061 (anti-CD4 mAb, Boehringer Ingelheim GmbH), Corus (inhaled lidocaine to decrease eosinophils, Gilead Sciences Inc), Prograf® (IL-2-mediated T-cell activation inhibitor, Astellas Pharma), Bimosiamose PFIZER INC (selectin inhibitor, Pfizer Inc), R411 (α4 β1/α4 β7 integrin antagonist, Roche Holdings Ltd), Tilade® (inflammatory mediator inhibitor, Sanofi-Aventis), Orenica® (T-cell co-stimulation inhibitor, Bristol-Myers Squibb Company), Soliris® (anti-CS, Alexion Pharmaceuticals Inc), Entorken® (Farmacija d.o.o.), Excellair® (Syk kinase siRNA, ZaBeCor Pharmaceuticals, Baxter International Inc), KB003 (anti-GMCSF mAb, KaloBios Pharmaceuticals), Cromolyn sodiums (inhibit release of mast cell mediators): Cromolyn sodium BOEHRINGER (Boehringer Ingelheim GmbH), Cromolyn sodium TEVA (Teva Pharmaceutical Industries Ltd), Intal (Sanofi-Aventis), BI1744CL (oldaterol (β2-adrenoceptor antagonist) and tiotropium, Boehringer Ingelheim GmbH), NFκ-B inhibitors, CXR2 antagaonists, FILE inhibitors, HMG-CoA reductase inhibitors and the like.

Anti-inflammatory agents also include compounds that inhibit/decrease cell signaling by inflammatory molecules like cytokines (e.g., IL-1, IL-4, IL-5, IL-6, IL-9, IL-13, IL-18 IL-25, IFN-α, IFN-β, and others), CC chemokines CCL-1-CCL28 (some of which are also known as, for example, MCP-1, CCL2, RANTES), CXC chemokines CXCL1-CXCL17 (some of which are also know as, for example, IL-8, MIP-2), growth factors (e.g., GM-CSF, NGF, SCF, TGF-β, EGF, VEGF and others) and/or their respective receptors.

Some examples of the aforementioned anti-inflammatory antagonists/inhibitors include ABN912 (MCP-1/CCL2, Novartis AG), AMG761 (CCR4, Amgen Inc), Enbrel® (TNF, Amgen Inc, Wyeth), huMAb OX40L GENENTECH (TNF superfamily, Genentech Inc, AstraZeneca PLC), R4930 (TNF superfamily, Roche Holding Ltd), SB683699/Firategrast (VLA4, GlaxoSmithKline PLC), CNT0148 (TNFα, Centocor, Inc, Johnson & Johnson, Schering-Plough Corp); Canakinumab (IL-1β, Novartis); Israpafant MITSUBISHI (PAF/IL-5, Mitsubishi Tanabe Pharma Corporation); IL-4 and IL-4 receptor antagonists/inhibitors: AMG317 (Amgen Inc), BAY169996 (Bayer AG), AER-003 (Aerovance), APG-201 (Apogenix); IL-5 and IL-5 receptor antagonists/inhibitors: MEDI563 (AstraZeneca PLC, MedImmune, Inc), Bosatria® (GlaxoSmithKline PLC), Cinquil® (Ception Therapeutic), TMC120B (Mitsubishi Tanabe Pharma Corporation), Bosatria (GlaxoSmithKline PLC), Reslizumab SCHERING (Schering-Plough Corp); MEDI528 (IL-9, AstraZeneca, MedImmune, Inc); IL-13 and IL-13 receptor antagonists/inhibitors: TNX650 GENENTECH (Genentech), CAT-354 (AstraZeneca PLC, MedImmune), AMG-317 (Takeda Pharmaceutical Company Limited), MK6105 (Merck & Co Inc), IMA-026 (Wyeth), IMA-638 Anrukinzumab (Wyeth), MILR1444A/Lebrikizumab (Genentech), QAX576 (Novartis), CNTO-607 (Centocor), MK-6105 (Merck, CSL); Dual IL-4 and IL-13 inhibitors: AIR645/ISIS369645 (ISIS Altair), DOM-0910 (GlaxoSmithKline, Domantis), Pitrakinra/AER001/Aerovant™ (Aerovance Inc), AMG-317 (Amgen), and the like.

Suitable steroids include corticosteroids, combinations of corticosteroids and LABAs, combinations of corticosteroids and LAMAs, combinations of corticosteroids, LABAs and LAMAs, and the like.

Suitable corticosteroids include budesonide, fluticasone, flunisolide, triamcinolone, beclomethasone, mometasone, ciclesonide, dexamethasone, and the like.

Examples of budesonide formulations include Captisol-Enabled® Budesonide Solution for Nebulization (AstraZeneca PLC), Pulmicort® (AstraZeneca PLC), Pulmicort® Flexhaler (AstraZeneca Plc), Pulmicort® HFA-MDI (AstraZeneca PLC), Pulmicort Respules® (AstraZeneca PLC), Inflammide (Boehringer Ingelheim GmbH), Pulmicort® HFA-MDI (SkyePharma PLC), Unit Dose Budesonide ASTRAZENECA (AstraZeneca PLC), Budesonide Modulite (Chiesi Farmaceutici S.p.A), CHF5188 (Chiesi Farmaceutici S.p.A), Budesonide ABBOTT LABS (Abbott Laboratories), Budesonide clickhaler (Vestura Group PLC), Miflonide (Novartis AG), Xavin (Teva Pharmaceutical Industries Ltd.), Budesonide TEVA (Teva Pharmaceutical Industries Ltd.), Symbicort® (AstraZeneca K.K., AstraZeneca PLC), VR632 (Novartis AG, Sandoz International GmbH), and the like.

Examples of fluticasone propionate formulations include Flixotide Evohaler (GlaxoSmithKline PLC), Flixotide Nebules (GlaxoSmithKline Plc), Flovent® (GlaxoSmithKline Plc), Flovent® Diskus (GlaxoSmithKline PLC), Flovent® HFA (GlaxoSmithKline PLC), Flovent® Rotadisk (GlaxoSmithKline PLC), Advair® HFA (GlaxoSmithKline PLC, Theravance Inc), Advair Diskus® (GlaxoSmithKline PLC, Theravance Inc.), VR315 (Novartis AG, Vectura Group PLC, Sandoz International GmbH), and the like. Other formulations of fluticasone include fluticasone as Flusonal (Laboratorios Almirall, S.A.), fluticasone furoate as GW685698 (GlaxoSmithKline PLC, Thervance Inc.), Plusvent (Laboratorios Almirall, S.A.), Flutiform® (Abbott Laboratories, SkyePharma PLC), and the like.

Examples of flunisolide formulations include Aerobid® (Forest Laboratories Inc), Aerospan® (Forest Laboratories Inc), and the like. Examples of triamcinolone include Triamcinolone ABBOTT LABS (Abbott Laboratories), Azmacort® (Abbott Laboratories, Sanofi-Aventis), and the like. Examples of beclomethasone dipropionate include Beclovent (GlaxoSmithKline PLC), QVAR® (Johnson & Johnson, Schering-Plough Corp, Teva Pharmaceutical Industries Ltd), Asmabec clickhaler (Vectura Group PLC), Beclomethasone TEVA (Teva Pharmaceutical Industries Ltd), Vanceril (Schering-Plough Corp), BDP Modulite (Chiesi Farmaceutici S.p.A.), Clenil (Chiesi Farmaceutici S.p.A), Beclomethasone dipropionate TEVA (Teva Pharmaceutical Industries Ltd), and the like. Examples of mometasone include QAB149 Mometasone furoate (Schering-Plough Corp), QMF149 (Novartis AG), Fomoterol fumarate, mometoasone furoate (Schering-Plough Corp), MFF258 (Novartis AG, Merck & Co Inc), Asmanex® Twisthaler (Schering-Plough Corp), and the like. Examples of cirlesonide include Alvesco® (Nycomed International Management GmbH, Sepracor, Sanofi-Aventis, Tejin Pharma Limited), Alvesco® Combo (Nycomed International Management GmbH, Sanofi-Aventis), Alvesco® HFA (Nycomed International Management GmbH, Sepracor Inc), and the like. Examples of dexamethasone include DexPak® (Merck), Decadron® (Merck), Adrenocot, CPC-Cort-D, Decaject-10, Solurex and the like. Other corticosteroids include Etiprednol dicloacetate TEVA (Teva Pharmaceutical Industries Ltd), and the like.

Combinations of corticosteroids and LABAs include salmeterol with fluticasone, formoterol with budesonide, formoterol with fluticasone, formoterol with mometasone, indacaterol with mometasone, and the like.

Examples of salmeterol with fluticasone include Plusvent (Laboratorios Almirall, S.A.), Advair® HFA (GlaxoSmithKline PLC), Advair® Diskus (GlaxoSmithKline PLV, Theravance Inc), VR315 (Novartis AG, Vectura Group PLC, Sandoz International GmbH) and the like. Examples of vilanterol with fluticasone include GSK642444 with fluticasone and the like. Examples of formoterol with budesonide include Symbicort® (AstraZeneca PLC), VR632 (Novartis AG, Vectura Group PLC), and the like. Examples of formoterol with fluticasone include Flutiform® (Abbott Laboratories, SkyePharma PLC), and the like. Examples of formoterol with mometasone include Dulera®/MFF258 (Novartis AG, Merck & Co Inc), and the like. Examples of indacaterol with mometasone include QAB149 Mometasone furoate (Schering-Plough Corp), QMF149 (Novartis AG), and the like. Combinations of corticosteroids with LAMAS include fluticasone with tiotropium, budesonide with tiotropium, mometasone with tiotropium, salmeterol with tiotropium, formoterol with tiotropium, indacaterol with tiotropium, vilanterol with tiotropium, and the like. Combinations of corticosteroids with LAMAs and LABAs include, for example, fluticasone with salmeterol and tiotropium.

Other anti-asthma molecules include: ARD111421 (VIP agonist, AstraZeneca PLC), AVE0547 (anti-inflammatory, Sanofi-Aventis), AVE0675 (TLR agonist, Pfizer, Sanofi-Aventis), AVE0950 (Syk inhibitor, Sanofi-Aventis), AVE5883 (NK1/NK2 antagonist, Sanofi-Aventis), AVE8923 (tryptase beta inhibitor, Sanofi-Aventis), CGS21680 (adenosine A2A receptor agonist, Novartis AG), ATL844 (A2B receptor antagonist, Novartis AG), BAY443428 (tryptase inhibitor, Bayer AG), CHF5407 (M3 receptor inhibitor, Chiesi Farmaceutici S.p.A.), CPLA2 Inhibitor WYETH (CPLA2 inhibitor, Wyeth), IMA-638 (IL-13 antagonist, Wyeth), LAS100977 (LABA, Laboratorios Almirall, S.A.), MABA (M3 and β2 receptor antagonist, Chiesi Farmaceutici S.p.A), R1671 (mAb, Roche Holding Ltd), CS003 (Neurokinin receptor antagonist, Daiichi Sankyo Company, Limited), DPC168 (CCR antagonist, Bristol-Myers Squibb), E26 (anti-IgE, Genentech Inc), HAE1 (Genentech), IgE inhibitor AMGEN (Amgen Inc), AMG853 (CRTH2 and D2 receptor antagonist, Amgen), IPL576092 (LSAID, Sanofi-Aventis), EPI2010 (antisense adenosine 1, Chiesi Farmaceutici S.p.A.), CHF5480 (PDE-4 inhibitor, Chiesi Farmaceutici S.p.A.), KI04204 (corticosteroid, Abbott Laboratories), SVT47060 (Laboratorios Salvat, S.A.), VML530 (leukotriene synthesis inhibitor, Abbott Laboratories), LAS35201 (M3 receptor antagonist, Laboratorios Almirall, S.A.), MCC847 (D4 receptor antagonist, Mitsubishi Tanabe Pharma Corporation), MEM 1414 (PDE-4 inhibitor, Roche), TA270 (5-LO inhibitor, Chugai Pharmaceutical Co Ltd), TAK661 (eosinophil chemotaxis inhibitor, Takeda Pharmaceutical Company Limited), TBC4746 (VLA-4 antagonist, Schering-Plough Corp), VR694 (Vectura Group PLC), PLD177 (steroid, Vectura Group PLC), KI03219 (corticosteroid+LABA, Abbott Laboratories), AMG009 (Amgen Inc), AMG853 (D2 receptor antagonist, Amgen Inc);

AstraZeneca PLC: AZD1744 (CCR3/histamine-1 receptor antagonist, AZD1419 (TLR9 agonist), Mast Cell inhibitor ASTRAZENECA, AZD3778 (CCR antagonist), DSP3025 (TLR7 agonist), AZD1981 (CRTh2 receptor antagonist), AZD5985 (CRTh2 antagonist), AZD8075 (CRTh2 antagonist), AZD1678, AZD2098, AZD2392, AZD3825 AZD8848, AZD9215, ZD2138 (5-LO inhibitor), AZD3199 (LABA);

GlaxoSmithKline PLC: GW328267 (adenosine A2 receptor agonist), GW559090 (α4 integrin antagonist), GSK679586 (mAb), GSK597901 (adrenergic β2 agonist), AM103 (5-LO inhibitor), GSK256006 (PDE4 inhibitor), GW842470 (PDE-4 inhibitor), GSK870086 (glucocorticoid agonist), GSK159802 (LABA), GSK256066 (PDE-4 inhibitor), GSK642444 (LABA, adrenergic β2 agonist), GSK64244 and Revolair (fluticasone/vilanterol), GSK799943 (corticosteroid), GSK573719 (mAchR antagonist), and GSK573719.

Pfizer Inc: PF3526299, PF3893787, PF4191834 (FLAP antagonist), PF610355 (adrenergic β2 agonist), CP664511 (α4β1/VCAM-1 interaction inhibitor), CP609643 (inhibitor of α4β1/VCAM-1 interactions), CP690550 (JAK3 inhibitor), SAR21609 (TLR9 agonist), AVE7279 (Th1 switching), TBC4746 (VLA-4 antagonist); R343 (IgE receptor signaling inhibitor), SEP42960 (adenosine A3 antagonist);

Sanofi-Aventis: MLN6095 (CrTH2 inhibitor), SAR137272 (A3 antagonist), SAR21609 (TLR9 agonist), SAR389644 (DPI receptor antagonist), SAR398171 (CRTH2 antagonist), SSR161421 (adenosine A3 receptor antagonist);

Merck & Co Inc: MK0633, MK0633, MK0591 (5-LO inhibitor), MK886 (leukotriene inhibitor), BIO1211 (VLA-4 antagonist); Novartis AG: QAE397 (long-acting corticosteroid), QAK423, QAN747, QAP642 (CCR3 antagonist), QAX935 (TLR9 agonist), NVA237 (LAMA).

Suitable expectorants include guaifenesin, guaiacolculfonate, ammonium chloride, potassium iodide, tyloxapol, antimony pentasulfide and the like.

Suitable vaccines include nasally inhaled influenza vaccines and the like.

Suitable macromolecules include proteins and large peptides, polysaccharides and oligosaccharides, and DNA and RNA nucleic acid molecules and their analogs having therapeutic, prophylactic or diagnostic activities. Proteins can include antibodies such as monoclonal antibodies. Nucleic acid molecules include genes, antisense molecules such as siRNAs that bind to complementary DNA, RNAi, shRNA, microRNA, RNA, or ribosomes to inhibit transcription or translation. Preferred macromolecules have a molecular weight of at least 800 Da, at least 3000 Da or at least 5000 Da.

Selected macromolecule drugs for systemic applications: Ventavis® (Iloprost), Calcitonin, Erythropoietin (EPO), Factor IX, Granulocyte Colony Stimulating Factor (G-CSF), Granulocyte Macrophage Colony, Stimulating Factor (GM-CSF), Growth Hormone, Insulin, Interferon Alpha, Interferon Beta, Interferon Gamma, Luteinizing Hormone Releasing Hormone (LHRH), follicle stimulating hormone (FSII), Ciliary Neurotrophic Factor, Growth Hormone Releasing Factor (GRF), Insulin-Like Growth Factor, Insulinotropin, Interleukin-1 Receptor Antagonist, Interleukin-3, Interleukin-4, Interleukin-6, Macrophage Colony Stimulating Factor (M-CSF), Thymosin Alpha 1, IIb/IIIa Inhibitor, Alpha-1 Antitrypsin, Anti-RSV Antibody, palivizumab, motavizumab, and ALN-RSV, Cystic Fibrosis Transmembrane Regulator (CFTR) Gene, Deoxyribonuclease (DNase), Heparin, Bactericidal/Permeability Increasing Protein (BPI), Anti-Cytomegalovirus (CMV) Antibody, Interleukin-1 Receptor Antagonist, and the like. GLP-1 analogs (liraglutide, exenatide, etc.), Domain antibodies (dAbs), Pramlintide acetate (Symlin), Leptin analogs, Synagis (palivizumab, MedImmune) and cisplatin.

Selected therapeutics helpful for chronic maintenance of CF include antibiotics/macrolide antibiotics, bronchodilators, inhaled LABAs, and agents to promote airway secretion clearance. Suitable examples of antibiotics/macrolide antibiotics include tobramycin, azithromycin, ciprofloxacin, colistin, aztreonam and the like. Another exemplary antibiotic/macrolide is levofloxacin. Suitable examples of bronchodilators include inhaled short-acting beta$_2$ agonists such as albuterol, and the like. Suitable examples of inhaled LABAs include salmeterol, formoterol, and the like. Suitable examples of agents to promote airway secretion clearance include Pulmozyme (dornase alfa, Genentech), hypertonic saline, DNase, heparin and the like. Selected therapeutics helpful for the prevention and/or treatment of CF include VX-770 (Vertex Pharmaceuticals) and amiloride.

Selected therapeutics helpful for the treatment of idiopathic pulmonary fibrosis include Metelimumab (CAT-192) (TGF-β1 mAb inhibitor, Genzyme), Aerovant™ (AER001, pitrakinra) (Dual IL-13, IL-4 protein antagonist, Aerovance), Aeroderm™ (PEGylated Aerovant, Aerovance), microRNA, RNAi, and the like.

In preferred embodiments, the respirable dry powder or respirable dry particle comprises an antibiotic, such as telavancin, tuberculosis-*mycobacterium* antibiotics, tobramycin, azithromycin, ciprofloxacin, colistin, and the like. In a further preferred embodiment, the respirable dry powder or respirable dry particle comprises levofloxacin. In a further preferred embodiment, the respirable dry powder or respirable dry particle comprises aztreonam or a pharmaceutically acceptable salt thereof (i.e., Cayston®). In a further preferred embodiment, the respirable dry powder or respirable dry particle does not comprise tobramycin. In a further preferred embodiment, the respirable dry powder or respirable dry particle does not comprise levofloxacin. In a further preferred embodiment, the respirable dry powder or respirable dry particle does not comprise Cayston®.

In preferred embodiments, the respirable dry powder or respirable dry particle comprises a LABA, such as salmeterol, formoterol and isomers (e.g. arformoterol), clenbuterol, tulobuterol, vilanterol (Revolair™), indacaterol, carmoterol, isoproterenol, procaterol, bambuterol, milveterol, and the like. In a further preferred embodiment, the respirable dry powder or respirable dry particle comprises formoterol. In a further preferred embodiment, the respirable dry powder or respirable dry particle comprises salmeterol. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

In preferred embodiments, the respirable dry powder or respirable dry particle comprises a LAMA, such as tiotropium, glycopyrrolate, aclidinium, ipratropium and the like. In a further preferred embodiment, the respirable dry powder or respirable dry particle comprises tiotropium.

In preferred embodiments, the respirable dry powder or respirable dry particle comprises a corticosteroid, such as budesonide, fluticasone, flunisolide, triamcinolone, beclomethasone, mometasone, ciclesonide, dexamethasone, and the like. In a further preferred embodiment, the respirable dry powder or respirable dry particle comprises fluticasone.

In preferred embodiments, the respirable dry powder or respirable dry particle comprises a combination of two or more of the following; a LABA, a LAMA, and a corticosteroid. In a further preferred embodiment, the respirable dry powder or respirable dry particle comprises fluticasone and salmeterol. In a further preferred embodiment, the respirable dry powder or respirable dry particle comprises fluticasone, salmeterol, and tiotropium.

When an additional therapeutic agent is administered to a patient with a dry powder or dry particles disclosed herein, the agent and the dry powder or dry particles are administered to provide substantial overlap of pharmacological activity, and the additional therapeutic agent can be administered to the patient before, substantially at the same time, or after the dry powder or dry particles described herein. For example, a LABA such as formoterol, or a short-acting beta agonist such as albuterol can be administered to the patient before a dry powder or dry particle, as described herein, is administered.

In preferred embodiments, the respirable dry powder or respirable dry particle does not comprise a surfactant, such as L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, or alkylated sugars.

It is generally preferred that the respirable dry particles and dry powders do not contain salts, excipients, or other active ingredients that have a molecular weight of greater than about 1 kilodalton (1000 dalton, Da). For example, the respirable particles of the invention preferably do not contain a protein, a polypeptide, oligopeptides, nucleic acid or an oligonucleotide with a molecular weight of greater than 1 KDa, great than about 900 Da, greater than about 800 Da, greater than about 700 Da, or greater than about 600 Da.

Because the respirable dry powders and respirable dry particles described herein contain salts, they may be hygroscopic. Accordingly it is desirable to store or maintain the respirable dry powders and respirable dry particles under conditions to prevent hydration of the powders. For example, if it is desirable to prevent hydration, the relative humidity of the storage environment should be less than 75%, less than 60%, less than 50%, less than 40%, less than 30%, less than 25%, less than 20%, less than 15%, less than 10%, or less than 5% humidity. The respirable dry powders and respirable dry particles can be packaged (e.g., in sealed capsules, blisters, vials) under these conditions.

The invention also relates to respirable dry powders or respirable dry particles produced by preparing a feedstock solution, emulsion or suspension and spray drying the feedstock according to the methods described herein. The feedstock can be prepared using (a) a calcium salt, such as calcium lactate or calcium chloride, in an amount of at least about 25% by weight (e.g., of total solutes used for preparing the feedstock) and (b) a sodium salt, such as sodium citrate, sodium chloride or sodium sulfate, in an amount of at least about 1% by weight (e.g., of total solutes used for preparing the feedstock). If desired, one or more excipient, such as leucine can be added to the feedstock in an amount of about 74% or less by weight (e.g., of total solutes used for preparing the feedstock). For example, the calcium salt used for preparing the feedstock can be in an amount of at least about 30%, at least about 35%, at least about 40%, at least about 50%, at least about 60% or at least about 70% by weight of total solutes used for preparing the feedstock. The sodium salt used for preparing the feedstock, for example, can be in an amount of at least about 2%, at least about 3%, at least about 4%, at least about 5%, at least about 6%, at least about 7%, at least about 8%, at least about 9%, at least about 10%, at least about 20%, at least about 25%, at least about 30%, at least about 40%, at least about 50%, at least about 55% or at least about 65% by weight of total solutes used for preparing the feedstock. The excipient added to the feedstock, for example, can be in an amount about 50% or less, about 30% or less, about 20% or less, about 10% or less, about 9% or less, about 8% or less, about 7% or less, about 6% or less, about 5% or less, about 4% or less, about 3% or less, about 2% or less, or about 1% or less by weight of total solutes used for preparing the feedstock. Alternatively, the excipient can be about 10% to about 90%, about 10% to about 50%, about 20% to about 40%, about 50% to about 90%, about 60% to about 80%, about 40% to about 60% of total solute used for preparing the feedstock.

In an embodiment, the respirable dry powders or respirable dry particles of the invention can be obtained by (1) preparing a feedstock comprising (a) a dry solute containing in percent by weight of the total dry solute about 10.0% leucine, about 35.1% calcium chloride and about 54.9% sodium citrate and (b) one or more suitable solvents for dissolution of the solute and formation of the feedstock, and (2) spray drying the feedstock. In another embodiment, the respirable dry powders or respirable dry particles of the invention can be obtained by (1) preparing a feedstock comprising (a) a dry solute containing in percent by weight of the total dry solute about 10.0% leucine, about 58.6% calcium lactate and about 31.4% sodium chloride and (b) one or more suitable solvents for dissolution of the solute and formation of the feedstock, and (2) spray drying the feedstock. In another embodiment, the respirable dry powders or respirable dry particles of the invention can be obtained by (1) preparing a feedstock comprising (a) a dry solute containing in percent by weight of the total dry solute about 10.0% leucine, about 39.6% calcium chloride and about 50.44% sodium sulfate and (b) one or more suitable solvents for dissolution of the solute and formation of the feedstock and (2) spray drying the feedstock. In another embodiment, the respirable dry powders or respirable dry particles of the invention can be obtained by (1) preparing a feedstock comprising (a) a dry solute containing in percent by weight of the total dry solute about 10.0% maltodextrin, about 58.6% calcium lactate and about 31.4% sodium chloride and (b) one or more suitable solvents for dissolution of the solute and formation of the feedstock, and (2) spray drying the feedstock. In another embodiment, the respirable dry powders or respirable dry particles of the invention can be obtained by (1) preparing a feedstock comprising (a) a dry solute containing in percent by weight of the total dry solute about 20.0% leucine, about 75.0% calcium lactate and about 5.0% sodium chloride and (b) one or more suitable solvents for dissolution of the solute and formation of the feedstock, and (2) spray drying the feedstock. In another embodiment, the respirable dry powders or respirable dry particles of the invention can be obtained by (1) preparing a feedstock comprising (a) a dry solute containing in percent by weight of the total dry solute about 37.5% leucine, about 58.6% calcium lactate and about 3.9% sodium chloride and b) one or more suitable solvents for dissolution of the solute and formation of the feedstock, and (2) spray drying the feedstock. In another embodiment, the ratio of $Ca^{2+}$ to $Na^{+}$ on a molar basis is about 8:1 to about 2:1 or about. As described herein, various methods (e.g., static mixing, bulk mixing) can be used for mixing the solutes and solvents to prepare feedstocks, which are known in the art. If desired, other suitable methods of mixing may be used. For example, additional components that cause or facilitate the mixing can be included in the feedstock. For example, carbon dioxide produces fizzing or effervescence and thus can serve to promote physical mixing of the solute and solvents. Various salts of carbonate or bicarbonate can promote the same effect that carbon dioxide produces and, therefore, can be used in preparation of the feedstocks of the invention. If desired, when a solid component (solute) of the formulation does not fully dissolve in the solvent or alternatively begins to precipitate out from solution prior to atomization, the resulting suspension can be spray dried.

In preferred embodiments, the respirable dry powders or respirable dry particles of the invention possess aerosol characteristics that permit effective delivery of the respirable dry particles to the respiratory system without the use of propellants.

In an embodiment, the respirable dry powders or respirable dry particles of the invention can be produced through an ion exchange reaction. In certain embodiments of the invention, two saturated or sub-saturated solutions are fed into a static mixer in order to obtain a saturated or supersaturated solution post-static mixing. Preferably, the post-mixed solution is supersaturated. The two solutions may be aqueous or organic, but are preferably substantially aqueous. The post-static mixing solution is then fed into the atomizing unit of a spray dryer. In a preferable embodiment, the post-static mixing solution is immediately fed into the atomizer unit. Some examples of an atomizer unit include a two-fluid nozzle, a rotary atomizer, or a pressure nozzle. Preferably, the atomizer unit is a two-fluid nozzle. In one embodiment, the two-fluid nozzle is an internally mixing nozzle, meaning that the gas impinges on the liquid feed before exiting to the most outward orifice. In another embodiment, the two-fluid nozzle is an externally mixing nozzle, meaning that the gas impinges on the liquid feed after exiting the most outward orifice.

Salts of divalent metal cations (e.g., calcium, magnesium) can be co-formulated with an excipient, and optionally salts of monovalent metal cations and/or an additional therapeutic agent to form respirable dry particles. Suitable excipients include, for example, sugars (e.g., lactose, trehalose, maltodextrin), polysaccharides (e.g. dextrin, maltodextrin, dextran, raffinose), sugar alcohols (e.g., mannitol, xylitol, sorbitol), and amino acids (e.g., glycine, alanine, leucine, isoleucine). Other suitable excipients include, for example, dipalmitoylphosphosphatidylcholine (DPPC), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, alkylated sugars, sodium phosphate, maltodextrin, human serum albumin (e.g., recombinant human serum albumin), biodegradable polymers (e.g., PLGA), dextran, dextrin, citric acid, sodium citrate, and the like.

Preferably, the excipients are chosen from one or more of the following; sugars (e.g., lactose, trehalose), polysaccharide (e.g. dextrin, maltodextrin, dextran, raffinose), sugar alcohols (e.g., mannitol, xylitol, sorbitol), and amino acids (e.g., glycine, alanine, leucine, isoleucine). More preferably, the excipients are chosen from one or more of the following: leucine, mannitol, and maltodextrin. In one aspect of the invention, the excipient is not a phospholipid, e.g. dipalmitoylphosphosphatidylcholine (DPPC), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC). In another aspect of the invention, the excipient is not a carboxylate acid or its salt form, e.g. citric acid, sodium citrate.

The dry particles of the invention can be blended with another therapeutic agent or co-formulated with another therapeutic agent to maintain the characteristic high dispersibility of the dry particles and dry powders of the invention. Such blended or co-formulated preparations can provide dry particles that deliver a therapeutic divalent metal cation (e.g., calcium ion) and one or more additional therapeutic agents, or that are carrier particles that deliver one or more therapeutic agents that are not divalent metal cations, and can be produced in a variety of ways. For example, respirable dry particles of the invention can be blended with an additional therapeutic agent or the components of the dry particles and dry powders described herein can be co-spray dried with an additional therapeutic agent, such as any one or combination of the additional thereapeutic agents disclosed herein, to produce a dry powder. Blended dry powders contain particles of the dry powders and dry particles described herein and particles that contain an additional therapeutic agent. Preferred additional therapeutic agents are LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

As described in exemplified herein, dry powders that contain certain divalent metal cations (e.g., calcium ions) have anti-viral, anti-bacterial and anti-inflammatory activities. These activities are enhanced in dry powders that also contain an monovalent metal cation salt (e.g. sodium chloride) and in which the ratio of divalent metal cation to monovalent metal cation (mole:mole) fall within certain ranges. For example, dry powders that contain a calcium salt (e.g. calcium lactate) and a sodium salt (e.g., sodium chloride) and in which the ratio of calcium ion to sodium ion (mole:mole) is about 1:1 to about 16:1, or about 1:1 to about 8:1, or about 1:1 to about 4:1, or about 1:1 to about 3.9:1, or about 1:1 to about 3.5:1, or about 2:1 to about 8:1, or about 2:1 to about 4:1, or about 2:1 to about 3.9:1, or about 2:1 to about 3:5, or about 4:1 can have superior activity relative to other proportions of calcium salts and sodium salts.

Thus, co-formulated dry powders that can be administered to a subject to provide the benefits of a divalent metal cation (e.g., calcium) and another therapeutic agent, can comprise respirable dry particles that include a divalent metal cation salt (e.g. a calcium salt), a monovalent metal cation salt (e.g., a sodium salt), one or more additional therapeutic agents, and optionally an excipient. Preferably, the ratio of calcium ion to sodium ion (mole:mole) in such a respirable dry particle is within one or more of the ranges described above (for example, the ratio can be about 4:1). This can be accomplished in several way, for example, by co-spray drying an additional therapeutic agent with the divalent salt and monovalent salt components, and optionally all or a portion of the excipient component, if present, of the dry powders and dry particles described herein (e.g., any of the particular formulations described herein). For example, in some embodiments, the dry particle can contain 0% to about 1% excipient.

Respirable dry particles that contain a divalent metal cation salt (e.g. a calcium salt), a monovalent metal cation salt (e.g., a sodium salt), one or more additional therapeutic agents, and optionally an excipient, in which the ratio of divalent metal cation to monovalent metal cation is within one or more of the ranges described herein, can contain any desired amount of therapeutic agent. It is generally desirable to maintain a high load of divalent metal cation salt (e.g. a calcium salt) in the respirable dry particles (e.g. at least about 50% (w/w) calcium salt), however, when high loads of the additional therapeutic agent are desired, the respirable dry particles can contain lower amounts of divalent metal cation salt (e.g., about 10% to about 50%) and a sufficient amount of monovalent cation salt to produce the desired ratio of divalent metal cation to monovalent metal cation.

In some embodiments, the respirable dry particles contain a calcium salt, a sodium salt and an additional therapeutic agent, wherein the additional therapeutic agent is present in a concentration of about 0.01% (w/w) to about 10% (w/w), or about 0.01% (w/w) to about 20% (w/w), or about 0.01% to about 90% (w/w), or about 20% (w/w) to about 90% (w/w), or about 20% (w/w) to about 80% (w/w), or about 20% (w/w) to about 60% (w/w), or about 20% (w/w) to about 50% (w/w), or about 50% (w/w) to about 90% (w/w), or about 50% (w/w) to about 80% (w/w), or about 60% (w/w) to about 90% (w/w), or about 60% (w/w) to about 80% (w/w), and the ratio of calcium ion to sodium ion (mole:mole) is about 1:1 to about 16:1, or about 1:1 to about 8:1, or about 1:1 to about 4:1, or about 1:1 to about 3.9:1, or about 1:1 to about 3.5:1, or about 2:1 to about 8:1, or about 2:1 to about 4:1, or about 2:1 to about 3.9:1, or about 2:1 to about 3:5, or about 4:1. The respirable dry particles preferably are small (e.g., VMGD at 1.0 bar of 10 μm or less, preferably 5 μm or less) and dispersible (i.e., possessing 1/4 bar and/or 0.5/4 bar ratios of 2.2 or less, as described herein). Preferably, the MMAD of the respirable dry particles is from about 0.5 μm to about 10 μm, more preferably from about 1 μm to about 5 μm. Preferably, the respirable dry particles are also calcium dense, and/or have a tap density of about 0.4 g/cc to about 1.2 g/cc, preferably between about 0.55 g/cc and about 1.0 g/cc. The therapeutic agent in these embodiments are preferably one or more agents independently selected from the group consisting of LABAs (e.g., formoterol, salmeterol), short-acting beta agonists (e.g., albuterol), corticosteroids (e.g., fluticasone), LAMAs (e.g., tiotropium), antibiotics (e.g., levofloxacin), and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

In more particular embodiments, the respirable dry particles contain a calcium salt (e.g. calcium lactate), a sodium salt (e.g., sodium chloride) and an additional therapeutic agent wherein the additional therapeutic agent is an antibiotic (e.g., levofloxacin) that is present in a concentration of about 20% (w/w) to about 90% (w/w), or about 20% (w/w) to about 80% (w/w), or about 20% (w/w) to about 60% (w/w), or about 20% (w/w) to about 50% (w/w), or about 50% (w/w) to about 90% (w/w), or about 50% (w/w) to about 80% (w/w), or about 60% (w/w) to about 90% (w/w), or about 60% (w/w) to about 80% (w/w), and the ratio of calcium ion to sodium ion (mole:mole) is about 1:1 to about 16:1, or about 1:1 to about 8:1, or about 1:1 to about 4:1, or about 1:1 to about 3.9:1, or about 1:1 to about 3.5:1, or about 2:1 to about 4:1, or about 2:1 to about 3.9:1, or about 2:1 to about 3:5, or about 4:1.

When it is desirable to retain the relative proportions of divalent salt, monovalent salt and excipient of any of the particular dry powders and dry particle formulations described herein, the additional therapeutic agent can be added to a solution of the components of the dry powder and the resulting solution spray dried to produce dry particles that contain the additional therapeutic agent. In such particles the amount of divalent salt, monovalent salt and excipient in the dry particles will each be lower than the amounts in the dry powders or dry particles described herein, due to the addition of the additional therapeutic agent. In one example, the formulation can contain up to about 20% (w/w) additional therapeutic agent, and the amount of each of divalent salt, monovalent salt and excipient are reduced proportionally, but the ratio of the amounts (wt %) of divalent salt:monovalent salt:excipient is the same as in the dry powders or dry particles described herein. In another example, the formulation can contain up to about 6% (w/w) additional therapeutic agent. In a further example, the formulation can contain up to about 1% (w/w) additional therapeutic agent.

In exemplary embodiments, the dry particles are based on Formulation VIII and contain up to about 6% (w/w) of one or more additional therapeutic agents, about 70% to about 75% (w/w) calcium lactate, about 3% to about 5% (w/w) sodium chloride and about 17% to about 20% (w/w) leucine. In other exemplary embodiments, the dry particles are based on Formulation VII and contain up to about 6% (w/w) of one or more additional therapeutic agent, about 45.0% to about 58.6% (w/w) calcium lactate, about 1.9% to about 3.9% (w/w) sodium chloride and about 27.5% to about 37.5% (w/w) leucine. In further exemplary embodiments, the dry particles are based on Formulation VIII and contain up to about 20% (w/w) of one or more additional therapeutic agents, about 60% to about 75% (w/w) calcium lactate, about 2% to about 5% (w/w) sodium chloride and about 15% to about 20% (w/w) leucine. In other exemplary embodiments, the dry particles are based on Formulation VII and contain up to about 20% (w/w) of one or more additional therapeutic agent, about 54.6% to about 58.6% (w/w) calcium lactate, about 1.9% to about 3.9% (w/w) sodium chloride and about 34.5% to about 37.5% (w/w) leucine. When the additional therapeutic agent is potent, a small amount may be used such as 0.01% to about 1% (w/w), and the composition of the dry particles is substantially the same as Formulation VIII or VII. The additional therapeutic agent can be any of the additional therapeutic agents described herein. Preferred additional therapeutic agents are LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

In dry powders that contain an additional therapeutic agent, all or a portion of the excipient component in the dry powders or dry particles described herein can be replaced with one or more additional therapeutic agents. This approach is particularly advantageous for additional therapeutic agents that require a higher effective dose, e.g., are not highly potent, and produces dry particles that deliver the beneficial effects of calcium cation in the respiratory tract and of the beneficial effects of the additional therapeutic agent(s). In exemplary embodiments, the dry particles are based on Formulation VIII and contain about 0.01% to about 20% (w/w) of one or more additional therapeutic agent, about 75% (w/w) calcium lactate, about 5% (w/w) sodium chloride and about 20% (w/w) or less leucine. In other exemplary embodiments, the dry particles are based on Formulation VII and contain about 0.01% to about 37.5% (w/w) of one or more additional therapeutic agents, about 58.6% (w/w) calcium lactate, about 3.9% (w/w) sodium chloride and about 37.5% (w/w) or less leucine. The additional therapeutic agent can be any of the additional therapeutic agents described herein. Preferred additional therapeutic agent are LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), and combinations thereof. Particular examples of dry powder of this type are disclosed herein as Formulations X-XX.

In one aspect, salts of divalent cations (e.g., calcium, magnesium) can be co-formulated with a non-calcium active agent, to make small, highly dispersible powders or large, porous particles. Optionally, these particles may include a monovalent cationic salt (e.g., sodium, potassium), and also optionally an excipient (e.g., leucine, maltodextrin, mannitol, lactose). The components can be mixed (e.g., mixed as one solution, static mixed as two solutions) together in order to produce a single particle after spray drying.

Some respirable dry powders of the invention comprise respirable dry particles that contain a divalent metal cation or salt thereof that does not on its own have a pharmacological effect, or is present in an amount that does not produce therapeutic efficacy (e.g., a sub-therapeutic amount such as a low % of divalent metal cation salt (e.g., less than about 20%, 15%, 10%, 5% or 3% (w/w)). For example, the respirable dry particles can contain magnesium ion or a magnesium salt such as magnesium lactate, magnesium sulfate, magnesium citrate, magnesium carbonate, magnesium chloride, magnesium phosphate, or any combinations thereof. Magnesium lactate and magnesium sulfate are preferred. Respirable dry particles of this type can be large and dispersible, but are preferably small and dispersible and dense in mass (e.g., have a high tap density or envelope density) as described herein. Such particles can be used as carrier particles to deliver other therapeutic agents, for example, by blending with a therapeutic agent or by incorporating a therapeutic agent into the particle (e.g., by co-spray drying). Preferred therapeutic agents that can be delivered using these types of particles, particularly when co-spray dried with the other particle components, are LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof. Additionally, the respirable dry particle may also contain an excipient, e.g. a monovalent salt, a sugar, a polysaccharide, a sugar alcohol, an amino acid, and any combination thereof.

The relative proportions of divalent metal cation or salt thereof, therapeutic agent and any excipients are selected to provide a sufficient amount of the therapeutic agent in the dry powder to allow an effective dose of the therapeutic agent to be conveniently administered to a subject, for example by inhalation of the dry powder contained in one or two capsules or blisters (e.g., 50 mg capsule, 40 mg capsules). Accordingly, the amount of therapeutic agent can vary from about 0.01% (w/w) for a potent therapeutic agent (or low molecular weight therapeutic agent) such as tiotropium, to about 90% (w/w) for therapeutic agents with lower potency (or higher molecular weight) such as many antibiotics (e.g., levofloxacin). For example, LABAs (e.g., formoterol, salmeterol), corticosteroids (e.g., fluticasone), and LAMAs (e.g., tiotropium), are generally highly potent and the respirable dry particle can contain from about 0.01% (w/w) to about 20% (w/w), preferably about 0.01% (w/w) to about 10% (w/w), or about 0.01% (w/w) to about 5% (w/w) of these therapeutic agents (i.e., alone or in any combination). Antibiotics are generally less potent and require higher doses for therapeutic efficacy. Accordingly, the respirable dry particle can contain from about 10% (w/w) to about 99% (w/w) antibiotic. Preferably, respirable dry particles that contain antibiotic contain from about 10% (w/w) to about 80% (w/w), about 25% (w/w) to about 80% (w/w), or about 25% (w/w) to about 75% (w/w) antibiotic.

A sufficient amount of one or more divalent metal cation salts and excipients (e.g., a monovalent salt, a sugar, a polysaccharide, a sugar alcohol, an amino acid, and any combination thereof) are present in such respirable dry particles (by % (w/w)) to provide the desired particle properties (e.g., size, dispersibility, tap density). In general, the amount of divalent metal cation salt in the respirable dry particle is sufficient to provide divalent metal cation in an amount of at least about 5% (w/w), for example the respirable dry particle can contain from about 20% to about 90% (w/w) divalent metal cation salt. The dry particles may contain about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, or about 5% to about 8% divalent metal cation. In a preferred aspect, the dry particles contain about 5% to about 20% divalent cation, in a more preferred aspect, the dry particles contain about 5% to about 15% divalent cation. Excipients, are generally present in the respirable dry particles in an amount of 0% to about 50%, preferably about 10% to about 50%.

Accordingly, in some embodiments the invention is a respirable dry powder that comprise respirable dry particles that contain a magnesium salt and a therapeutic agent, and optionally an excipient (e.g, a monovalent metal salt, a sugar, a polysaccharide, a sugar alcohol, an amino acid, and any combination thereof). The respirable dry particles preferably are small (e.g., VMGD at 1.0 bar of 10 µm or less, preferably 5 µm or less) and dispersible (1/4 bar and/or 0.5/4 bar of 2.2 or less, as described herein). Preferably, the MMAD of the respirable dry particles is from about 0.5 µm to about 10 µm, more preferably from about 1 µm to about 5 µm. Preferably, the respirable dry particles are also dense, and have a tap density of about 0.4 g/cc to about 1.2 g/cc, preferably between about 0.55 g/cc and about 1.0 g/cc. The magnesium salt can be magnesium lactate, magnesium sulfate, magnesium citrate, magnesium carbonate, magnesium chloride, magnesium phosphate or any combination of the forgoing. In preferred embodiments, the magnesium salt is magnesium lactate or magnesium sulfate. The therapeutic agent in these embodiments are preferably one or more agents independently selected from the group consisting of LABAs (e.g., formoterol, salmeterol), short-acting beta agonists (e.g., albuterol), corticosteroids (e.g., fluticasone), LAMAs (e.g., tiotropium), antibiotics (e.g., levofloxacin), and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

In more particular embodiments, the respirable dry powder contains respirable dry particles that contain at least about 5% (w/w) magnesium ion, and 1) about 5% to about 45% excipient, about 20% to about 90% magnesium salt, and about 0.01% to about 20% therapeutic agent; 2) about 0.01% to about 30% excipient, about 20% to about 80% magnesium salt, and about 20% to about 60% therapeutic agent; or 3) about 0.01% to about 20% excipient, about 20% to about 60% magnesium salt, and about 60% to about 99% therapeutic agent. The respirable dry particles preferably are small (e.g., VMGD at 1.0 bar of 10 μm or less, preferably 5 μm or less) and dispersible (1/4 bar and/or 0.5/4 bar of 2.2 or less, as described herein). Preferably, the MMAD of the respirable dry particles is from about 0.5 μm to about 10 μm, more preferably from about 1 μm to about 5 μm. Preferably, the respirable dry particles are also dense, and have a tap density of about 0.4 g/cc to about 1.2 g/cc, preferably between about 0.55 g/cc and about 1.0 g/cc. The magnesium salt can be magnesium lactate, magnesium sulfate, magnesium citrate, magnesium carbonate, magnesium chloride, magnesium phosphate or any combination of the forgoing. In preferred embodiments, the magnesium salt is magnesium lactate or magnesium chloride. The therapeutic agent in these embodiments are preferably one or more agents independently selected from the group consisting of LABAs (e.g., formoterol, salmeterol), short-acting beta agonists (e.g., albuterol), corticosteroids (e.g., fluticasone), LAMAs (e.g., tiotropium), antibiotics (e.g., levofloxacin), and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

Alternatively, the particles may be large, e.g. the dry powder has a geometric diameter (VMGD) between 5 microns and 30 microns. Optionally, the particles are large and the tap density may be between 0.01 g/cc and 0.4 glee, or between 0.05 Wee and 0.3 g/cc. For small or large VMGD particles, the MMAD of the dry powder can be between 0.5 and 10 microns, more preferably between 1 and 5 microns.

In another aspect, the dry particles of the invention are large, porous, and are dispersible. The size of the dry particles can be expressed in a variety of ways. The particles may have VMGD between 5 to 30 μm, or between 5 and 20 μm, with a tap density of less than 0.5 g/cc, preferably less than 0.4 g/cc.

Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, milling (e.g., jet milling), blending, solvent extraction, solvent evaporation, phase separation, simple and complex coacervation, interfacial polymerization, suitable methods that involve the use of supercritical carbon dioxide ($CO_2$), sonocrystallization, nanoparticle aggregate formation, other suitable methods, and any combination thereof. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

The respirable dry particles are preferably spray dried. Suitable spray-drying techniques are described, for example, by K. Masters in "Spray Drying Handbook", John Wiley & Sons, New York (1984). Generally, during spray-drying, heat from a hot gas such as heated air or nitrogen is used to evaporate a solvent from droplets formed by atomizing a continuous liquid feed. When hot air is used, the moisture in the air is at least partially removed before its use. When nitrogen is used, the nitrogen gas can be run "dry", meaning that no additional water vapor is combined with the gas. If desired the moisture level of the nitrogen or air can be set before the beginning of spray dry run at a fixed value above "dry" nitrogen. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. The nozzle can be a two-fluid nozzle, which is in an internal mixing setup and an external mixing setup. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by Niro, Inc. (Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C., and preferably is about 220° C. to about 285° C. Another preferable range is between 130° C. to about 200° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. Another preferable range is between 65° C. to about 110° C., more preferably about 75° C. to about 100° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the invention, generally, a solution, emulsions or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feed stock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophillic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer. Alternatively, the atomizing step is performed on a bulk mixed solution.

In one example, respirable dry particles that contain calcium citrate, sodium chloride and leucine are prepared by spray drying. A first phase is prepared that comprises an aqueous solution of sodium citrate and leucine. A second phase is prepared that comprises calcium chloride in an appropriate solvent. One or both solutions may be separately heated as needed to assure solubility of their components. The first and second phases are then combined in a static mixer to form a combination. The combination is spray dried to form respirable dry particles.

The feed stock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions.

The feed stock or components of the feed stock can have any desired pH, viscosity or other properties. If desired, a pH buffer can be added to the solvent or co-solvent or to the formed mixture. Generally, the pH of the mixture ranges from about 3 to about 8.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD.

The diameter of the respirable dry particles, for example, their VMGD, can be measured using an electrical zone sensing instrument such as a Multisizer IIe, (Coulter Electronic, Luton, Beds, England), or a laser diffraction instrument such as a HELOS system (Sympatec, Princeton, N.J.) or a Mastersizer system (Malvern, Worcestershire, UK). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Aerosol Particle Sizer (APS) Spectrometer (TSI Inc., Shoreview, Minn.) can be used to measure aerodynamic diameter. The APS measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor and the multi-stage liquid impinger (MSLI) methods. The methods and instruments for measuring particle aerodynamic diameter are well known in the art.

Tap density is an accepted approximate measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture, high particle cohesiveness and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopia convention, Rockville, Md., $10^{th}$ Supplement, 4950-4951, 1999.

Fine particle fraction can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages 0 and 2 of the eight-stage ACI, as well as the final collection filter, and allows for the collection of two separate powder fractions. Specifically, a two-stage collapsed ACI is calibrated so that the fraction of powder that is collected on stage two is composed of respirable dry particles that have an aerodynamic diameter of less than 5.6 microns and greater than 3.4 microns. The fraction of powder passing stage two and depositing on the final collection filter is thus composed of respirable dry particles having an aerodynamic diameter of less than 3.4 microns. The airflow at such a calibration is approximately 60 L/min. The FPF (<5.6) has been demonstrated to correlate to the fraction of the powder that is able to reach the lungs of the patient, while the FPF (<3.4) has been demonstrated to correlate to the fraction of the powder that reaches the deep lung of a patient. These correlations provide a quantitative indicator that can be used for particle optimization.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose. The FPF_TD (<5.0) is the ratio of the interpolated amount of powder depositing below 5.0 μm on the ACI to the nominal dose. The FPF_RD (<5.0) is the ratio of the interpolated amount of powder depositing below 5.0 μm on the ACI to either the gravimetric recovered dose or the analytical recovered dose.

Another way to approximate emitted dose is to determine how much powder leaves its container, e.g. capsule or blister, upon actuation of a dry powder inhaler (DPI). This takes into account the percentage leaving the capsule, but does not take into account any powder depositing on the DPI. The emitted powder mass is the difference in the weight of the capsule with the dose before inhaler actuation and the weight of the capsule after inhaler actuation. This measurement can be called the capsule emitted powder mass (CEPM) or sometimes termed "shot-weight".

A Multi-Stage Liquid Impinger (MSLI) is another device that can be used to measure fine particle fraction. The Multi-Stage Liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

The geometric particle size distribution can be measured for the respirable dry powder after being emitted from a dry powder inhaler (DPI) by use of a laser diffraction instrument such as the Malvern Spraytec. With the inhaler adapter in the closed-bench configuration, an airtight seal is made to the DPI, causing the outlet aerosol to pass perpendicularly through the laser beam as an internal flow. In this way, known flow rates can be drawn through the DPI by vacuum pressure to empty the DPI. The resulting geometric particle size distribution of the aerosol is measured by the photodetectors with samples typically taken at 1000 Hz for the duration of the inhalation and the DV50, GSD, FPF<5.0 μm measured and averaged over the duration of the inhalation.

The invention also relates to a method for producing a respirable dry powder comprising respirable dry particles that contain calcium citrate or calcium sulfate. The method comprises a) providing a first liquid feed stock comprising an aqueous solution of calcium chloride, and a second liquid feed stock comprising an aqueous solution of sodium sulfate or sodium citrate; b) mixing the first liquid feed stock and the second liquid feed stock to produce a mixture in which an anion exchange reaction occurs to produce a saturated or supersaturated solution comprising calcium sulfate and sodium chloride, or calcium citrate and sodium chloride; and c) spray drying the saturated or supersaturated solution produced in b) to produce respirable dry particles. The first liquid feed stock and the second liquid feed stock can be batch mixed or preferably, static mixed. In some embodiments, the resulting mixture is spray dried, and atomized within 60 minutes, within 30 minutes, within 15 minutes, within 10 minutes, within 5 minutes, within 4 minutes, within 3 minutes, within 2 minutes, within 1 minute, within 45 seconds, within 30 seconds, within 15 seconds, within 5 seconds of mixing, preferably static mixing.

The invention also relates to a respirable dry powder or respirable dry particles produced using any of the methods described herein.

The respirable dry particles of the invention can also be characterized by the chemical stability of the salts or the excipients that the respirable dry particles comprise. The chemical stability of the constituent salts can affect important characteristics of the respirable particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC). Respirable dry particles of the invention include salts that are generally stable over a long period of time.

If desired, the respirable dry particles and dry powders described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. The maltodextrin may act as an amporphous phase stabilizer and inhibit the components from converting from an amorphous to crystalline state. Alternatively, a post-processing step to help the particles through the crystallization process in a controlled way (e.g., on the baghouse at elevated humidity) can be employed with the resultant powder potentially being further processed to restore its dispersibility if agglomerates formed during the crystallization process, such as by passing the particles through a cyclone to break apart the agglomerates. Another possible approach is to optimize around process conditions that lead to manufacturing particles that are more crystalline and therefore more stable. Another approach is to use different excipients, or different levels of current excipients to attempt to manufacture more stable forms of the salts.

The respirable dry particles and dry powders described herein are suitable for inhalation therapies. The respirable dry particles may be fabricated with the appropriate material, surface roughness, diameter and tap density for localized delivery to selected regions of the respiratory system such as the deep lung or upper or central airways.

In order to relate the dispersion of powder at different inhalation flow rates, volumes, and from inhalers of different resistances, the energy required to perform the inhalation maneuver can be calculated. Inhalation energy can be calculated from the equation $E=R^2Q^2V$ where E is the inhalation energy in Joules, R is the inhaler resistance in $kPa^{1/2}/LPM$, Q is the steady flow rate in L/min and V is the inhaled air volume in L.

The respirable dry powders and dry particles described herein are characterized by a high emitted dose (e.g., CEPM of at least 75%, at least 80%, at least 85%, at least 90%, at least 95%) from a dry powder inhaler when a total inhalation energy of less than about 2 Joules or less than about 1 Joule, or less than about 0.8 Joule, or less than about 0.5 Joule, or less than about 0.3 Joule is applied to the dry powder inhaler. For example, an emitted dose of at at least 75%, at least 80%, at least 85%, at least 90%, at least 95% CEPM of Formulation I or Formulation II contained in a unit dose container, containing about 50 mg or about 40 mg of the appropriate formulation, in a dry powder inhaler can be achieved when a total inhalation energy of less than about 1 Joule (e.g., less than about 0.8 Joule, less than about 0.5 Joule, less than about 0.3 Joule) is applied to the dry powder inhaler. An emitted dose of at least about 70% CEPM of respirable dry powder contained in a unit dose container, containing about 50 mg or about 40 mg of the respirable dry powder, in a dry powder inhaler can be achieved when a total inhalation energy of less than about 0.28 Joule is applied to the dry powder inhaler. The dry powder can fill the unit dose container, or the unit dose container can be at least 40% full, at least 50% full, at least 60% full, at least 70% full, at least 80% full, or at least 90% full. The unit dose container can be a capsule (e.g. size 000, 00, 0E, 0, 1, 2, 3, and 4, with respective volumetric capacities of 1.37 ml, 950 μl, 7704 680 μl, 480 μl, 360 μl, 270 μl, and 200 μl). Alternatively, the unit dose container can be a blister. The blister can be packaged as a single blister, or as part of a set of blisters, for example, 7 blisters, 14 blisters, 28 blisters, or 30 blisters.

Healthy adult populations are predicted to be able to achieve inhalation energies ranging from 2.9 Joules for comfortable inhalations to 22 Joules for maximum inhalations by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa1/2/LPM, with a inhalation volume of 2 L based on both FDA guidance documents for dry powder inhalers and on the work of Tiddens et al. (Journal of Aerosol Med, 19(4), p. 456-465, 2006) who found adults averaging 2.2 L inhaled volume through a variety of DPIs.

Mild, moderate and severe adult COPD patients are predicted to be able to achieve maximum inhalation energies of 5.1 to 21 Joules, 5.2 to 19 Joules, and 2.3 to 18 Joules respectively. This is again based on using measured PIFR values for the flow rate Q in the equation for inhalation energy. The PIER achievable for each group is a function of the inhaler resistance that is being inhaled through. The work of Broeders et al. (Eur Respir J, 18, p. 780-783, 2001) was used to predict maximum and minimum achievable PIER through 2 dry powder inhalers of resistances 0.021 and 0.032 kPa1/2/LPM for each.

Similarly, adult asthmatic patients are predicted to be able to achieve maximum inhalation energies of 7.4 to 21 Joules based on the same assumptions as the COPD population and PIFR data from Broeders et al.

Healthy adults and children, COPD patients, asthmatic patients ages 5 and above, and CF patients, for example, are capable of providing sufficient inhalation energy to empty and disperse the dry powder formulations of the invention. For example, a 50 mg dose of Formulation I or Formulation II was found to require only 0.28 Joules to empty more than 70% of the fill weight in a single inhalation. All the adult patient populations listed above were calculated to be able to achieve greater than 2 Joules, 7 times more than the inhalational energy required. For example, a 25 mg dose of Formulation II was found to require only 0.16 Joules to empty 80% of the fill weight in a single inhalation well deagglomerated as illustrated by a Dv50 within 1 micrometer of that at much higher inhalation energies. All the adult patient populations listed above were calculated to be able to achieve greater than 2 Joules, more than an order of magnitude more inhalational energy than required.

An advantage of the invention is the production of powders that disperse well across a wide range of flowrates and are relatively flowrate independent. The dry particles and powders of the invention enable the use of a simple, passive DPI for a wide patient population.

Methods

The respirable dry powders and respirable dry particles of the present invention are for administration to the respiratory tract. The dry powders and dry particles of the invention can be administered to a subject in need thereof for the treatment of respiratory (e.g., pulmonary) diseases, such as asthma, airway hyperresponsiveness, seasonal allergic allergy, brochiectasis, chronic bronchitis, emphysema, chronic obstructive pulmonary disease, cystic fibrosis, pulmonary parenchyal inflammatory conditions and the like, and for the treatment and/or prevention of acute exacerbations of these chronic diseases, such as exacerbations caused by viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Burkholderis* ssp., *Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, including pollen and cat dander, airborne particulates, and the like).

The dry powders and dry particles of the invention can be administered to a subject in need thereof for the treatment and/or prevention and/or reducing contagion of infectious diseases of the respiratory tract, such as pneumonia (including community-acquired pneumonia, nosocomial pneumonia (hospital-acquired pneumonia, HAP: health-care associated pneumonia, HCAP), ventilator-associated pneumonia (VAP)), ventilator-associated tracheobronchitis (VAT), bronchitis, croup (e.g., postintubation croup, and infectious croup), tuberculosis, influenza, common cold, and viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, airborne particulates, and the like). Similarly, the respirable dry particles or dry powders can be administered to a subject in need thereof to prevent or treat chronic infections like bacterial colonization and biofilm formation that are often seen in those with chronic respiratory diseases like cystic fibrosis and chronic obstructive pulmonary disease. Without wishing to be bound by particular theory, it is believed that the respirable dry particles or dry powders described herein may activate cation-regulated ion channels like, for example, TRP channels (e.g., TRPV, TRPC, TRPM, TRPA channels) and mediate the eventual induction of anti-microbial defenses like, for example, the secrection of anti-microbial peptides (e.g., alpha-, beta-, theta-defensins), thereby preventing and/or treating microbial infections.

The respirable dry particles and dry powders can be administered to alter the biophysical and/or biological properties of the mucosal lining of the respiratory tract (e.g, the airway lining fluid) and underlying tissue (e.g., respiratory tract epithelium). These properties include, for example, gelation at the mucus surface, surface tension of the mucosal lining, surface elasticity and/or viscosity of the mucosal lining, bulk elasticity and/or viscosity of the mucosal lining. Without wishing to be bound by a particular theory, it is believed that the benefits produced by the respirable dry particles or dry powder and the methods described herein (e.g., therapeutic and prophylactic benefits), result from an increase in the amount of calcium cation ($Ca^{2+}$ provided by the calcium salts in the respirable dry particles or dry powder) in the respiratory tract (e.g., lung mucus or airway lining fluid) after administration of the respirable dry particles or dry powder.

The respirable dry powders and dry particles can be administered to increase the rate of mucociliary clearance. Clearance of microbes and inhaled particles is an important function of airways to prevent respiratory infection and exposure to or systemic absorption of potentially noxious agents. This is performed as an integrated function by epithelial, mucus-secreting, and immunologic response cells present at the airway surface. It prominently includes the cilia at the epithelial cell airway surface, whose function is to beat synchronously to transport the overlying liquid mucus blanket proximally (toward the mouth), where it exits the airway and is swallowed or expectorated.

The respirable dry powders and dry particles can be administered to assist in all of these functions. By increasing surface viscoelasticity, the respirable dry powders and dry particles retain microbes and particulates at the surface of the airway mucus blanket, where they do not gain systemic exposure to the host. Dry powders and dry particles induce water/liquid transport out of the airway epithelial cells, making the periciliary liquid layer less viscous and rendering ciliary beating more effective in moving and clearing the overlying mucus blanket. Dry particles and dry powders that contain calcium salts as the pharmacologically active agent, also cause an increase in both ciliary beat frequency and the force or vigor of ciliary contractions, with resultant increase in clearance velocity of the overlying mucus stream.

Mucociliary clearance is measured by a well-established technique that measures the function and speed of clearance quantitatively using safe, inhaled radioisotope preparation (e.g., Technitium ($^{99m}$Tc)) in solution. The radioisotope is measured quantitatively by external scintigraphy. Serial measurements over minutes to several hours allow for the assessment of velocity of clearance and effect of a drug vs. baseline/control value.

In some aspects, the invention is a method for treating a pulmonary disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention is a method for treating and/or reducing the severity of pulmonary parenchyal inflammatory/fibrotic conditions, such as idiopathic pulmonary fibrosis, pulmonary interstitial inflammatory conditions (e.g., sarcoidosis, allergic interstitial pneumonitis (e.g., Farmer's Lung)), fibrogenic dust interstitial diseases (e.g., asbestosis, silicosis, beryliosis), eosinophilic granulomatosis/histiocytosis X, collagen vascular diseases (e.g., rheumatoid arthritis, scleroderma, lupus), Wegner's granulomatosis, and the like, comprising administering to the respiratory tract of a subject in need thereof an effective amount of respirable dry particles or dry powder, as described herein.

In other aspects, the invention is a method for the treatment or prevention of acute exacerbations of a chronic pulmonary disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention is a method for treating, preventing and/or reducing contagion of an infectious disease of the respiratory tract, comprising administering to the respiratory tract of a subject in need thereof an effective amount of respirable dry particles or dry powder, as described herein.

In still other aspects, the invention is a method for reducing inflammation comprising administering to the respiratory tract of a subject in need thereof an effective amount of respirable dry particles or dry powders as described herein. Thus, the respirable dry particles and dry powders can be used to broadly prevent or treat acute and/or chronic inflammation and, in particular, inflammation that characterizes a number of pulmonary diseases and conditions including, asthma, airway hyperresponsiveness, seasonal allergic allergy, bronchiectasis, chronic bronchitis, emphysema, chronic obstructive pulmonary disease (COPD), cystic fibrosis (CF), pulmonary parenchyal inflammatory diseases/conditions, and the like. The dry particles and dry powders can be administered to prevent or treat both the inflammation inherent in diseases like asthma, COPD and CF and the increased inflammation caused by acute exacerbations of those diseases, both of which play a primary role in the pathogenesis of the diseases.

In certain particular embodiments of the methods described herein, the respirable dry powders or dry particles described herein are administered to a patient who has been pretreated with a bronchodilator, or is administered concurrently with a bronchodilator. When the patient is pretreated with a bronchodilator it is preferred that the respirable dry powder or dry particle is administered at a time after the bronchodilator when the onset of bronchodilatory effect is evident or, more preferably, maximal. For example, a short acting $beta_2$ agonist such as albuterol, can be administered about 10 minutes to about 30 minutes, preferably, about 15 minutes, prior to administration of the respirable dry powder or dry particles. Pretreatment with a short acting $beta_2$ agonist such as albuterol is particularly preferred for CF patients. Some patients may already be taking bronchodilators, such as LABAs (e.g, fomoterol). Patients with COPD frequently take LABAs to manage their disease. Patients that are taking LABAs already receive some degree of bronchorelaxation due to the effects of the LABAs, and therefore further bronchodilation (e.g., using a short acting $beta_2$ agonist) may not be required or desired. For these types of patients, respirable dry powder or dry particles can be administered at substantially the same time or concurrently with the LABA, for example, in a single formulation.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, North Carolina), FlowCapss® (Hovione, Loures, Portugal), Inhalators® (Boehringer-Ingelheim, Germany), Aerolizer® (Novartis, Switzerland), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 µl, 770 µl, 680 µl, 480 µl, 360 µl, 270 µl, and 200 µl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders, are preferably administered in a single, breath-activated step using a breath-activated DPI. When this type of device is used, the energy of the subject's inhalation both disperses the respirable dry particles and draws them into the respiratory tract.

The respirable dry particles or dry powders can be delivered by inhalation to a desired area within the respiratory tract, as desired. It is well-known that particles with an aerodynamic diameter of about 1 micron to about 3 microns, can be delivered to the deep lung. Larger aerodynamic diameters, for example, from about 3 microns to about 5 microns can be delivered to the central and upper airways.

In certain embodiments, a dry powder formulation is administered to the small airways. In these embodiments, the dry powder preferably contains respirable particles that have a VMDG and/or MMAD that is suitable for delivery to the small airways, such as a VMGD and/or MMAD of about 0.5 µm to about 3 µm, about 0.75 µm to about 2 µm, or about 1 µm to about 1.5 µm.

It is believed that when some dry powders that contain divalent metal salts as active ingredients are administered, there is a possibility that at least some of the respirable dry powder will deposit in the oral cavity and produce an unpleasant "salty mouth" sensation. It is envisioned that this sensation could lead patients to not comply with therapeutic instructions or to discontinue therapy. An advantage of the respirable dry powders of this invention is that they are small and highly dispersible, and therefore, deposition in the oral cavity is reduced and the occurrence of an unpleasant salty mouth sensation is reduced or prevented.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors which contribute to oral deposition of a powder include the size distribution of the individual particles and the dispersibility of the powder. If the MMAD of the individual particles is too large, e.g. above 5 µm, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of 5 microns or less), the size distribution of the inhaled powder may have an MMAD of greater than 5 µm, leading to enhanced oral cavity deposition.

Therefore, it is desirable to have a powder in which the particles are small (e.g., MMAD of 5 microns or less, e.g. between 1 to 5 microns), and are highly dispersible (e.g. 1/4 bar or alternatively, 0.5/4 bar of 2.0, and preferably less than 1.5). More preferably, the respirable dry powder is comprised of respirable dry particles with an MMAD between 1 to 4 microns or 1 to 3 microns, and have a 1/4 bar less than 1.4, or less than 1.3, and more preferably less than 1.2.

The absolute geometric diameter of the particles measured at 1 bar using the HELOS system is not critical provided that the particle's envelope density is sufficient such that the MMAD is in one of the ranges listed above, wherein MMAD is VMGD times the square root of the envelope density (MMAD=VMGD*sqrt(envelope density)). If it is desired to deliver a high unit dose of salt using a fixed volume dosing container, then, particles of higher envelope density are desired. High envelope density allows for more mass of powder to be contained within the fixed volume dosing container. Preferable envelope densities are greater than 0.1 g/cc, greater than 0.25 g/cc, greater than 0.4 g/cc, greater than 0.5 g/cc, and greater than 0.6 g/cc.

The respirable dry powders and particles of the invention can be employed in compositions suitable for drug delivery via the respiratory system. For example, such compositions can include blends of the respirable dry particles of the invention and one or more other dry particles or powders, such as dry particles or powders that contain another active agent, or that consist of or consist essentially of one or more pharmaceutically acceptable excipients.

Respirable dry powders and dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry powders or particles deposit in the deep lung. In another embodiment of the invention, delivery is primarily to the central airways. In another embodiment, delivery is to the upper airways.

The respirable dry particles or dry powders of the invention can be delivered by inhalation at various parts of the breathing cycle (e.g., laminar flow at mid-breath). An advantage of the high dispersibility of the dry powders and dry particles of the invention is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they are released later in the inhalation.

The highly dispersible powders of this invention provide advantages for targeting the timing of drug delivery in the breathing cycle and also location in the human lung. Because the respirable dry powders of the invention can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate which diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Esevier, Amsterdam (1985).

As described herein, it is believed that the therapeutic and prophylactic effects of the respirable dry particles and dry powders are the result of an increased amount of calcium in the respiratory tract (e.g., lung) following administration of respirable dry particles and dry powders. Accordingly, since the amount of calcium provided can vary depending upon the particular salt selected, dosing can be based on the desired amount of calcium to be delivered to the lung. For example, one mole of calcium chloride ($CaCl_2$) dissociates to provide one mole of $Ca^{2+}$, but one mole of calcium citrate can provide three moles of $Ca^{2+}$.

Generally, an effective amount of a pharmaceutical formulation will deliver a dose of about 0.001 mg $Ca^{2+}$/kg body weight/dose to about 2 mg $Ca^{2+}$/kg body weight/dose, about 0.002 mg $Ca^{2+}$/kg body weight/dose to about 2 mg $Ca^{2+}$/kg body weight/dose, about 0.005 mg $Ca^{2+}$/kg body weight/dose to about 2 mg $Ca^{2+}$/kg body weight/dose, about 0.01 mg $Ca^{2+}$/kg body weight/dose to about 2 mg $Ca^{2+}$/kg body weight/dose, about 0.01 mg $Ca^{2+}$/kg body weight/dose to about 60 mg $Ca^{2+}$/kg body weight/dose, about 0.01 mg $Ca^{2+}$/kg body weight/dose to about 50 mg $Ca^{2+}$/kg body weight/dose, about 0.01 mg $Ca^{2+}$1 kg body weight/dose, about 0.01 mg $Ca^{2+}$/kg body weight/dose to about 40 mg $Ca^{2+}$/kg body weight/dose, about 0.01 mg $Ca^{2+}$/kg body weight/dose to about 30 mg $Ca^{2+}$/kg body weight/dose, about 0.01 mg $Ca^{2+}$/kg body weight/dose to about 20 mg $Ca^{2+}$/kg body weight/dose, about 0.01 mg $Ca^{2+}$/kg body weight/dose to about 10 mg $Ca^{2+}$/kg body weight/dose, about 0.01 mg $Ca^{2+}$/kg body weight/dose to about 5 mg $Ca^{2+}$/kg body weight/dose, about 0.01 mg $Ca^{2+}$/kg body weight/dose to about 2 mg $Ca^{2+}$/kg body weight/dose, about 0.02 mg $Ca^{2+}$/kg body weight/dose to about 2 mg $Ca^{2+}$/kg body weight/dose, about 0.03 mg $Ca^{2+}$/kg body weight/dose to about 2 mg $Ca^{2+}$/kg body weight/dose, about 0.04 mg $Ca^{2+}$/kg body weight/dose to about 2 mg $Ca^{2+}$/kg body weight/dose, about 0.05 mg $Ca^{2+}$/kg body weight/dose to about 2 mg $Ca^{2+}$/kg body weight/dose, about 0.1 mg $Ca^{2+}$/kg body weight/dose to about 2 mg $Ca^{2+}$/kg body weight/dose, about 0.1 mg $Ca^{2+}$/kg body weight/dose to about 1 mg $Ca^{2+}$/kg body weight/dose, about 0.1 mg $Ca^{2+}$/kg body weight/dose to about 0.5 mg $Ca^{2+}$/kg body weight/dose, about 0.2 mg $Ca^{2+}$/kg body weight/dose to about 0.5 mg $Ca^{2+}$/kg body weight/dose, about 0.18 mg $Ca^{2+}$/kg body weight/dose, about 0.001 mg $Ca^{2+}$/kg body weight/dose, about 0.005 mg $Ca^{2+}$/kg body weight/dose, about 0.01 mg $Ca^{2+}$/kg body weight/dose, about 0.02 mg $Ca^{2+}$/kg body weight/dose, or about 0.5 mg $Ca^{2+}$/kg body weight/dose.

In some embodiments the amount of calcium delivered to the respiratory tract (e.g., lungs, respiratory airway) is about 0.001 mg $Ca^{2+}$/kg body weight/dose to about 2 mg $Ca^{2+}$/kg body weight/dose, about 0.002 mg $Ca^{2+}$/kg body weight/dose to about 2 mg $Ca^{2+}$/kg body weight/dose, about 0.005 mg $Ca^{2+}$/kg body weight/dose to about 2 mg $Ca^{2+}$/kg body weight/dose, about 0.01 mg $Ca^{2+}$/kg body weight/dose to about 2 mg $Ca^{2+}$/kg body weight/dose, about 0.01 mg $Ca^{2+}$/kg body weight/dose to about 60 mg $Ca^{2+}$/kg body weight/dose, about 0.01 mg $Ca^{2+}$/kg body weight/dose to about 50 mg $Ca^{2+}$/kg body weight/dose, about 0.01 mg $Ca^{2+}$/kg body weight/dose to about 40 mg $Ca^{2+}$/kg body weight/dose, about 0.01 mg $Ca^{2+}$/kg body weight/dose to about 30 mg $Ca^{2+}$/kg body weight/dose, about 0.01 mg $Ca^{2+}$/kg body weight/dose to about 20 mg $Ca^{2+}$/kg body weight/dose, about 0.01 mg $Ca^{2+}$/kg body weight/dose to about 10 mg $Ca^{2+}$/kg body weight/dose, about 0.01 mg $Ca^{2+}$/kg body weight/dose to about 5 mg $Ca^{2+}$/kg body weight/dose, about 0.01 mg $Ca^{2+}$/kg body weight/dose to about 2 mg $Ca^{2+}$/kg body weight/dose, about 0.02 mg $Ca^{2+}$/kg body weight/dose to about 2 mg $Ca^{2+}$/kg body weight/dose, about 0.03 mg $Ca^{2+}$/kg body weight/dose to about 2 mg $Ca^{2+}$/kg body weight/dose, about 0.04 mg $Ca^{2+}$/kg body weight/dose to about 2 mg $Ca^{2+}$/kg body weight/dose, about 0.05 mg $Ca^{2+}$/kg body weight/dose to about 2 mg $Ca^{2+}$/kg body weight/dose, about 0.1 mg $Ca^{2+}$/kg body weight/dose to about 2 mg $Ca^{2+}$/kg body weight/dose, about 0.1 mg $Ca^{2+}$/kg body weight/dose to about 1 mg $Ca^{2+}$/kg body weight/dose, about 0.1 mg $Ca^{2+}$/kg body weight/dose to about 0.5 mg $Ca^{2+}$/kg body weight/dose, about 0.2 mg $Ca^{2+}$/kg body weight/dose to about 0.5 mg $Ca^{2+}$/kg body weight/dose, about 0.18 mg $Ca^{2+}$/kg body weight/dose, about 0.001 mg $Ca^{2+}$/kg body weight/dose, about 0.005 mg $Ca^{2+}$/kg body weight/dose, about 0.01 mg $Ca^{2+}$/kg body weight/dose, about 0.02 mg $Ca^{2+}$/kg body weight/dose, or about 0.5 mg $Ca^{2+}$/kg body weight/dose.

In other embodiments the amount of calcium delivered to the upper respiratory tract (e.g., nasal cavity) is of about 0.001 mg $Ca^{2+}$/kg body weight/dose to about 2 mg $Ca^{2+}$/kg body weight/dose, about 0.002 mg $Ca^{2+}$/kg body weight/dose to about 2 mg $Ca^{2+}$/kg body weight/dose, about 0.005 mg $Ca^{2+}$/kg body weight/dose to about 2 mg $Ca^{2+}$/kg body weight/dose, about 0.01 mg $Ca^{2+}$/kg body weight/dose to about 2 mg $Ca^{2+}$/kg body weight/dose, about 0.01 mg $Ca^{2+}$/kg body weight/dose to about 60 mg $Ca^{2+}$/kg body weight/dose, about 0.01 mg $Ca^{2+}$/kg body weight/dose to about 50 mg $Ca^{2+}$/kg body weight/dose, about 0.01 mg $Ca^{2+}$/kg body weight/dose to about 40 mg $Ca^{2+}$/kg body weight/dose, about 0.01 mg $Ca^{2+}$/kg body weight/dose to about 30 mg $Ca^{2+}$/kg body weight/dose, about 0.01 mg $Ca^{2+}$/kg body weight/dose to about 20 mg $Ca^{2+}$/kg body weight/dose, about 0.01 mg $Ca^{2+}$/kg body weight/dose to about 10 mg $Ca^{2+}$/kg body weight/dose, about 0.01 mg $Ca^{2+}$/kg body weight/dose to about 5 mg $Ca^{2+}$/kg body weight/dose, about 0.01 mg $Ca^{2+}$/kg body weight/dose to about 2 mg $Ca^{2+}$/kg body weight/dose, about 0.02 mg $Ca^{2+}$/kg body weight/dose to about 2 mg $Ca^{2+}$/kg body weight/dose, about 0.03 mg $Ca^{2+}$/kg body weight/dose to about 2 mg $Ca^{2+}$/kg body weight/dose, about 0.04 mg $Ca^{2+}$/kg body weight/dose to about 2 mg $Ca^{2+}$/kg body weight/dose, about 0.05 mg $Ca^{2+}$/kg body weight/dose to about 2 mg $Ca^{2+}$/kg body weight/dose, about 0.1 mg $Ca^{2+}$/kg body weight/dose to about 2 mg $Ca^{2+}$/kg body weight/dose, about 0.1 mg $Ca^{2+}$/kg body weight/dose to about 1 mg $Ca^{2+}$/kg body weight/dose, about 0.1 mg $Ca^{2+}$/kg body weight/dose to about 0.5 mg $Ca^{2+}$/kg body weight/dose, about 0.2 mg $Ca^{2+}$/kg body weight/dose to about 0.5 mg $Ca^{2+}$/kg body weight/dose, about 0.18 mg $Ca^{2+}$/kg body weight/dose, about 0.001 mg $Ca^{2+}$/kg body In addition, when the respirable dry particles and dry powders include a sodium salt, the respirable dry particles and dry powders can be administered in an amount sufficient to deliver a dose of about 0.001 mg $Na^+$/kg body weight/dose to about 10 mg $Na^+$/kg body weight/dose, or about 0.01 mg $Na^+$/kg body weight/dose to about 10 mg $Na^+$/kg body weight/dose, or about 0.1 mg $Na^+$/kg body weight/dose to about 10 mg $Na^+$/kg body weight/dose, or about 1.0 mg $Na^+$/kg body weight/dose to about 10 mg $Na^+$/kg body weight/dose, or about 0.001 mg $Na^+$/kg body weight/dose to about 1 mg $Na^+$/kg body weight/dose, or about 0.01 mg $Na^+$/kg body weight/dose to about 1 mg $Na^+$/kg body weight/dose, or about 0.1 mg $Na^+$/kg body weight/dose to about 1 mg $Na^+$/kg body weight/dose, about 0.2 to about 0.8 mg $Na^+$/kg body weight/dose, about 0.3 to about 0.7 mg $Na^+$/kg body weight/dose, or about 0.4 to about 0.6 mg $Na^+$/kg body weight/dose.

In some embodiments the amount of sodium delivered to the respiratory tract (e.g., lungs, respiratory airway) is about 0.001 mg/kg body weight/dose to about 10 mg/kg body weight/dose, or about 0.01 mg/kg body weight/dose to about 10 mg/kg body weight/dose, or about 0.1 mg/kg body weight/dose to about 10 mg/kg body weight/dose, or about 1 mg/kg body weight/dose to about 10 mg/kg body weight/dose, or about 0.001 mg/kg body weight/dose to about 1 mg/kg body weight/dose, or about 0.01 mg/kg body weight/dose to about 1 mg/kg body weight/dose, or about 0.1 mg/kg body weight/dose to about 1 mg/kg body weight/dose, or about 0.2 to about 0.8 mg/kg body weight/dose, or about 0.3 to about 0.7 mg/kg body weight/dose, or about 0.4 to about 0.6 mg/kg body weight/dose.

In other embodiments the amount of sodium delivered to the upper respiratory tract (e.g., nasal cavity) is about 0.001 mg/kg body weight/dose to about 10 mg/kg body weight/dose, or about 0.01 mg/kg body weight/dose to about 10 mg/kg body weight/dose, or about 0.1 mg/kg body weight/dose to about 10 mg/kg body weight/dose, or about 1 mg/kg body weight/dose to about 10 mg/kg body weight/dose, or about 0.001 mg/kg body weight/dose to about 1 mg/kg body weight/dose, or about 0.01 mg/kg body weight/dose to about 1 mg/kg body weight/dose, or about 0.1 mg/kg body weight/dose to about 1 mg/kg body weight/dose, or about 0.2 to about 0.8 mg/kg body weight/dose, or about 0.3 to about 0.7 mg/kg body weight/dose, or about 0.4 to about 0.6 mg/kg body weight/dose.

Suitable intervals between doses that provide the desired therapeutic effect can be determined based on the severity of the condition (e.g., infection), overall well being of the subject and the subject's tolerance to respirable dry particles and dry powders and other considerations. Based on these and other considerations, a clinician can determine appropriate intervals between doses. Generally, respirable dry particles and dry powders are administered once, twice or three times a day, as needed.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

Another advantage provided by the respirable dry powders and respirable dry particles described herein, is that dosing efficiency can be increased as a result of hygroscopic growth of particles inside the lungs, due to particle moisture growth. The propensity of the partially amorphous, high salt compositions of the invention to take up water at elevated humidities can also be advantageous with respect to their deposition profiles in vivo. Due to their rapid water uptake at high humidities, these powder formulations can undergo hygroscopic growth do the absorbance of water from the humid air in the respiratory tract as they transit into the lungs. This can result in an increase in their effective aerodynamic diameters during transit into the lungs, which will further facilitate their deposition in the airways.

EXEMPLIFICATION

Materials used in the following Examples and their sources are listed below. Calcium chloride dihydrate, calcium lactate pentahydrate, sodium chloride, L-leucine, maltodextrin, mannitol, lactose and trehalose were obtained from Sigma-Aldrich Co. (St. Louis, Mo.) or Spectrum Chemicals (Gardena, Calif.); sodium sulfate from EMD Chemicals (Gibbstown, N.J.), Sigma-Aldrich Co. (St. Louis, Mo.) or Spectrum Chemicals (Gardena, Calif.); and sodium citrate dihydrate from J.T. Baker (Phillipsburg, N.J.), Mallinckrodt Baker (Phillipsburg, N.J.) or Spectrum Chemicals (Gardena, Calif.). Ultrapure water was from a water purification system (Millipore Corp., Billerica, Mass.).

Methods:

Geometric or Volume Diameter.

Volume median diameter (×50 or Dv50), which may also be referred to as volume median geometric diameter (VMGD), was determined using a laser diffraction technique. The equipment consisted of a HELOS diffractometer and a RODOS dry powder disperser (Sympatec, Inc., Princeton, N.J.). The RODOS disperser applies a shear force to a sample of particles, controlled by the regulator pressure (typically set at 1.0 bar) of the incoming compressed dry air. The pressure settings may be varied to vary the amount of energy used to disperse the powder. For example, the regulator pressure may be varied from 0.2 bar to 4.0 bar; and the orifice ring pressure may be varied from 5.00 mbar to 115.00 mbar. Powder sample is dispensed from a microspatula into the RODOS funnel. The dispersed particles travel through a laser beam where the resulting diffracted light pattern produced is collected, typically using an R1 lens, by a series of detectors. The ensemble diffraction pattern is then translated into a volume-based particle size distribution using the Fraunhofer diffraction model, on the basis that smaller particles diffract light at larger angles. Using this method geometric standard deviation (GSD) for the volume mean geometric diameter was also determined.

Volume median diameter can also be measured using a method where the powder is emitted from a dry powder inhaler device. The equipment consisted of a Spraytec laser diffraction particle size system (Malvern, Worcestershire, UK), "Spraytec". Powder formulations were filled into size 3

HPMC capsules (Capsugel V-Caps) by hand with the fill weight measured gravimetrically using an analytical balance (Mettler Tolerdo XS205). A capsule based passive dry powder inhalers (RS-01 Model 7, High resistance Plastiape S.p.A.) was used which had specific resistance of 0.036 kPa$^{1/2}$ LPM$^{-1}$. Flow rate and inhaled volume were set using a timer controlled solenoid valve with flow control valve (TPK2000, Copley Scientific). Capsules were placed in the dry powder inhaler, punctured and the inhaler sealed to the inlet of the laser diffraction particle sizer. The steady air flow rate through the system was initiated using the TPK2000 and the particle size distribution was measured via the Spraytec at 1 kHz for at least 2 seconds and up to the total inhalation duration. Particle size distribution parameters calculated included the volume median diameter (Dv50) and the geometric standard deviation (GSD) and the fine particle fraction (FPF) of particles less than 5 micrometers in diameter. At the completion of the inhalation duration, the dry powder inhaler was opened, the capsule removed and re-weighed to calculate the mass of powder that had been emitted from the capsule during the inhalation duration (capsule emitted powder mass or CEPM).

The previous description of the use of the Spraytec was for what is described as its "closed bench configuration". Alternatively, the Spraytec can be used in its "open bench configuration". In the open bench configuration, capsules were placed in the dry powder inhaler, punctured and the inhaler sealed inside a cylinder. The cylinder was connected to a positive pressure air source with steady air flow through the system again measured with a mass flow meter and its duration controlled with a timer controlled solenoid valve. The exit of the dry powder inhaler was exposed to room pressure and the resulting aerosol jet passed through the laser of the diffraction particle sizer (Spraytec) in its open bench configuration before being captured by a vacuum extractor. The steady air flow rate through the system was initiated using the solenoid valve and the particle size distribution was measured via the Spraytec at 1 kHz for the duration of the single inhalation maneuver with a minimum of 2 seconds, as in the closed bench configuration. When data are reported in the examples as being measured by the Spraytec, they are from the closed bench configuration unless otherwise noted.

Emitted Geometric or Volume Diameter.

The volume median diameter (Dv50) of the powder after it emitted from a dry powder inhaler, which may also be referred to as volume median geometric diameter (VMGD), was determined using a laser diffraction technique via the Spraytec diffractometer (Malvern, Inc., Worcestershire, UK). Powder was filled into size 3 capsules (V-Caps, Capsugel) and placed in a capsule based dry powder inhaler (RS01 Model 7 High resistance, Plastiape, Italy), or DPI, which was connected with an airtight seal to the inhaler adapter of the Spraytec. A steady airflow rate was drawn through the DPI typically at 60 L/min for a set duration, typically of 2 seconds controlled by a timer controlled solenoid (TPK2000, Copley, Scientific, UK). Alternatively, the airflow rate drawn through the DPI was sometimes run at 15 L/min, 20 L/min, or 30 L/min. The outlet aerosol then passed perpendicularly through the laser beam as an internal flow. The resulting geometric particle size distribution of the aerosol was calculated from the software based on the measured scatter pattern on the photodetectors with samples typically taken at 1000 Hz for the duration of the inhalation. The Dv50, GSD, FPF<5.0 μm measured were then averaged over the duration of the inhalation.

Fine Particle Fraction.

The aerodynamic properties of the powders dispersed from an inhaler device were assessed with a Mk-II 1 ACFM Andersen Cascade Impactor (Copley Scientific Limited, Nottingham, UK). The instrument was run in controlled environmental conditions of 22±2° C. and relative humidity (RH) between 30±5%. The instrument consists of eight stages that separate aerosol particles based on inertial impaction. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain, called the "final collection filter". Gravimetric and/or chemical analyses can then be performed to determine the particle size distribution. A short stack cascade impactor, also referred to as a collapsed cascade impactor, is also utilized to allow for reduced labor time to evaluate two aerodynamic particle size cut-points. With this collapsed cascade impactor, stages are eliminated except those required to establish fine and coarse particle fractions.

The impaction techniques utilized allowed for the collection of two or eight separate powder fractions. The capsules (HPMC, Size 3; Shionogi Qualicaps, Madrid, Spain or Capsugel Vcaps, Peapack, N.J.) were approximately half-filled with powder and placed in a hand-held, breath-activated dry powder inhaler (DPI) device, the high resistance RS-01 DPI (Plastiape, Osnago, Italy). The capsule was punctured and the powder was drawn through the cascade impactor operated at a flow rate of 60.0 L/min for 2.0 s. At this flowrate, the calibrated cut-off diameters for the eight stages are 8.6, 6.5, 4.4, 3.3, 2.0, 1.1, 0.5 and 0.3 microns and for the two stages used with the short stack cascade impactor, the cut-off diameters are 5.6 microns and 3.4 microns. The fractions were collected by placing filters in the apparatus and determining the amount of powder that impinged on them by gravimetric measurements or chemical measurements on an HPLC, as labeled in the tables. The fine particle fraction of the total dose of powder (FPF_TD) less than or equal to an effective cut-off aerodynamic diameter was calculated by dividing the powder mass recovered from the desired stages of the impactor by the total particle mass in the capsule. Results are reported as the fine particle fraction of less than 5.6 microns (FPF <5.6 microns) and the fine particle fraction of less than 3.4 microns (FPF <3.4 microns). The fine particle fraction can alternatively be calculated relative to the recovered or emitted dose of powder by dividing the powder mass recovered from the desired stages of the impactor by the total powder mass recovered.

Aerodynamic Diameter.

Mass median aerodynamic diameter (MMAD) was determined using the information obtained by the Andersen Cascade Impactor. The cumulative mass under the stage cut-off diameter is calculated for each stage and normalized by the recovered dose of powder. The MMAD of the powder is then calculated by linear interpolation of the stage cut-off diameters that bracket the 50th percentile.

Fine Particle Dose.

The fine particle dose was determined using the information obtained by the ACI. The cumulative mass deposited on the final collection filter, and stages 6, 5, 4, 3, and 2 for a single dose of powder actuated into the ACI is equal to the fine particle dose less than 4.4 microns (FPD<4.4 μm).

Capsule Emitted Powder Mass.

A measure of the emission properties of the powders was determined by using the information obtained from the Andersen Cascade Impactor tests. The filled capsule weight was recorded at the beginning of the run and the final capsule weight was recorded after the completion of the run. The difference in weight represented the amount of powder emitted from the capsule (CEPM or capsule emitted powder mass). The emitted dose was calculated by dividing the amount of powder emitted from the capsule by the total initial particle mass in the capsule. While the standard CEPM was measured at 60 L/min, it was also measured at 15 L/min, 20 L/min, or 30 L/min.

Tap Density.

Two methods were utilized to measure tap density. (1) A modified method requiring smaller powder quantities was initially used, following USP <616> with the substitution of a 1.5 cc microcentrifuge tube (Eppendorf AG, Hamburg, Germany) or a 0.3 cc section of a disposable serological polystyrene micropipette (Grenier Bio-One, Monroe, N.C.) with polyethylene caps (Kimble Chase, Vineland, N.J.) to cap both ends and hold the powder. (2) USP <616> was used, utilizing a 100 cc graduated cylinder. Instruments for measuring tap density, known to those skilled in the art, include but are not limited to the Dual Platform Microprocessor Controlled Tap Density Tester (Vankel, Cary, N.C.) or a GeoPyc instrument (Micrometrics Instrument Corp., Norcross, Ga.). Tap density is a standard, approximated measure of the envelope mass density. The envelope mass density of an isotropic particle is defined as the mass of the particle divided by the minimum spherical envelope volume within which it can be enclosed.

Bulk Density.

Bulk density was estimated prior to tap density measurement procedure by dividing the weight of the powder by the volume of the powder, as estimated using the volumetric measuring device.

Hausner Ratio.

This is a dimensionless number, which was calculated by dividing the tap density by the bulk density. It is a number that is correlated to the flowability of a powder.

Scanning Electron Microscopy (SEM).

SEM was performed using a FE Quanta 200 scanning electron microscope (Hillsboro, Oreg.) equipped with an Everhart Thornley (ET) detector. Images were collected and analysed using xTm (v. 2.01) and XT Docu (v. 3.2) software, respectively. The magnification was verified using a NIST traceable standard. Each sample was prepared for analysis by placing a small amount on a carbon adhesive tab supported on an aluminum mount. Each sample was then sputter coated with Au/Pd using a Cressington 108 auto Sputter Coater at approximately 20 mA and 0.13 mbar (Ar) for 75 seconds. The data acquisition parameters are displayed in the information bar at the bottom of each image. The magnification reported on each image was calculated upon the initial data acquisition. The scale bar reported in the lower portion of each image is accurate upon resizing and should be used when making size determinations.

Liquid Feedstock Preparation for Spray Drying.

Spray drying homogenous particles requires that the ingredients of interest be solubilized in solution or suspended in a uniform and stable suspension. Certain calcium salts, such as calcium chloride, calcium acetate and calcium lactate, are sufficiently water-soluble to prepare suitable spray drying solutions. However, other calcium salts, such as calcium sulfate, calcium citrate and calcium carbonate, have a low solubility in water. The solubility in water of exemplary calcium salts are listed in Table 1. As a result of these low solubilities, formulation feedstock development work was necessary to prepare solutions or suspensions that could be spray dried. These solutions or suspensions included combinations of salts in an appropriate solvent, typically water but also ethanol and water mixtures or other solvents as described earlier in the specification.

TABLE 1

Calcium Salts' Solubility in Water
Calcium Salt Solubility in Water
(at 20-30° C., 1 bar)

| Salt | Water solubility (g/L) |
|---|---|
| Calcium chloride | 1368[1,2] |
| Calcium acetate | 347[1] |
| Calcium lactate | 105[1] |
| Calcium gluconate | 33.23[3] |
| Calcium sulate | 2.98[1] |
| Calcium citrate | 0.96[1] |
| Calcium phosphate dibasic | 0.2[1] |
| Calcium carbonate | Pract. Insol.[2] |
| Calcium stearate | Pract. Insol.[2] |
| Calcium alginate | Not applicable |
| Sodium Carbonate | 505[1] |
| Sodium Chloride | 360[1] |
| Sodium Citrate | 910[1] |
| Sodium Sulfate | 194[1] |

[1]Perry, Robert H., Don W. Green, and James O. Maloney. *Perry's Chemical Engineers' Handbook*, 7th ed. New York: McGraw-Hill, 1997, Print.
[2]Solubility at 60° C.
[3]O'Neil, Maryadele J. *The Merck Index: an Encyclopedia of Chemicals, Drugs, and Biologicals*, 14th ed. Whitehouse Station, N.J.: Merck, 2006. Print.

As mentioned previously, calcium chloride has high water solubility. Sodium salts, such as sodium sulfate, sodium citrate and sodium carbonate, are also very soluble in water. As will be discussed further in the following examples, calcium chloride and sodium salts (the "starting materials") are combined in solution or suspension to obtain stable calcium salts in final dry powder form. When combining the calcium chloride and sodium salt in solution, the calcium and the anion contributed from the sodium salt may react in a precipitation reaction to produce the desired calcium salt (i.e., $CaCl_2$+ $2NaXX \rightarrow CaXX+2NaCl$). In this case, the maximum solids concentration that maintained a clear solution or a stable suspension were used for spray drying. Certain calcium salts were soluble enough to be dissolved in water and then spray dried alone. The same concept may be applied to, for example, magnesium salts by using magnesium chloride, potassium salts using potassium chloride, and sodium salts.

The starting materials may be provided in molar amounts where the full precipitation reaction may proceed to completion, termed 'reaction to completion.' The weight percent of calcium ion in exemplary calcium salts are further listed in Table 2.

TABLE 2

Weight Percent of $Ca^{2+}$ in Salt Molecules
Weight % of Calcium ion in Salt Molecule

| Salt | Formula | MW | Weight % of $Ca^{2+}$ in molecule |
|---|---|---|---|
| Calcium carbonate | $CaCO_3$ | 100.09 | 40.0 |
| Calcium chloride | $CaCl_2$ | 110.98 | 36.0 |
| Calcium phosphate dibasic | $CaHPO_4$ | 136.06 | 29.4 |
| Calcium sulfate | $CaSO_4$ | 136.14 | 29.4 |
| Calcium acetate | $Ca(C_2H_3O_2)_2$ | 158.17 | 25.3 |
| Calcium citrate | $Ca_3(C_6H_5O_7)_2$ | 498.46 | 24.1 |
| Calcium lactate | $Ca(C_3H_5O_3)_2$ | 218.218 | 18.3 |

TABLE 2-continued

Weight Percent of $Ca^{2+}$ in Salt Molecules
Weight % of Calcium ion in Salt Molecule

| Salt | Formula | MW | Weight % of $Ca^{2+}$ in molecule |
|---|---|---|---|
| Calcium sorbate | $CaC_{12}H_{14}O_4$ | 262.33 | 15.2 |
| Calcium gluconate | $CaC_{12}H_{22}O_{14}$ | 430.373 | 9.3 |
| Calcium stearate | $CaC_{36}H_{70}O_4$ | 607.02 | 6.6 |
| Calcium alginate | $[Ca(C_6H_7O_6)_2]_n$ | NA | NA |

Alternatively, excess calcium chloride may be added for an incomplete reaction, or 'reaction not to completion,' where a given amount of calcium chloride is present in the final powder form. While calcium chloride is hygroscopic, its high water solubility may be beneficial to have in small amounts in the final product to increase the solubility of the final product, to be able to tailor the dissolution profile, and to increase the relative calcium ion ratio to sodium or other cations present in the formulation. For ease of formulation development, the required molar ratios of calcium chloride and sodium salt were converted to mass ratios of calcium chloride and sodium salt. An example is for calcium citrate (i.e., calcium chloride+ sodium citrate), where the precipitation reaction proceeds forward as follows:

$$3CaCl_2 + 2Na_3C_6H_5O_7 \rightarrow Ca_3(C_6H_5O_7)_2 + 6NaCl$$

This reaction results in a 1:2 molar ratio of Ca:Na ions. For the reaction to proceed to completion, 3 moles of calcium chloride and 2 moles of sodium citrate are required. To convert to mass in grams and a weight ratio, the moles of salts are multiplied by the molecular weight of the salts in grams per mole:

For calcium chloride: 3 mol $CaCl_2 \times 111$ g/mol=333 g $CaCl_2$

For sodium citrate: 2 mol $Na_3C_6H_5O_7 \times 258$ g/mol=516 g $Na_3C_6H_5O_7$ Therefore, a 1:1.55 or 39:61 weight ratio of $CaCl_2$: $Na_3C_6H_5O_7$ is required for a complete reaction. These ratios were solubilized and spray dried to produce 'pure salt' formulations. In addition, dry powders were produced with an additional excipient, such as leucine or lactose. The ratio of calcium to sodium salt remained the same so as to produce a 'reaction to completion.' For example, for a formulation of 50% (w/w) leucine, the remainder is composed of salts, such as calcium citrate (i.e., $CaCl_2$:$Na_3C_6H_5O_7$) where the 39:61, $CaCl_2$:$Na_3C_6H_5O_7$ weight ratio is maintained. Thus, for that reaction: 50% (w/w) leucine, 19.5% (w/w) $CaCl_2$ and 30.5% (w/w) $Na_3C_6H_5O_7$ will be added. For a spray drying process, the salts and other excipients will be dissolved or suspended in a solvent (i.e., water). The solids concentration (w/v) can be chosen depending on the solubility of the different components. For the citrate formulation, a concentration of 5 mg/mL was appropriate, given the limited solubility of calcium citrate: 0.95 mg/mL. Therefore, 5 g of solids (i.e., 2.5 g leucine, 0.975 g calcium chloride and 1.525 g of sodium citrate) were dissolved in 1 L of ultrapure water.

In addition, when preparing spray drying solutions, the water weight of the hydrated starting material must be accounted for. The ratios used for formulations were based on the molecular weight of the anhydrous salts. For certain salts, hydrated forms are more readily available than the anhydrous form. This required an adjustment in the ratios originally calculated, using a multiplier to correlate the molecular weight of the anhydrous salt with the molecular weight of the hydrate. An example of this calculation is included below.

For the example above, calcium chloride anhydrous molecular weight is 110.98 g/mol and the dihydrate molecular weight is 147.01 g/mol. Sodium citrate anhydrous molecular weight is 258.07 g/mol and the dihydrate molecular weight is 294.10 g/mol.

The multiplier is analogous to the ratio of the dihydrate to anhydrous molecular weight, e.g., 1.32 for calcium chloride and 1.14 for sodium citrate. Therefore, adjusting for the dihydrate forms results in: 2.5 g leucine, 1.287 g (i.e., 0.975 g×1.32) calcium chloride dihydrate and 1.738 g (i.e., 1.525 g×1.14) of sodium citrate dihydrate were dissolved and spray dried.

Spray Drying Using Niro Spray Dryer.

Dry powders were produced by spray drying utilizing a Niro Mobile Minor spray dryer (GEA Process Engineering Inc., Columbia, Md.) with powder collection from a cyclone, a product filter or both. Atomization of the liquid feed was performed using a co-current two-fluid nozzle either from Niro (GEA Process Engineering Inc., Columbia, Md.) or a Spraying Systems (Carol Stream, Ill.) two-fluid nozzle with gas cap 67147 and fluid cap 2850SS, although other two-fluid nozzle setups are also possible. For example, the two-fluid nozzle can be in an internal mixing setup or an external mixing setup. Additional atomization techniques include rotary atomization or a pressure nozzle. The liquid feed was fed using gear pumps (Cole-Parmer Instrument Company, Vernon Hills, Ill.) directly into the two-fluid nozzle or into a static mixer (Charles Ross & Son Company, Hauppauge, N.Y.) immediately before introduction into the two-fluid nozzle. An additional liquid feed technique includes feeding from a pressurized vessel. Nitrogen or air may be used as the drying gas, provided that moisture in the air is at least partially removed before its use. Pressurized nitrogen or air can be used as the atomization gas feed to the two-fluid nozzle. The process gas inlet temperature can range from 100° C. to 300° C. and outlet temperature from 50° C. to 120° C. with a liquid feedstock rate of 20 mL/min to 100 mL/min. The gas supplying the two-fluid atomizer can vary depending on nozzle selection and for the Niro co-current two-fluid nozzle can range from 8 kg/hr to 15 kg/hr and be set a pressures ranging from 0.5 bar to 2.0 bar or for the Spraying Systems two-fluid nozzle with gas cap 67147 and fluid cap 2850SS can range from 40 to 100 g/min. For example, the Niro two fluid nozzle discussed above can range from 5 kg/hr to 50 kg/hr. The atomizing gas rate can be set to achieve a certain gas to liquid mass ratio, which directly affects the droplet size created. The pressure inside the drying drum can range from +3 "WC to −6 "WC. Spray dried powders can be collected in a container at the outlet of the cyclone, onto a cartridge or baghouse filter, or from both a cyclone and a cartridge or baghouse filter.

Spray Drying Using Büchi Spray Dryer.

Dry powders were prepared by spray drying on a Büchi B-290 Mini Spray Dryer (BÜCHI Labortechnik AG, Flawil, Switzerland) with powder collection from either a standard or High Performance cyclone. The system used the Büchi B-296 dehumidifier to ensure stable temperature and humidity of the air used to spray dry. Furthermore, when the relative humidity in the room exceeded 30% RH, an external LG dehumidifier (model 49007903, LG Electronics, Englewood Cliffs, N.J.) was run constantly. Atomization of the liquid feed utilized a Büchi two-fluid nozzle with a 1.5 mm diameter. Inlet temperature of the process gas can range from 100° C. to 220° C. and outlet temperature from 80° C. to 120° C. with a liquid feedstock flowrate of 3 mL/min to 10 mL/min. The two-fluid atomizing gas ranges from 25 mm to 45 mm (300 LPH to 530 LPH) and the aspirator rate from 70% to 100% (28 m³/hr to 38 m³/hr).

Table 3 provides feedstock formulations used in preparation of some dry powders described herein.

TABLE 3

Feedstock Formulations

| Formulation | Feedstock Composition (w/w) | Ca:Na molar ratio |
|---|---|---|
| I | 10.0% leucine, 35.1% calcium chloride, 54.9% sodium citrate [12.7% $Ca^{2+}$ (w/w); 14.7% $Na^+$ (w/w)] | 1:2 |
| II | 10.0% leucine, 39.6% calcium chloride, 50.4% sodium sulfate [14.3% $Ca^{2+}$ (w/w); 8.2% $Na^+$ (w/w)] | 1:2 |
| III | 10.0% leucine, 58.6% calcium lactate, 31.4% sodium chloride [10.8% $Ca^{2+}$ (w/w); 12.4% $Na^+$ (w/w)] | 1:2 |
| IV | 10.0% maltodextrin, 58.6% calcium lactate, 31.4% sodium chloride [10.8% $Ca^{2+}$ (w/w); 12.4% $Na^+$ (w/w)] | 1:2 |
| V | 10.0% mannitol, 58.6% calcium lactate, 31.4% sodium chloride [10.8% $Ca^{2+}$ (w/w); 12.4% $Na^+$ (w/w)] | 1:2 |
| VI | 39.4% leucine, 58.6% calcium lactate, 2.0% sodium chloride [10.8% $Ca^{2+}$ (w/w); 0.8% $Na^+$ (w/w)] | 8:1 |
| VII | 37.5% leucine, 58.6% calcium lactate, 3.9% sodium chloride [10.8% $Ca^{2+}$ (w/w); 1.5% $Na^+$ (w/w)] | 4:1 |
| VIII | 20% leucine, 75.0% calcium lactate, 5.0% sodium chloride [13.8% $Ca^{2+}$ (w/w); 2.0% $Na^+$ (w/w)] | 4:1 |
| IX | 33.6% leucine, 58.6% calcium lactate, 7,8% sodium chloride [10.8% $Ca^{2+}$ (w/w); 3.1% $Na^+$ (w/w)] | |

Table 4 provides expected final dry powder compositions. These compositions are based on the expectation that the ion exchange reaction described above goes to completion for Formulations I and III. Without wishing to be bound by any particular theory, the evaporation of the droplet that occurs during spray drying is expected to drive the least soluble salt to precipitate first, which is the calcium citrate and calcium sulfate in Formulations I and II, respectively.

TABLE 4

Dry Powder Products of Spray Drying

| Formulation | Composition (w/w) |
|---|---|
| I | 10.0% leucine, 52.8% calcium citrate, 37.2% sodium chloride |
| II | 10.0% leucine, 48.4% calcium sulfate, 41.6% sodium chloride |
| III | 10.0% leucine, 58.6% calcium lactate, 31.4% sodium chloride |
| IV | 10.0% maltodextrin, 58.6% calcium lactate, 31.4% sodium chloride |
| V | 10.0% mannitol, 58.6% calcium lactate, 31.4% sodium chloride |
| VI | 39.4% leucine, 58.6% calcium lactate, 2.0% sodium chloride |
| VII | 37.5% leucine, 58.6% calcium lactate, 3.9% sodium chloride |
| VIII | 20% leucine, 75.0% calcium lactate, 5.0% sodium chloride |

Description of Placebo:

Placebo formulations comprising 100 weight percent leucine or 98 weight percent leucine with 2 weight percent sodium chloride were produced by spray drying. An aqueous phase was prepared for a batch process by dissolving leucine in ultrapure water with constant agitation until the materials were completely dissolved in the water at room temperature. For a static mixing process, the ultrapure water was divided in half and half of the total required leucine was dissolved in each volume of water. The solutions were then spray dried using a Niro or a Büchi spray dryer. For the Placebo formulation, two batches (A and B) of feedstock were prepared and spray dried. The total solids concentration for Batch A was 15 g/L and for Batch B was 5 g/L. The process conditions used for spray drying Batch A (Placebo-A) on the Niro Mobile Minor spray dryer were similar to the conditions used to spray dry Formulation 1-A in Example 1. The process conditions used for spray drying Batch B (Placebo-B) were similar to the conditions used to spray dry Formulation I-C in Example 1, with the exception that the outlet temperature was about 82° C. for Formulation Placebo-B. Additional information relating to process conditions and properties of the Formulation Placebo-A and Placebo-B powders and/or particles prepared in this example are provided in the Tables or graphs shown in FIGS. 1A-1F and 2-4.

Example 1

This example describes the preparation of dry powders using feedstock of Formulation I: 10.0 weight percent leucine, 35.1 weight percent calcium chloride and 54.9 weight percent sodium citrate.

An aqueous phase was prepared for a hatch process by dissolving leucine in ultrapure water, then sodium citrate dihydrate, and finally calcium chloride dihydrate. The solution or suspension was kept agitated throughout the process until the materials were completely dissolved in the water at room temperature. For a static mixing process, the sodium salt and calcium salt were kept in separate solutions. The ultrapure water was divided in half and half of the total required leucine was dissolved in each volume of water. The sodium citrate dihydrate was dissolved in one aqueous phase and the calcium chloride dihydrate dissolved in the second aqueous phase. The solutions or suspensions were kept agitated throughout the process until the materials were completely dissolved in the water at room temperature. The solutions or suspensions were then spray dried using a Niro or a Büchi spray dryer. For each formulation, three batches (A, B & C) of feedstock were prepared and spray dried. Details on the liquid feedstock preparations for each of the three hatches are shown in Table 5, where the total solids concentration is reported as the total of the dissolved anhydrous material weights. Batch A and D particles were prepared using batch A and D feedstock, respectively, on a Niro spray dryer. Batch B and C particles were prepared using the corresponding feedstocks on a Büchi spray dryer.

TABLE 5

Summary of liquid feedstock preparations of four batches of particles for Formulation I.

| Formulation: | I-A | I-B | I-C | I-D |
|---|---|---|---|---|
| Liquid feedstock mixing | Static mixed | Batch mixed | Batch mixed | Static mixed |
| Total solids concentration | 10 g/L | 5 g/L | 5 g/L | 15 g/L |
| Total solids | 380 g | 6.25 g | 10.50 g | 570 g |
| Total volume water | 38.0 L | 1.25 L | 2.1 L | 38 L |
| Amount leucine in 1 L | 1.00 g | 0.50 g | 1.05 g | 1.5 g |
| Amount sodium citrate dihydrate in 1 L | 6.26 g | 3.13 g | 3.13 g | 9.39 g |
| Amount calcium chloride dihydrate in 1 L | 4.65 g | 2.32 g | 2.32 g | 6.98 g |

Batch A (I-A) dry powders were produced by spray drying on the Niro Mobile Minor spray dryer (GEA Process Engineering Inc., Columbia, Md.) with powder collection from a product cartridge filter. Atomization of the liquid feed used a co-current two-fluid nozzle from Niro (GEA Process Engineering Inc., Columbia, Md.) with 1.0 mm insert. The liquid feed was fed using gear pumps (Cole-Parmer Instrument Company, Vernon Hills, Ill.) into a static mixer (Charles Ross & Son Company, Hauppauge, N.Y.) immediately before introduction into the two-fluid nozzle. Nitrogen was used as the drying gas. The process gas inlet temperature was set to 282° C., with the outlet temperature reading about 98° C. The gas supplying the two-fluid atomizer was set at a flowrate of 14.5 kg/hr and a pressure of 2 psi, the process gas flowrate was set at 85 kg/hr and a pressure of 25 psi, and the pressure inside the drying drum was at −2 "WC. The liquid feed stock total flowrate was 70 mL/min, with each stream being fed at 35 mL/min. Spray dried powders were collected from a product collection cartridge filter.

Batch B (I-B) and Batch C (I-C) dry powders were prepared by spray drying on a Büchi B-290 Mini Spray Dryer (BÜCHI Labortechnik AG, Flawil, Switzerland) with a Büchi two-fluid nozzle with a 1.5 mm diameter and powder collection from a High Performance cyclone. The system used the Büchi B-296 dehumidifier to ensure stable temperature and humidity of the air used to spray dry. Inlet temperature of the process gas was set at 220° C. with a liquid feedstock flowrate of 6.7 mL/min for Formulation I-B and 7 mL/min for Formulation I-C. The outlet temperature was about 108° C. for Formulation I-B and about 95° C. for Formulation I-C. The two-fluid atomizing gas was at 40 mm and the aspirator rate at 90%.

Batch D (I-D) dry powders were produced by spray drying on the Niro Mobile Minor spray dryer (GEA Process Engineering Inc., Columbia, Md.) with powder collection from a product filter membrane. Atomization of the liquid feed used a two-fluid nozzle from Spraying Systems (Carol Stream, Il,) with gas cap 67147 and fluid cap 2850SS. The liquid feed was fed using gear pumps (Cole-Parmer Instrument Company, Vernon Hills, Ill.) into a static mixer (Charles Ross & Son Company, Hauppauge, N.Y.) immediately before introduction into the two-fluid nozzle. Nitrogen was used as the drying gas. The process gas inlet temperature was set to approximately 265° C., with the outlet temperature reading about 99° C. The gas supplying the two-fluid atomizer was set at a flowrate of 80 g/min, the process gas flowrate was set at 80 kg/hr and the pressure inside the drying drum was at −2 "WC. The liquid feed stock total flowrate was 66 mL/min, with each stream being fed at 33 mL/min. Spray dried powders were collected from a product collection filter membrane.

Some of the physical properties of the particles obtained in four separate batches (Formulation I-A, I-B, I-C and I-D) are summarized in Table 6. In addition to the data provided in Table 5, further data related to the dry powders prepared from feedstock formulation I-A is summarized as follows. The fine particle fraction (FPF) as measured by a full 8-stage Andersen Cascade Impactor with gravimetric analysis was on average 56.2% for FPF less than 5.6 microns and 41.7% for FPF less than 3.4 microns. The aerodynamic diameter was also measured with a full-stage ACI with gravimetric analysis. The average value for the mass median aerodynamic diameter (MMAD) was 2.72 microns. The volume size was determined by laser diffraction on the HELOS/RODOS sizing equipment and the average value for the volume median diameter (×50) at a pressure of 1 bar was 2.57 microns. In addition, the powder displayed relatively flowrate independent behavior as can be seen from the ratio of ×50 measured at 0.5 bar to ×50 measured at 4.0 bar, which was 1.19. The value for 1/4 bar for these particles was 1.17.

Additional properties of the dry powders prepared from feedstock Formulation I-D are summarized as follows. The fine particle fraction (FPF) as measured by a full 8-stage Andersen Cascade Impactor with gravimetric analysis was on average 58.8% for FPF less than 5.6 microns and 46.7% for FPF less than 3.4 microns. The aerodynamic diameter was also measured with a full-stage ACI with gravimetric analysis. The average value for the mass median aerodynamic diameter (MMAD) was 2.38 microns. The volume size was determined by laser diffraction on the HELOS/RODOS sizing equipment and the average value for the volume median diameter (×50) at a pressure of 1 bar was 2.45 microns. In addition, the powder displayed relatively flowrate independent behavior as can be seen from the ratio of ×50 measured at 0.5 bar to ×50 measured at 4.0 bar, which was 1.12. The value for 1/4 bar for these particles was 1.09.

TABLE 6

Summary of ACI-2 data for the four batches of particles for Formulation I.

| Formulation: | I-A | I-B | I-C | I-D |
|---|---|---|---|---|
| FPF less than 5.6 μm on ACI-2 (%) | 61.6 | 49.2 | 64.8 | 672 |
| FPF less than 3.4 μm on ACI-2 (%) | 45.7 | 33.3 | 52.1 | 54.8 |

Additional information relating to properties of the Formulation I-A powder and/or particles prepared in this example are provided in the Tables or graphs shown in FIGS. 1A-1F and 2-4. In FIG. 1D, GSD refers to geometric standard deviation. In FIG. 1F, Dv50 refers to volume median geometric diameter (VMGD) as measured by Spraytec instrument; V refers to volume. SEM was performed as described above (FIG. 5A).

Example 2

This example describes the preparation of dry powders using feedstock of Formulation III: 10.0 weight percent leucine, 58.6 weight percent calcium lactate and 31.4 weight percent sodium chloride.

An aqueous phase was prepared for a batch process by dissolving leucine in ultrapure water, then sodium chloride, and finally calcium lactate pentahydrate. The solution was kept agitated throughout the process until the materials were completely dissolved in the water at room temperature. For the calcium lactate formulation, four batches (A, B, C and D) of feedstock were prepared and spray dried. Details on the liquid feedstock preparations for each of the four batches are shown in Table 7, where the total solids concentration is reported as the total of the dissolved anhydrous material weights. Batch A and D particles were prepared using batch A and D feedstock, respectively on a Niro spray dryer. The process conditions used for spray drying Batch A (III-A) were similar to the conditions used to spray dry Formulation I-A in Example 1 and those for Batch D (III-D) were similar to the conditions used to spray dry Formulation 1-D in Example 1. Batch B and C particles were prepared using the corresponding feedstocks on a Büchi Mini spray dryer with process conditions similar to those used to spray dry for Formulations I-B and I-C in Example 1, with the exception of the following process conditions. The liquid feedstock flowrate was set at 5.2 mL/min for Formulation III-B and 6 mL/min for Formulation III-C. The outlet temperature was about 91° C. to 109° C. for Formulation III-B and about 100° C. for Formulation III-C.

TABLE 7

Summary of liquid feedstock preparations of four batches of particles for Formulation III.

| Formulation: | III-A | III-B | III-C | III-D |
|---|---|---|---|---|
| Liquid feedstock mixing | Static mixed | Batch mixed | Batch mixed | Static mixed |
| Total solids concentration | 10 g/L | 5 g/L | 5 g/L | 15 g/L |
| Total solids | 400 g | 10.0 g | 9.20 g | 570 g |
| Total volume water | 40.0 L | 2.00 L | 1.84 L | 38 L |
| Amount leucine in 1 L | 1.00 g | 0.50 g | 0.50 g | 1.5 g |
| Amount sodium chloride in 1 L | 3.14 g | 1.57 g | 1.57 g | 4.71 g |
| Amount calcium lactate pentahydrate in 1 L | 8.28 g | 4.13 g | 4.13 g | 12.42 g |

Some of the physical properties of the particles obtained in four separate batches (Formulation III-A, III-B, III-C and III-D) are summarized in Table 8. In addition to the data provided in Table 8, further data about the dry particles prepared by feedstock Formulation III-A is summarized as follows. The fine particle fraction (FPF) as measured by a full 8-stage Andersen Cascade Impactor with gravimetric analysis was on average 55.3% for FPF less than 5.6 microns and 39.7% for FPF less than 3.4 microns. The aerodynamic diameter was also measured with a full-stage ACI with gravimetric analysis. The average value for the mass median aerodynamic diameter (MMAD) was 2.89 microns. The volume size was determined by laser diffraction on the HELOS/RODOS sizing equipment and the average value for the volume median diameter (×50) at a pressure of 1 bar was 1.51 microns. In addition, the powder displayed relatively flowrate independent behavior as can be seen from the ratio of ×50 measured at 0.5 bar to ×50 measured at 4.0 bar, which was 1.12. The value for 1/4 bar for these particles was 1.08.

Additional properties of the dry powders prepared by feedstock formulation III-D are summarized as follows. The fine particle fraction (FPF) as measured by a full 8-stage Andersen Cascade Impactor with gravimetric analysis was on average 62.2% for FPF less than 5.6 microns and 45.3% for FPF less than 3.4 microns. The aerodynamic diameter was also measured with a full-stage ACI with gravimetric analysis. The average value for the mass median aerodynamic diameter (MMAD) was 2.72 microns. The volume size was determined by laser diffraction on the HELOS/RODOS sizing equipment and the average value for the volume median diameter (×50) at a pressure of 1 bar was 1.47 microns. In addition, the powder displayed relatively flowrate independent behavior as can be seen from the ratio of ×50 measured at 0.5 bar to ×50 measured at 4.0 bar, which was 1.08. The value for 1/4 bar for these particles was 1.03.

TABLE 8

Summary of ACI-2 data for the four batches of particles for Formulation III.

| Formulation: | III-A | III-B | III-C | III-D |
|---|---|---|---|---|
| FPF less than 5.6 µm on ACI-2 (%) | 63.5 | 55.4 | 56.5 | 71.4 |
| FPF less than 3.4 µm on ACI-2 (%) | 43.4 | 35.5 | 34.7 | 49.7 |

Figure 5A:
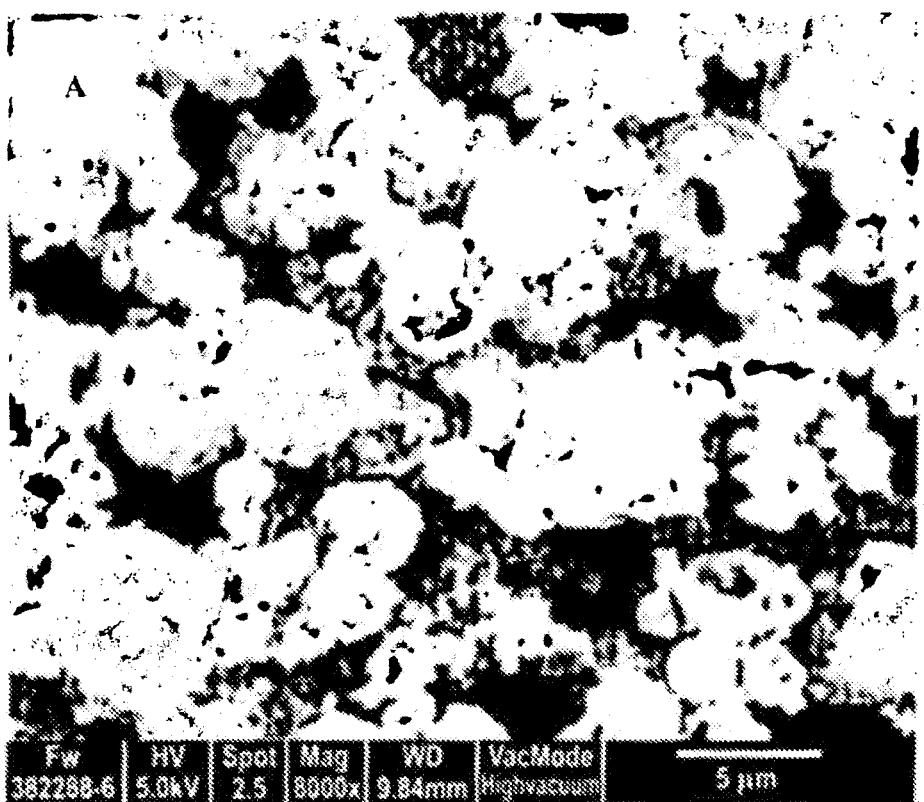
FIG. 5A-D are electron micrographs of Formulation I (FIG. 5A); Formulation III (FIG. 5B); Formulation II (FIG. 5C); and Formulation IV (FIG. 5D)
Figure 5B:
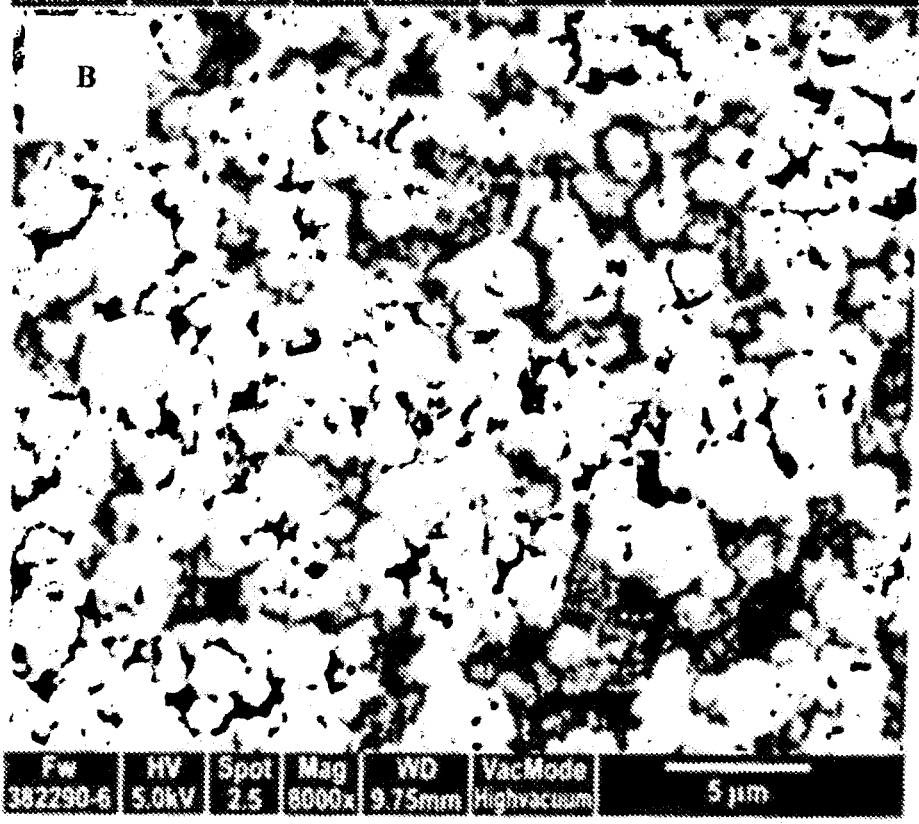

Additional information relating to properties of the Formulation III powders and/or particles prepared in this example are provided in the Tables or graphs shown in FIGS. 1A-1F and 2-4. SEM was performed as described above (FIG. 5B).

Example 3

This example describes the preparation of dry powders using feedstock of Formulation II: 10 weight percent leucine, 39.6 weight percent calcium chloride and 50.4 weight percent sodium sulfate.

An aqueous phase was prepared for a batch process by dissolving leucine in ultrapure water, then sodium sulfate, and finally calcium chloride dihydrate. The solution or suspension was kept agitated throughout the process until the materials were completely dissolved in the water at room temperature. For a static mixing process, the sodium salt and calcium salt were kept in separate solutions. The ultrapure water was divided in half and half of the total required leucine was dissolved in each volume of water. The sodium sulfate was dissolved in one aqueous phase and the calcium chloride dihydrate dissolved in the second aqueous phase. The solutions or suspensions were kept agitated throughout the process until the materials were completely dissolved in the water at room temperature. The solutions or suspensions were then spray dried using a Niro or a Büchi spray dryer. For each formulation, four batches (A, B, C and D) of feedstock were prepared and spray dried. Details on the liquid feedstock preparations for each of the four batches are shown in Table 9, where the total solids concentration is reported as the total of the dissolved anhydrous material weights. Batch A and D particles were prepared using batch A and D feedstock, respectively on a Niro spray dryer. Batch B and C particles were prepared using the corresponding feedstocks on a Büchi spray dryer. The process conditions used for spray drying Batch A (II-A) were similar to the conditions used to spray dry Formulation I-A in Example 1 and the process conditions used for spray drying Batch D (II-D) were similar to the conditions used to spray dry Formulation I-D in Example 1. Batch B and C particles were prepared using the corresponding feedstocks on a Büchi Mini spray dryer with process conditions similar to those used to spray dry Formulations I-B and I-C in Example 1, with the exception of the following process conditions. The liquid feedstock flowrate was set at 8.3 mL/min for Formulation II-B and 7 mL/min for Formulation II-C. The outlet temperature was about 83° C. for Formulation II-B and about 92° C. for Formulation II-C. The aspirator was set at 80% for Formulation II-B.

TABLE 9

Summary of liquid feedstock preparations of four batches of particles for Formulation II.

| Formulation: | II-A | II-B | II-C | II-D |
|---|---|---|---|---|
| Liquid feedstock mixing | Static mixed | Batch mixed | Batch mixed | Static mixed |

TABLE 9-continued

Summary of liquid feedstock preparations of four batches of particles for Formulation II.

| Formulation: | II-A | II-B | II-C | II-D |
|---|---|---|---|---|
| Total solids concentration | 10 g/L | 5 g/L | 5 g/L | 15 g/L |
| Total solids | 400 g | 2.5 g | 9.5 g | 185 g |
| Total volume water | 40 L | 0.5 L | 1.9 L | 37 L |
| Amount leucine in 1 L | 1.00 g | 0.5 g | 0.5 g | 0.5 g |
| Amount sodium sulfate in 1 L | 5.04 g | 2.52 g | 2.52 g | 2.52 g |
| Amount calcium chloride dihydrate in 1 L | 5.25 g | 2.61 g | 2.61 g | 2.61 g |

The physical properties of the particles obtained in four separate batches (Formulation II-A, II-B, II-C and II-D) are summarized in Table 10. In addition to the data provided in Table 10, further data about the dry powders prepared from feedstock Formulation 11-A is summarized as follows. The fine particle fraction (FPF) as measured by a full 8-stage Andersen Cascade Impactor with gravimetric analysis was on average 68.7% for FPF less than 5.6 microns and 51.5% for FPF less than 3.4 microns. The aerodynamic diameter was also measured with a full-stage ACI with gravimetric analysis. The average value for the mass median aerodynamic diameter (MMAD) was 2.59 microns. The volume size was determined by laser diffraction on the HELOS/RODOS sizing equipment and the average value for the volume median diameter (×50) at a pressure of 1 bar was 2.50 microns. In addition, the powder displayed relatively flowrate independent behavior as can be seen from the ratio of ×50 measured at 0.5 bar to ×50 measured at 4.0 bar, which was 1.47. The value for 1/4 bar for these particles was 1.42.

Additional properties of the dry powders prepared by feedstock Formulation II-D are summarized as follows. The fine particle fraction (FPF) as measured by a full 8-stage Andersen Cascade Impactor with gravimetric analysis was on average 77.9% for FPF less than 5.6 microns and 68.3% for FPF less than 3.4 microns. The aerodynamic diameter was also measured with a full-stage ACI with gravimetric analysis. The average value for the mass median aerodynamic diameter (MMAD) was 2.17 microns. The volume size was determined by laser diffraction on the HELOS/RODOS sizing equipment and the average value for the volume median diameter (×50) at a pressure of 1 bar was 1.90 microns. In addition, the powder displayed relatively flowrate independent behavior as can be seen from the ratio of ×50 measured at 0.5 bar to ×50 measured at 4.0 bar, which was 1.17. The value for 1/4 bar for these particles was 1.63.

TABLE 10

Summary of ACI_2 data for the four batches of particles for Formulation II.

| Formulation: | II-A | II-B | II-C | II-D |
|---|---|---|---|---|
| FPF less than 5.6 μm on ACI-2 (%) | 82.7 | 62.0 | 69.0 | 82.8 |
| FPF less than 3.4 μm on ACI-2 (%) | 60.1 | 47.4 | 53.2 | 70.9 |

Figure 5C:
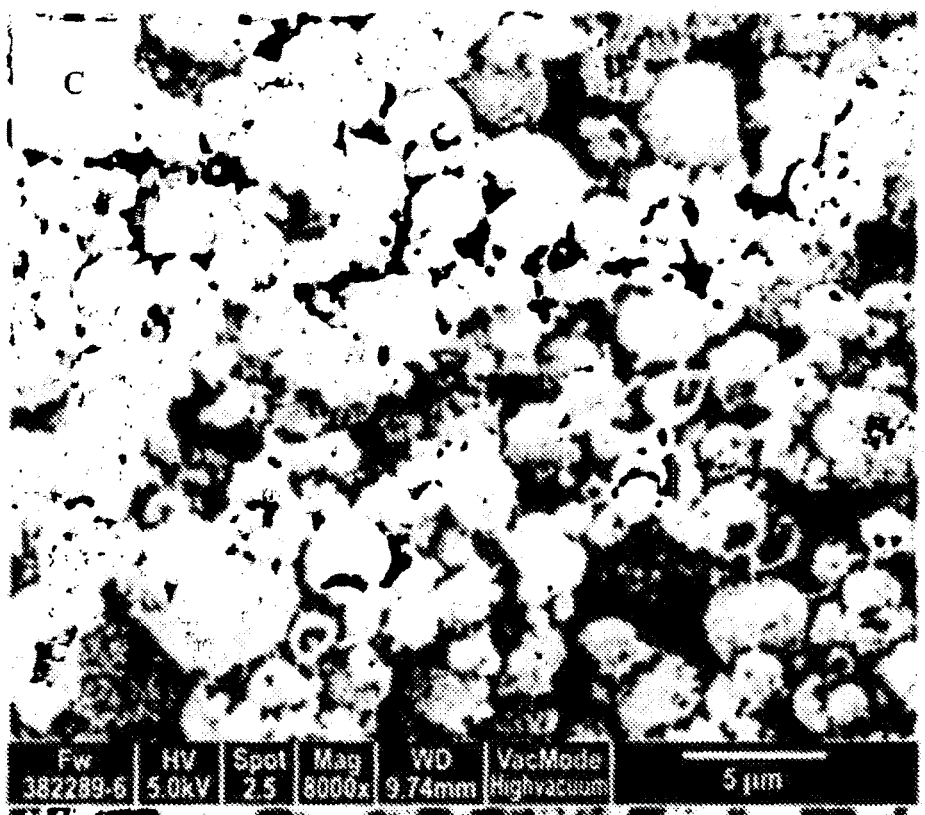
Figure 5D:
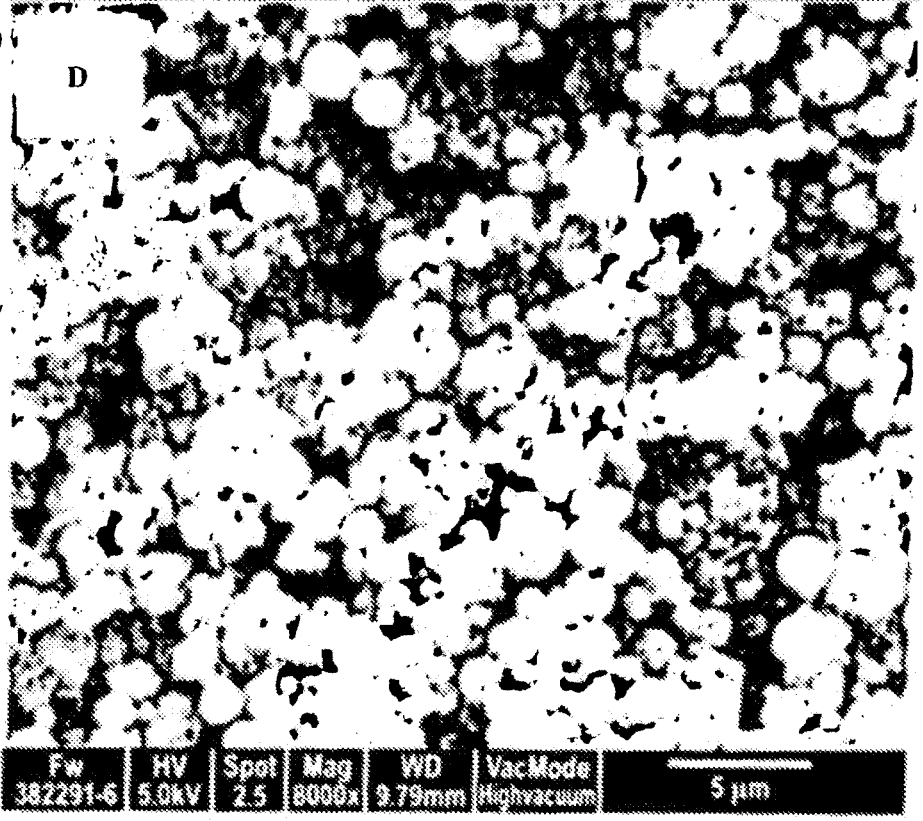

Additional information relating to properties of the Formulation H powders and/or particles prepared in this example is provided in the Tables or graphs shown in FIGS. 1A-1F and 2-4. SEM was performed as described above (FIG. 5C)

Example 4

This example describes the dose emission of powders of formulation batches I-B, II-B, and III-B from a dry powder inhaler at room and elevated conditions.

Method: Spray dried powders of the three different formulations (I-B, II-B, and III-B) were filled into size 2 HPMC capsules (Quali-V, Qualicaps, Whitsett, N.C.) to approximately half full (13-30 mg depending on powder). Capsules were punctured prior to loading into one of four capsule DPIs in order to ensure adequate hole openings in the capsule. The capsules were loaded horizontally into the inhalers which were then connected to the custom chamber. Each dry powder inhaler had a pressure transducer connected to it to monitor the flow rate through the inhaler during the test. When the test was begun, an airflow of 45 L/min was drawn through each inhaler for 3 short bursts of 0.3 seconds each, separated by 1 minute. During each burst, the air drawn through the inhaler caused the capsule to spin and emit the powder in it into one of 4 sub-chambers which had one row of 3 tissue culture wells forming the floor of the sub-chamber. The aerosol cloud was allowed to settle for one minute before the next subsequent burst for a total of 3 bursts and a total air volume of 0.68 L being drawn through the inhaler. The duration and total airflow rate was controlled with a flow controller (TPK-2000, MSP Corporation, Shoreview, Minn.) and recorded with an air mass flow meter (model#3063, TSI Inc., Shoreview, Minn.). Individual inhaler airflow rates were monitored with pressure sensors (model #ASCX01DN, Honeywell International Inc., Morristown, N.J.) which had been previously calibrated and whose signal was converted to flow rate via a custom Lab-view code. In one case, the custom chamber was located on the lab bench at room conditions, while in another 2 cases it was located in a stability chamber (Darwin Chambers Company, St. Louis, Mo.) set to 37° C. and 90% RH. For the first case in the stability chamber, the capsules were punctured and loaded into inhalers at room conditions, the door of the chamber was opened, the inhalers attached and the flow rate was actuated ~30 seconds after the capsules entered the chamber. In the second case, the capsules were first placed unpunctured in the stability chamber for 3 minutes, then removed from the chamber, punctured and loaded at room conditions, attached in the chamber and actuated within 30 seconds of the second entry into the chamber. Following each test, the capsules were removed from the inhalers and weighed and used to calculate the percentage of powder emitted from the capsule. For each of the 3 sets of conditions, two 12 well tissue culture plates (each plate required 4 capsules in 4 inhalers delivering powder to 3 wells each) were exposed to powder for each of the powder formulations tested, giving a total of 8 capsule emissions for each powder at each temperature and humidity setting.

As shown in Table 11 below, for all three powder batches (I-B, II-B, and III-B) the average amount of powder emitted from the capsule is greater than 99% based on the weight change of the capsule.

TABLE 11

Emitted Dose Percent

| Powder Batch | Emitted Dose % |
|---|---|
| I-B | 99.45 |
| III-B | 100.0 |
| II-B | 99.38 |

Example 5

This example describes the dispersion properties and density properties of formulations I-A, II-A, III-A, and Leucine formulation for placebo as summarized in Table 12. All the data found in Table 12 can also be found in FIGS. 1A through 1E. As evidenced by the results shown in Table 12, all formulations are highly dispersible, meaning that their measured volume sizes are relatively independent of pressure on the HELOS/RODOS. As shown in Table 12, the ratio of the volume median sizes obtained at low dispersion pressures (0.5 bar or 1.0 bar) and at a high dispersion pressure (4.0 bar) can be used as an indicator of dispersibility. These values are referred to as the 0.5 bar/4.0 bar ratio or the 1.0 bar/4.0 bar ratio.

The tap density was determined by the modified USP<616> method using a 1.5 cc microcentrifuge tube and the average value for tap density at 1,000 taps were 0.29, 0.69, 0.34, and 0.04 g/cc, respectively. The MMAD, as measured by a full-stage (eight-stage) Andersen Cascade Impactor (ACI), were 2.72, 2.89, 2.59, and 4.29 um, respectively. The FPF below 3.4 um, as measured on a full-stage ACI, were 41.7%, 39.7%, 51.5%, and 17.4%, respectively, and below 5.6 um were 56.2%, 55.3%, 68.7%, and 32.5%, respectively. The volume size was determined by laser diffraction and the average values for the volume median diameter (×50) at a pressure of 1 bar were 2.57 microns, 1.51 microns, 2.50 microns, and 6.47 microns, respectively. Values for pressure values at 0.5 bar, 2.0 bar, and 4.0 bar can be seen in Table 12. In addition, the powder displayed relatively flowrate independent behavior as can be seen from the ratio of ×50 measured at 0.5 bar to ×50 measured at 4.0 bar as shown in Table 12. The values are 1.19, 1.12, 1.47, and 1.62, respectively. The table also includes values for the ratio of 1.0 bar to 4.0 bar, for the sake of comparison to other art, since this is another measure of flowrate dependency.

TABLE 12

Dispersion and Density Properties of Formulations I-A, II-A, III-A

| Formulation | Density Tap density (g/cc) Ave | ACI-8, Gravimetric MMAD (um) Ave | ACI-8, Gravimetric FPF_TD <3.4 um Ave | ACI-8, Gravimetric FPF_TD <5.6 um Ave | Spraytec Dv50 (um) Ave | HELOS/RODOS Regulator pressure (bar) | HELOS/RODOS x50 (μm) Ave | HELOS/RODOS 0.5 bar/4 bar | HELOS/RODOS 1 bar/4 bar |
|---|---|---|---|---|---|---|---|---|---|
| Formulation I-A | 0.29 | 2.72 | 41.7% | 56.2% | 3.07 | 0.5 | 2.62 | 1.19 | 1.17 |
| | | | | | | 1.0 | 2.57 | | |
| | | | | | | 2.0 | 2.49 | | |
| | | | | | | 4.0 | 2.20 | | |
| Formulation III-A | 0.69 | 2.89 | 39.7% | 55.3% | 1.78 | 0.5 | 1.57 | 1.12 | 1.08 |
| | | | | | | 1.0 | 1.51 | | |
| | | | | | | 2.0 | 1.47 | | |
| | | | | | | 4.0 | 1.40 | | |
| Formulation II-A | 0.34 | 2.59 | 51.5% | 68.7% | 3.05 | 0.5 | 2.59 | 1.47 | 1.42 |
| | | | | | | 1.0 | 2.50 | | |
| | | | | | | 2.0 | 2.17 | | |
| | | | | | | 4.0 | 1.76 | | |
| Placebo (100% leucine) | 0.04 | 4.29 | 17.4% | 32.5% | 21.77 | 0.5 | 7.68 | 1.62 | 1.37 |
| | | | | | | 1.0 | 6.47 | | |
| | | | | | | 2.0 | 5.69 | | |
| | | | | | | 4.0 | 4.74 | | |

Example 6

This example describes the preparation of dry powders using feedstock Formulations 6.1-6.9 as listed in Table 13 below.

TABLE 13

Feedstock Formulations 6.1-6.9

| Formulation | Composition and Weight % (w/w) |
|---|---|
| 6.1 | 10.0% leucine, 58.6% calcium lactate, 31.4% sodium chloride |
| 6.2 | 50.0% leucine, 48.4% calcium lactate, 1.6% sodium chloride |
| 6.3 | 10.0% leucine, 66.6% calcium lactate, 23.4% sodium chloride |
| 6.4 | 10.0% leucine, 35.1% calcium chloride, 54.9% sodium citrate |
| 6.5 | 67.1% leucine, 30.0% calcium chloride, 2.9% sodium citrate |
| 6.6 | 39.0% calcium chloride, 61.0% sodium citrate |
| 6.7 | 10.0% leucine, 39.6% calcium chloride, 50.4% sodium sulfate |
| 6.8 | 67.6% leucine, 30.0% calcium chloride, 2.4% sodium sulfate |
| 6.9 | 44.0% calcium chloride, 56.0% sodium sulfate |

The general mode of preparation of the dry powders in this example is similar to what was described for the powders in the above examples with the exception that all of the dry powders in this example were spray dried using a Büchi B-290 spray dryer with High Performance cyclone. Formulations 6.1, 6.4, and 6.7 in this Example correspond to Formulations III-B, I-B, and II-B in the Examples above, respectively.

The physical properties of the powders and/or particles obtained in this example are summarized in the Tables shown in FIGS. 6A and 6B. Formulations 6.1-6.9 in Table 13 correspond to Formulations 6.1-6.9 in FIGS. 6A and 6B, respectively. In FIG. 6A, ×50 and Dv50 refer to volume median diameter or volume median geometric diameter (VMGD); and GSD refers to geometric standard deviation. In FIG. 6B, yield % refers to percentage of the weight of the recovered product in the collection jar attached to the High Performance cyclone divided by the weight of the solutes in the feedstock. All other abbreviations are described elsewhere in the application.

Example 7

This example describes the dose emission of powders prepared by feedstock Formulations 6.1-6.9 from a dry powder inhaler at room and elevated conditions. Some of this data is also presented above, in Example 4.

Method: Spray dried powders of the nine feedstock formulations 6.1-6.9 were separately filled into size 2 HPMC capsules (Quali-V, Qualicaps, Whitsett, N.C.) to approximately half full (13-30 mg depending on powder). Capsules were punctured prior to loading into one of four capsule based DPIs in order to ensure adequate hole openings in the capsule. The capsules were loaded horizontally into the inhalers which were then connected to the custom chamber. Each dry powder inhaler had a pressure transducer connected to it to monitor the flow rate through the inhaler during the test. When the test was begun, an airflow of 45 L/min was drawn through each inhaler for 3 short bursts of 0.3 seconds each, separated by 1 minute. During each burst, the air drawn through the inhaler caused the capsule to spin and emit the powder in it into one of 4 sub-chambers which had one row of 3 tissue culture wells forming the floor of the sub-chamber. The aerosol cloud was allowed to settle for one minute before the next subsequent burst for a total of 3 bursts and a total air volume of 0.68 L being drawn through the inhaler. The duration and total airflow rate was controlled with a flow controller (TPK-2000, MSP Corporation, Shoreview, Minn.) and recorded with an air mass flow meter (model#3063, TSI Inc., Shoreview, Minn.). Individual inhaler airflow rates were monitored with pressure sensors (model #ASCX01DN, Honeywell International Inc., Morristown, N.J.) which had been previously calibrated and whose signal was converted to flow rate via a custom Lab-view code. In one case, the custom chamber was located on the lab bench at room conditions, while in another 2 cases it was located in a stability chamber (Darwin Chambers Company, St. Louis, Mo.) set to 37° C. and 90% RH. For the first case in the stability chamber, the capsules were punctured and loaded into inhalers at room conditions, the door of the chamber was opened, the inhalers attached and the flow rate was actuated ~30 seconds after the capsules entered the chamber. In the second case, the capsules were first placed unpunctured in the stability chamber for 3 minutes, then removed from the chamber, punctured and loaded at room conditions, attached in the chamber and actuated within 30 seconds of the second entry into the chamber. Following each test, the capsules were removed from the inhalers and weighed and used to calculate the percentage of powder emitted from the capsule. For each of the 3 sets of conditions, two 12 well tissue culture plates (each plate required 4 capsules in 4 inhalers delivering powder to 3 wells each) were exposed to powder for each of the powder formulations tested, giving a total of 8 capsule emissions for each powder at each temperature and humidity setting.

As shown in Table 14 below, for all nine powder batches (obtained using feedstock Formulations 6.1-6.9) the average amount of powder emitted from the capsule is greater than 98% based on the weight change of the capsule.

TABLE 14

| Emitted Dose Percent | |
|---|---|
| Formulation | Emitted Dose (%) |
| 6.1 | 100.00% |
| 6.2 | 98.86% |
| 6.3 | 99.85% |
| 6.4 | 99.45% |
| 6.5 | 99.68% |
| 6.6 | 100.00% |
| 6.7 | 99.38% |
| 6.8 | 98.05% |
| 6.9 | 100.00% |

Example 8

This example describes the results of a short-term stability study that was conducted for the dry powders prepared by feedstock Formulations 6.1, 6.4 and 6.7.

An important characteristic of pharmaceutical dry powders is stability at different temperature and humidity conditions. One property that may lead to an unstable powder is the powder's tendency to absorb moisture from the environment, which then will likely lead to agglomeration of the particles, thus altering the apparent particle size of the powder at similar dispersion conditions. Spray dried powders were held at a range of conditions for periods of one week to three or more months and periodically tested for particle size distribution. Storage conditions included closed capsules in vials at 25° C. and 60% RH, closed capsules in vials at 40° C. and 75% RH, closed capsules at room temperature and 40% RH, open capsules at 30° C. and 65% RH and open capsules at 30° C. and 75% RH. Size 3 HPMC capsules (Quali-V, Qualicaps, Whitsett, N.C.) were half filled with each dry powder. One sample was tested immediately in the Spraytec (Malvern Instruments Inc., Westborough, Mass.), a laser diffraction spray particle sizing system where dry powders can be dispersed from an inhaler using the inhaler cell setup. Approximately 16 capsules were filled with each powder prepared using feedstock solutions 6.1, 6.4 and 6.7. Capsules were kept in the lab at controlled humidity and temperature conditions (~23-28% RH), and also in the outside lab at varying temperature and relative humidity (~40-75% RH). Capsules kept at storage conditions of 25° C. and 60% RH, 40° C. and 75% RH, 30° C. and 65% RH and 30° C. and 75% RH were held in stability chambers (Darwin Chambers Company, St. Louis, Mo.) set at those conditions. At specific time points (ranging from 30 min to 3 months), one to three capsules from each condition were tested on the Spraytec for geometric particle size distribution and the ACI-2 for aerodynamic particle size properties.

Generally, the powders that were in closed capsules in vials remained stable for a long period of time, longer than three months. Powders that were in open capsules with no vials showed agglomeration after exposure to higher humidity conditions. The stability data are summarized in Table 15 below.

TABLE 15

Short-term Stability Data

| Formulation | Counter ion | Excipient | closed capsules in vials | | closed capsules, no vials | | open capsules, no vials | | | |
|---|---|---|---|---|---|---|---|---|---|---|
| | | | 25 C./60% RH | 40 C./75% RH | Spraytec 40% RH | ACI-2 40% RH | Spraytec 30 C./65% RH | ACI-2 30 C./65% RH | Spraytec 30 C./75% RH | ACI-2 30 C./75% RH |
| 6.1 | Lactate | 10% Leucine | >3 months | 0.5-1 month | >8 days | 4-6 days | >30 min | >30 min | >30 min | >30 min |
| 6.4 | Citrate | 10% Leucine | >3 months | 1-3 months | >7 days | N/A | >30 min | >30 min | <30 min | >30 min |
| 6.7 | Sulfate | 10% Leucine | >3 months | 1-3 months | 2-7 days | N/A | >30 min | >30 min | >30 min | >30 min |

Example 9

This example describes a Bacterial Pass-Through Assay performed using dry powders prepared using feedstock Formulations A-E found in Table 16.

Method: To test the effect of aerosolized dry powder formulations on bacterial movement across mucus, a pass-through model was used. In this model, 200 µL of 4% sodium alginate (Sigma-Aldrich, St. Louis, Mo.) was added to the apical surface of a 12 mm Costar Transwell membrane (Corning, Lowell, Mass.; 3.0 µm pore size) and subsequently exposed to dry powder formulations. Dry powders were aerosolized into the chamber using a dry powder insufflator (Penn-Century, Inc., Philadelphia, Pa.) and allowed to settle by gravity over a 5 minute period. Following this exposure, 10 µL of *Klebsiella pneumoniae* (~$10^7$ CFU/mL in saline) was added to the apical surface of the mimetic. At various time points after the addition of bacteria, aliquots of the basolateral buffer were removed and the number of bacteria in each aliquot was determined by serially diluting and plating on blood agar plates. A schematic of this method is shown in FIG. 7. The concentration of salt that was delivered to each Transwell was quantified by HPLC. For this purpose, empty wells of the 12 well cell culture plate that were next to each Transwell and were exposed to the same dose of formulation were rinsed with sterile water and diluted 1:1 with acetic acid to solubilize the calcium salts in each powder.

The effect of calcium containing powders on *K. pneumoniae* movement through sodium alginate mucus mimetic was tested. Dry powder formulations comprising calcium salts with different solubility profiles, together with leucine and sodium chloride, were screened for activity. Table 16 (below) lists the feedstock formulations of the powders that were tested. A 50.0% (w/w) leucine loading in the composition was necessary, as opposed to the 10.0% (w/w) leucine loading in the formulations described in the examples above, due to dosing and detection limitations in the pass through model. The calcium and sodium molar ratio was chosen for each formulation to target a 1:1 molar ratio, while not needing to go too low on the relative weights of any particular salt. Therefore, the lactate, citrate, and acetate formulations used were not in a 1:1 molar ratio in order to keep the weights of the sodium chloride and the calcium chloride in those formulations, respectively, above about 10% by weight.

TABLE 16

Feedstock Formulations

| Formulation | Composition (w/w) | Ca:Na mole ratio |
|---|---|---|
| A | 50.0% leucine, 22.0% calcium chloride, 28.0% sodium sulfate | 1.0:2.0 |
| B | 50.0% leucine, 25.5% calcium chloride, 24.5% sodium carbonate | 1.0:2.0 |
| C | 50.0% leucine, 19.5% calcium chloride, 30.5% sodium citrate | 1.0:2.0 |
| D | 50.0% leucine, 37.0% calcium lactate, 13.0% sodium chloride | 1.0:1.3 |
| E | 50.0% leucine, 33.75% calcium acetate, 16.25% sodium chloride | 1.0:1.8 |

Figure 8A:
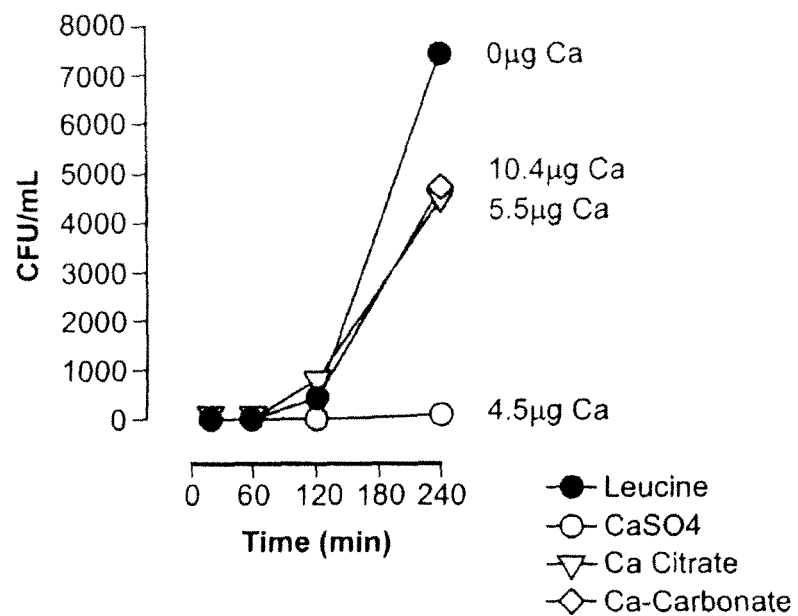
FIG. 8A is a graph showing the results of the bacterial pass-through model with exposure to dry powders. A calcium sulfate-containing powder (4.5 ug Ca/cm$^2$ delivered dose) reduced bacterial movement through sodium alginate mimetic.
Figure 8B:
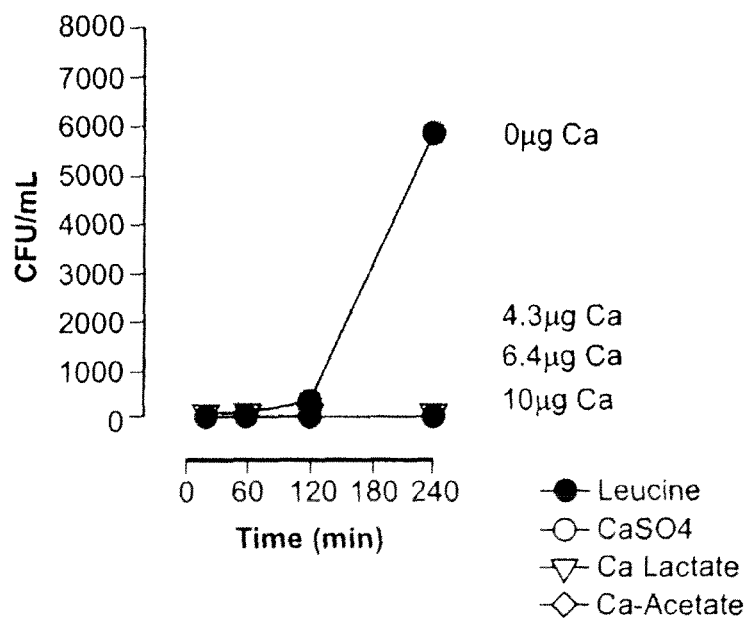
FIG. 8B is a graph showing the results of the bacterial pass-through model with exposure to dry powders. The calcium salt dry powders, prepared from the feedstock formulations A-E, tested contained 0 ug, 4.3 ug, 6.4 ug or 10 ug of calcium. Calcium sulfate (4.3 ug Ca/cm$^2$ delivered dose), calcium acetate (10 ug Ca/cm$^2$ delivered dose) and calcium lactate (6.4 ug Ca/cm$^2$ delivered dose) containing powders reduced bacterial movement through sodium alginate mimetic.

The results for this test are shown in FIGS. 8A and 8B. The two different figures represent two different sets of experiments, run at the same conditions. The leucine control and sulfate data allow for relative comparison between the two sets of experiments. The powders containing the anions sulfate, lactate, and acetate, i.e., the dry powders prepared from feedstock formulations A, D, and E, respectively, reduced the movement of bacteria across the mimetic, whereas the powders containing the anions carbonate and citrate, i.e., dry powders prepared from feedstock formulations B and C, exhibited no effect. These finding correlated with the known solubility of the calcium salts in water, suggesting that the possible failure of carbonate and citrate salts to inhibit the movement of *K. pneumoniae* could be related to the solubility of these powders at the surface of the sodium alginate mimetic. This conclusion is also based on the plausible assumption that the ion exchange reaction described previously goes to completion during spray drying, and that the form of the calcium salt in Formulations A through E is calcium sulfate, calcium carbonate, calcium citrate, calcium lactate, and calcium acetate, respectively. The solubility of these salts from least soluble to most soluble: calcium carbonate<calcium citrate<calcium sulfate<calcium lactate<calcium acetate. (See Table 1 above.)

Example 10

This example describes the performance of dry powders in reducing viral replication utilizing a viral replication model.

In this example, a series of dose response studies with different dry powder prepared from feedstock formulations consisting of different calcium salts are described. Dry powders were made with leucine, a calcium salt (lactate or chloride), and sodium salt (chloride, sulfate, citrate or carbonate). Feedstock formulations listed 10-1, 10-2 and 10-3 were spray dried on a Büchi B-290 mini spray dryer. The system used the Büchi B-296 dehumidifier to ensure stable temperature and humidity of the air used to spray dry. Feedstock Formulation 10-4 was spray dried on a Niro Mobile Minor Spray Dryer in an open cycle with nitrogen.

Four liquid feedstocks were prepared with the following components and ratios (weight percentage) as listed in Table 17.

TABLE 17

Feedstock Formulations

| Formulation | Feedstock Composition (w/w) | Ca:Na mole ratio |
|---|---|---|
| 10-1 | 50.0% leucine, 37.0% calcium lactate, 13.0% sodium chloride | 1.0:1.3 |
| 10-2 | 50.0% leucine, 22.0% calcium chloride, 28.0% sodium sulfate | 1.0:2.0 |
| 10-3 | 50.0% leucine, 19.5% calcium chloride, 30.5% sodium citrate | 1.0:2.0 |
| 10-4 | 50.0% leucine, 25.5% calcium chloride, 24.5% sodium carbonate | 1.0:2.0 |

A 50.0% (w/w) leucine loading in the composition was necessary, as opposed to the 10.0% (w/w) leucine loading in the formulations described in the examples above, due to dosing and detection limitations in the viral replication model. The calcium and sodium mole ratio was chosen for each formulation to target a 1:1 molar ratio, while not needing to go too low on the relative weights of any particular salt. Therefore, the lactate and citrate formulations used were not in a 1:1 mole ratio in order to keep the weights of the sodium chloride and the calcium chloride in those formulations, respectively, above about 10% by weight.

Formulations 10-1, 10-2 and 10-3 were spray dried with feedstock solids concentrations of 5 g/L, while the exact amount of salts and excipient dissolved in ultrapure water and its specific volume varied. The following process settings were used: inlet temperature of 220° C., liquid flow rate of approximately 10mL/min, room conditions at 23.2-24.6° C. and 19-21% RH, and dehumidifier air at 3-5° C. and 30% RH. The outlet temperature, cyclone and aspirator rate varied. Formulation 10-1 was spray dried using a high performance cyclone with the aspirator at 80% and an outlet temperature of 93° C. Dry powder formulations 10-2 and 10-3 were made with the regular cyclone, an aspirator at 100% and an outlet temperature of 111-115° C. Formulation 10-4 was spray dried with a solids concentration of 2.7 g/L and the following process settings: inlet temperature of 140° C., outlet temperature of 75° C., liquid feedstock flowrate of 30 ml/min, process gas flowrate of 100 kg/hr, atomizer gas flowrate of 20 g/min and a spray drying drum chamber pressure of −2 "WC.

A cell culture model of Influenza infection was used to study the effects of Formulations 1 through 4. Calu-3 cells (American Type Culture Collection, Manassas, Va.) were cultured on permeable membranes (12 mm Transwells; 0.4 μm pore size, Corning Lowell, Mass.) until confluent (the membrane was fully covered with cells) and air-liquid interface (ALI) cultures were established by removing the apical media and culturing at 37° C./5% $CO_2$. Cells were cultured for >2 weeks at ALI before each experiment. Prior to each experiment the apical surface of each Transwell was washed 3× with PBS (Hyclone, Logan, Utah). Calu-3 cells were exposed to dry powders using a proprietary dry powder sedimentation chamber. In order to expose cells to equivalent doses of calcium, capsules were filled with different amounts of each powder. The high, medium, and low fill weights were calculated based on matching the amount of calcium delivered by each powder (4.23 mg, 1.06 mg, and 0.35 mg). For each dry powder condition tested, two capsules were weighed as empty, filled, and after exposure in order to determine emitted dose of the powder. Table 18 (below) shows the capsule fill weights before and after exposure and the concentration of calcium delivered to cells as determined by HPLC measurements. Immediately after exposure, the basolateral media (media on the bottom side of the Transwell) was replaced with fresh media. Triplicate wells were exposed to dry powders from each feedstock formulation in each test. A second cell culture plate was exposed to the same dry powders from the feedstock formulations to quantify the delivery of total salt or calcium to cells. One hour after exposure, cells were infected with 104 of Influenza A/WSN/33/1 (H1N1) or Influenza A/Panama/2007/99 (H3N2) at a multiplicity of infection of 0.1-0.01 (0.1-0.01 virions per cell). Four hours after aerosol treatment, the apical surfaces were washed to remove excess dry powders and unattached virus and cells were cultured for an additional 20 h at 37° C. plus 5% $CO_2$. Twenty-four hours after aerosol treatment, virus released onto the apical surface of infected cells was collected in culture media or PBS and the concentration of virus in the apical wash was quantified by $TCID_{50}$ (50% Tissue Culture Infectious Dose) assay. The $TCID_{50}$ assay is a standard endpoint dilution assay that is used to quantify how much of a virus is present in a sample.

Dry powder formulations were tested to evaluate their effect on Influenza A/WSN/33/1 infection in a cell culture model (Table 18). To deliver an equivalent amount of calcium ion $Ca^{2+}$, the desired fill weight was calculated for each dry powder formulation. Qualicap capsules were weighed empty, filled, and after exposure to determine the emitted dose. Triplicate wells were exposed to each capsule and after wells were washed. HPLC analysis of these samples determined the amount of $Ca^{2+}$ delivered to cells. * denotes the use of two capsules in order to achieve desired fill weight. [a] denotes n=3, [b] denotes n=1

TABLE 18

Dry powder, prepared from feedstock formulations 10-1 to 10-4, tested to evaluate their effect on Influenza A/WSN/33/1 infection in a cell culture model.

| Feedstock Formulation (for Dry Powders) | Intended Fill (mg) | Empty Capsule (mg) | Filled Capsule (mg) | Capsule after Exposure (mg) | Calcium ion concentration determined by HPLC (μg/cm²) |
|---|---|---|---|---|---|
| 10-2 (50.0% leucine, 22.0% calcium chloride, 28.0% sodium sulfate) | 53.18 | 31.7 | 83.0 | 31.9 | 20.5 ± 0.7[a] |
|  | 13.29 | 32.5 | 45.9 | 33.9 | 5.8[b] |
|  | 4.43 | 33.3 | 38.4 | 33.9 | 2.8[b] |
| 10-1 (50.0% | 62.17 | 64.972, 63.122* | 99.649, 98.881* | 64.994, 63.679* | 50.9 ± 1.1[a] |

TABLE 18-continued

Dry powder, prepared from feedstock formulations 10-1 to 10-4, tested to evaluate their effect on Influenza A/WSN/33/1 infection in a cell culture model.

| Feedstock Formulation (for Dry Powders) | Intended Fill (mg) | Empty Capsule (mg) | Filled Capsule (mg) | Capsule after Exposure (mg) | Calcium ion concentration determined by HPLC ($\mu g/cm^2$) |
|---|---|---|---|---|---|
| leucine, 37.0% calcium lactate, 13.0% sodium chloride) | 15.54<br>5.18 | 63.525<br>62.453 | 81.926<br>67.796 | 68.141<br>62.49 | $12.7 \pm 1.7^a$<br>$4.0^b$ |
| 10-3 (50.0% leucine, 19.5% calcium chloride, 30.5% sodium citrate) | 60.0<br>14.99<br>5.00 | 64.4<br>64.0<br>63.5 | 123.6<br>78.5<br>70.3 | 81.994<br>65.388<br>63.829 | $20.5 \pm 5.7^a$<br>$7.6 \pm 0.9^a$<br>$3.6 \pm 1.5^a$ |
| 10-4 (50.0% leucine, 25.5% calcium chloride, 24.5% sodium carbonate) | 45.88<br>11.47<br>3.82 | 64.6<br>61.5<br>61.8 | 104.7<br>72.0<br>62.6 | 66.685<br>63.186<br>63.341 | $28.1 \pm 7.3^a$<br>$8.1 \pm 2.6^a$<br>$5.62 \pm 2.7^a$ |

Example 10A

Dry powders, prepared from feedstock formulations 10-1 to 10-4, reduce Influenza A/WSN/33/1 (H1N1) infection in a dose-dependent manner.

To test the effect of dry powder formulations on Influenza infection in a cell culture model Calu-3 cells were exposed to four different dry powder formulations each consisting of 50% leucine, a calcium salt and sodium chloride. Viral infection was assessed by quantifying the amount of viral replication over a 24 h period. The specific powders tested are listed in Table 18 (above), and included carbonate, lactate, sulfate and citrate salts. In an attempt to expose cells to equivalent amounts of calcium of each of the four calcium containing powders, capsules were filled to appropriate fill weights prior to dosing. Cells exposed to no formulation (Air) were used as control cells.

Figure 9:
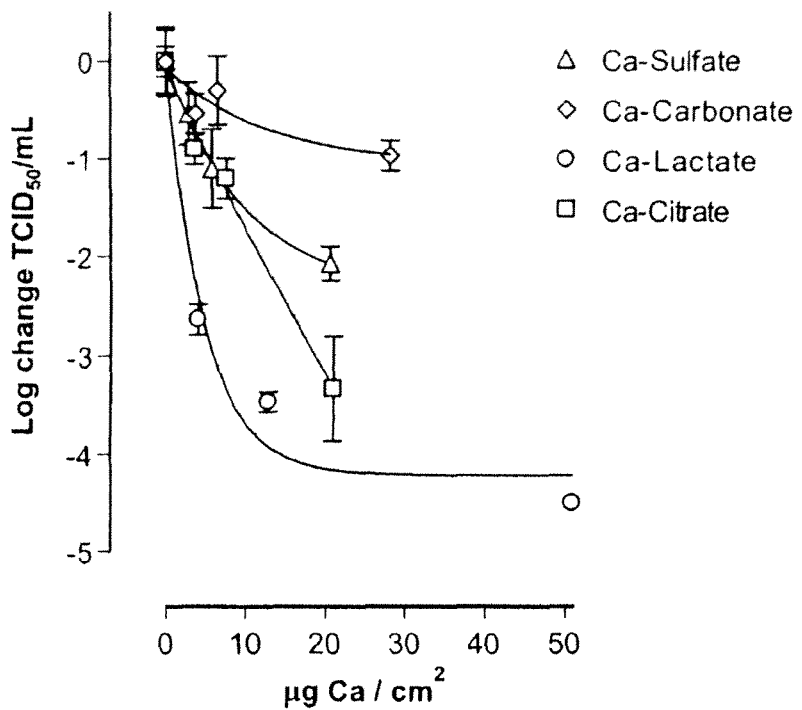
FIG. 9 is a graph that shows the effect of the respirable dry powders, prepared from feedstock formulations 10-1 to 10-4 in Example 10A, on Influenza A/WSN/33 (H1N1) infection in a dose-dependent manner.

As seen in FIG. 9, each powder exhibited a dose-responsive reduction in influenza infection; however, the magnitude of the effect was different among the four powders tested. At low calcium concentrations calcium lactate was most efficacious suggesting that it was the most potent of the powders tested. At higher concentrations of calcium, the calcium lactate and calcium citrate powders exhibited similar efficacy. Additional testing of the calcium citrate powder at even higher concentrations may demonstrate that it is the most efficacious powder. The calcium sulfate powder exhibited an intermediate effect and was comparable to calcium citrate at several concentrations. Calcium carbonate had only a minimal effect on viral replication even at the highest concentration (less than 10-fold). Of note, calcium carbonate is the least soluble of the powders tested.

As shown in FIG. 9, the dry powders prepared for this reduce Influenza infection in a dose-dependent manner.

Calu-3 cells exposed to no formulation were used as a control and compared to Calu-3 cells exposed to dry powder formulations at different fill weights. The concentration of virus released by cells exposed to each aerosol formulation was quantified. Bars represent the mean and standard deviation of triplicate wells for each condition. Data were analyzed statistically by one way ANOVA and Tukey's multiple comparison post-test.

Example 10B

Dry powder, prepared from feedstock formulations 10-1 to 10-4 in Table 19, reduce Influenza A/Panama/2007/99 (H3N2) infection in a dose-dependent manner.

To extend these studies, the same powders were tested with a second influenza strain [Influenza A/Panama/2007/99 (H3N2)]. Similar to Example 10A, Calu-3 cells were exposed to four different dry powder formulations each consisting of 50% leucine, a calcium salt and sodium chloride. Viral infection was assessed by quantifying the amount of viral replication over a 24 h period. The specific powders tested are listed in Table 19 (below) and included carbonate, lactate, sulfate and citrate salts. In an attempt to expose cells to equivalent amounts of calcium of each of the four calcium containing powders, capsules were filled to appropriate fill weights prior to dosing. Cells exposed to no formulation (Air) were used as control cells.

Figure 10:
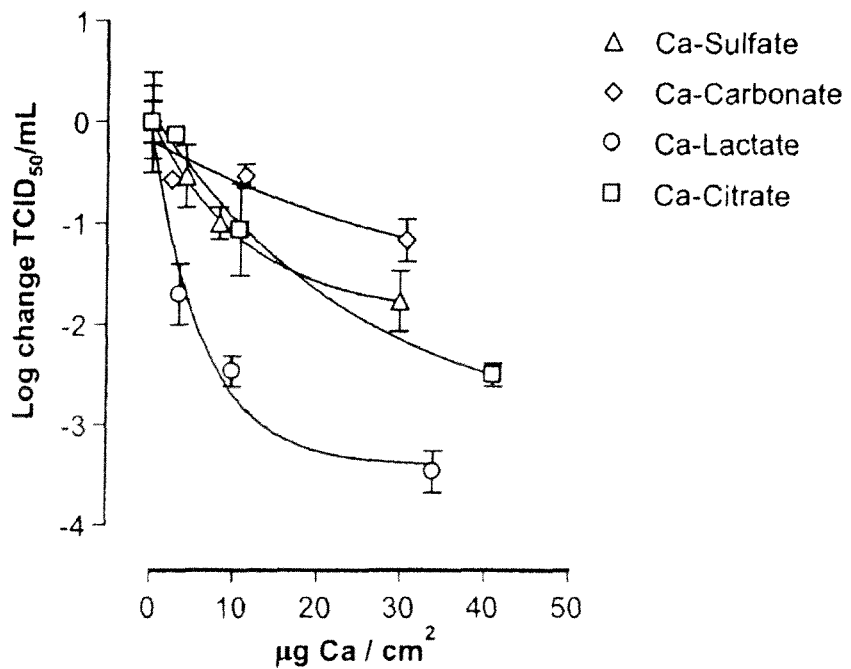
FIG. 10 is a graph that shows the effect of the respirable dry powders prepared for Example 10B on Influenza A/Panama/99/2007 (H3N2) infection in a dose-dependent manner.

As seen in FIG. 10, using this strain, similar efficacy was observed for each powder: calcium lactate was the most efficacious, calcium citrate and calcium sulfate exhibited intermediate efficacy and the calcium carbonate powder was only minimally efficacious. These data support the broad activity of Ca:Na dry powders against multiple influenza strains.

Dry powders, prepared from feedstock formulations 10-1 to 10-4, tested to evaluate their effect on Influenza A/Panama/99/2007 (II3N2) infection in a cell culture model (Table 19). To deliver equivalent amount of $Ca^{2+}$, the desired fill weight was calculated for each dry powder formulation. Qualicap capsules were weighed empty, filled, and after exposure to determine the emitted dose. Triplicate wells were exposed to each capsule and after wells were washed. HPLC analysis of these samples determined the amount of $Ca^{2+}$ delivered to cells.

TABLE 19

| Feedstock Formulation (for Dry Powders) | Desired Fill (mg) | Empty Capsule (mg) | Filled Capsule (mg) | Capsule after Exposure (mg) | Calcium ion concentration determined by HPLC ($\mu g/cm^2 \pm SD)^a$ |
|---|---|---|---|---|---|
| 10-2 (50.0% leucine, 22.0% calcium chloride, 28.0% sodium sulfate) | 53.18<br>13.29<br>4.43 | 61.358<br>60.602<br>65.102 | 121.417<br>76.804<br>70.789 | 62.591<br>62.167<br>65.670 | $40.8 \pm 5.0$<br>$10.5 \pm 2.3$<br>$2.9 \pm 0.6$ |
| 10-1 (50.0% leucine, 37.0% calcium lactate, 13.0% sodium chloride) | 62.17<br>15.54<br>5.18 | 64.037<br>65.358<br>66.046 | 125.465<br>82.474<br>72.455 | 67.043<br>65.632<br>66.324 | $33.8 \pm 3.5$<br>$9.7 \pm 1.4$<br>$3.4 \pm 0.9$ |

TABLE 19-continued

| Feedstock Formulation (for Dry Powders) | Desired Fill (mg) | Empty Capsule (mg) | Filled Capsule (mg) | Capsule after Exposure (mg) | Calcium ion concentration determined by HPLC ($\mu g/cm^2 \pm SD$)[a] |
|---|---|---|---|---|---|
| 10-3 | 60.0 | 62.581 | 108.035 | 63.841 | 29.6 ± 10.1 |
| (50.0% leucine, | 14.99 | 63.393 | 75.770 | 64.085 | 8.1 ± 1.4 |
| 19.5% calcium chloride, 30.5% sodium citrate) | 5.00 | 65.910 | 70.062 | 66.204 | 4.1 ± 0.8 |
| 10-4 | 45.88 | 64.506 | 115.876 | 65.004 | 30.4 ± 11.9 |
| (50.0% leucine, | 13.47 | 64.319 | 77.627 | 65.080 | 11.1 ± 4.3 |
| 25.5% calcium chloride, 24.5% sodium carbonate) | 3.82 | 66.495 | 71.398 | 66.698 | 2.4 ± 1.0 |

As shown in FIG. 10, the dry powders prepared for this Example reduce Influenza A/Panama/99/2007 (H3N2) infection in a dose-dependent manner. Calu-3 cells exposed to no formulation (0 µg $Ca^{2+}/cm^2$) were used as a control and compared to Calu-3 cells exposed to dry powder formulations at different fill weights and therefore different concentrations of calcium. The concentration of calcium delivered to cells in each experiment for each fill weight was determined using HPLC measurements of calcium in washes from empty plates exposed to each condition. The concentration of virus released by cells exposed to each aerosol formulation 24 h after dosing was quantified by $TCID_{50}$ assay. Each data point represents the mean and standard deviation of triplicate wells for each condition.

Example 11

In Vivo Influenza Model

This example demonstrates that dry powder formulations comprised of calcium salts and sodium chloride reduce the severity of influenza infection in ferrets. The formulations tested are shown in Table 20. Control ferrets were exposed to a powder comprised of 100% leucine under the same exposure conditions. In preliminary in vitro studies, this control powder had no effect on viral replication. Calcium powders and control (Formulation I, Formulation II, Formulation III and Leucine control) were aerosolized with a Palas Rotating Brush Generator 1000 solid particle disperser (RBG, Palas GmbH, Karlsruhe, Germany). Ferrets (n=8 per group) were exposed to ~0.2 mg Ca/kg and the severity of infection was evaluated over time. Each formulation was dispersed in a nose-only exposure system 1 hour before infection, 4 hours after infection and then BID for 4 days (d1-4). The study was terminated on day 10. Body temperatures were determined twice a day beginning on day 0 of the study. Ferrets infected with influenza typically show increases in body temperature within 2 days of infection, drop body weight over the course of the study and show clinical signs of infection such as lethargy and sneezing. These changes coincide with an increase in influenza viral titers shed from the nasal cavity and increases in nasal inflammation.

TABLE 20

Formulations tested for efficacy in ferrets

| Formulation | Composition |
|---|---|
| Formulation I | 10.0% leucine, 35.1% calcium chloride, 54.9% sodium citrate (Active with 12.7% calcium ion) |
| Formulation II | 10.0% leucine, 39.6% calcium chloride, 50.4% sodium sulfate (Active with 14.3% calcium ion) |
| Formulation III | 10.0% leucine, 58.6% calcium lactate, 31.4% sodium chloride (Active with 10.8% calcium ion) |

Figure 11A:
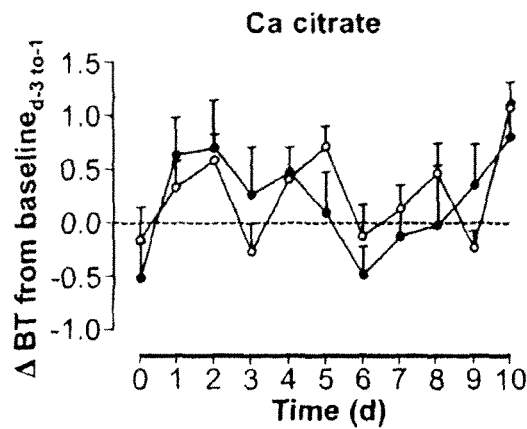
FIGS. 11A-D are graphs showing that dry powder formulations comprised of calcium salts and sodium chloride reduce the severity of influenza in ferrets.
Figure 11B:
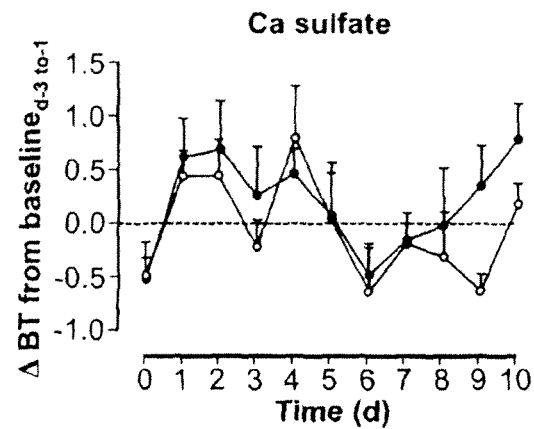
Figure 11C:
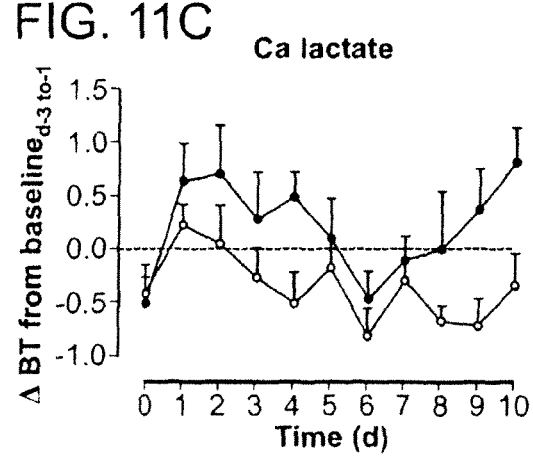
Figure 11D:
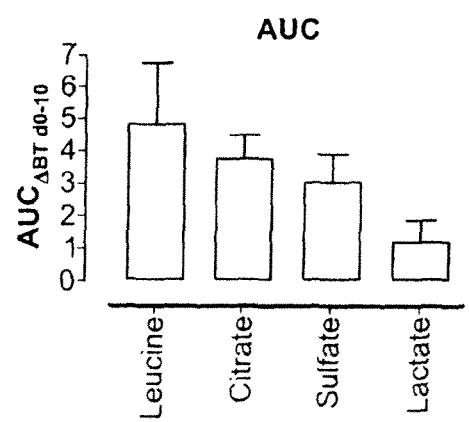

On study day −4, ferrets were implanted with a microchip subcutaneously in the right rear flank and another in the shoulder for redundancy. The transponder chip (IPTT-300 Implantable Programmable Temperature and Identification Transponder; Bio Medic Data Systems, Inc, Seaford, Del. 19973) allows for ferret identification and provides subcutaneous body temperature data throughout the study using a BMDS electronic proximity reader wand (WRS-6007; Biomedic Data Systems Inc, Seaford, Del.). Subcutaneous body temperatures taken on day −3 to −1 were used as baseline temperatures and used to calculate the change from baseline for each animal over the course of the study. Treatment with a dry powder formulation comprised of leucine (excipient), Ca-lactate (Formulation III), and NaCl had a significant impact on body temperature increases (FIG. 11C). The mean body temperature changes in this group remained at or below baseline measurements for the course of the study and the area under the curve (AUC) measurements were approximately 5-fold lower than the control (FIG. 11D). The two other powders tested exhibited less pronounced efficacy that was limited to differences from the control on specific days of the study. In particular, both the Ca citrate and Ca sulfate treated groups had lower body temperatures than the control animals on day 3 of the study (FIGS. 11A and 11B, respectively) and the Ca sulfate group had lower body temperatures over the final three days of the study.

Example 12

This example demonstrates that dry powder formulations comprised of different excipients reduce influenza infection, but at higher doses than formulations comprised of leucine.

To assess the impact of the excipient on efficacy in vitro we tested two dry powder formulations (Table 21) that varied in excipient and compared their efficacy to Formulation III (containing leucine) using the influenza replication model. These formulations contained the same concentration of calcium lactate and sodium chloride and the same weight percentage of excipient (10%).

TABLE 21

Formulations used to evaluate efficacy against multiple influenza viruses and to test different excipients

| Formulation | Feedstock Composition (w/w) | Ca:Na molar ratio | Spray Dryer |
|---|---|---|---|
| I | 10.0% leucine, 35.1% calcium chloride, 54.9% sodium citrate (Active with 12.7% calcium ion) | 1:2 | Niro |
| II | 10.0% leucine, 39.6% calcium chloride, 50.4% sodium sulfate (Active with 14.3% calcium ion) | 1:2 | Niro |

TABLE 21-continued

Formulations used to evaluate efficacy against multiple influenza viruses and to test different excipients

| Formulation | Feedstock Composition (w/w) | Ca:Na molar ratio | Spray Dryer |
|---|---|---|---|
| III | 10.0% leucine, 58.6% calcium lactate, 31.4% sodium chloride (Active with 10.8% calcium ion) | 1:2 | Niro |
| V | 10.0% marmitol, 58.6% calcium lactate, 31.4% sodium chloride (Active with 10.8% calcium ion) | 1:2 | Büchi |
| IV | 10.0% maltodextrin, 58.6% calcium lactate, 31.4% sodium chloride (Active with 10.8% calcium ion) | 1:2 | Büchi |

Figure 12:
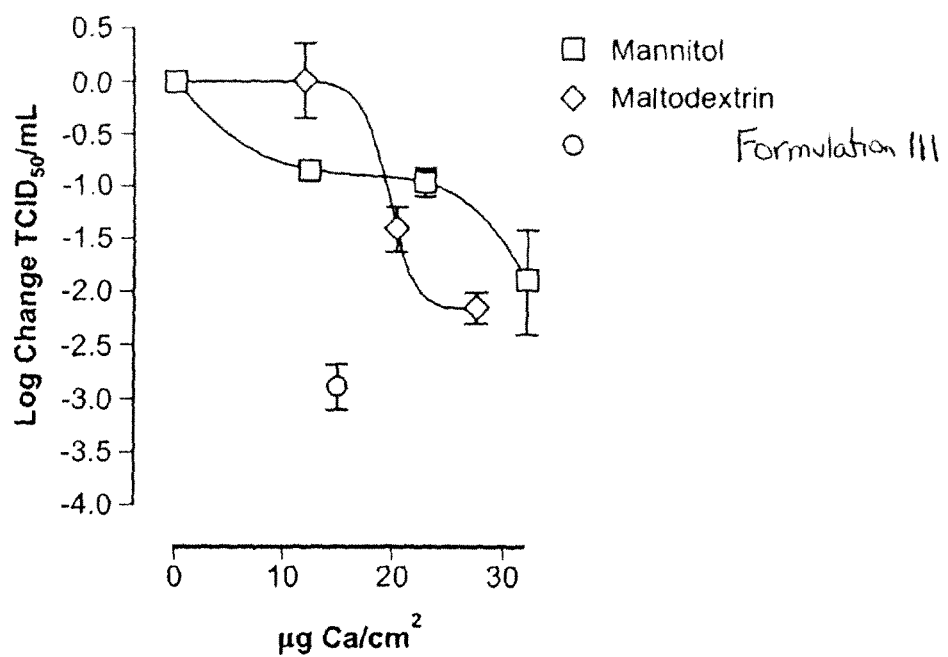
FIG. 12 is a graph showing dry powder formulations consisting of different excipients (mannitol, maltodextrin) with calcium lactate and sodium chloride reduced influenza titer at higher concentrations than the Formulation III powder alone.

Calu-3 cells exposed to no formulation were used as a control and compared to Calu-3 cells exposed to dry powder comprised of calcium lactate and sodium chloride with different excipients. Three different fill weights of the mannitol and maltodextrin powders were used to cover a dose range between 10 to 30 μg Ca2+/cm2. The concentration of virus released by cells exposed to each aerosol formulation was quantified (FIG. 12). Each data point represents the mean and standard deviation of duplicate wells for each concentration. Data were analyzed by one-way ANOVA and Tukey's multiple comparisons post-test. The data for the low dose of each powder is representative of two independent experiments.

Both the mannitol and maltodextrin containing formulations reduced influenza infection in a dose responsive manner, however, they were significantly less potent than the leucine containing powder. At a dose of 14.8 μg $Ca^{2+}/cm^2$, the leucine containing powder reduced influenza infection by 2.9±0.2 $\log_{10}$ $TCID_{50}/mL$, whereas the mannitol powder at a comparable dose (12.2 μg $Ca^{2+}/cm^2$) reduced infection by 0.85±0.0 $\log_{10}$ $TCID_{50}/mL$ and the maltodextrin powder (11.9 μg $Ca^{2+}/cm^2$) had no effect on replication (FIG. 12). Even at higher doses (>27 μg $Ca^{2+}/cm^2$), the maximal reduction for mannitol (1.9±0.50 log 10 $TCID_{50}/mL$) and maltodextrin (2.2±0.14 $\log_{10}$ $TCID_{50}/mL$) was less than that of the leucine powder. Of note, previous testing using powders comprised of 100% leucine found no effect of the excipient alone on viral replication. These data suggest that the nature of the excipient can impact the efficacy of calcium containing formulations.

Example 13

This example demonstrates the efficacy of dry powder formulations comprising calcium salt, calcium lactate, calcium sulfate or calcium citrate powders with respect to treatment of influenza, parainfluenza or rhinovirus.

The Formulation I, Formulation II, and Formulation III powders were produced by spray drying utilizing a Mobile Minor spray dryer (Niro, GEA Process Engineering Inc., Columbia, Md.). All solutions had a solids concentration of 10 g/L and were prepared with the components listed in Table 22. Leucine and calcium salt were dissolved in DI water, and leucine and sodium salt were separately dissolved in DI water with the two solutions maintained in separate vessels. Atomization of the liquid feed was performed using a co-current two-fluid nozzle (Niro, GEA Process Engineering Inc., Columbia, Md.). The liquid feed was fed using gear pumps (Cole-Parmer Instrument Company, Vernon Hills, Ill.) into a static mixer (Charles Ross & Son Company, Hauppauge, N.Y.) immediately before introduction into the two-fluid nozzle. Nitrogen was used as the drying gas and dry compressed air as the atomization gas feed to the two-fluid nozzle. The process gas inlet temperature was 282° C. and outlet temperature was 98° C. with a liquid feedstock rate of 70 mL/min. The gas supplying the two-fluid atomizer was approximately 14.5 kg/hr. The pressure inside the drying chamber was at −2 "WC. Spray dried product was collected in a container from a filter device.

TABLE 22

Formulations used to evaluate efficacy against different respiratory viruses

| Formulation | Feedstock Composition (w/w) | Ca:Na molar ratio | Spray Dryer |
|---|---|---|---|
| I | 10.0% leucine, 35.1% calcium chloride, 54.9% sodium citrate (Active with 12.7% calcium ion) | 1:2 | Niro |
| II | 10.0% leucine, 39.6% calcium chloride, 50.4% sodium sulfate (Active with 14.3% calcium ion) | 1:2 | Niro |
| III | 10.0% leucine, 58.6% calcium lactate, 31.4% sodium chloride (Active with 10.8% calcium ion) | 1:2 | Niro |

A cell culture model of Influenza A/Panama/2007/99, human parainfluenza type 3 (hPIV3) or Rhinovirus (Rv16) infection was used to evaluate the efficacy of dry powder formulations. This model has been described in detail previously (See, Example 10) and utilizes Calu-3 cells grown at air-liquid interface as a model of influenza infection of airway epithelial cells. Calu-3 cells were exposed to dry powders using a dry powder sedimentation chamber. The amount of calcium ion (Ca2+) delivered to each well was determined by HPLC using dry powder recovered from an empty well in the cell culture plate. The concentration of calcium deposited in each study is shown in Table 23.

TABLE 23

Calcium Deposition

| | Formulation I (μg Ca/cm²) | | | Formulation II (μg Ca/cm²) | | | Formulation III (μg Ca/cm²) | | |
|---|---|---|---|---|---|---|---|---|---|
| | Low | Medium | High | Low | Medium | High | Low | Medium | High |
| Influenza | 12.74 | 17.12 | 28.85 | 11.37 | 15.84 | 27.73 | 10.93 | 16.01 | 26.61 |
| Parainfluenza | 10.58 | 16.19 | 25.04 | 12.26 | 15.71 | 25.32 | 11.03 | 16.81 | 26.33 |
| Rhinovirus | 11.63 | 16.25 | 24.11 | 10.86 | 15.01 | 23.89 | 11.49 | 15.22 | 24.69 |

One hour after exposure, cells were infected with 10 μL of Influenza A/Panama/99/2007 at a multiplicity of infection of 0.1-0.01 (0.1-0.01 virions per cell), human parainfluenza type 3 (hPIV3) at a multiplicity of infection of 0.1-0.01 (0.1-0.01 virions per cell), or 10 μL of rhinovirus (Rv16) at a multiplicity of infection of 0.1-0.01 (0.1-0.01 virions per cell). Four hours after dry powder treatment, the apical surfaces were washed to remove excess formulation and unattached virus, and cells were cultured for an additional 20 hours at 37° C. plus 5% $CO_2$. The next day (24 hours after infection) virus released onto the apical surface of infected cells was collected in culture media and the concentration of virus in the apical wash was quantified by $TCID_{50}$ (50% Tissue Culture Infectious Dose) assay. The $TCID_{50}$ assay is a standard endpoint dilution assay that is used to quantify how much of a given virus is present in a sample. For each of the three powders, Calu-3 cells were exposed to three different $Ca^{2+}$ doses and the replication of each virus was assessed.

Influenza

Figure 13A:
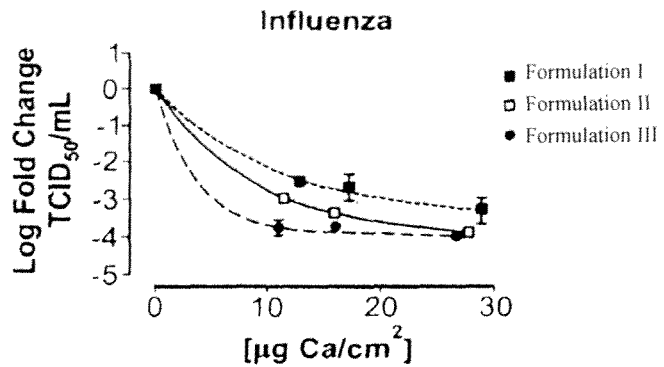
FIGS. 13A-C are graphs showing calcium dry powder formulations vary in efficacy against different viral pathogens. Calu-3 cells exposed to no formulation were used as a control and compared to Calu-3 cells exposed to Formulation I, Formulation II, and Formulation III. The concentration of virus released by cells exposed to each aerosol formulation was quantified. Symbols represent the mean and standard deviation of duplicate wells for each test.

In the influenza model, all three powders significantly reduce viral titer to comparable levels at the highest dose tested: Formulation I, Formulation II, and Formulation III reduced viral titer up to 3.25, 3.80, and 3.95 $\log_{10} TCID_{50}/$ mL, respectively (FIG. 13A). It is important to note that while at the highest dose tested these powders exhibited similar activity against influenza, at lower doses the data suggests the most efficacious powder was Formulation III (comprised of leucine, calcium lactate and sodium chloride). Formulation III reduced viral titers 3.70 and 3.75 log $TCID_{50}$/mL at low and medium doses, whereas low doses of Formulation I and Formulation II reduced viral titer 2.50 and 2.95 $\log_{10} TCID_{50}/$ mL, and mid doses of Formulation I and Formulation II reduced viral titers 2.65 and 3.30 $\log_{10} TCID_{50}$/mL, respectively.

Parainfluenza

Figure 13B:
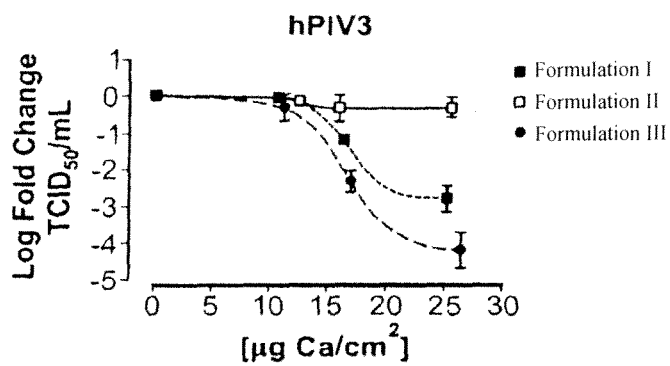

Formulation I, Formulation II, and Formulation III were tested over a similar dose range against parainfluenza. The parainfluenza titer in the Formulation II treated cell cultures was comparable to the control cells (FIG. 13B) at doses of calcium similar to those used in the influenza experiment, indicating that the calcium sulfate based formulation may exhibit activity only against specific pathogens. In contrast, Formulation I and Formulation III treatment resulted in a dose dependent reduction in parainfluenza infection. At high doses, Formulation I and Formulation III reduced infection by 2.70 and 4.10 $\log_{10} TCID_{50}$/mL, respectively, compared to the control cells. Similarly, Formulation III exhibited greater efficacy than Formulation I at the middle dose tested, however, neither formulation reduced infection at the lowest dose tested (FIG. 13B; Table 25). Collectively, these data demonstrate that calcium based dry powder formulations effectively reduce the infectivity of parainfluenza. These effects are specific to certain calcium salts and the efficacious dose ranges differ significantly from that observed for influenza.

Rhinovirus

Figure 13C:
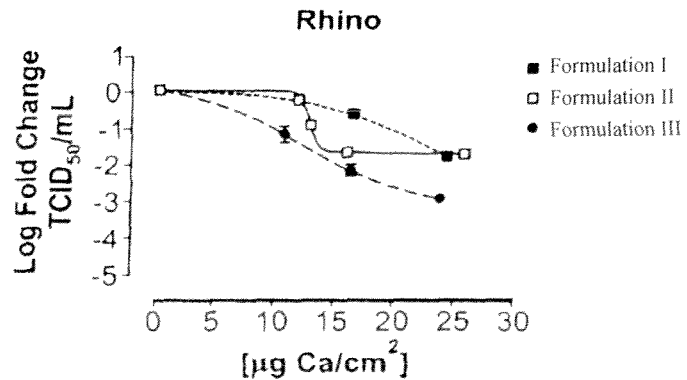

Influenza and parainfluenza are enveloped viruses. To test the broad spectrum activity of calcium dry powder formulations and extend these findings to nonenveloped viruses, the same powders were tested against rhinovirus. All three formulations reduced rhinovirus to some extent, with the Formulation III powder demonstrating the greatest activity (FIG. 13C). Formulation III treatment resulted in a significant, 2.80 $\log_{10} TCID_{50}$/mL viral reduction at the highest dose tested. Low and medium doses of this powder reduced titer 1.15 and 2.10 $\log_{10} TCID_{50}$/mL, respectively, compared to control cells. Formulation I and Formulation II treatment also reduced rhinovirus infection, albiet to a lesser extent than Formulation III. At the highest dose tested, Formulation I reduced infection by 1.70 $\log_{10} TCID_{50}$/mL and Formulation II reduced infection 1.60 $\log_{10} TCID_{50}$/mL. Together these results indicate that calcium based dry powder formulations can be broadly applied to diverse viral infections.

The above data suggests that by increasing the delivered dose of calcium dry powder formulations exhibit more activity than was previously observed at lower doses. Influenza infection was reduced by all three powders tested, although the calcium lactate based formulation (Formulation III) exhibited greater potency than the calcium sulfate (Formulation II) and calcium citrate (Formulation I) formulations. Additionally, across all three viral strains, Formulation III treatment resulted in the greatest reduction in viral titer. At higher doses Formulation I effectively reduced viral titer in all three viral strains, but the effect was much more pronounced with influenza and parainfluenza, suggesting a difference in mechanism that may be related to viral strain specificity. Formulation II treatment was active against parainfluenza, but exhibited better activity against both influenza and rhinovirus, suggesting that the specific calcium counterions may have some role in the optimal activity of the formulation.

Example 14

Calcium Lactate, Sodium Chloride, Maltodextrin Dry Powder

This example describes the preparation of dry powders using feedstock of Formulation IV: 10.0 weight percent maltodextrin, 58.6 weight percent calcium lactate and 31.4 weight percent sodium chloride.

An aqueous phase was prepared for a batch process by dissolving maltodextrin in ultrapure water, then calcium lactate pentahydrate, and finally sodium chloride. The solution was kept agitated throughout the process until the materials were completely dissolved in the water at room temperature. For the maltodextrin and calcium lactate formulation, three batches (A, B & C) of feedstock were prepared and spray dried. Details on the liquid feedstock preparations for each of the three hatches are shown in Table 24, where the total solids concentration is reported as the total of the dissolved anhydrous material weights. The solutions or suspensions were then spray dried using a BUN spray dryer. For each formulation, three batches (A, B & C) of feedstock were prepared and spray dried. Batch A, B and C particles were prepared using the corresponding feedstocks on a Büchi Mini spray dryer with process conditions similar to those used to spray dry for Formulations I-B and I-C in Example 1, with the exception of the following process conditions. The liquid feedstock flow rate was set at 5.2 mL/min for Formulation IV-A and Formulation IV-B and 5.6 mL/min for Formulation IV-C. The outlet temperature was about 90° C. to 98° C. for Formulation IV-A, about 100° C. to for Formulation IV-B and about 100° C. 106° C. for Formulation IV-C.

TABLE 24

Summary of liquid feedstock preparations of three batches of particles for Formulation IV.

| Formulation: | IV-A | IV-B | IV-C |
|---|---|---|---|
| Liquid feedstock mixing | Batch mixed | Batch mixed | Batch mixed |
| Total solids concentration | 5 g/L | 5 g/L | 5 g/L |
| Total solids | 5 g | 5 g | 20 g |
| Total volume water | 1.0 L | 1.0 L | 4.0 L |
| Amount leucine in 1 L | 0.5 g | 0.5 g | 0.5 g |
| Amount sodium chloride in 1 L | 1.55 g | 1.55 g | 1.55 g |

TABLE 24-continued

Summary of liquid feedstock preparations of three
batches of particles for Formulation IV.

| Formulation: | IV-A | IV-B | IV-C |
|---|---|---|---|
| Amount calcium lactate pentahydrate in 1 L | 4.13 g | 4.13 g | 4.13 g |

Figure 14:
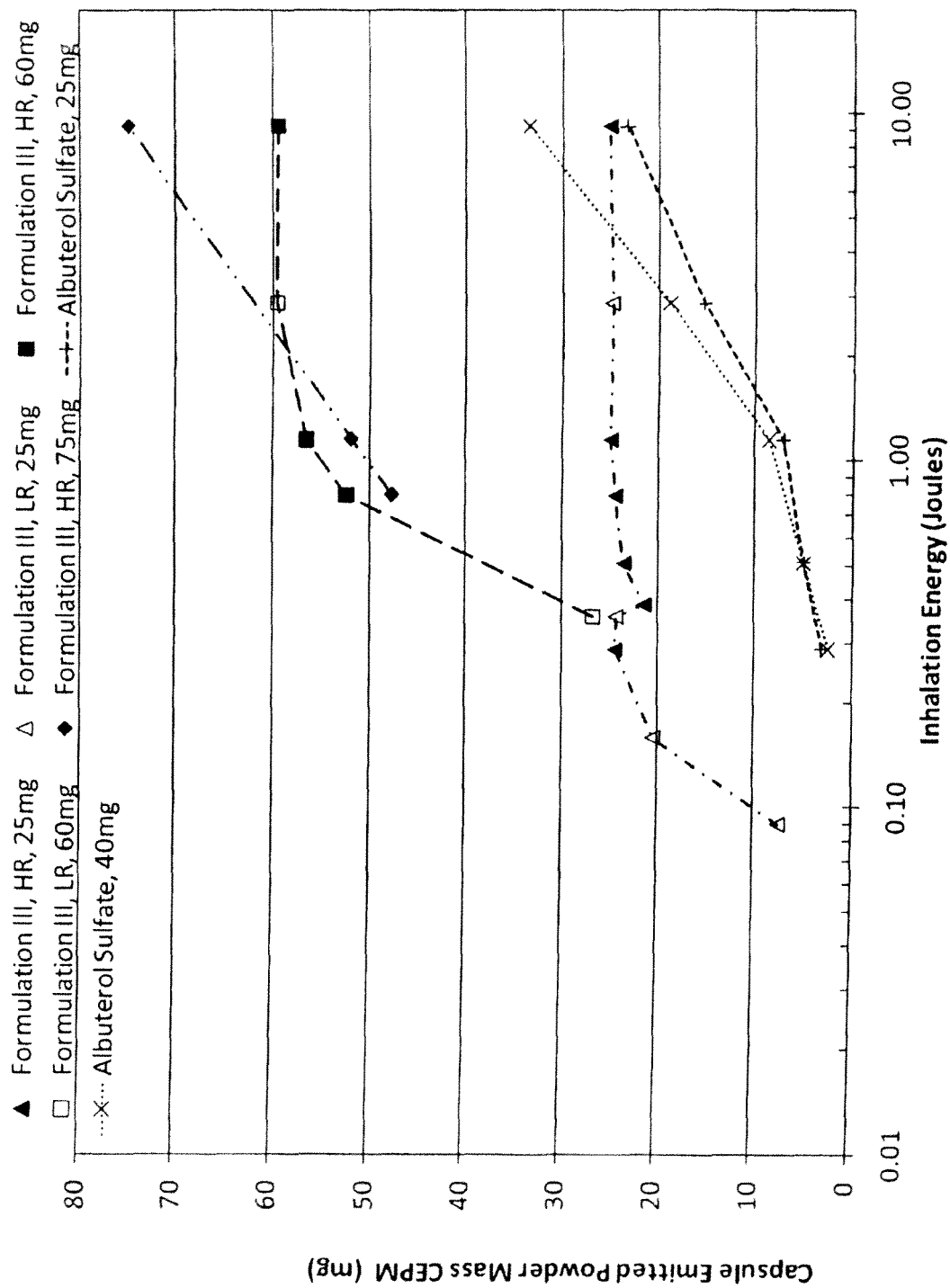
FIG. 14 is a graph showing the emitted dose of Formulation III powder at three different capsule fill weights (25 mg, 60 mg, 75 mg) at varying inhalation energies.
Figure 15:
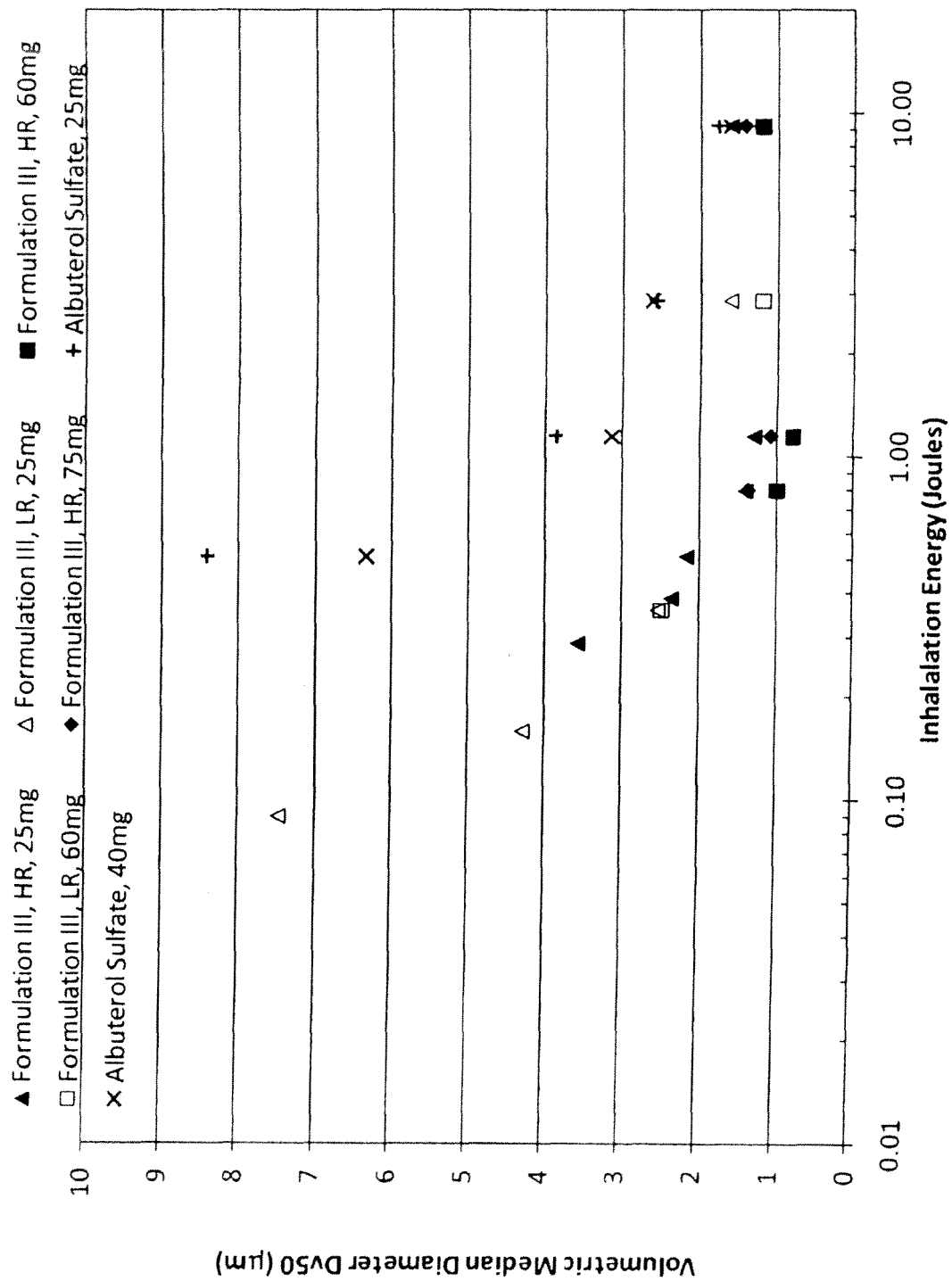
FIG. 15 is a graph showing the particle size distribution of calcium lactate (Formulation III) powders emitted from different inhalers, characterized by the volume median diameter (Dv50) and plotted against the inhalation energy applied. Consistent values of Dv50 at decreasing energy values indicate that the powder is well dispersed since additional energy does not result in additional deagglomeration of the emitted powder.

Some of the physical properties of the particles obtained in three separate batches (Formulation IV-A, IV-B, and IV-C) are summarized in Table 25. In addition to the data provided in Table 25, further data about the dry particles prepared by feedstock formulation IV-A is summarized as follows. The fine particle fraction (FPF) as measured by a collapsed 2-stage Andersen Cascade Impactor with gravimetric analysis was on average 71.3% for FPF less than 5.6 microns and 47.5% for FPF less than 3.4 microns. The volume size was determined by laser diffraction on the HELOS/RODOS sizing equipment and the average value for the volume median diameter (×50) at a pressure of 1 bar was 1.40 microns. In addition, the powder displayed flowrate independent behavior as can be seen from the ratio of ×50 measured at 0.5 bar to ×50 measured at 4.0 bar, which was 1.04. The value for 1/4 bar for these particles was 1.00, demonstrating the that particles were highly dispersable.

TABLE 25

| Summary of ACI-2 data for the three batches of particles for Formulation IV. | | | |
|---|---|---|---|
| Formulation: | IV-A | IV-B | IV-C |
| FPF less than 5.6 μm on ACI-2 (%) | 71.3 | 66.6 | 68.2 |
| FPF less than 3.4 μm on ACI-2 (%) | 47.5 | 44.8 | 48.7 |

Additional information relating to properties of the Formulation IV powder and/or particles prepared in this example are provided in the Tables or graphs shown in FIGS. 1A-1F

Example 15

Dispersibility

This example demonstrates the dispersibility of dry powder formulations comprising calcium lactate, calcium sulfate or calcium citrate powders when delivered from different dry powder inhalers over a range of inhalation maneuvers and relative to a traditional micronized drug product similarly dispersed.

The dispersibility of various powder formulations was investigated by measuring the geometric particle size and the percentage of powder emitted from capsules when inhaling on dry powder inhalers with flow rates representative of patient use. The particle size distribution and weight change of the filled capsules were measured for multiple powder formulations as a function of flow rate, inhaled volume and fill weight in 2 passive dry powder inhalers.

Powder formulations were filled into size 3 HPMC capsules (Capsugel V-Caps) by hand with the fill weight measured gravimetrically using an analytical balance (Mettler Toledo XS205). Fill weights of 25 and 35 mg were filled for Formulation I (lot #26-190-F), 25, 60 and 75 mg for Formulation III (Lot#69-191-1), 25 and 40 mg for Formulation II (Lot #65-009-F), 10 mg for a spray dried leucine powder (lot#65-017-F) and 25 mg of micronized albuterol sulfate (Cirrus lot#073-001-02-039A). Two capsule based passive dry powder inhalers (RS-01 Model 7, Low resistance Plastiape S.p.A. and RS-01 Model 7, High resistance Plastiape S.p.A.) were used which had specific resistances of 0.020 and 0.036 kPa1/2/LPM which span the typical range of dry powder inhaler resistance. Flow rate and inhaled volume were set using a timer controlled solenoid valve with flow control valve (TPK2000, Copley Scientific). Capsules were placed in the appropriate dry powder inhaler, punctured and the inhaler sealed to the inlet of the laser diffraction particle sizer (Spraytec, Malvern). The steady air flow rate through the system was initiated using the TPK2000 and the particle size distribution was measured via the Spraytec at 1 kHz for the durations at least 2 seconds and up to the total inhalation duration. Particle size distribution parameters calculated included the volume median diameter (Dv50) and the geometric standard deviation (GSD) and the fine particle fraction (FPF) of particles less than 5 micrometers in diameter. At the completion of the inhalation duration, the dry powder inhaler was opened, the capsule removed and re-weighed to calculate the mass of powder that had been emitted from the capsule during the inhalation duration. At each testing condition, 5 replicate capsules were measured and the results of Dv50, FPF and capsule emitted powder mass (CEPM) were averaged.

In order to relate the dispersion of powder at different flow rates, volumes, and from inhalers of different resistances, the energy required to perform the inhalation maneuver was calculated and the particle size and dose emission data plotted against the inhalation energy. Inhalation energy was calculated as $E=R^2Q^2V$ where E is the inhalation energy in Joules, R is the inhaler resistance in $kPa^{12}$/LPM, Q is the steady flow rate in L/min and V is the inhaled air volume in L.

FIG. 14 shows the dose emitted from a capsule for Formulation III powder at 3 different capsule fill weights, using both the high resistance and low resistance RS-01 dry powder inhalers. At each fill weight, steady inhalations ranged from a maximum energy condition of 9.2 Joules which was equivalent to a flow rate of 60 L/min through the high resistance inhaler (R=0.036 $kPa^{1/2}$/LPM) with a total volume of 2 L down to lower energies with reduced volumes down to 1 L, reduced flow rates down to 15 L/min and inhaler resistance down to R=0.020 $kPa^{12}$/LPM. As can be seen from FIG. 14, the entire mass of powder filled into the capsule empties out of the capsule in a single inhalation for all 3 fill weights of 25, 60 and 75 mg of Formulation III at the highest energy condition tested. For the 25 mg fill weight, greater than 80% of the fill weight empties on average for all inhalation conditions down to 0.16 Joules. At 60 mg, the capsule dose emission drops below 80% of the fill weight at 0.36 Joules. At a capsule fill weight of 75 mg, the capsule dose emission drops below 80% of the fill weight at 1.2 Joules.

Also shown in FIG. 14 are 2 fill weights of 25 mg and 40 mg of a micronized albuterol sulfate drug formulation which was jet milled to an average particle size of 1.8 micrometers, hand filled into size 3 capsules and dispersed in the high resistance RS-01 inhaler. As can be seen for both the 25 and 40 mg fill weights, at an inhalation energy of 9.2 Joules (steady inhalation of 60 L/min for 2 L) the average CEPM is above 80% of the capsule fill weight (93% for the 25 mg fill weight and 84% for the 40 mg fill weight). However, at all measured lower energies, the CEPM drops to below 10 mg (<30% of capsule fill weight) for both fill weights and monotonically decreases with decreases in inhalation energy.

FIG. 15 shows the particle size distribution of the Formulation III powders that are emitted from the inhalers characterized by the volume median diameter (Dv50) and plotted against the inhalation energy applied. Consistent values of Dv50 at decreasing energy values indicate that the powder is well dispersed since additional energy does not result in additional deagglomeration of the emitted powder. The Dv50 values are consistent for all three fill weights of 75, 60 and 25 mg at all high energy values, with the Dv50 remaining below 2 micrometers down to 0.51 Joules for all 3 fill weights (FIG. 15). Taking into account that at the 60 and 75 mg fill weights, inhalations in the 0.5 to 1.2 Joule range did not fully emit the powder from the capsule (FIG. 14), it is clear that the powder which was emitted was still fully dispersed by the DPI (FIG. 15). In this range, the Dv50 is not significantly increased in size, which would be expected if the emitting powder contained a lot of agglomerates and was not well dispersed.

Also shown in the FIG. 15 are fill weights of 25 mg (x) and 40 mg (+) of a micronized albuterol sulfate drug formulation which was jet milled to an average particle size of 1.8 micrometers, hand filled into size 3 capsules and dispersed in the high resistance RS-01 inhaler. As can be seen for both the 25 and 40 mg fill weights, at an inhalation energy of 9.2 Joules (steady inhalation of 60 L/min for 2 L) the average Dv50 is below 2 micrometers (1.8 and 1.6 μm respectively) for both fill weights, demonstrating good dispersion and relatively few agglomerates. However, at all measured lower energies, the Dv50 increases to greater than 2 micrometers (3.9 and 3.1 μm respectively) and continues to monotonically increase with decreasing inhalation energy, demonstrating agglomeration and poor dispersion of the primary particles.

Additional powders were tested at all of the test conditions and average CEPM and Dv50 were determined (Table 26) These results demonstrate the ability of the powder formulations to be fully emptied and deagglomerated at inhalation energies down to approximately 0.5 Joules.

TABLE 26

Mean CEPM, Dv(50) and FPF as a function of fill weight, flowrate and duration for Formulations I to III, placebo, and micronized albuterol sulfate.

| Powder | DPI | Fill Weight (mg) | Flow Rate (LPM) | Duraton (s) | Inhalation Energy, $E = R^2Q^2V$ (Joules) | Mean CEPM (mg) | Mean Dv(50) (μm) | Mean FPF, % <5 μm |
|---|---|---|---|---|---|---|---|---|
| Formulation I | RS.01.HR | 25 | 15 | 4 | 0.29 | 15.84 | 4.77 | 52.09 |
| Formulation I | RS.01.HR | 25 | 20 | 3 | 0.51 | 22.88 | 3.46 | 65.79 |
| Formulation I | RS.01.HR | 25 | 30 | 2 | 1.15 | 24.75 | 2.94 | 72.88 |
| Formulation I | RS.01.HR | 25 | 60 | 2 | 9.18 | 24.72 | 2.93 | 73.39 |
| Formulation I | RS.01.LR | 25 | 15 | 4 | 0.09 | 4.30 | 7.29 | 31.97 |
| Formulation I | RS.01.LR | 25 | 20 | 3 | 0.16 | 8.05 | 5.10 | 48.98 |
| Formulation I | RS.01.LR | 25 | 30 | 2 | 0.36 | 19.94 | 3.28 | 71.09 |
| Formulation I | RS.01.LR | 25 | 60 | 2 | 2.85 | 24.75 | 2.51 | 80.26 |
| Formulation I | RS.01.HR | 35 | 30 | 2 | 1.15 | 33.77 | 2.17 | 83.17 |
| Formulation I | RS.01.HR | 35 | 60 | 2 | 9.18 | 34.73 | 2.33 | 81.42 |
| Formulation I | RS.01.LR | 35 | 30 | 2 | 0.36 | 13.07 | 3.16 | 73.22 |
| Formulation I | RS.01.LR | 35 | 60 | 2 | 2.85 | 34.57 | 2.34 | 83.15 |
| Placebo | RS.01.HR | 10 | 15 | 4 | 0.29 | 3.87 | 25.71 | 6.22 |
| Placebo | RS.01.HR | 10 | 20 | 3 | 0.51 | 8.79 | 22.80 | 8.64 |
| Placebo | RS.01.HR | 10 | 30 | 2 | 1.15 | 9.42 | 22.95 | 11.83 |
| Placebo | RS.01.HR | 10 | 60 | 2 | 9.18 | 9.78 | 21.45 | 12.52 |
| Placebo | RS.01.LR | 10 | 15 | 4 | 0.09 | 1.87 | 40.36 | 3.17 |
| Placebo | RS.01.LR | 10 | 20 | 3 | 0.16 | 3.08 | 28.16 | 5.20 |
| Placebo | RS.01.LR | 10 | 30 | 2 | 0.36 | 7.01 | 18.62 | 9.39 |
| Placebo | RS.01.LR | 10 | 60 | 2 | 2.85 | 9.82 | 15.26 | 16.41 |
| Formulation III | RS.01.HR | 25 | 15 | 4 | 0.29 | 24.87 | 3.26 | 68.77 |
| Formulation III | RS.01.HR | 25 | 20 | 3 | 0.51 | 25.48 | 3.06 | 72.61 |
| Formulation III | RS.01.HR | 25 | 30 | 2 | 1.15 | 25.05 | 2.90 | 74.06 |
| Formulation III | RS.01.HR | 25 | 60 | 2 | 9.18 | 25.28 | 2.92 | 71.87 |
| Formulation III | RS.01.LR | 25 | 15 | 4 | 0.09 | 18.97 | 5.59 | 43.81 |
| Formulation III | RS.01.LR | 25 | 20 | 3 | 0.16 | 24.95 | 3.45 | 68.14 |
| Formulation III | RS.01.LR | 25 | 30 | 2 | 0.36 | 25.08 | 2.72 | 76.82 |
| Formulation III | RS.01.LR | 25 | 60 | 2 | 2.85 | 24.88 | 2.66 | 75.76 |
| Formulation III | RS.01.HR | 40 | 30 | 2 | 1.15 | 39.55 | 2.76 | 74.92 |

TABLE 26-continued

Mean CEPM, Dv(50) and FPF as a function of fill weight, flowrate and duration for Formulations I to III, placebo, and micronized albuterol sulfate.

| Powder | DPI | Fill Weight (mg) | Flow Rate (LPM) | Duraton (s) | Inhalation Energy, $E = R^2Q^2V$ (Joules) | Mean CEPM (mg) | Mean Dv(50) (μm) | Mean FPF, % <5 μm |
|---|---|---|---|---|---|---|---|---|
| Formulation III | RS.01.HR | 40 | 60 | 2 | 9.18 | 40.13 | 3.14 | 67.35 |
| Formulation III | RS.01.LR | 40 | 30 | 2 | 0.36 | 39.74 | 2.89 | 75.51 |
| Formulation III | RS.01.LR | 40 | 60 | 2 | 2.85 | 39.85 | 2.65 | 77.00 |
| Formulation II | RS.01.HR | 25 | 15 | 4 | 0.29 | 24.45 | 3.56 | 63.96 |
| Formulation II | RS.01.HR | 25 | 17.5 | 3.4 | 0.39 | 21.43 | 2.34 | 80.07 |
| Formulation II | RS.01.HR | 25 | 20 | 3 | 0.51 | 23.55 | 2.15 | 82.08 |
| Formulation II | RS.01.HR | 25 | 25 | 2.4 | 0.80 | 24.42 | 1.39 | 90.70 |
| Formulation II | RS.01.HR | 25 | 30 | 2 | 1.15 | 24.88 | 1.28 | 88.29 |
| Formulation II | RS.01.HR | 25 | 60 | 2 | 9.18 | 25.07 | 1.59 | 85.28 |
| Formulation II | RS.01.LR | 25 | 15 | 4 | 0.09 | 7.47 | 7.46 | 32.20 |
| Formulation II | RS.01.LR | 25 | 20 | 3 | 0.16 | 20.39 | 4.29 | 57.09 |
| Formulation II | RS.01.LR | 25 | 30 | 2 | 0.36 | 24.23 | 2.52 | 78.85 |
| Formulation II | RS.01.LR | 25 | 60 | 2 | 2.85 | 24.81 | 1.61 | 89.78 |
| Formulation II | RS.01.HR | 60 | 25 | 2.4 | 0.80 | 52.42 | 0.99 | 90.45 |
| Formulation II | RS.01.HR | 60 | 30 | 2 | 1.15 | 56.50 | 0.78 | 92.70 |
| Formulation II | RS.01.HR | 60 | 60 | 2 | 9.18 | 59.42 | 1.19 | 90.64 |
| Formulation II | RS.01.LR | 60 | 30 | 2 | 0.36 | 26.62 | 2.48 | 80.08 |
| Formulation II | RS.01.LR | 60 | 60 | 2 | 2.85 | 59.51 | 1.19 | 90.64 |
| Formulation II | RS.01.HR | 75 | 25 | 2.4 | 0.80 | 47.63 | 1.36 | 89.83 |
| Formulation II | RS.01.HR | 75 | 30 | 2 | 1.15 | 51.84 | 1.07 | 92.59 |
| Formulation II | RS.01.HR | 75 | 60 | 2 | 9.18 | 74.90 | 1.41 | 85.20 |
| Micronized Albuterol | RS.01.HR | 25 | 15 | 4 | 0.29 | 3.12 | 16.76 | 13.00 |
| Micronized Albuterol | RS.01.HR | 25 | 20 | 3 | 0.51 | 5.00 | 8.40 | 32.10 |
| Micronized Albuterol | RS.01.HR | 25 | 30 | 2 | 1.15 | 7.08 | 3.86 | 59.44 |
| Micronized Albuterol | RS.01.LR | 25 | 60 | 2 | 2.85 | 15.28 | 2.57 | 75.01 |
| Micronized Albuterol | RS.01.HR | 25 | 60 | 2 | 9.18 | 23.18 | 1.77 | 81.65 |
| Micronized Albuterol | RS.01.HR | 40 | 15 | 4 | 0.29 | 2.43 | 17.63 | 10.73 |
| Micronized Albuterol | RS.01.HR | 40 | 20 | 3 | 0.51 | 4.97 | 6.34 | 42.24 |
| Micronized Albuterol | RS.01.HR | 40 | 30 | 2 | 1.15 | 8.55 | 3.13 | 67.18 |
| Micronized Albuterol | RS.01.LR | 40 | 60 | 2 | 2.85 | 18.88 | 2.62 | 73.98 |
| Micronized Albuterol | RS.01.HR | 40 | 60 | 2 | 9.18 | 33.40 | 1.60 | 84.30 |

Example 16

Solid State Particle Analysis

A. X-Ray Powder Diffraction

Formulations I, II, III and IV were analyzed for amorphous/crystalline content and polymorphic form using high resolution X-ray powder diffraction (XRPD) and differential scanning calorimetry (DSC). For XRPD, phase identification was performed to identify any crystalline phases observed in each XRPD pattern. XRPD patterns were collected using a PANalytical X'Pert Pro diffractometer (Almelo, The Netherlands). The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop was used, along with helium purge in some cases, to minimize the background generated by air scattering. Soller slits were used for the incident and diffracted beams to minimize axial divergence. Diffraction patterns were collected using a scanning position-sensitive detector (X'Celerator) located 240 mm from the specimen. The data-acquisition parameters of each diffraction pattern are displayed above the image of each pattern in appendix C. Prior to the analysis a silicon specimen (NIST standard reference material 640c) was analyzed to verify the position of the silicon 111 peak. Calculated patterns for the potential crystalline components (including anhydrous and hydrated forms) were produced from either the Cambridge Structural Database or the International Center for Diffraction Data (ICDD) Database and compared to the experimental patterns. The crystalline components were qualitatively determined. XRPD was also performed on powders that had been conditioned at 75% RH for a period of three to four hours in a Dynamic Vapor Sorption system in order to assess the propensity for recrystallization of said powders upon short-term exposure to elevated humidities.

Differential scanning calorimetry (DSC) was performed using a TA Instruments differential scanning calorimeter Q2000 (New Castle, Del.). The sample was placed into an aluminum DSC pan, and the weight accurately recorded. The data acquisition and processing parameters are displayed on each thermogram. Indium metal was used as the calibration standard. The glass transition temperature ($T_g$) is reported from the inflection point of the transition/or/the half-height of the transition. Standard mode DSC experiments were initially conducted on the powders of interest in order to assess the overall thermal behavior of the powders. Cyclic mode DSC experiments were also performed in order to attempt to identify the occurrence of glass transitions occurring in these powders over temperature regions of interest identified in the standard DSC thermograms.

Figure 16:
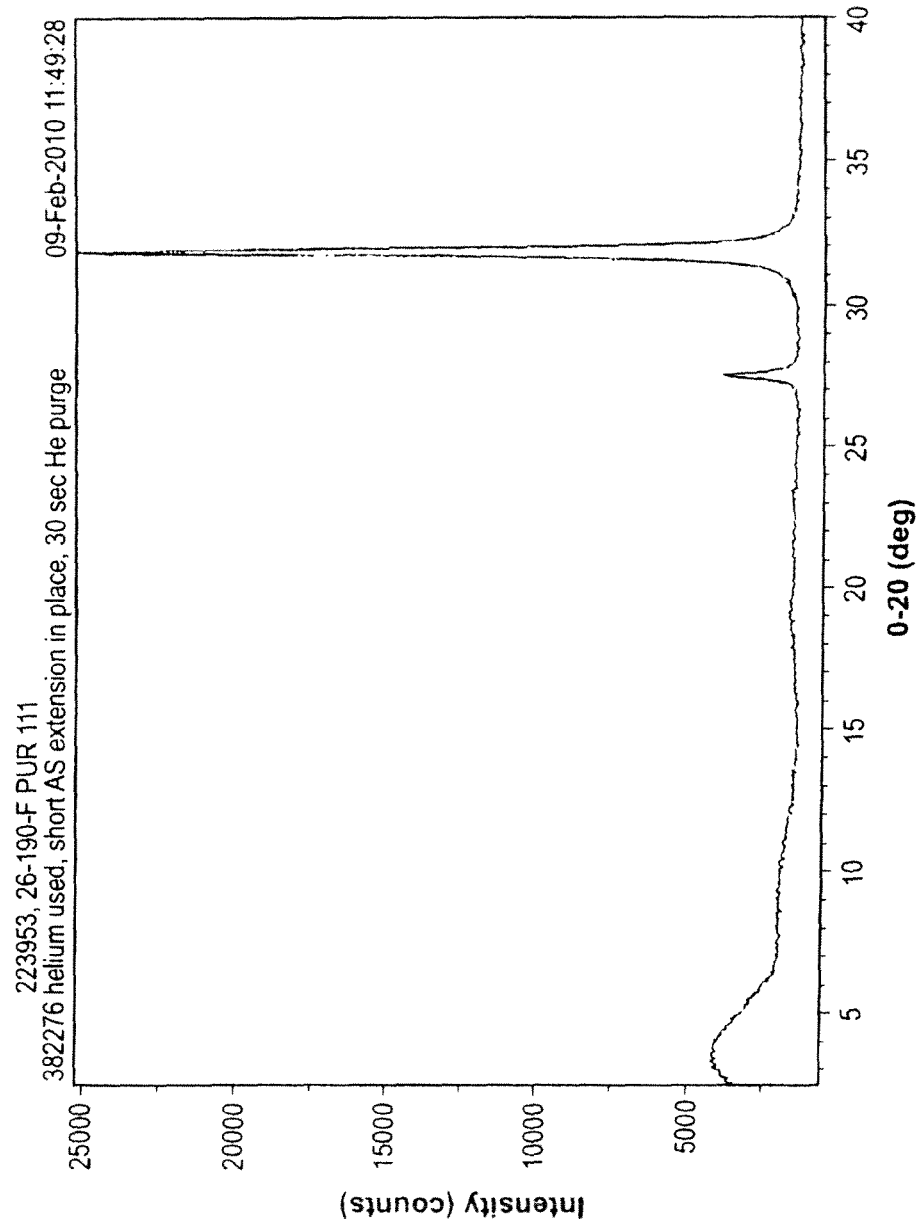
FIG. 16 shows a high resolution XRPD pattern of Formulation I powder. This pattern shows that Formulation I powder consists of a combination of crystalline sodium chloride and a poorly crystalline or amorphous calcium citrate and potentially calcium chloride-rich phase.
Figure 17:
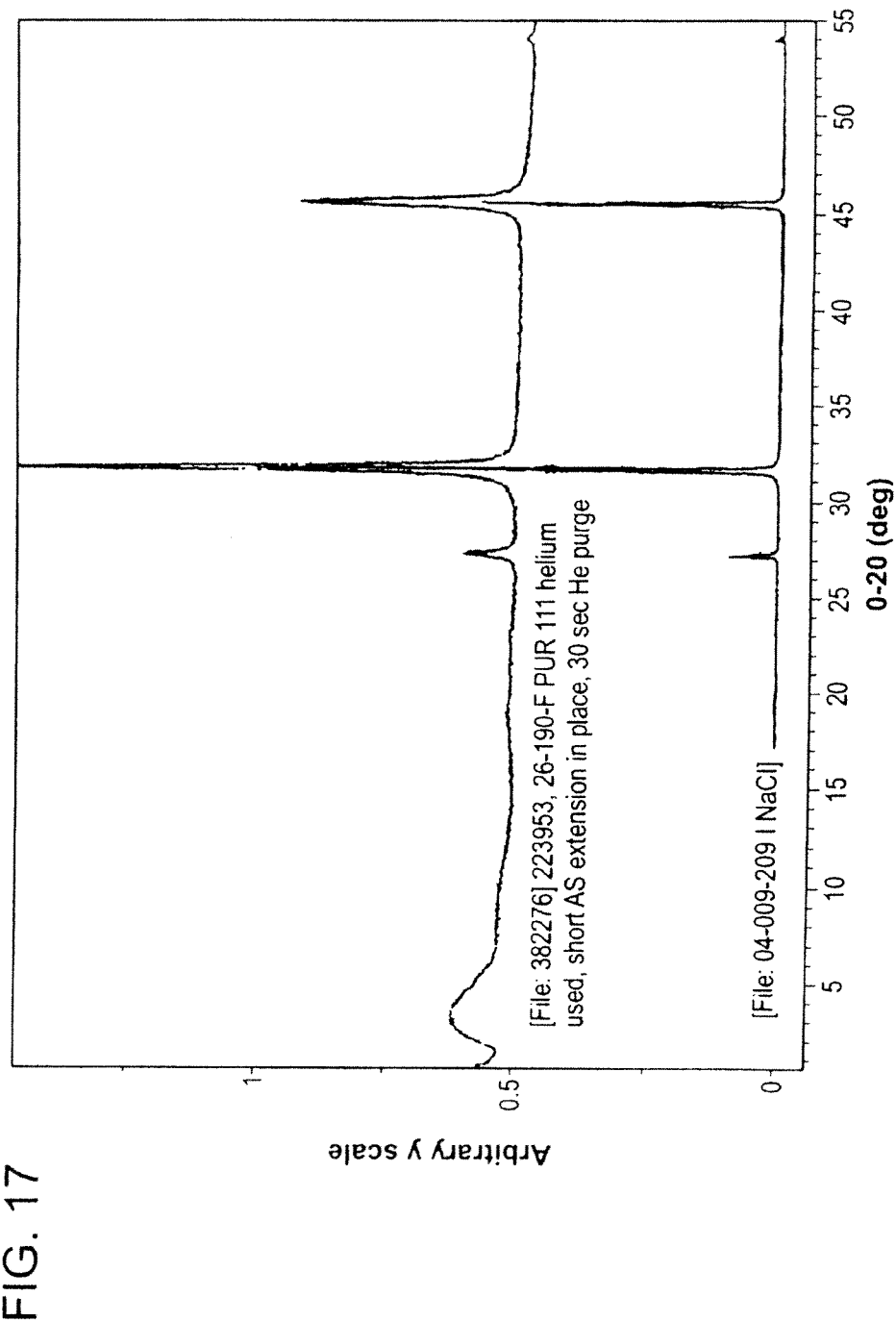
FIG. 17 shows a comparison of XRPD patterns for Formulation I powder with crystalline reflections from NaCl.
Figure 18:
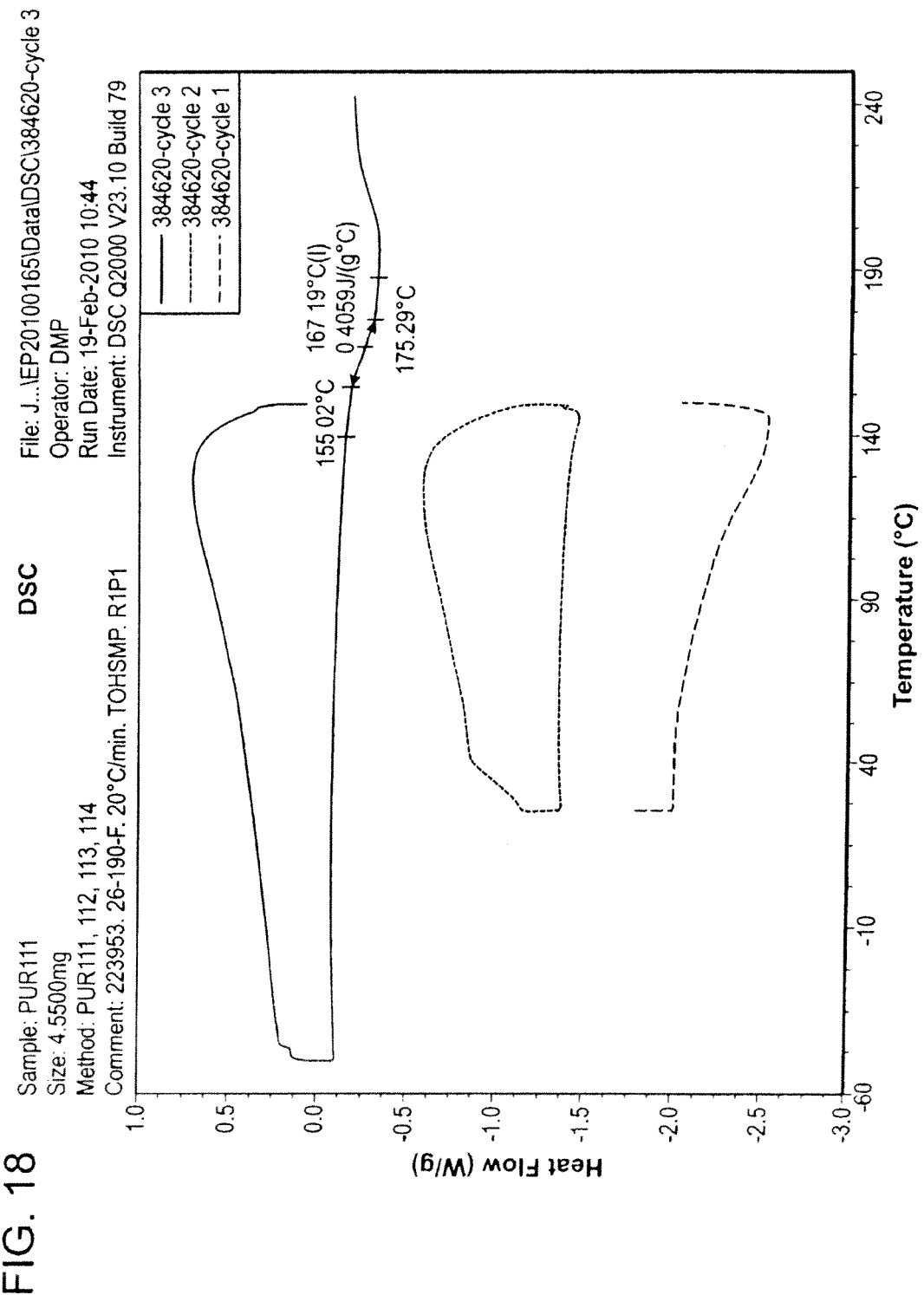
FIG. 18 shows an overlay of temperature cycling DSC thermogram of Formulation I. A glass transition temperature of approximately 167° C. was observed via cyclic DSC for the amorphous calcium-rich phase.

Surprisingly, high calcium and sodium salt content powders were produced that possessed a mixture of amorphous and crystalline content that possessed optimized properties with respect to their dispersibility and stability in the dry state and their dissolution and water absorption properties in the hydrated state. As shown in FIGS. 16 and 17, the Formulation I powder was observed via XRPD to consist of a combination of crystalline sodium chloride and a poorly crystalline or amorphous calcium citrate and potentially calcium chloride-rich phase (as evidenced by a lack of observance of any characteristic peaks for any calcium salt forms in this powder as well as the absence of any characteristic peaks for leucine). As shown in FIG. 18, a glass transition temperature of approximately 167° C. was observed via cyclic DSC for the amorphous calcium-rich phase, indicating that this amorphous phase should be relatively stable to crystalline conversion at standard conditions (25° C., 30% RH). The presence of crystalline sodium chloride in this powder in the dry state may enhance the dispersibility and stability of said powder. The presence of the calcium salt in a poorly crystalline or amorphous form in the Formulation I powder may also facilitate the rapid water uptake and dissolution properties of the Formulation I formulation upon deposition in the lungs (i.e., crystalline sodium chloride is readily soluble, whereas calcium citrate is poorly soluble). When a particle or powder is readily soluble, it dissolves rapidly. When a particle or powder is poorly soluble, it dissolves slowly.

Figure 19:
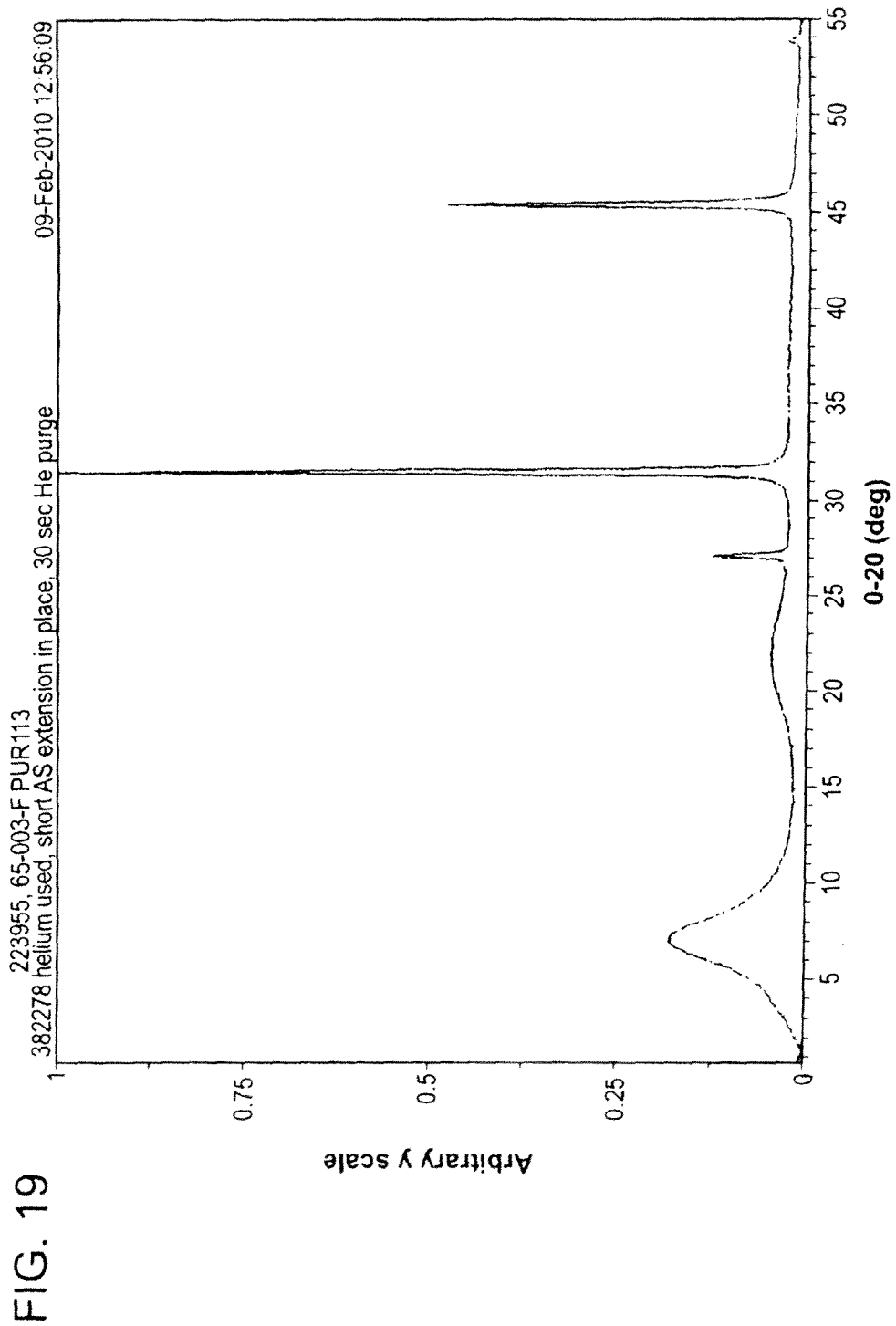
FIG. 19 shows a high resolution XRPD pattern of Formulation II powder. This pattern shows that Formulation III powder consists of a combination of crystalline sodium chloride and a poorly crystalline or amorphous calcium lactate and potentially calcium chloride-rich phase.
Figure 20:
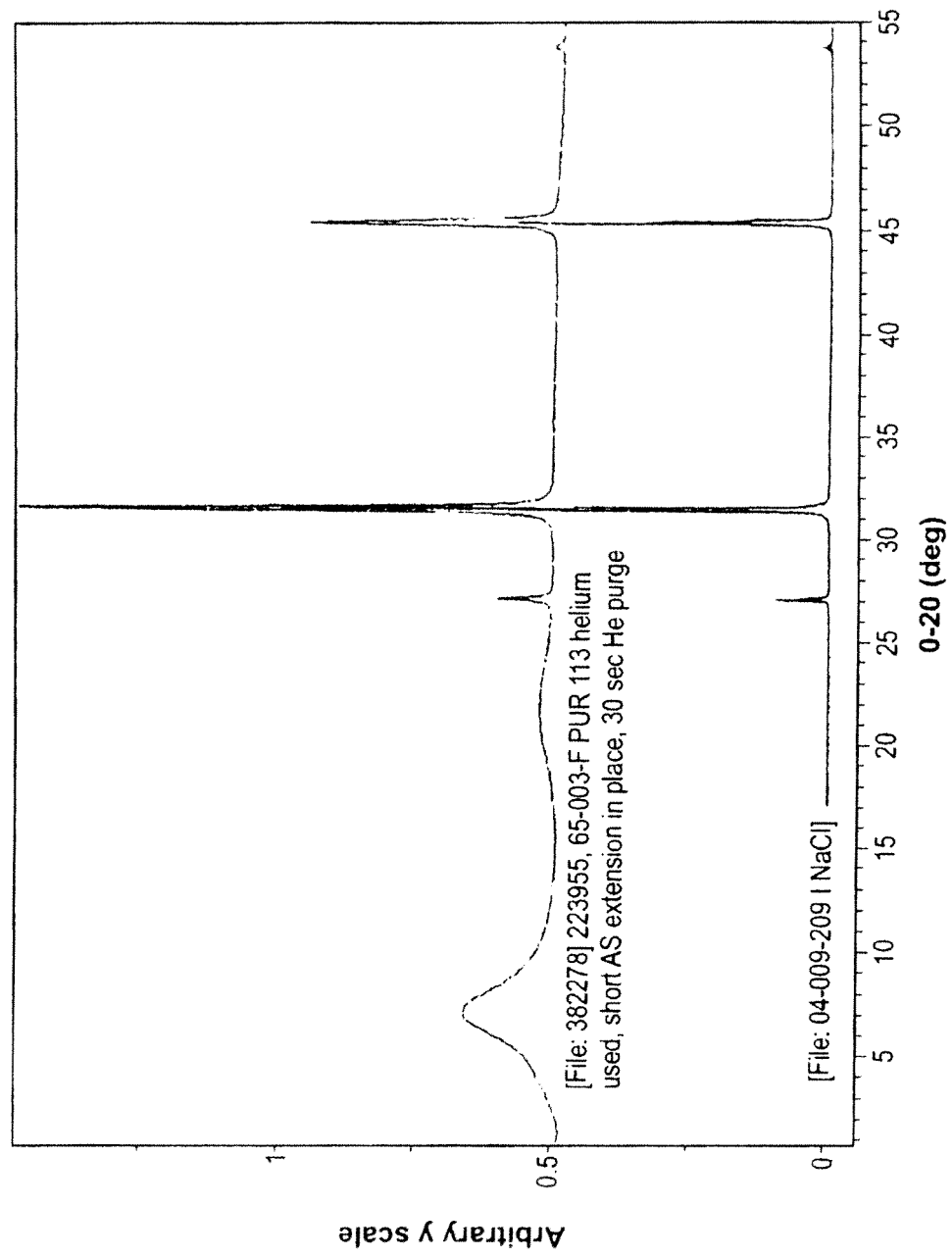
FIG. 20 shows a comparison of XRPD patterns for Formulation II powder with crystalline reflection from NaCl.
Figure 21:
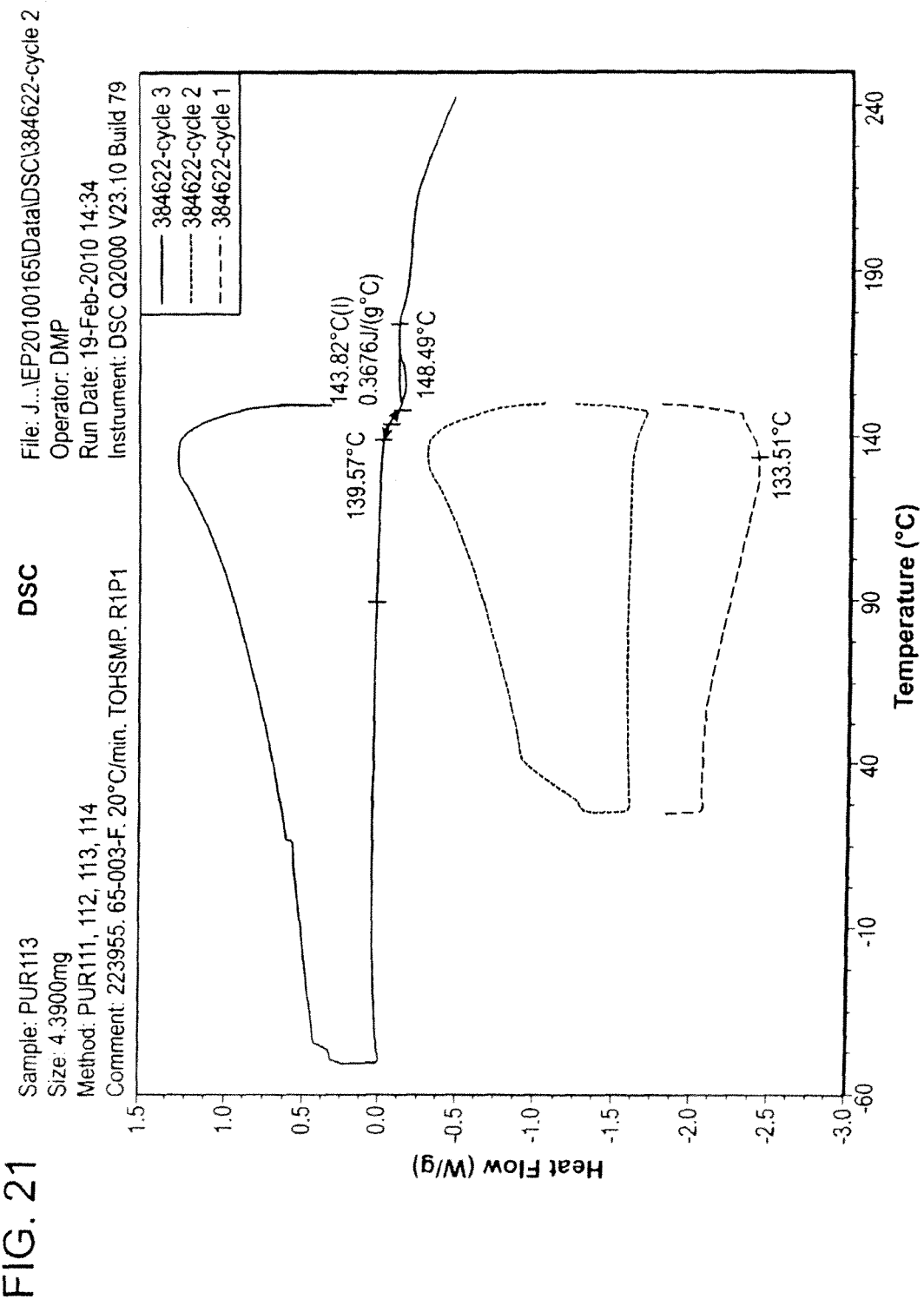
FIG. 21 shows an overlay of temperature cycling DSC thermogram of Formulation II. A glass transition temperature of approximately 144° C. was observed via cyclic DSC for the amorphous calcium-rich phase.
Figure 22:
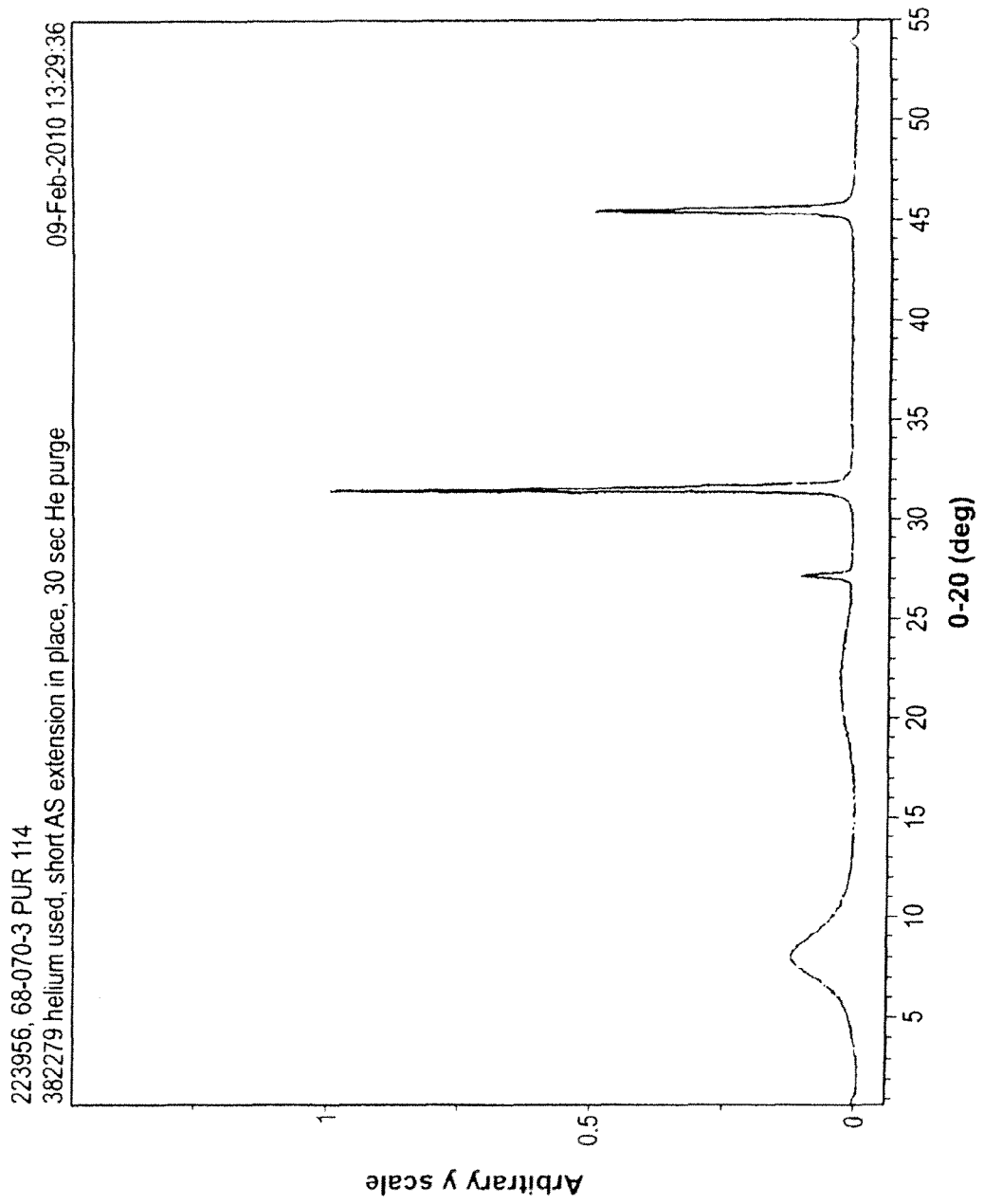
FIG. 22 shows a high resolution XRPD pattern of Formulation IV powder.
Figure 23:
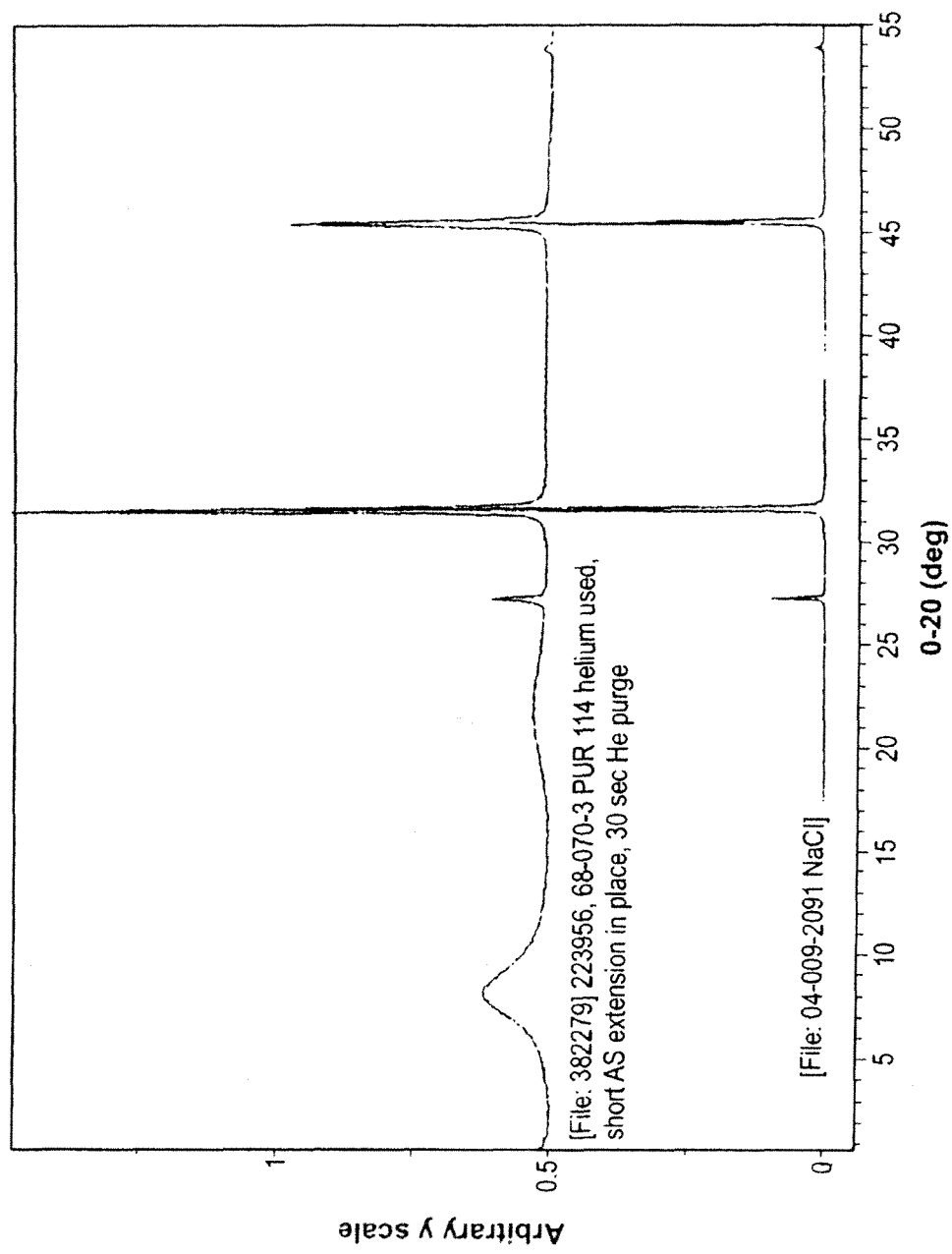
FIG. 23 shows a comparison of XRPD patterns for Formulation IV powder with crystalline reflection from NaCl.
Figure 24:
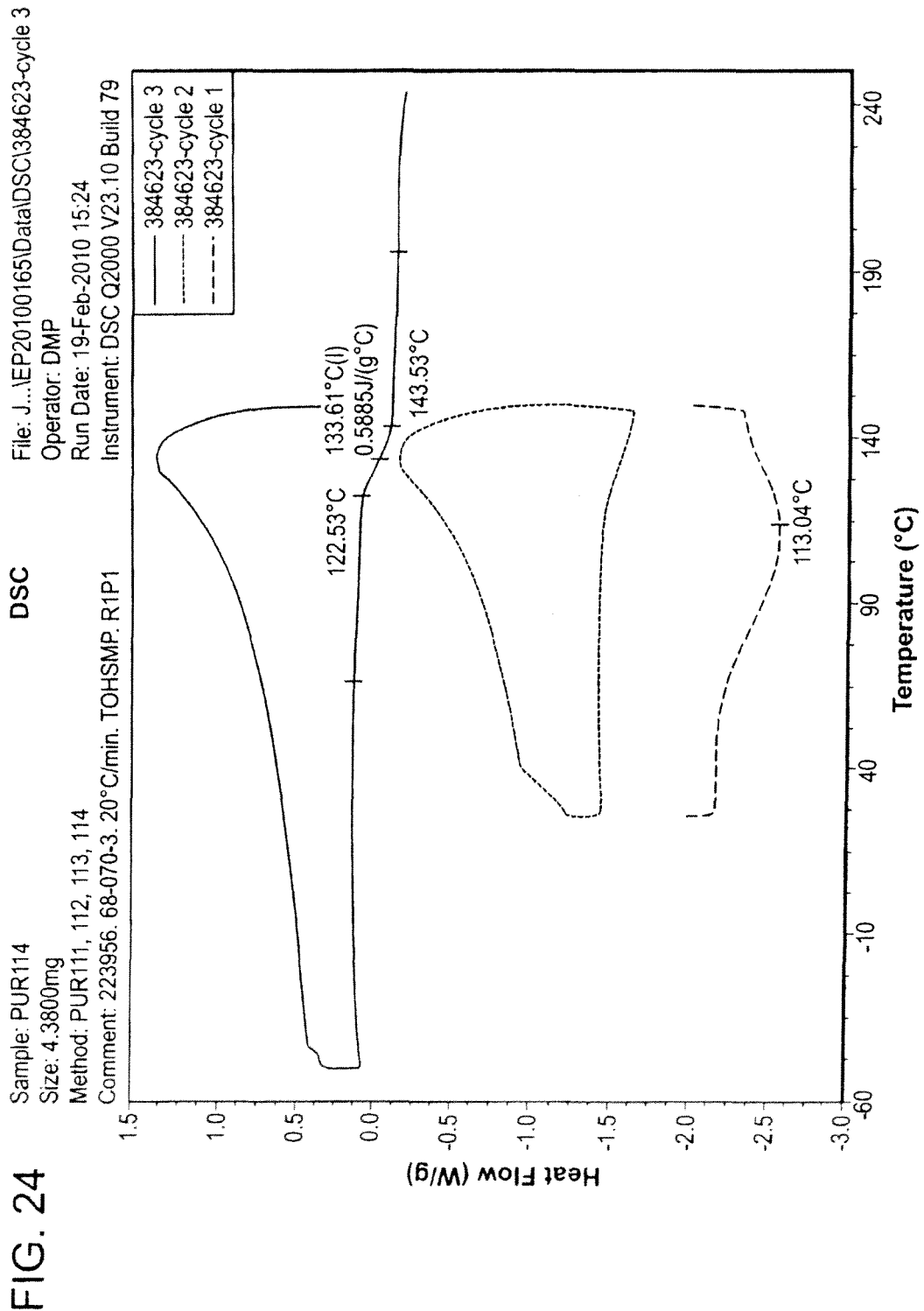
FIG. 24 shows an overlay of temperature cycling DSC thermogram of Formulation IV. A glass transition temperature of approximately 134° C. was observed via cyclic DSC for the amorphous calcium-rich phase.

Similar results were seen for powders Formulation III and Formulation IV. As shown in FIGS. 19 and 20, the Formulation III powder was observed via XRPD to consist of a combination of crystalline sodium chloride and a poorly crystalline or amorphous calcium lactate and potentially calcium chloride-rich phase (as evidenced by a lack of observance of any characteristic peaks for any calcium salt forms in this powder as well as the absence of any characteristic peaks for leucine). As shown in FIG. 21, a glass transition temperature of approximately 144° C. was observed via cyclic DSC for the amorphous calcium-rich phase, indicating that this amorphous phase should be relatively stable to crystalline conversion at standard conditions (25° C., 30% RH). Nearly identical results were seen for the Formulation IV powder which contained 10% maltodextrin versus 10% leucine (see FIGS. 22 and 23) for XRPD data as well as FIG. 24 which shows a glass transition temperature of approximately 134° C.

Figure 25A:
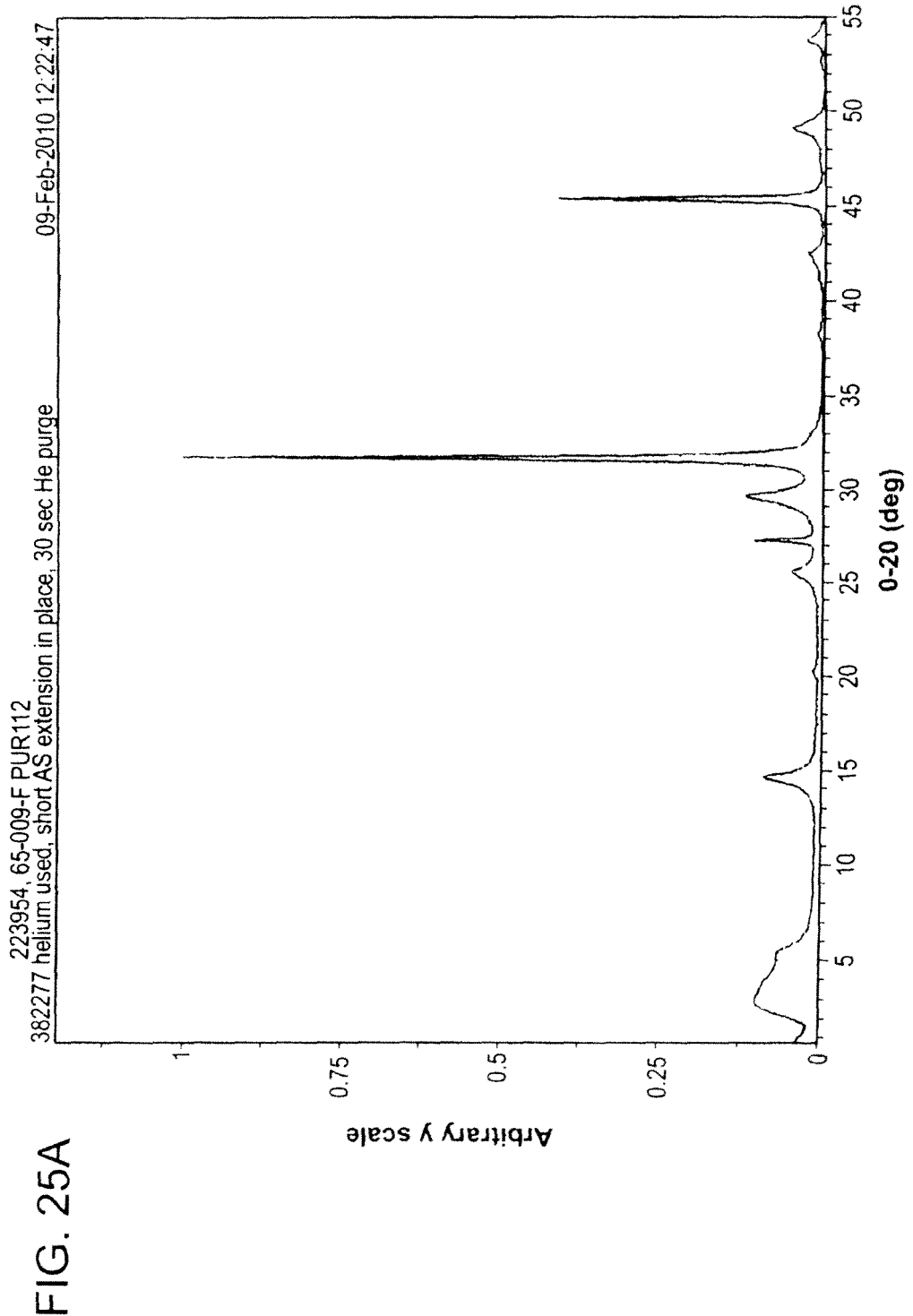
FIG. 25A shows a high resolution XRPD pattern of Formulation II powder. This pattern shows that Formulation II has some degree of crystalline calcium salt content (calcium sulfate) present, in addition to crystalline sodium chloride.
Figure 25B:
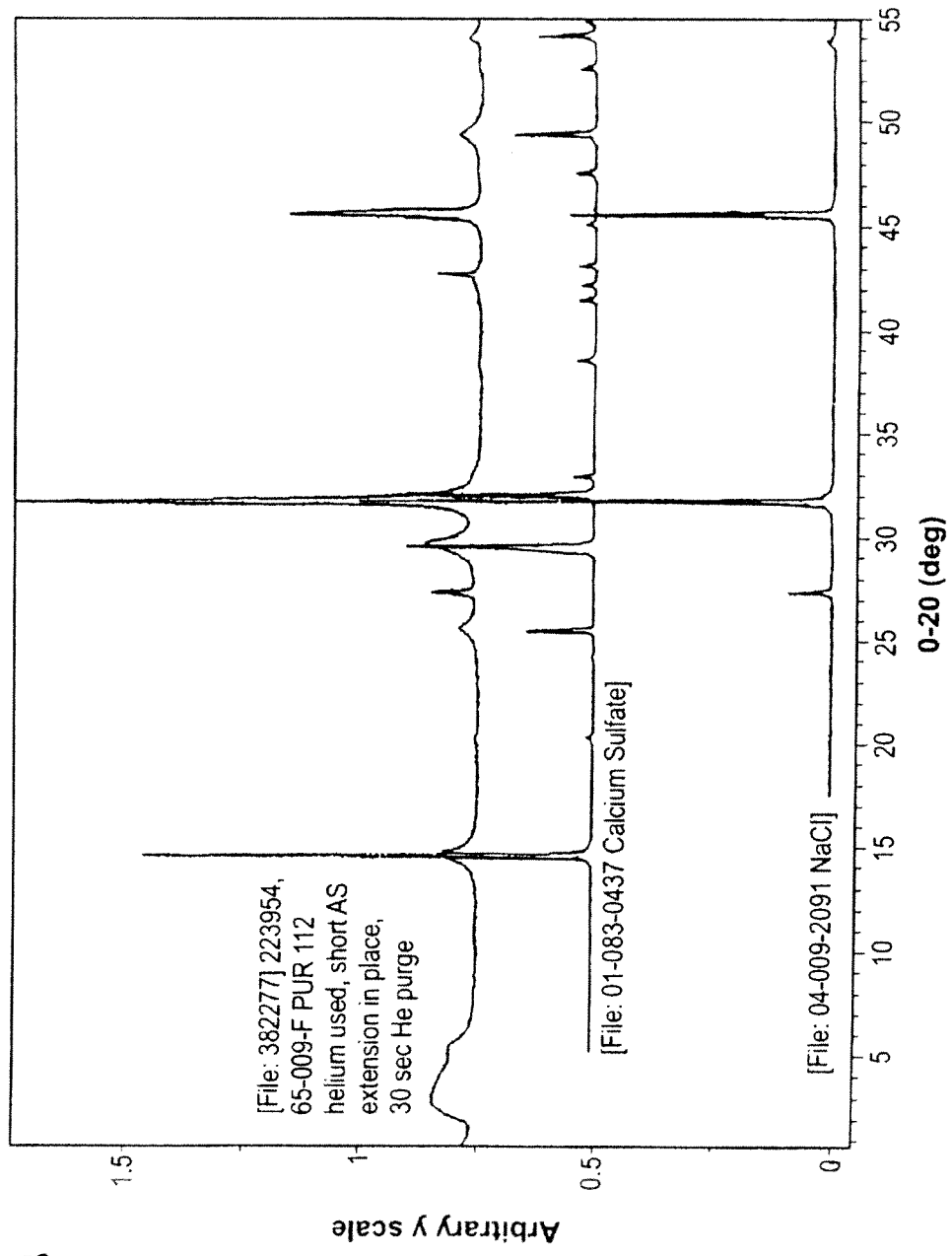
FIG. 25B shows a comparison of XRPD patterns for Formulation II powder with crystalline reflection from NaCl.
Figure 26:
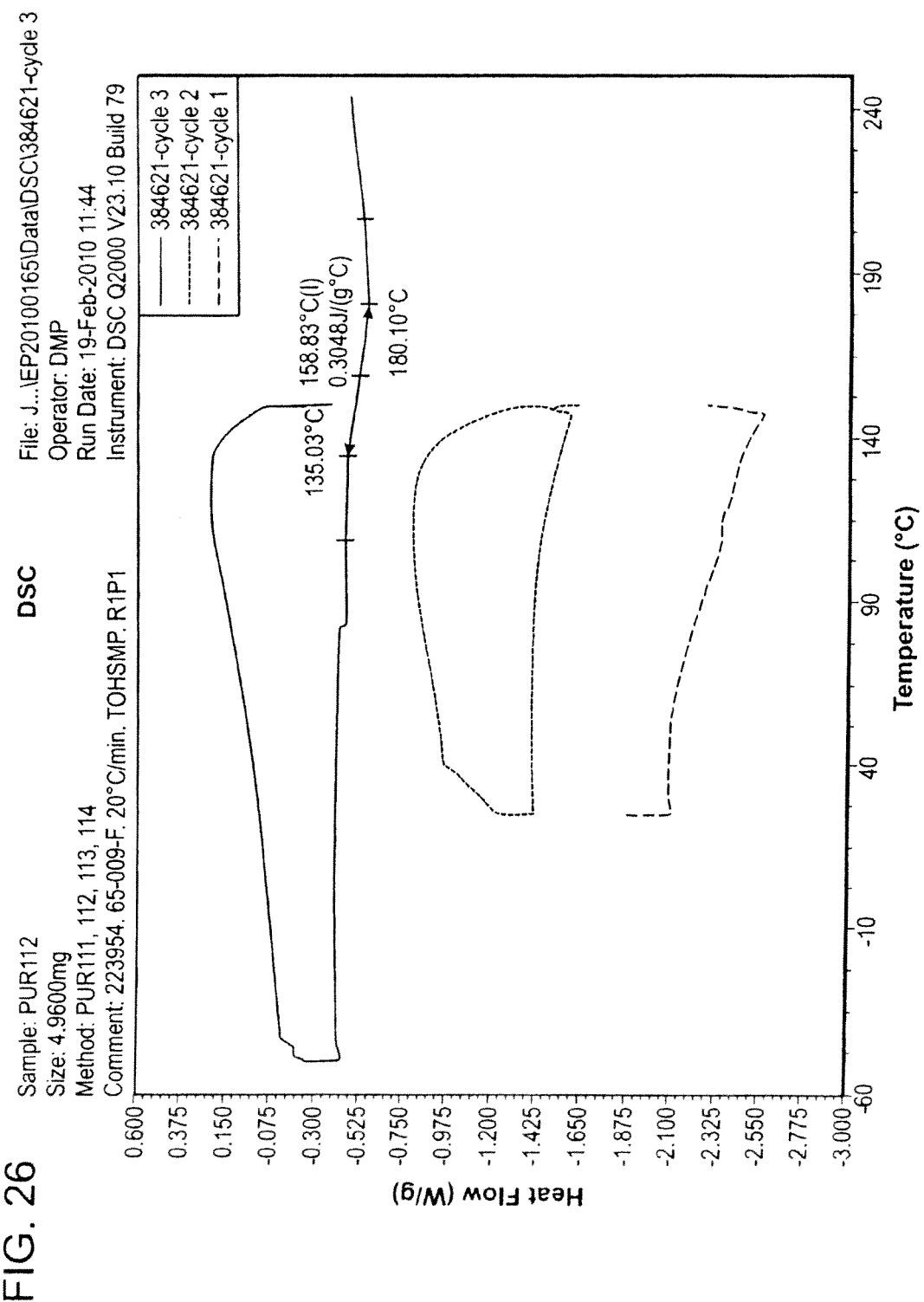
FIG. 26 shows an overlay of temperature cycling DSC thermogram of Formulation II. A glass transition temperature of approximately 159° C. was observed via cyclic DSC for the amorphous calcium-rich phase.

In contrast, the Formulation II formulation displayed the presence of some degree of crystalline calcium salt content (calcium sulfate) in addition to crystalline sodium chloride (see FIGS. 25A and 25B). However, this powder still possessed a significant degree of amorphous, calcium-rich phase content, as evidenced by the presence of a glass transition temperature of approximately 159° C. via DSC (see FIG. 26).

B. Surface RAMAN Mapping

Surface Mapping RAMAN experiments were conducted on samples of Formulations I through IV in order to determine the nature of the chemical composition at the surface of the particles comprising these formulations. Raman map spectra were acquired on a Renishaw inVia Ramascope (Gloucestershire, UK) equipped with a Leica DM LM microscope (Wetzlar, Germany). The instrument was calibrated using a silicon wafer standard. The samples were prepared for analysis on an aluminum-coated microscope slide. The excitation wavelength was 785 nm using a high-power near-infrared diode laser source. The data collection for Formulation I, Formulation III and Formulation IV was a static scan with a 30 second exposure time and 10 accumulations. The data collection for Formulation II was an extended scan with a 60 second exposure time and one accumulation. A Philips ToUcam Pro II camera (model PCVC 840K) (Amsterdam, the Netherlands) was used for image acquisition with a 50× objective. Renishaw WiRE 3.1 (service pack 9) software (Gloucestershire, UK) was used for data collection and processing.

Figure 27A:
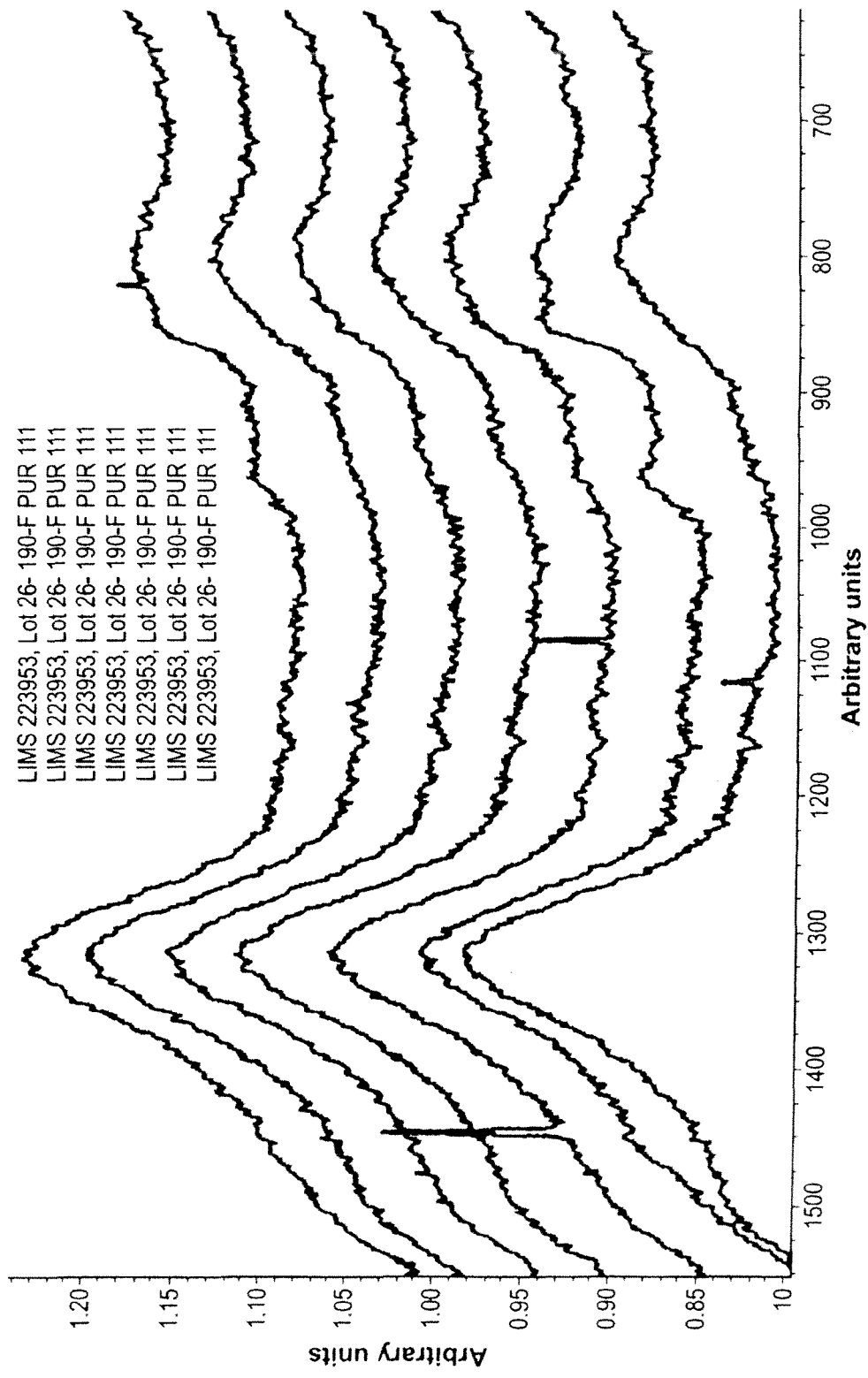
Figure 27B:
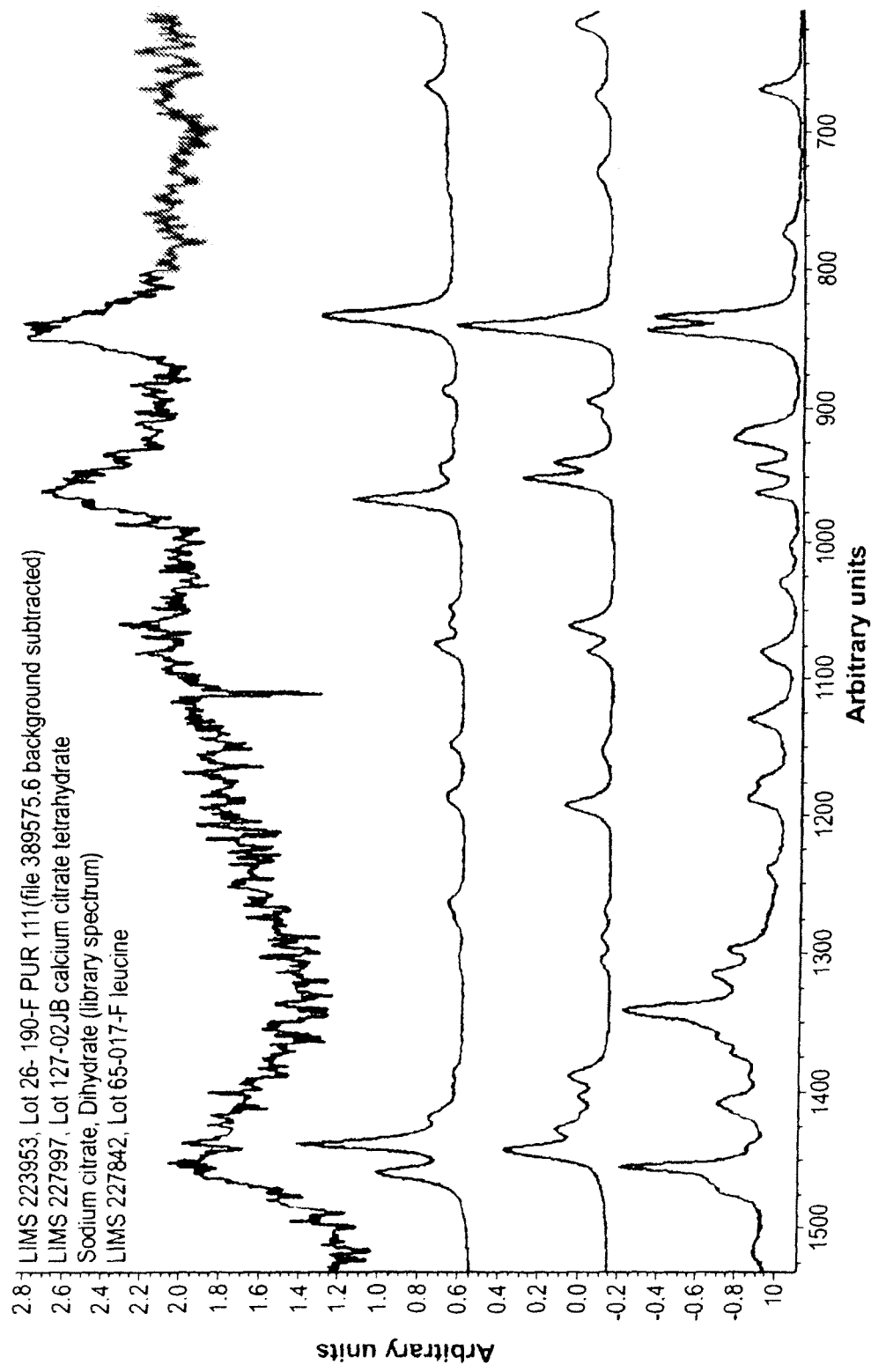

Raman spectra were acquired for six particles from the Formulation I sample, and are shown overlaid in FIG. 27A. Spectra files 389575-1 and 389575-6 are characterized by the presence of weak peaks at approximately 1450, 965 and 850 cm−1. These peaks are discernable as only very weak features in spectra file 389575-6, and are not detected in the remaining spectral data files. In FIG. 27B, spectrum 389575-6 is background subtracted and overlaid with the Raman spectra of calcium citrate tetrahydrate, sodium citrate, and leucine. The sample spectrum exhibits peaks at approximately 1450 and 850 cm−1 which are common to both leucine and the citrate salts. The sample spectrum displays an additional peak at approximately 965 cm−1, which is consistent with the relatively stronger intensity peak in the spectrum of the citrate salts (i.e., calcium citrate tetrahydrate and sodium citrate). The characteristic leucine peak at 1340 cm−1 is not observed in the sample spectra.

Raman spectra were acquired for eight particles from the Formulation II sample, and are shown overlaid in FIG. 27C. All particle spectra are characterized by the presence of a peak at approximately 1060 cm−1. An additional peak at approximately 670 cm−1 is observed in spectral file 388369-

4. The 670 cm−1 peak is also observable in spectral data files 388369-1, 3, and 8 after background subtraction (not shown). In FIG. 27D, spectrum 388369-4 is background subtracted and overlaid with the Raman spectra of calcium sulfate, calcium sulfate dihydrate, sodium sulfate anhydrous, and leucine. The background subtracted sample spectrum reveals a possible third peak near 520 cm−1. The peaks at 1060 and 670 cm−1 are present at similar positions to characteristic peaks of the sulfate ions displayed, but do not overlap precisely. The frequencies of the peaks at 1060 and 670 cm−1 in the sample spectrum are consistent with the stretching and bending modes, respectively, of a sulfate ion functional group. Peaks assignable to leucine are not detected in the particle spectra.

Figure 27E:
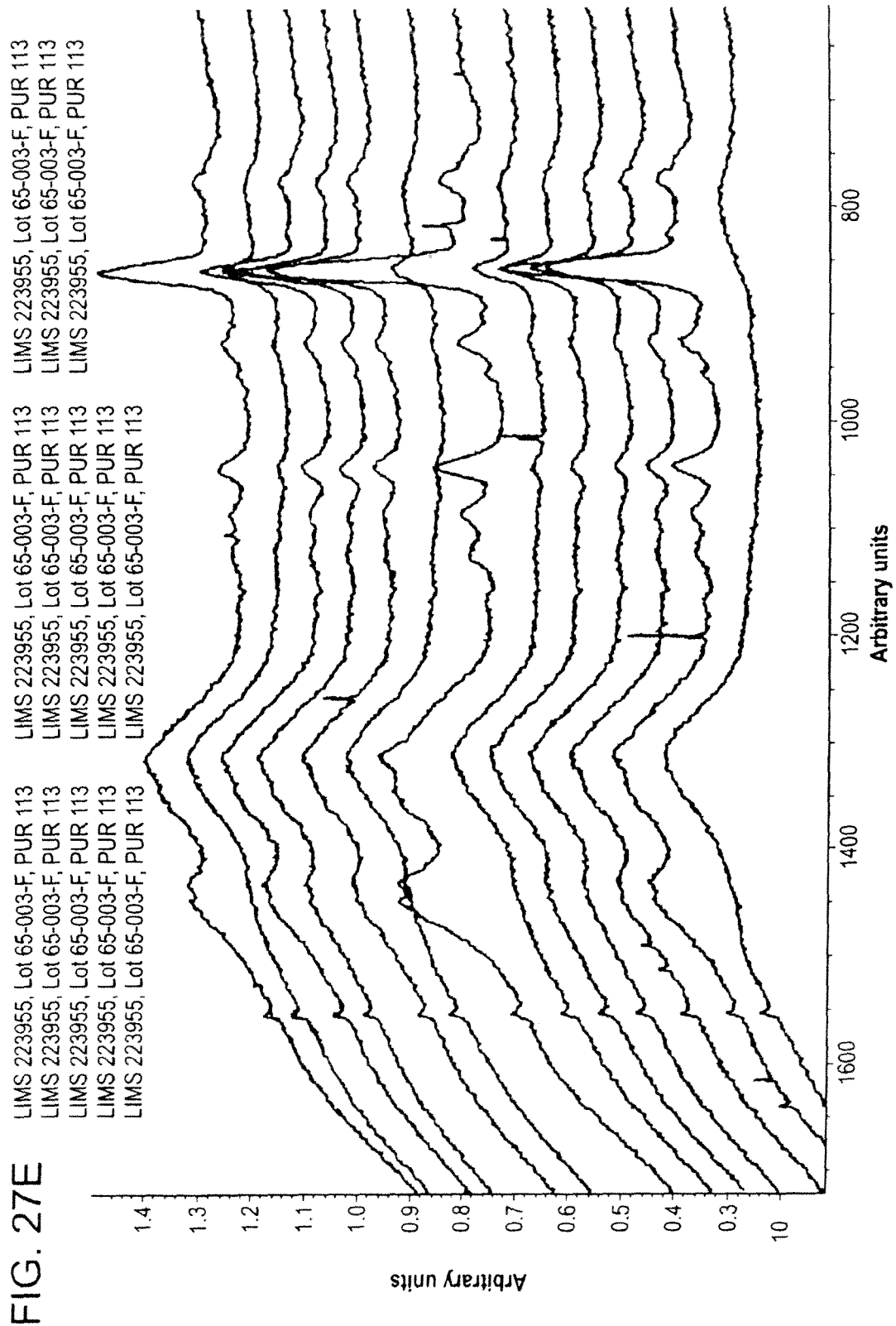

Raman spectra were acquired for twelve particles from the Formulation III sample, and are shown overlaid in FIG. 27E. All particle spectra are characterized by the presence of peaks at approximately 1045 and 860 cm−1. Additional peaks can be observed in various spectra at approximately 1450, 1435, 1125, 1095, 930, and 775 cm−1, which generally correlate in relatively intensity with the strong peak at 1045 cm−1. In FIG. 27F, spectra 389576-7 and 389576-12 are background subtracted and overlaid with the Raman spectra of calcium lactate pentahydrate, and leucine. A good correspondence is observed between the sample spectra and calcium lactate pentahydrate spectrum. However, the sample spectra display additional weak peaks at approximately 1345, 1170, 960, 830, and 760 cm−1 which are absent in the spectrum of calcium lactate pentahydrate. Similar peaks are present in the reference spectrum of leucine, although with slightly different relative intensities and frequencies.

Figure 27G:
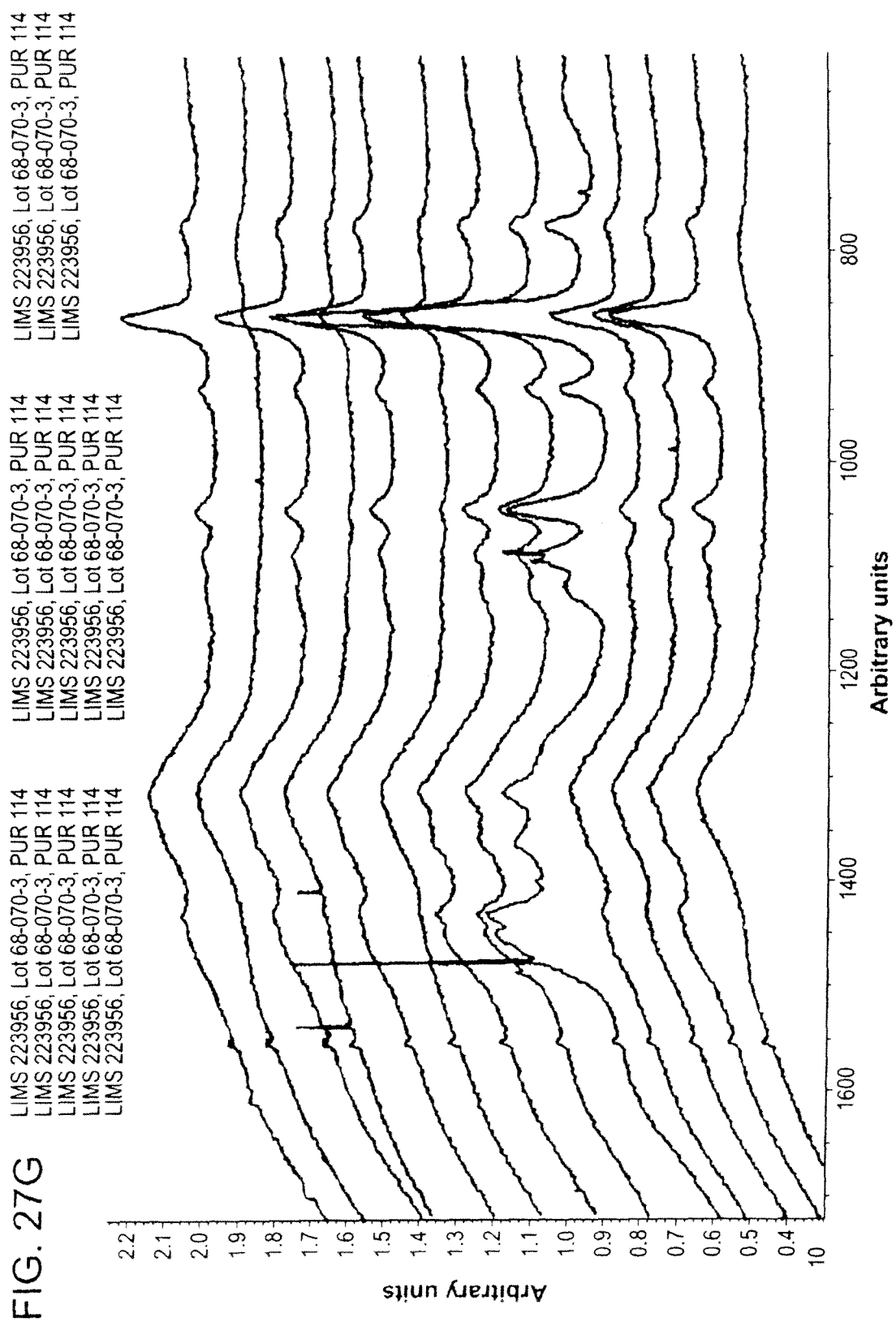
Figure 27H:
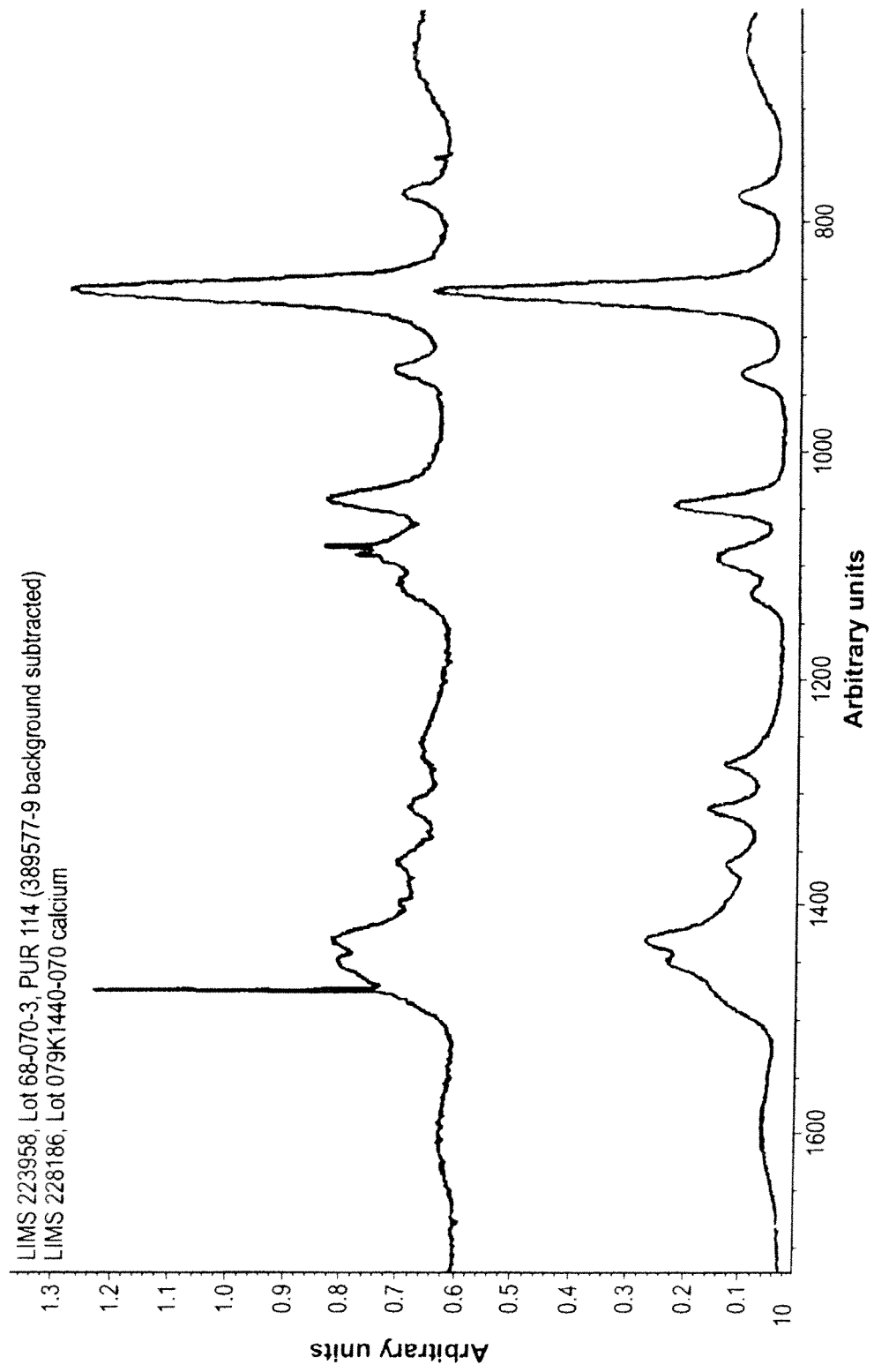
Figure 28:
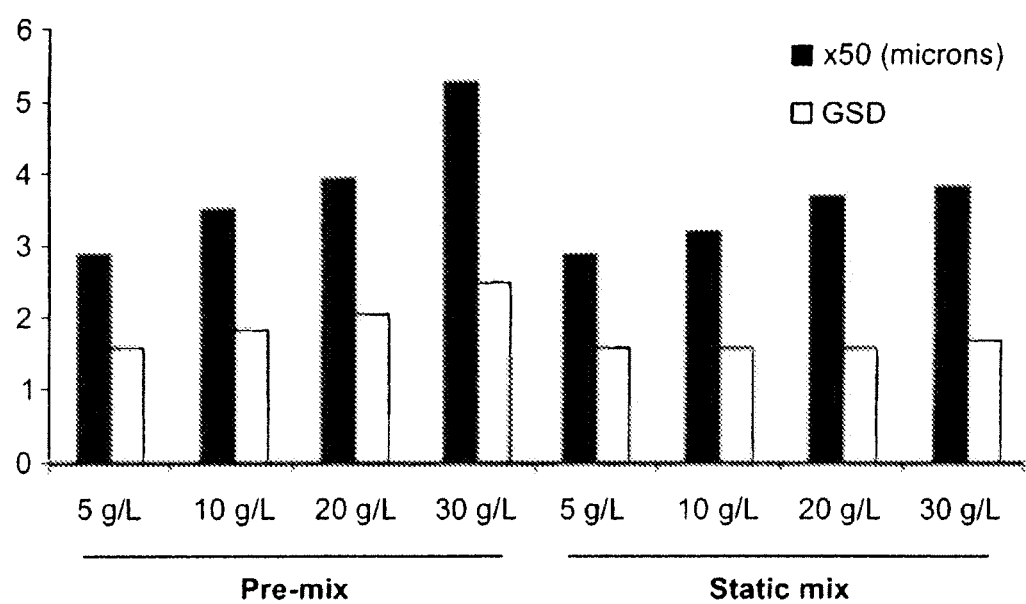
FIG. 28 is a graph showing volume particle size results for Formulation II (calcium sulfate) spray dried powders prepared from pre-mixed and static mixed liquid feed stocks with increasing solids concentrations. Particle size distribution broadens (increasing GSD) and median volume particle size significantly increases (×50) with increasing solids concentration in pre-mixed feed stocks. Particle size distribution remains constant with increasing solids concentration in static mixed feed stocks, while the median volume particle size increases slightly, as expected with increasing solids concentrations.
Figure 29:
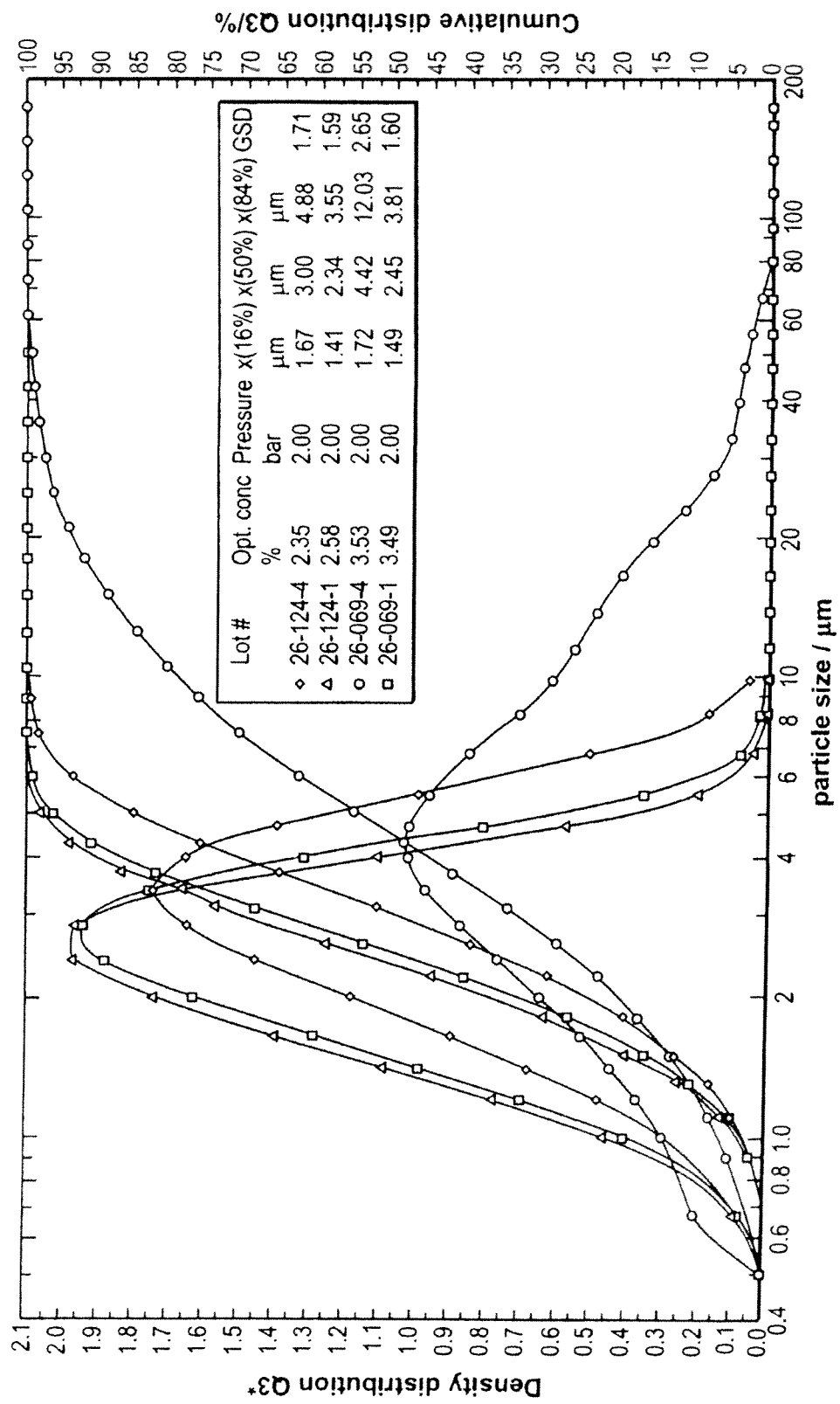
FIG. 29 is a graph showing volume particle size distribution results for Formulation II (calcium sulfate) spray dried powders prepared from pre-mixed and static mixed liquid feed stocks with increasing solids concentrations. Particle size distribution broadens with increasing solids concentration in pre-mixed feed stocks and remains narrow with increasing solids concentration in static mixed feed stocks. Triangles 5 g/L, static mixed; squares, 5 g/L, pre-mixed; diamonds, 30 g/L, static mixed; circles 30 g/L, pre-mixed.
Figure 30:
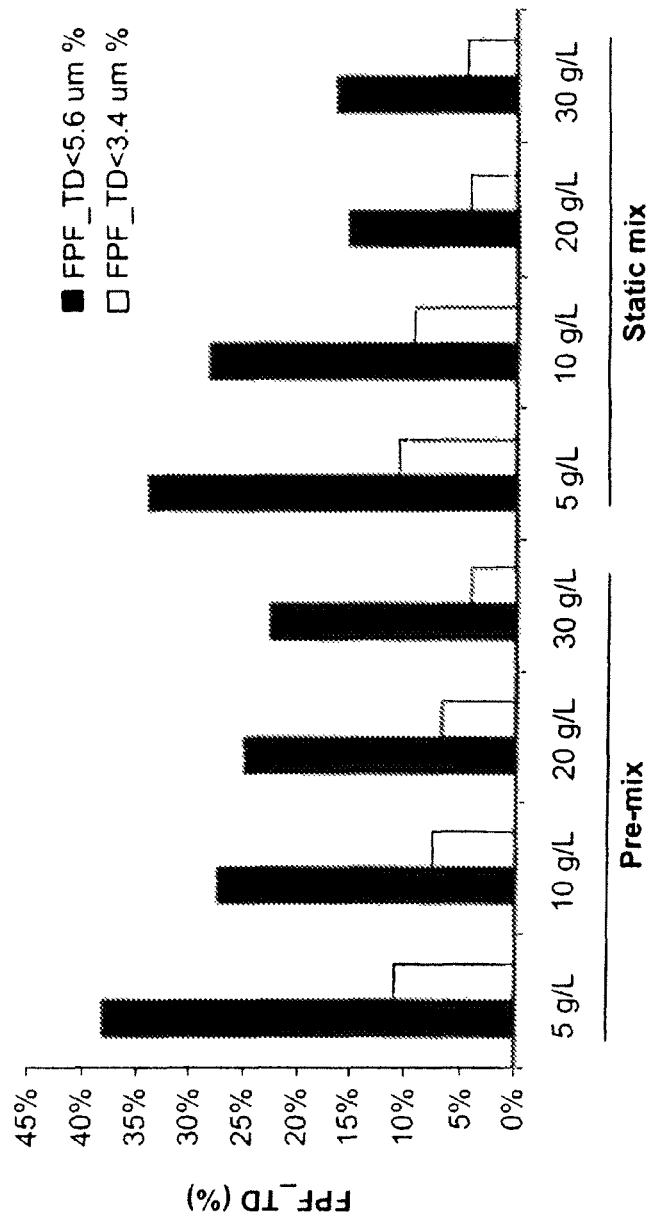
FIG. 30 is a graph showing aerosol characterization results for Formulation II (calcium sulfate) spray dried powders prepared from pre-mixed and static mixed liquid feed stocks with increasing solids concentration.
Figure 31A:
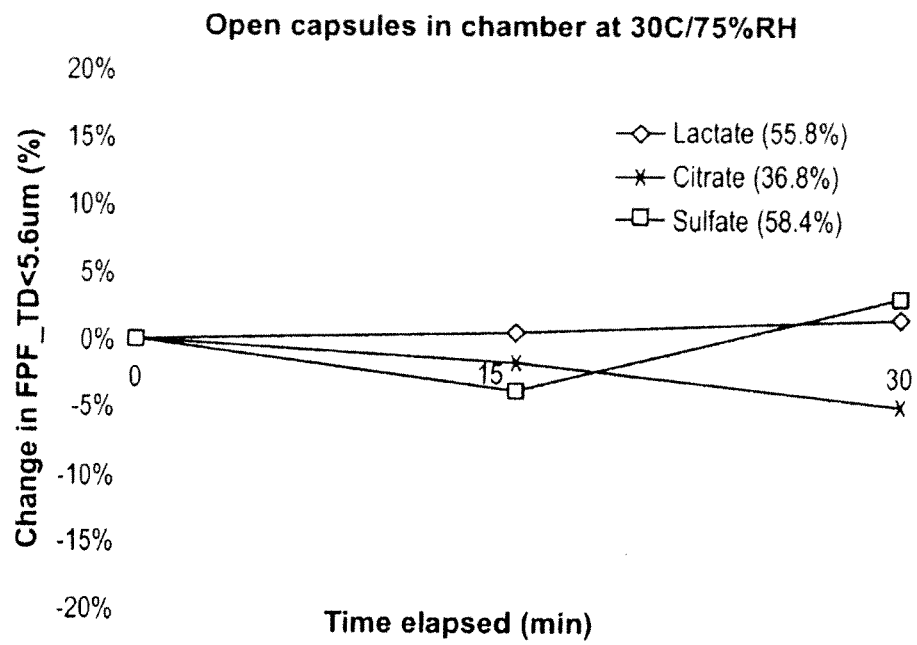
FIGS. 31A-B are graphs showing the change in fine particle fraction (FPF) of formulations Formulation I (calcium citrate), Formulation II (calcium sulfate), and Formulation III (calcium lactate) during in-use stability testing at extreme conditions. The graph compares change in FPF (total dose) <5.6 microns (%) versus time elapsed in the chamber at extreme temperature and humidity conditions (30° C., 75% RH). The values in the legend indicate the true value at time zero. The plots show fluctuation as a function of change as compared to time zero.
Figure 31B:
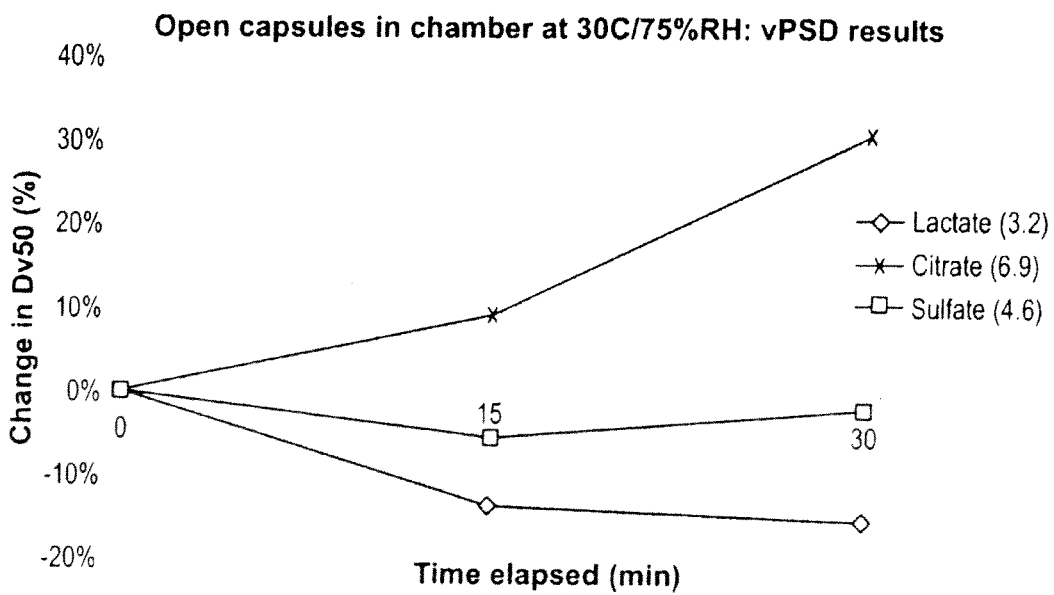
Figure 31C:
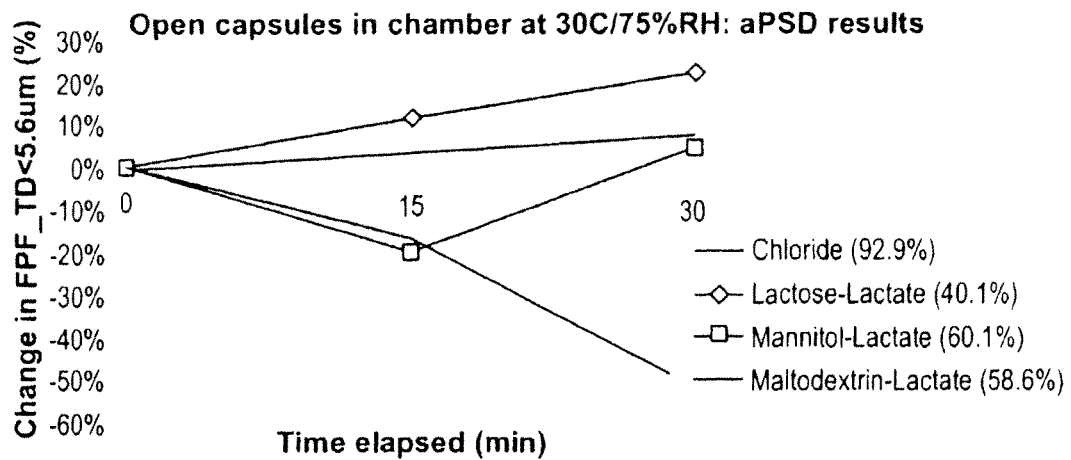
FIG. 31C,D show similar data for a second set of spray-dried formulations comprised of a control calcium chloride:sodium chloride:leucine powder and calcium lactate:sodium chloride powders containing 10% (i)
Figure 31D:
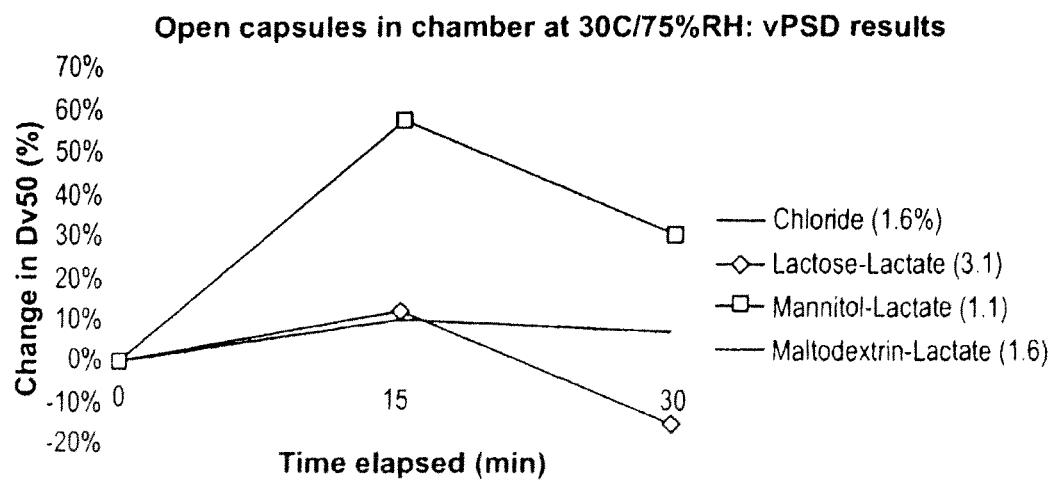
FIG. 31D is a graph showing changes in volume particle sizes of the second set of powders during in-use stability testing at extreme conditions. The graph compares change in median volume particle size versus time elapsed in the chamber at extreme temperature and humidity conditions (30° C., 75% RH). The values in the legend indicate the true value at time zero. The plots show fluctuation as a function of change as compared to time zero.
Figure 32:
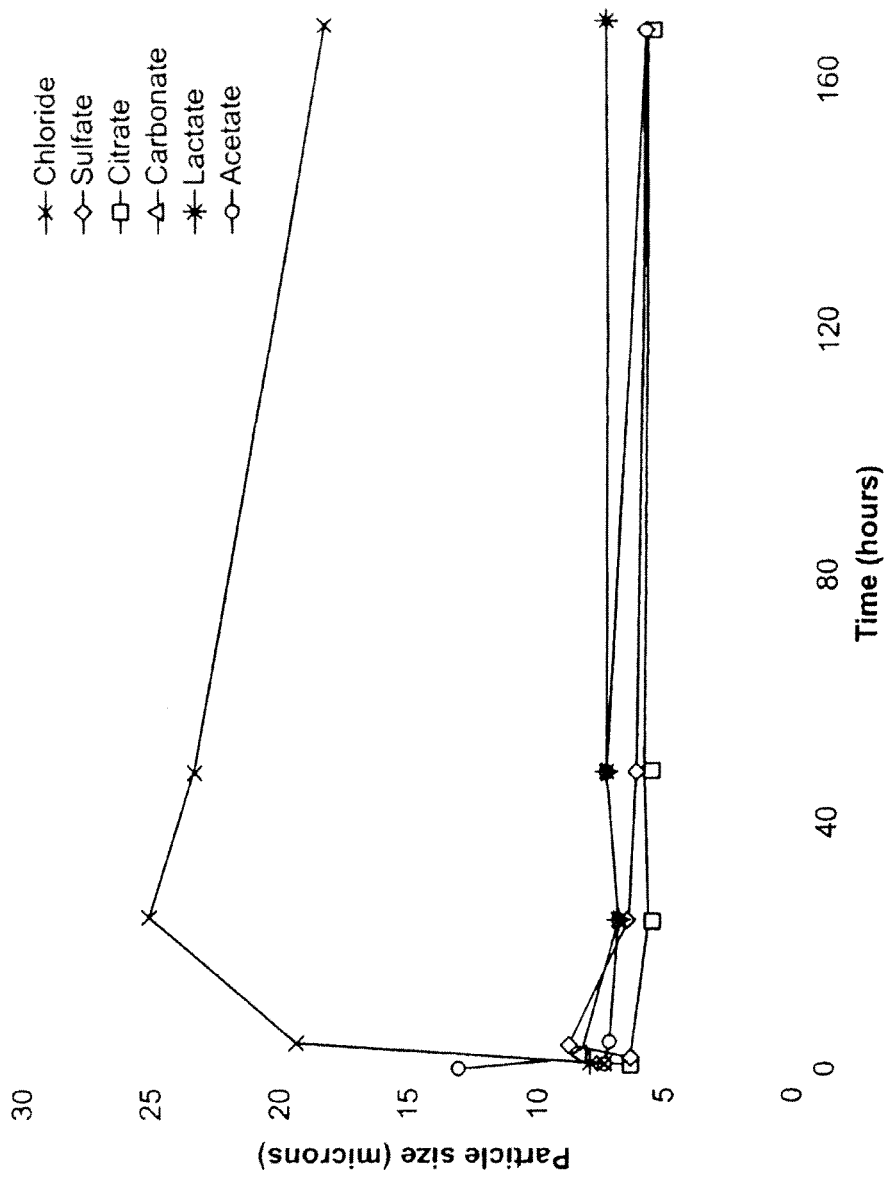
FIG. 32 is a graph showing powder stability for a range of different powders as measured by volume particle size upon exposure to ~40% RH conditions for up to one week.
Figure 33:
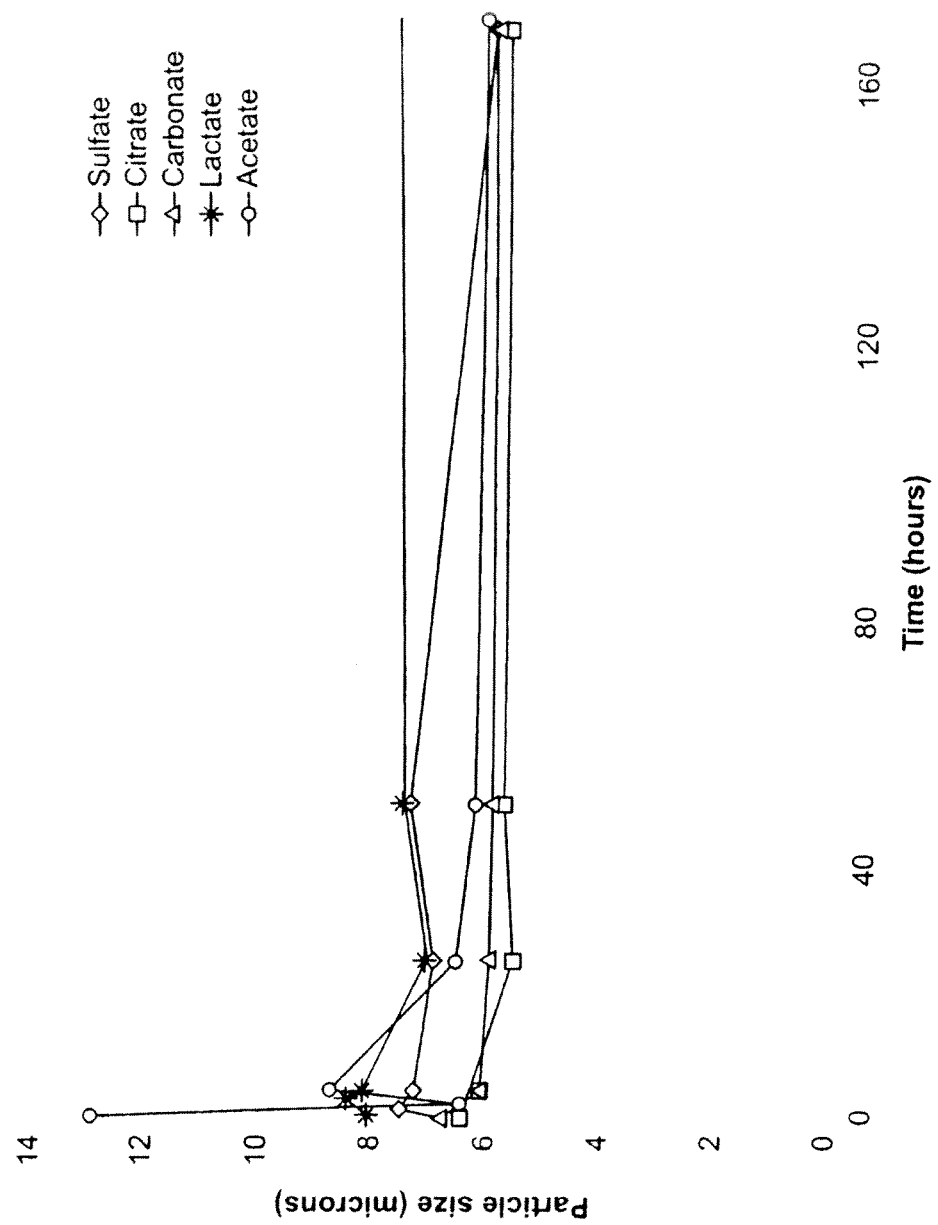
FIG. 33 is a graph showing volume particle size upon exposure to ~40% RH conditions for a range of different powders for up to one week. This figure is identical to FIG. 32, except that chloride was removed to allow for better detail.
Figure 34:
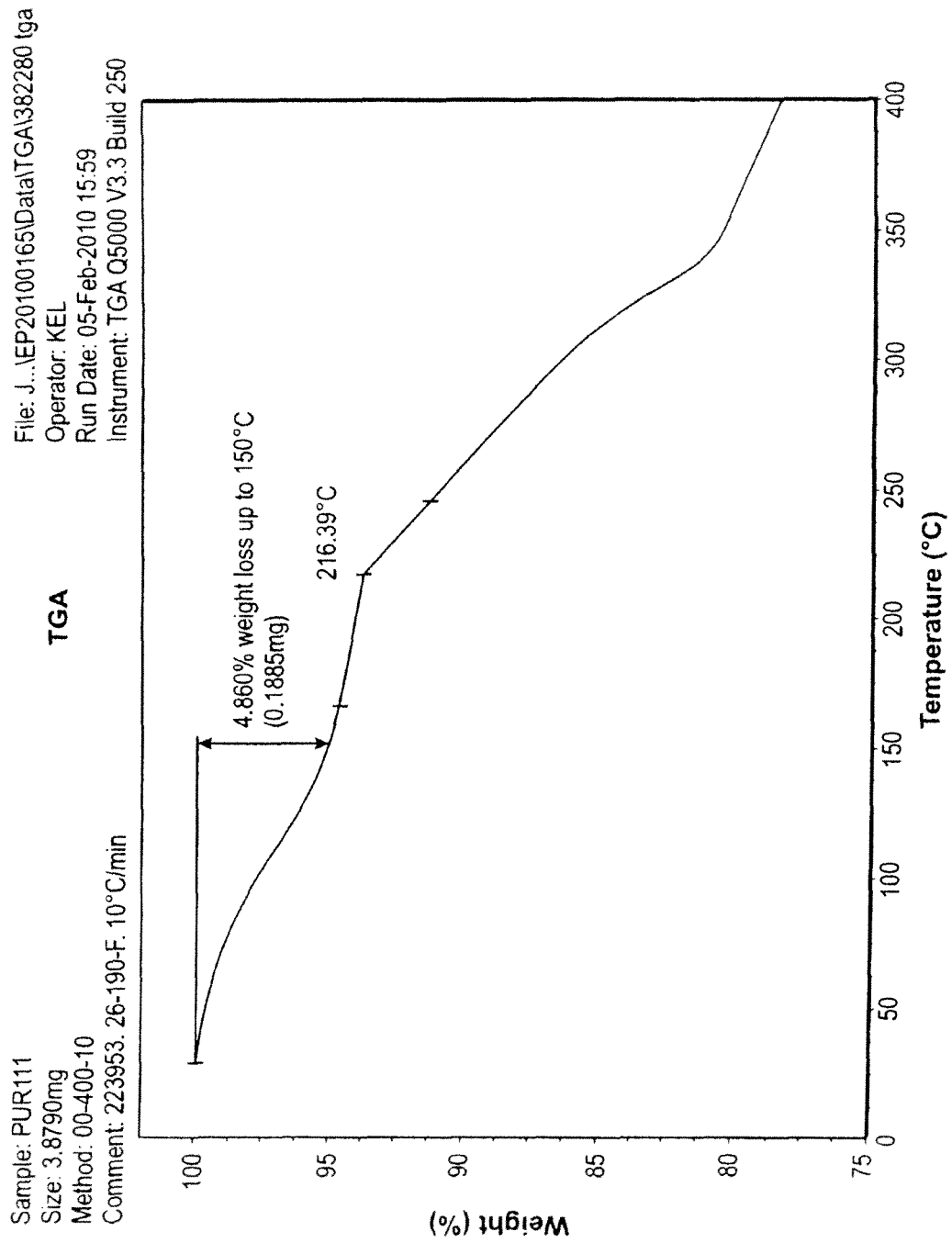
FIG. 34 is a graph showing a representative TGA thermogram for Formulation I.

Raman spectra were acquired for twelve particles from the Formulation IV sample, and are shown overlaid in FIG. 27G. All particle spectra are characterized by the presence of a peak at approximately 1045 cm−1. All particle spectra except file 389577-2 also display a peak at approximately 860 cm−1. Additional peaks can be observed in various spectra at approximately 1450, 1435, 1125, 1095, 930, and 775 cm−1, which generally correlate in relatively intensity with the strong peak at 1045 cm−1. In FIG. 27H, spectrum 389577-9 is background subtracted and overlaid with the Raman spectra of calcium lactate pentahydrate. A good correspondence is observed between the sample and calcium lactate pentahydrate spectra. Peaks assigned to maltodextrin (not shown) are not observed in the sample spectra.

Thus, RAMAN surface mapping analysis indicates that the surface composition of each of Formulations I though IV is dominated by the presence of the various calcium salts (calcium citrate for Formulation I, calcium sulfate for Formulation II and calcium lactate for Formulations III and IV). For the case of Formulations I through III, this is in contrast to the reported use of leucine as a dispersion-enhancing agent that increases the dispersibility of powders for aerosolization via being concentrated at the surface of the particles comprising said powders. For the formulations disclosed herein, it does not appear that leucine is acting as a dispersibility enhancer in this fashion, as also evidenced by the similar results seen for Formulations III (leucine-containing calcium lactate formulation) and IV (maltodextrin-containing calcium lactate formulation) with respect to surface content and dispersibility.

Example 17

Ion Exchange Reaction for Spray Drying Supersaturated Calcium Citrate and Calcium Sulfate Saturated or super-saturated stocks of aqueous calcium sulfate or calcium citrate were prepared for spray drying using calcium chloride and sodium sulfate or calcium chloride or sodium citrate as starting materials. A range of total solids concentrations from 5 to 30 g/L were prepared both by (i) pre-mixing both salts in water and (ii) keeping the calcium and sodium salt in separate aqueous solutions, with static mixing in-line immediately before spray drying. All of the liquid feed stocks prepared contained saturated or supersaturated calcium sulfate amounts, (where the solubility limit of calcium sulfate in water is 2.98 g/L) and saturated or supersaturated calcium citrate amounts (where the solubility limit of calcium citrate in water is 0.96 g/L). Considering the calcium chloride and sodium sulfate precipitation reaction proceeds to completion ($CaCl_2+Na_2SO_4 \rightarrow CaSO_4+2NaCl$), the corresponding final concentrations of calcium sulfate are listed in Table 24. Similar results for the calcium chloride and sodium citrate precipitation reaction ($3CaCl_2+2Na_3C_6H_5O_7 \rightarrow Ca_3(C_6H_5O_7)_2+6\ NaCl$) are also shown in Table 27.

TABLE 27

Liquid feedstock total solids concentrations and final calcium sulfate or calcium citrate concentrations, where the aqueous solubility limit of calcium sulfate is 2.98 g/L and calcium citrate is 0.96 g/L

| Total solids concentration (g/L) | Final calcium sulfate concentration (g/L) | Final calcium citrate concentration (g/L) |
| --- | --- | --- |
| 5 | 2.7 | 2.9 |
| 10 | 5.4 | 5.9 |
| 15 | 8.1 | 8.8 |
| 20 | 10.8 | 11.7 |
| 30 | 16.1 | 17.6 |

Formulations of 44 weight percent calcium chloride and 56 weight percent sodium sulfate were produced by spray drying utilizing a Mobile Minor spray dryer (Niro, GEA Process Engineering Inc., Columbia, Md.). The liquid feed stocks were prepared at a range of solids concentration from 5-30 g/L. For pre-mixed feeds, sodium salt then calcium salt was dissolved in DI water with constant stirring on a magnetic stirplate. For static mixed feeds, calcium salt was dissolved in DI water, and sodium salt was separately dissolved in DI water with the two solutions maintained in separate vessels with constant agitation. Atomization of the liquid feed was performed using a co-current two-fluid nozzle (Niro, GEA Process Engineering Inc., Columbia, Md.). The liquid feed was fed using gear pumps (Cole-Parmer Instrument Company, Vernon Hills, Ill.) either directly into the two-fluid nozzle for pre-mixed feeds or into a static mixer (Charles Ross & Son Company, Hauppauge, N.Y.) immediately before introduction into the two-fluid nozzle for static mixed feeds. Nitrogen was used as the drying gas and dry compressed air as the atomization gas feed to the two-fluid nozzle. The process gas inlet temperature was 240-250° C. and outlet temperature was 94-98° C. with a liquid feedstock rate of 50-70 mL/min. The gas supplying the two-fluid atomizer was approximately 11 kg/hr. The pressure inside the drying chamber was at −2 "WC. Spray dried product was collected from a cyclone and analyzed for volume particle size by laser diffraction using a HELOS with RODOS attachment and for aerosol properties using a collapsed two-stage ACI.

Pre-mixed feeds were assessed for solution stability and clarity. At a total solids concentration of 5 g/L, where the final calcium sulfate concentration would be slightly over the solubility limit of calcium sulfate, the solution stayed clear during the 30 minute duration of mixing and spray drying. As the total solids concentration increased and the final calcium sulfate concentration greatly exceeded the solubility limit, the feed stock became cloudy and precipitation was evident. At 10 g/L the liquid was slightly cloudy, at 20 g/L the liquid was clear for approximately 5-10 minutes before becoming increasingly cloudy over the course of 10 minutes and at 30 g/L the liquid was clear for approximately 2 minutes after mixing, with visible precipitation appearing after approximately 5 minutes.

The pre-mixed and static mixed liquid feed stocks were spray dried and the resulting dry powder collected from the cyclone. Results from the HELOS with RODOS are shown in FIG. 28 with representative particle size distributions shown in FIG. 29. While an increase in particle size is expected with increasing feed stock solids concentrations (as seen in the static mixed feeds), the significant particle size increase and broadened particle size distribution in the pre-mixed feeds is undesirable.

Results for aerosol characterization of the dry powders using the collapsed ACI are shown in FIG. 30.

Unstable solutions with continued precipitation may negatively affect reproducible particle formation during spray drying and also result in a broad particle size distribution. The supersaturated, clear solutions evident for 2-10 minutes for the higher solids concentration suggest that the solutions could be static mixed to achieve a higher spray drying throughput while reproducibly producing a narrow particle size distribution.

Similar results were exemplified for calcium citrate, as demonstrated in Example 1 for the formulation comprising 10.0 weight percent leucine, 35.1 weight percent calcium chloride and 54.9 weight percent sodium citrate (Formulation I-A). The precipitation reaction will result in a formulation comprising 10.0 weight percent leucine, 52.8 weight percent calcium citrate and 37.2 weight percent sodium chloride. At a total solids concentration of 10 g/L, the final calcium citrate concentration would be 5.3 g/L, which exceeds the solubility limit of calcium citrate in water of 0.96 g/L. As can be seen from the properties of the spray dried powder (FIGS. 1A-1E and 2-4), this supersaturated solution resulted in respirable particles with narrow size distribution.

Example 18

Small, dispersible particles were made from calcium-containing formulations with and without leucine, as well as magnesium-containing and sodium only formulations.

The following powders were spray dried on the Büchi B-290 using the high performance cyclone with an air feed rate of 30 mm air, aspirator at 90% rate and the small glass collection vessel. The inlet temperature was 220° C. and the outlet temperature was between 96-102° C. The solids concentration was 5 g/L and all were mixed in D.I. water by fully dissolving one component at a time, before adding the next in the order in which they are listed.

18-1) 10.0% lactose, 30.6% magnesium chloride, 59.4% sodium citrate, Ca:Na ratio=1:2

18-2) 63.4% magnesium lactate, 36.6% sodium chloride, Ca:Na ratio=1:2

18-3) 10.0% leucine, 58.4% magnesium lactate, 31.6% sodium chloride, Ca:Na ratio=1:2

18-4) 50.0% leucine, 50% calcium lactate 18-5) 10% leucine, 90% sodium chloride 18-6) 60% leucine, 40% sodium chloride 18-7) 10.0% albuterol, 58.6% calcium lactate, 31.4% sodium chloride 18-8) 90.0% albuterol, 5.9% calcium lactate, 3.1% sodium chloride Characterization results for these powders are shown in Table 28 below. All eight powders exhibited good dispensability with respect to ×50 0.5/4 and 1/4 ratios. FPF's<5.6 microns ranged from a low of 18.7% to 75.6%.

TABLE 28

Assorted sodium, calcium and magnesium-based formulations.

| Formulation | Method | x50 (μm) @ 1 bar | GSD @ 1 bar | 1/4 bar | 0.5/4 bar | FPF_TD <3.4 um % | FPF_TD <5.6 um % | % Mass collected | yield % |
|---|---|---|---|---|---|---|---|---|---|
| lact: MgCl2: Na3Cit 10:30.6:59.4 | Buchi HP | 2.9 | 2.3 | 1.1 | 1.1 | 18.1% | 37.8% | 55.7% | 88.9% |
| leucine: MgLact: NaCl 10:58.6:31.4 | Buchi HP | 2.7 | 2.4 | 0.8 | 1.1 | 14.5% | 32.3% | 53.0% | 80.0% |
| MgLact: NaCl 63.4:36.6 | Buchi HP | 3.3 | 2.1 | 1.0 | 1.0 | 16.5% | 39.3% | 59.8% | 78.0% |
| leu:CaLact 50:50 | Buchi HP | 3.5 | 2.2 | 1.1 | 1.1 | 19.2% | 38.5% | 60.4% | 76.0% |
| leu:NaCl 10:90 | Buchi HP | 1.1 | 1.7 | 1.0 | 1.2 | 53.0% | 71.0% | 78.6% | 67.9% |
| leu:NaCl 60:40 | Buchi HP | 1.4 | 2.2 | 1.1 | 1.2 | 49.7% | 75.6% | 85.2% | 54.3% |
| albuterol: CaLact:NaCl 10:58.6:31.4 | Buchi HP | 2.8 | 2.3 | 0.9 | 1.0 | 16.0% | 38.6% | 60.2% | 81.5% |
| albuterol: CaLact:NaCl 90:5.9:3.1 | Buchi HP | 3.5 | 2.3 | 1.0 | 1.1 | 8.9% | 18.7% | 29.1% | 40.5% |

Several additional calcium-free exemplary formulations were produced utilizing various spray-dryer systems (Buchi, LabPlant and Niro systems) following similar procedures those described above. Selected characterization results for the resultant powders are shown in Table 29 (cells with blank values indicates no value was measured for that powder).

TABLE 29

Non-calcium formulations of small, dispersible powders

| Lot | Formulation | Method | x50 (μm) @1 bar | GSD @1 bar | 1/4 bar | 0.5/4 bar | water % | FPF_TD <3.4 um % | FPF_TD <5.6 um % | % Mass collected | yield % |
|---|---|---|---|---|---|---|---|---|---|---|---|
| | | | | NaCl | | | | | | | |
| 2.26.2 | NaCl, 100 | Labplant | 2.9 | 1.4 | | | 0.5% | | | | |
| 27.115.4 | NaCl 100 | Niro | 4.5 | 1.9 | 1.4 | | 0.6% | 5.2% | 22.0% | 43.1% | 61.3% |
| | | | | Magnesium Salts | | | | | | | |
| 27.33.2 | MgCl2 + NaCl | Labplant | 4.3 | 1.9 | 1.2 | | 29.9% | 2.3% | 5.7% | 14.0% | 17.9% |
| 27.15.4 | MgCl2:Na2CO3, 47:53 | Labplant | 2.3 | 1.4 | 1.1 | | 87.4% | | | | 17.6% |
| 68.124.1 | lactose:MgCl2:Na3Cit 10:30.6:59.4 | Buchi HP | 2.9 | 2.3 | 1.1 | 1.1 | | 18.1% | 37.8% | 55.7% | 88.9% |
| 68.129.1 | leucine:MgLact:NaCl 10:58.6:31.4 | Buchi HP | 2.7 | 2.4 | 0.8 | 1.1 | | 14.5% | 32.3% | 53.0% | 80.0% |
| 68.129.2 | MgLact:NaCl 63.4:36.6 | Buchi HP | 3.3 | 2.1 | 1.0 | 1.0 | | 16.5% | 39.3% | 59.8% | 78.0% |
| | | | | Leucine | | | | | | | |
| 26.155.1 | Leucine, 100 | Buchi HP | 4.1 | 2.3 | 1.1 | | | 33.6% | 58.5% | 71.8% | 56.7% |

Further, several additional examples of compositions containing either no excipients or non-leucine excipients were also produced utilizing various spray-dryer systems (Buchi, Labplant and Niro-based systems) following similar procedures those described above. Selected characterization results for the resultant powders are shown in Table 30 (cells with blank values indicates no value was measured for that powder).

TABLE 30

Non-leucine salt formulations of small, dispersible powders

| Lot | Formulation | Method | x50 (μm) @1 bar | GSD @1 bar | 1/4 bar | 0.5/4 bar | water % | FPF_TD <3.4 um % | FPF_TD <5.6 um % | % Mass collected | yield % |
|---|---|---|---|---|---|---|---|---

TABLE 30-continued

Non-leucine salt formulations of small, dispersible powders

| Lot | Formulation | Method | x50 (μm) @ 1 bar | GSD @ 1 bar | 1/4 bar | 0.5/4 bar | water % | FPF_TD <3.4 um % | FPF_TD <5.6 um % | % Mass collected | yield % |
|---|---|---|---|---|---|---|---|---|---|---|---|
| 27.154.1 | CaCl2:Na2SO4 44:56 | Buchi | 3.1 | 1.9 | 1.3 | | | 14.0% | 31.6% | 55.1% | 50.3% |
| 27.114.6 | CaCl2:Na2SO4:Rhod B 44:56.1 | Niro | 3.9 | 1.9 | 1.0 | | 7.2% | 7.4% | 25.5% | 52.4% | 44.2% |
| 27.114.1 | lact:CaCl2:Na2SO4 90:4.4:5.6 | Niro | 3.9 | 2.5 | 1.2 | | 17.9% | 12.0% | 28.5% | 42.5% | 13.3% |
| 27.114.2 | lact:CaCl2:Na2SO4 50:22:28 | Niro | 4.5 | 2.0 | 1.1 | | 12.6% | 10.2% | 29.1% | 44.5% | 58.0% |
| 27.115.3 | CaSO4 100 | Niro | 3.8 | 1.7 | 1.2 | | 14.0% | 15.8% | 38.2% | 57.0% | 47.5% |
| 27.185.2 | Ca(OH)2:Sulf acid:NaCl 41.3:54.6:4.1 | Buchi | 2.5 | 1.8 | 1.3 | | | 17.5% | 45.2% | 65.2% | 44.1% |
| 27.185.3 | Ca(OH)2:Sulf acid 43:57 | Buchi | 2.9 | 2.3 | 1.1 | | | 15.3% | 38.9% | 59.4% | 16.1% |
| 27.183.1 | CaLact:NaCl 96.8:3.2 | Buchi | 3.1 | 2.0 | 1.1 | | | 22.4% | 50.9% | 69.5% | 35.0% |
| 27.115.2 | CaCl2:Na2CO3 51:49 | Niro | 3.9 | 2.1 | 1.4 | | 1.7% | 8.4% | 22.4% | 38.9% | 27.3% |
| 27.184.3 | CaGluc:NaCl 98.3:1.7 | Buchi | 2.9 | 2.0 | 1.0 | | | 13.5% | 26.7% | 48.3% | 47.6% |
| 27.15.2 | MgCl2:Na3Cit, 36:64 | Labplant | 3.1 | 1.4 | 1.0 | | 13.2% | | | | 28.6% |
| 27.33.3 | MgCl2:Na3Cit, 36:64 | Labplant | 4.0 | 2.2 | 1.2 | | 15.7% | 21.4% | 53.7% | 68.2% | 26.2% |
| 27.15.3 | MgCl2:Na2SO4, 40:60 | Labplant | 3.9 | 2.3 | 1.3 | | 11.1% | | | | 31.8% |
| 27.33.9 | MgCl2:Na2CO3, 47:53 | Labplant | 2.7 | 3.7 | 1.4 | | 7.9% | 21.0% | 46.0% | 58.3% | 18.8% |
| 27.15.4 | MgCl2:Na2CO3, 47:53 | Labplant | 2.3 | 1.4 | 1.1 | | 87.4% | | | | 17.6% |
| 68.124.1 | lact:MgCl2:Na3Cit 10:30.6:59.4 | Buchi HP | | | | | | 18.1% | 37.8% | 55.7% | 88.9% |
| 68.129.2 | MgLact:NaCl 63.4:36.6 | Buchi HP | | | | | | 16.5% | 39.3% | 59.8% | 78.0% |

Table 31 contains characterization data for additional leucine and calcium containing small and dispersible powder compositions made via using a Buchi or a Niro spray-drying system per procedures similar to those described above (cells with blank values indicates no value was measured for that powder).

TABLE 31

Leucine and calcium-containing formulations of small, dispersible particles

| Lot | Formulation | Method | x50 (μm) @ 1 bar | GSD @ 1 bar | 1/4 bar | 0.5/4 bar | water % | FPF_TD <3.4 um % | FPF_TD <5.6 um % | % Mass collected | yield % | Tapped density (g/cc) |
|---|---|---|---|---|---|---|---|---|---|---|---|---|
| | | | | | Chloride | | | | | | | |
| 26.010.2 | leu:CaCl2:NaCl 50:29.5:20.5 | Niro | 4.8 | 2.2 | 1.1 | | | 15.8% | 35.9% | 50.8% | 64.1% | |
| 26.041.3 | leu:CaCl2:NaCl 50:29.5:20.5 | Niro | 4.9 | 2.4 | | | | 14.7% | 28.0% | 43.0% | 50.2% | |
| | | | | | Citrate | | | | | | | |
| 26.013.1 | leu:CaCl2:Na3Cit2 50:19.5:30.5 | Niro | 4.2 | 2.1 | 1.6 | | | 16.8% | 35.2% | 53.8% | 56.1% | |
| 26.013.2 | leu:CaCl2:Na3Cit2 10:35.1:54.9 | Niro | 4.8 | 1.8 | 1.3 | | | 20.8% | 39.6% | 52.2% | 57.5% | |
| 26-190-F | Leucine:CaCl2:Na3Cit2 10.0:35.1:54.9 | Niro | 2.6 | 1.9 | 1.2 | 1.2 | | 45.7% | 61.6% | 66.3% | 74.8% | 0.29 |
| | | | | | Sulfate | | | | | | | |
| 26.013.4 | leu:CaCl2:Na2SO4 10:39.6:50.4 | Niro | 3.7 | 2.0 | 1.4 | | | 19.6% | 39.4% | 60.9% | 73.1% | |
| 26.060.2 | leu:CaCl2:Na2SO4 10:39.6:50.4 | Niro | 2.9 | 1.9 | 1.2 | | | 16.2% | 35.2% | 53.2% | 46.5% | 0.18 |
| 26.060.4 | leu:CaCl2:Na2SO4 10:39.6:50.4 | Niro | 2.9 | 1.7 | 1.3 | | | 18.8% | 45.1% | 64.4% | 49.9% | 0.17 |
| 27.154.2 | leu:CaCl2:Na2SO4 10:39.6:50.4 | Buchi | 3.8 | 1.9 | 1.1 | | | 17.2% | 37.5% | 55.5% | 56.1% | 0.30 |
| 65-009-F | Leucine:CaCl2:Na2SO4 10.0:39.6:50.4 | Niro | 2.5 | 2.2 | 1.4 | 1.5 | | 60.1% | 82.7% | 88.6% | 74.2% | 0.34 |
| 26.053.1 | leucine:CaCl2:Na2SO4 50:22:28 | Niro | 4.2 | 2.0 | 1.5 | | 3.3% | 23.0% | 39.6% | 52.0% | 59.6% | |
| 27.114.4 | leu:CaCl2:Na2SO4 50:22:28 | Niro | 4.7 | 1.8 | 1.9 | | 3.8% | 21.2% | 44.6% | 59.6% | 59.6% | |

TABLE 31-continued

Leucine and calcium-containing formulations of small, dispersible particles

| Lot | Formulation | Method | x50 (μm) @ 1 bar | GSD @ 1 bar | 1/4 bar | 0.5/4 bar | water % | FPF_TD <3.4 um % | FPF_TD <5.6 um % | % Mass collected | yield % | Tapped density (g/cc) |
|---|---|---|---|---|---|---|---|---|---|---|---|---|
| 27.155.1 | leu:CaCl2:Na2SO4 50:22:28 | Buchi | 3.7 | 1.9 | 1.2 | | | 15.7% | 42.9% | 68.8% | 47.6% | 0.35 |
| Calcium sulfate | | | | | | | | | | | | |
| 26.019.4 | leu:CaSO4 50:50 | Niro | 4.1 | 2.1 | 1.4 | | | 11.9% | 28.0% | 56.0% | 101.8% | |
| Carbonate | | | | | | | | | | | | |
| 26.019.1 | leu:CaCl2:NaCO3 50:25.5:24.5 | Niro | 3.4 | 1.9 | 1.7 | | | 9.6% | 22.2% | 35.9% | 46.3% | |
| 26.019.2 | leu:CaCl2:NaCO3 10:45.9:44.1 | Niro | 2.7 | 1.8 | 1.4 | | | 10.6% | 23.8% | 37.5% | 51.0% | |
| Lactate | | | | | | | | | | | | |
| 26.041.4 | leu:CaLact:NaCl 50:36.8:13.1 | Niro | 5.0 | 1.9 | | | | 9.7% | 25.9% | 46.6% | 56.5% | |
| 27.183.2 | Leu:CaLact:NaCl 50:48.4:1.6 | Buchi | 3.7 | 1.8 | 1.1 | | | 24.9% | 48.9% | 62.7% | 34.1% | |
| 27.185.1 | Leu:CaLact:NaCl 10:66.6:23.4 | Buchi | 3.0 | 1.9 | 1.0 | | | 26.1% | 53.7% | 70.0% | 44.8% | |
| 45.19.1 | leu:CaLact:NaCl 10:66.6:23.4 | Buchi HP | 3.4 | 2.3 | 0.9 | | 5.2% | 12.8% | 29.1% | 50.3% | 75.6% | 0.74 |
| 45.76.1 | leu:CaLact:NaCl 10:58.6:31.4 | Buchi HP | 3.8 | 2.1 | 1.0 | | 5.0% | 8.6% | 20.9% | 36.6% | 78.5% | |
| 45.78.1 | leu:CaLact:NaCl 10:58.6:31.4 | Buchi HP | 1.5 | 1.9 | 1.1 | | 4.8% | 30.6% | 53.4% | 62.9% | 60.8% | |
| 45.80.1 | leu:CaLact:NaCl 10:58.6:31.4 | Buchi HP | 1.5 | 1.9 | 1.1 | | 4.4% | 30.3% | 53.5% | 63.8% | 71.0% | |
| 45.81.1 | leu:CaLact:NaCl 10:58.6:31.4 | Buchi HP | 2.4 | 2.8 | 1.3 | | 7.2% | 19.3% | 34.1% | 44.3% | 64.6% | |
| 68.70.1 | leu:CaLact:NaCl 10:58.6:31.4 | Buchi HP | 1.5 | 1.9 | 1.0 | | | 42.8% | 63.2% | 67.8% | 73.9% | |
| 65-003-F | Leucine:CaLact:NaCl 10.0:58.6:31.4 | Niro | 1.5 | 2.5 | 1.1 | 1.1 | | 43.4% | 63.5% | 69.7% | 62.9% | 0.69 |
| Gluconate | | | | | | | | | | | | |
| 27.184.1 | Leu:CaGluc:NaCl 50:49.15:0.85 | Buchi | 3.4 | 2.1 | 1.0 | | | 35.0% | 61.4% | 76.3% | 51.9% | |
| 27.184.4 | leu:CaGluc:NaCl 50:42.35:7.65 | Buchi | 3.5 | 2.0 | 1.2 | | | 34.1% | 60.7% | 71.5% | 46.3% | |
| 27.184.2 | Leu:CaGluc:NaCl 10:88.5:1.5 | Buchi | 2.7 | 2.0 | 1.0 | | | 24.9% | 52.2% | 64.2% | 51.0% | |

Example 19

Pure calcium chloride was spray dried in the LabPlant spray drying system with an inlet temperature of 180° C. The liquid feed consisted of 20 g/L solids concentration of calcium chloride dihydrate in D.I. water. Water condensed in the collection vessel as the calcium chloride deliquesced and no powder could be collected. Pure calcium chloride was deemed too hygroscopic for spray drying from an aqueous solution with high water content in the exhaust drying gas. The liquid feed was then changed to 70% ethanol to reduce humidity in the exhaust gas, keeping the solids concentration at 20 g/L, the inlet temperature at 200° C. and outlet temperature at 69° C. Water still condensed in the collection vessel and the powder looked wet. It was concluded that calcium chloride is too hygroscopic to be spray dried without mixing with other salts or with an excipient to reduce the calcium chloride content in the final powder.

Pure magnesium chloride was spray dried in the Labplant system with an inlet temperature of 195° C. and outlet temperature of 68° C. The liquid feed consisted of 20 g/L solids concentration of magnesium chloride hexahydrate in D.I. water. The dry powder in the collection vessel looked wet and the median particle size measured on the HELOS/RODOS system was 21 microns. The liquid feed was then changed to 70% ethanol to reduce humidity in the exhaust drying gas, keeping the solids concentration at 50 g/L, the inlet temperature at 200° C. and an outlet temperature of 74° C. This magnesium chloride powder did not look wet and had a median volume particle size of 4 microns, but the powder appeared granular and had a fine particle fraction less than 5.6 microns of 19%, indicating that the powder was not sufficiently respirable.

Example 20

Large, Porous Particles

TABLE 32

Large Porous Particle formulations

| Formulation | Method | x50 (μm) @ 1 bar | GSD @ 1 bar | Spray-tec dV50 (μm) | Spraytec GSD | water % | FPF_TD <3.4 um % | FPF_TD <5.6 um % | % Mass collected | yield % | Tap density (g/cc) |
|---|---|---|---|---|---|---|---|---|---|---|---|
| leucine:Cacl2:NaCl 50:29.5:20.5 | Niro | 25.9 | 5.8 | | | | 18.2% | 29.0% | 48.6% | 43.2% | |
| leucine:Cacl2:NaCl 50:29.5:20.5 | Niro | 12.2 | 6.3 | | | | | | | 35.4% | |
| leu:CaCl2:Na2SO4 90:4.4:5.6 | Niro | 10 | 2.4 | | | 1.8% | 5.0% | 16.5% | 34.7% | 84.8% | |
| leu:CaLact:NaCl 10:66.6:23.4 | Buchi HP | | | 22.4 | 4.4 | | 4.9% | 7.3% | 13.1% | 72.0% | |
| leu:CaCl2:Na2SO4 67.6:30:2.4 | Buchi HP | | | 21.2 | 3 | | 13.2% | 25.2% | 47.7% | n/a | 0.22 |

Example 21

Stability

Dry powders were tested for in-use stability under extreme temperature and humidity conditions (ICH, Climatic Zone XIV), defined as 30° C. and 75% RH. Approximately 25 mg of Formulation I, Formulation II and Formulation III were filled into capsules. The capsules were left opened and then were placed in a stability chamber at the defined conditions for 15 and 30 minutes. The capsules were removed at the appropriate time, closed and tested for aerodynamic particle size distribution (aPSD) using the collapsed 2-stage ACI and for geometric particle size distribution (gPSD) using the Malvern Spraytec. Both tests were run at 60LPM for 2 seconds. Each timepoint was repeated n=2. The results were compared with aPSD/gPSD data from the powder at room temperature and 25-30% RH.

All formulations (Formulation I, Formulation II and Formulation III) showed less than +/−5% change from the fine particle fraction of the total dose (FPFTD) less than 5.6 microns at standard conditions (22° C., 25-30% RH), after a 30 minute exposure to extreme temperature and humidity conditions (30° C., 75% RH). For gPSD, Formulation I showed an increase of approximately 30% after 30 minutes, while Formulation II remained mostly stable and Formulation III had a decrease in Dv50 of approximately 15% after 30 minutes.

While insignificant changes in aerosol properties of the three formulations were seen upon exposure to 30° C., 75% RH for 30 minutes, changes in geometric particle size were more evident (FIGS. 31A and 31B). Formulation I (calcium citrate) particle size increased by approximately 30%, while Formulation III (calcium lactate) particle size decreased by approximately 15%. Formulation II (calcium sulfate) particle size decreased, but not significantly.

Additional formulations tested were a calcium chloride powder (38.4% leucine, 30.0% calcium chloride, 31.6% sodium chloride) and the calcium lactate powders using different excipients (lactose, mannitol, maltodextrin) matching the Formulation III formulation (10.0% excipient, 58.6% calcium lactate, 31.4% sodium chloride).

After a 30 minute exposure to extreme temperature and humidity conditions (30° C., 75% RH), the maltodextrin (Formulation IV) and mannitol formulations showed an overall change of less than +/−10% change from the fine particle fraction of the total dose smaller than 5.6 microns at standard conditions (22° C., 25-30% RH). The calcium chloride powder and lactose formulation appeared affected with a decrease of over 50% and an increase of approximately 20%, respectively, in fine particle fraction of the total dose smaller than 5.6 microns. (FIG. 31C) For gPSD, the results were opposite, where the calcium chloride powder and the lactose formulation showed an overall change of less than +/−10% change in $Dv_{50}$ after 30 minutes, while the mannitol formulation had an increase in $Dv_{50}$ of 30%-60% during the test. (FIG. 31D) The maltodextrin formulation was not tested for change in $Dv_{50}$.

Example 22

Short-Term Stability at Room Temperature and 30% and 40% RH

Spray dried powders were kept at room temperature at approximately 30% and 40% RH for a period of one week and periodically tested for particle size distribution. Size 3 HPMC capsules (Quali-V, Qualicaps, Whitsett, N.C.) were half filled with each dry powder. One sample was tested immediately in the Spraytec (Malvern Instruments Inc., Westborough, Mass.), a laser diffraction spray particle sizing system where dry powders can be dispersed from an inhaler using the inhaler cell setup. Approximately 16 capsules were filled with each powder. Half of the capsules were kept in the lab at controlled humidity and temperature conditions (~23-28% RH), while the other half were kept in the outside lab at varying temperature and relative humidity (~38-40% RH). At specific time points (t=1 hr, 2 hr, 4 hr, 24 hr, 48 hr, 1 week), one capsule from the environmental controlled room and one from the outside lab were tested on the Spraytec for volume particle size distribution.

Results for a selection of formulations containing 50% leucine and a combination of calcium chloride and the sodium salt indicated are shown in FIG. 32 and FIG. 33. The formulations containing calcium chloride and sodium chloride showed significant agglomeration after exposure to higher humidity conditions. The acetate formulation had variable results at the initial time points. The sulfate, citrate and carbonate formulations demonstrated good relative stability over the test period.

Dry powder formulations containing calcium chloride and sodium chloride were not stable when held at room temperature and 40% RH after an hour of exposure, while the acetate formulation also showed variable results in particle size. The sulfate and lactate powders increased slightly in size, while carbonate and citrate powders decreased slightly in size. Formulations containing only chloride and those containing acetate were not deemed suitably stable for further study.

Example 23

Dry Powder Flow Properties

The flowability of Formulation I, II, III and IV powders was also assessed using conventional methods in the art for the characterization of powder flowability. The Flowability Index for each powder was determined using a Flodex Powder Flowability Test Instrument (Hanson Research Corp., model 21-101-000). For any given run, the entire sample was loaded using a stainless steel funnel aimed at the center of the trap door hole in the cylinder. Care was taken not to disturb the column of powder in the cylinder. After waiting ~30 sec for the potential formation of flocculi, the trap door was released while causing as little vibration to the apparatus as possible. The test was considered a pass if the powder dropped through the trap door so that the hole was visible looking down through the cylinder from the top and the residue in the cylinder formed an inverted cone; if the hole was not visible or the powder fell straight through the hole without leaving a cone-shaped residue, the test failed. Enough flow discs were tested to find the minimum size hole the powder would pass through, yielding a positive test. The minimum-sized flow disc was tested two additional times to obtain 3 positive tests out of 3 attempts. The flowability index (FI) is reported as this minimum-sized hole diameter.

Bulk and tap densities were determined using a SOTAX Tap Density Tester model TD2. For any given run, the entire sample was introduced to a tared 100-mL graduated cylinder using a stainless steel funnel. The powder mass and initial volume ($V_0$) were recorded and the cylinder was attached to the anvil and run according to the USP I method. For the first pass, the cylinder was tapped using Tap Count 1 (500 taps) and the resulting volume $V_a$ was recorded. For the second pass, Tap Count 2 was used (750 taps) resulting in the new volume $V_{b1}$. If $V_{b1}$>98% of $V_a$, the test was complete, otherwise Tap Count 3 was used (1250 taps) iteratively until $V_{bn}$>98% of $V_{bn-1}$. Calculations were made to determine the powder bulk density ($d_B$), tap density ($d_T$), Hausner Ratio (H) and Compressibility Index (C), the latter two of which are standard measures of powder flowability. "H" is the tap density divided by the bulk density, and "C" is 100*(1−(bulk density divided by the tap density)). Skeletal Density measurement was performed by Micromeritics Analytical Services using an Accupyc II 1340 which used a helium gas displacement technique to determine the volume of the powders. The instrument measured the volume of each sample excluding interstitial voids in bulk powders and any open porosity in the individual particles to which the gas had access. Internal (closed) porosity was still included in the volume. The density was calculated using this measured volume and the sample weight which was determined using a balance. For each sample, the volume was measured 10 times and the skeletal density ($d_s$) was reported as the average of the 10 density calculations with standard deviation.

Results for these density and flowability tests are shown in Tables 34 and 35. All four of the powders tested possess Hausner Ratios and Compressibility Indices that are described in the art as being characteristic of powders with extremely poor flow properties (See, e.g., USP <1174>). It is thus surprising that these powders are highly dispersible and possess good aerosolization properties as described herein.

TABLE 33

Bulk and tap densities and flow properties of Formulation I-IV powders.

| Sample | FI (mm) | $d_B$ (g/mL) | $d_T$ (g/mL) | H | C |
|---|---|---|---|---|---|
| Formulation I | 26 | 0.193 | 0.341 | 1.77 | 43.4% |
| Formulation III | 22 | 0.313 | 0.722 | 2.31 | 56.7% |
| Formulation II | 18 | 0.177 | 0.388 | 2.19 | 54.3% |
| Formulation IV | >34 | 0.429 | 0.751 | 1.75 | 42.9% |

TABLE 34

Skeletal density measurements of powders Formulation I-IV.

| Sample | $d_{S1} \pm \sigma$ (g/mL) | $d_{S2} \pm \sigma$ (g/mL) |
|---|---|---|
| Formulation I | 1.7321 ± 0.0014 | 1.7384 ± 0.0042 |
| Formulation III | 1.6061 ± 0.0007 | 1.6074 ± 0.0004 |
| Formulation II | 2.1243 ± 0.0011 | 2.1244 ± 0.0018 |
| Formulation IV | 1.6759 ± 0.0005 | 1.6757 ± 0.0005 |

USP <1174> mentioned previously notes that dry powders with a Hausner Ratio greater than 1.35 are poor flowing powders. Flow properties and dispersibility are both negatively effected by particle agglomeration or aggregation. It is therefore unexpected that powders with Hausner Ratios of 1.75 to 2.31 would be highly dispersible

Example 24

Water Content and Hygroscopicity

The water content of Formulation I, II, III and IV powders was determined via both thermogravimetric analysis (TGA) and Karl Fischer analysis. Thermogravimetric analysis (TGA) was performed using a TA Instruments Q5000 IR thermogravimetric analyzer (New Castle, Del.). Sample was placed in an aluminum sample pan and inserted into the TG furnace. The data acquisition and processing parameters are displayed on each thermogram. Nickel and Alumel™ were used as the calibration standards. For TGA, the water content was determined from the loss of mass of the samples upon heating to a temperature of 150° C. (for TGA, since the spray-drying solvent used was 100% water, it was assumed that only water was present as a volatile component in these powders). A representative TGA thermogram for powder Formulation I is shown in FIG. 34 Coulometric Karl Fischer (KF) analysis for water determination was performed using a Mettler Toledo DL39 KF titrator (Greifensee, Switzerland). Sample was placed in the KF titration vessel containing Hydranal-Coulomat AD and mixed for 10 seconds to ensure dissolution. The sample was then titrated by means of a generator electrode which produces iodine by electrochemical oxidation: 2 I−=> $I_2$+2e. Generally, one range-finding run and two replicates were obtained to ensure reproducibility. Summary data for powder water contents using these methods are shown in Table 35.

TABLE 35

Water content data for FORMUALTIONS I, II, III and IV via TGA and Karl Fischer.

| Powder | Water Content via TGA | Water Content via Karl Fischer |
|---|---|---|
| Formulation I | 4.9% | 3.9% |
| Formulation III | 2.0% | 2.0% |
| Formulation II | 5.1% | 4.6% |
| Formulation IV | 2.2% | 2.1% |

A dynamic vapor sorption (DVS) step mode experiment was conducted to compare the hygroscopicity and water uptake potential of Formulation I, II, III and IV powders versus raw calcium chloride dihydrate, as well as a 1:2 calcium chloride:sodium chloride control powder made via spray-drying a formulation containing 38.4% leucine, 30.0% $CaCl_2$ and 31.6% NaCl (it was determined that 30 wt % was the highest loading level of calcium chloride that could be successfully incorporated into a spray-dried powder without undergoing deliquescence in the collection vehicle immediately after spray-drying). With respect to the DVS operating conditions, the powders were initially equilibrated at 0% RH then exposed to 30% RH for 1 hour followed by exposure to 75% RH for 4 hours. The mass % water uptake for each of the powders is shown in Table 36. As can be seen in Table 36, both raw calcium chloride dihydrate and the control powder were extremely hygroscopic, taking up approximately 14 to 15% water upon exposure to 30% RH for 1 hour and taking up well over 100% their mass in water after exposure to 75% RH. In contrast, the Formulation I, II, III and IV powders took up less than 2.5% water upon exposure to 30% RH for 1 hour and from 14% to 33% water upon exposure to 75% RH for 4 hours.

TABLE 36

% Change in mass due to water uptake after (i) 30% RH hold for 1 hour and (ii) 75% RH hold for 4 hours via DVS.

| Powder | % Change in Mass Due to Water Uptake after 30% RH for 1 hr | % Change in Mass Due to Water Uptake after 75% RH for 4 hrs |
|---|---|---|
| $CaCl_2*2H_2O$ (raw) | 13.7 | 146 |
| $CaCl_2$—control | 15.3 | 124 |
| Formulation I | 1.68 | 14.7 |
| Formulation III | 1.27 | 28.3 |
| Formulation II | 2.45 | 20.8 |
| Formulation IV | 1.36 | 32.8 |

Example 25

Heat of Solution

Heats of solution were obtained upon dissolution of samples of Formulations I through III in HBSS buffer in comparison to (i) a control powder comprised of 30% calcium chloride, 31.6% sodium chloride and 38.4% leucine, (ii) raw calcium chloride dihydrate and (iii) raw leucine. Heats of solution were also obtained for Formulations VII and VIII using the same method.

Figure 35:
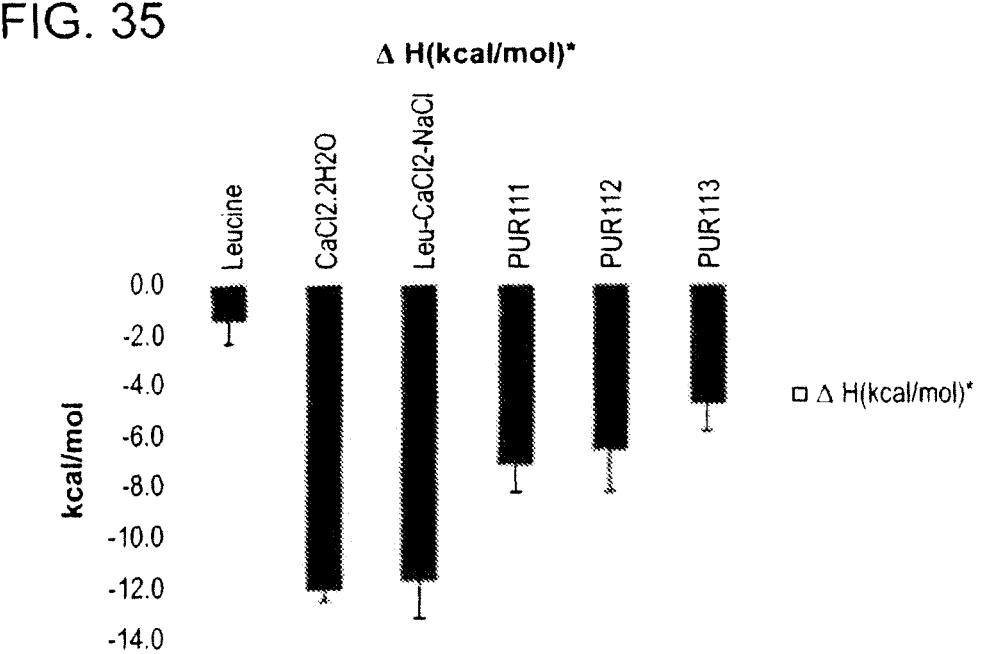
FIG. 35 is a graph showing heats of solution obtained upon dissolution of Formulations I through III. Formulations I through III resulted in significantly decreased heats of solution as compared to both raw calcium chloride dihydratedihydrate and a control calcium chloride:sodium chloride:leucine powder.

As shown in Table 37, masses of Formulation I, II, and III powder containing equivalent moles of calcium ion were tested for the calcium-containing samples. Results are shown in FIG. 35. As can be seen from the data shown in FIG. 35, Formulations I through III resulted in significantly decreased heats of solution as compared to both raw calcium chloride dihydrate and the control calcium powder. Calcium chloride dihydrate is known to possess a large exothermic heat of solution and to release a significant amount of heat upon contact with water. Under certain circumstances, such as when a large quantity of calcium chloride dihydrate, or other salts that have a large exothermic heat of solution, are rapidly dissolved a large amount of heat is released that can cause burns. Thus, there are safety concerns associated with contacting mucosal surfaces with calcium chloride dihydrate. These safety concerns can be alleviated by producing powders, such as Formulations I through III which do not have large exothermic heats of solution, and thus reduced potential for undesirable exothermic effects.

In Table 37, Formulations I, II, III, VII, and VIII had ΔH (kcal/mol) of −6.9, −8.3, −4.3, −3.6, and −4.4. Calcium chloride dehydrate was used as a control in both experiments, i.e. the first experiment, when Formulations I, II, and III were tested, and the second experiment, when Formulations VII and VIII were tested. The calcium chloride dehydrate had a ΔH (kcal/mol) of −12.1 in the first experiment, and a ΔH (kcal/mol) of −8.4 in the second experiment.

Like for Formulations I, II, and III, which each had a relatively low heat of solution compared to calcium chloride dehydrate, Formuations VII and VIII also had a relatively low heat of solution compared to calcium chloride dehydrate. Thus, dry powder Formulations VII and VIII which do not have large exothermic heats of solution, have a reduced potential for undesirable exothermic effects.

TABLE 37

Heat of solution data for Formulations I-III and VII-VIII, a control powder containing calcium chloride, raw calcium chloride dihydrate and raw leucine.

| Powder | Leucine | | CaCl2•2H2O (experiment #1) | | Leu-CaCl2—NaCl | |
|---|---|---|---|---|---|---|
| | Average | St. Dev. | Average | St. Dev. | Average | St. Dev. |
| g | 0.032 | 0.000 | 0.036 | 0.001 | 0.090 | 0.001 |
| mmol* | 0.244 | 0.001 | 0.242 | 0.004 | 0.242 | 0.001 |
| ΔT (deg. C.) | 0.003 | 0.002 | 0.024 | 0.001 | 0.023 | 0.003 |
| Q (cal) | 0.37 | 0.20 | 2.93 | 0.12 | 2.8 | 0.3 |

TABLE 37-continued

Heat of solution data for Formulations I-III and VII-VIII, a control powder containing calcium chloride, raw calcium chloride dihydrate and raw leucine.

| ΔH (kcal/mol)* | −1.5 | 0.8 | −12.1 | 0.4 | −11.7 | 1.4 |
|---|---|---|---|---|---|---|
| ΔH (kJ/mol)* | −6 | 4 | −50.5 | 1.6 | −49 | 6 |

*mol Ca for all powders except leucine, which is in mol Leu

| | Formulation I | | Formulation II | | Formulation III | |
|---|---|---|---|---|---|---|
| Powder | Average | St. Dev. | Average | St. Dev. | Average | St. Dev. |
| g | 0.077 | 0.000 | 0.032 | 0.000 | 0.090 | 0.000 |
| mmol* | 0.242 | 0.001 | 0.115 | 0.001 | 0.242 | 0.001 |
| ΔT (deg. C.) | 0.014 | 0.002 | 0.008 | 0.002 | 0.009 | 0.002 |
| Q (cal) | 1.7 | 0.2 | 1.0 | 0.3 | 1.0 | 0.3 |
| ΔH (kcal/mol)* | −6.9 | 1.0 | −8.3 | 2.5 | −4.3 | 1.1 |
| ΔH (kJ/mol)* | −29 | 4 | −35 | 10 | −18 | 4 |

*mol Ca for all powders

Example 26

In Vivo Pneumonia Model

Bacteria were prepared by growing cultures on tryptic soy agar (TSA) blood plates overnight at 37° C. plus 5% $CO_2$. Single colonies were resuspended to an $OD_{600}$ ~0.3 in sterile PBS and subsequently diluted 1:4 in sterile PBS (~$2\times10^7$ Colony forming units (CFU)/mL). Mice were infected with 50 μL of bacterial suspension (~$1\times10^6$ CFU) by intratracheal instillation while under anesthesia.

C57BL6 mice were exposed to aerosolized liquid formulations in a whole-body exposure system using either a high output nebulizer or Pari LC Sprint nebulizer connected to a pie chamber cage that individually holds up to 11 animals. Mice were treated with dry powder formulations (Table 38) 2 h before infection with S. pneumoniae. As a control, animals were exposed to a similar amount of 100% leucine powder. Twenty-four hours after infection mice were euthanized by pentobarbital injection and lungs were collected and homogenized in sterile PBS. Lung homogenate samples were serially diluted in sterile PBS and plated on TSA blood agar plates. CFU were enumerated the following day.

Figure 36:
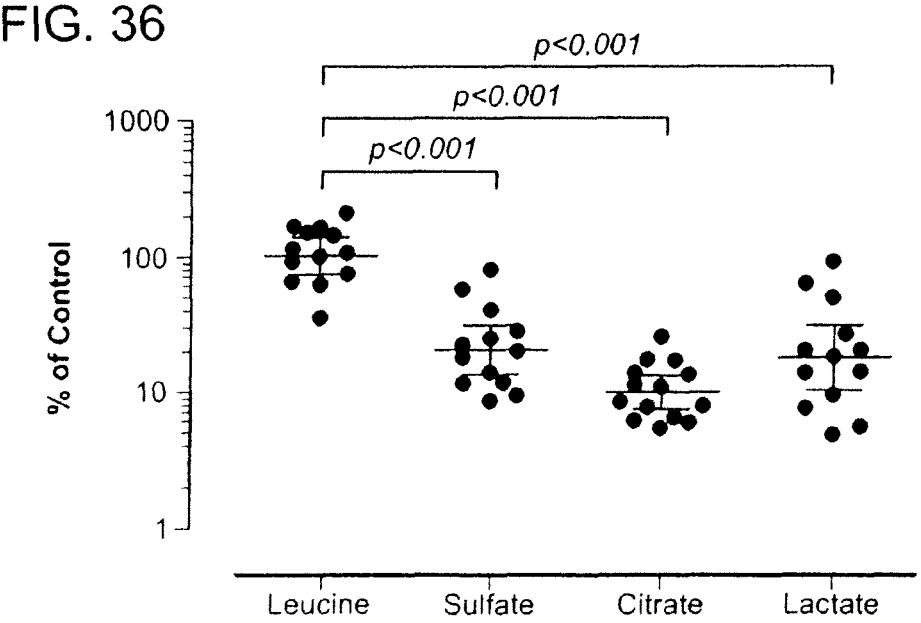
FIG. 36 is a graph showing the results of an in vivo pneumonia study. Animals treated with Formulation II (calcium sulfate) exhibited 5-fold lower bacterial titers, animals treated with Formulation I (calcium citrate) exhibited 10.4-fold lower bacterial titers, and animals treated with Formulation III (calcium lactate) exhibited 5.9-fold lower bacterial titers.

Compared to control animals, calcium dry powder treated animals exhibited reduced bacterial titers 24 hours after infection. Specifically, animals treated with a formulation comprised of calcium sulfate and sodium chloride (Formulation II) exhibited 5-fold lower bacterial titers, animals treated with a formulation comprised of calcium citrate and sodium chloride (Formulation I) exhibited 10.4-fold lower bacterial titers, and animals treated with a formulation comprised of calcium lactate and sodium chloride (Formulation III) exhibited 5.9-fold lower bacterial titers. (FIG. 36)

TABLE 38

Formulations used to evaluate efficacy

| Formulation | Composition |
|---|---|
| Formulation I | 10.0% leucine, 35.1% calcium chloride, 54.9% sodium citrate (Active with 12.7% calcium ion) |
| Formulation II | 10.0% leucine, 39.6% calcium chloride, 50.4% sodium sulfate (Active with 14.3% calcium ion) |
| Formulation III | 10.0% leucine, 58.6% calcium lactate, 31.4% sodium chloride (Active with 10.8% calcium ion) |

The data presented herein show that divalent metal cation salt-containing dry powders that are highly dispersible can be manufactured and used to treat bacterial and viral infections.

Example 27

3 Month Refrigerated, Standard and Accelerated Conditions Stability Study

A 3 month physical stability study was conducted utilizing representative samples of Formulations I through III filled into size 3 HPMC capsules (Shionogi Qualicaps, Madrid, Spain) and placed at the following conditions (i) 2-8° C. refrigerated storage, (ii) 25° C./60% RH, capsules stored under desiccant and (iii) 40° C./75% RH, capsules stored under desiccant. FPF <5.6 and 3.4 as well as Dv50 (Spraytec) and water content (Karl Fischer) were monitored out to a 3 month timepoint. As shown in Table 39, each of Formulations I through III displayed good stability with respect to the assessed physical properties under each of these conditions.

TABLE 39

3 month stability study results for Formulations I-III.

| | | Formulation I | | | | Formulation III | | | |
|---|---|---|---|---|---|---|---|---|---|
| Condition (° C./% RH) | Time (mo) | FPF < 3.4 μm | FPF < 5.6 μm | Spraytec Dv50 (μm) | Water content | FPF < 3.4 um | FPF < 5.6 um | Spraytec Dv50 (um) | Water content |
| Time zero | 0 | 50% | 63% | 3.1 | 6% | 42% | 61% | 1.8 | 4% |
| 25 C./60% RH | 1 | 47% | 68% | 1.5 | 7% | 42% | 60% | 2.0 | 4% |
| | 3 | 45% | 68% | 3.5 | 7% | 42% | 61% | 1.2 | 4% |

TABLE 39-continued 3 month stability study results for Formulations I-III.

| | | | | | | | | | |
|---|---|---|---|---|---|---|---|---|---|
| 40 C./75% RH | 0.5 | 43% | 66% | 5.3 | 8% | 39% | 58% | 1.8 | 6% |
| | 1 | 43% | 65% | 2.0 | 7% | 40% | 58% | 3.0 | 4% |
| | 3 | 46% | 68% | 3.3 | 7% | 47% | 61% | 1.5 | 4% |
| 2-8 C. | 3 | 46% | 60% | 2.4 | 5% | 43% | 63% | 1.3 | 2% |

| | Formulation II | | | |
|---|---|---|---|---|
| Condition (° C./% RH) | FPF < 3.4 um | FPF < 5.6 um | Spraytec (um) | Water content |
| Time zero | 55% | 73% | 3.1 | 5% |
| 25 C./60% RH | 56% | 74% | 3.6 | 6% |
| 40 C./75% RH | 57% | 73% | 2.4 | 6% |
| | 51% | 67% | 2.9 | 6% |
| | 56% | 70% | 3.9 | 5% |
| | 45% | 64% | 2.5 | 5% |
| 2-8 C. | 56% | 76% | 2.3 | 5% |

Formulations I and III were also tested for stability with bulk powder in vials stored with dessicant. Dry powders were produced by spray drying utilizing a Niro Mobile Minor spray dryer (GEA Process Engineering Inc., Columbia, Md.) with powder collection from a product filter. Atomization of the liquid feed was performed using a Spraying Systems (Carol Stream, Ill.) two-fluid nozzle with gas cap 67147 and fluid cap 2850SS. The liquid feed was fed using gear pumps (Cole-Parmer Instrument Company, Vernon Hills, Ill.) directly into a static mixer (Charles Ross & Son Company, Hauppauge, N.Y.) immediately before introduction into the two-fluid nozzle. Nitrogen was used as the drying gas. Pressurized nitrogen or air can be used as the atomization gas feed to the two-fluid nozzle. The process gas inlet temperature was 282° C. and outlet temperature was approximately 98° C. with a liquid feedstock rate of 70 mL/min. The process gas rate was 80 kg/hr and the atomization gas rate was set to 80 g/min. The atomizing gas rate can be set to achieve a certain gas to liquid mass ratio, which directly affects the droplet size created. The pressure inside the drying drum was −2 "WC. Spray dried powders were collected onto a powder collection filter. The liquid feedstock was prepared using 15 g/L solids concentration dissolved in ultrapure water.

A 6 month physical stability study was then conducted with the powders utilizing representative samples of Formulations I, H and III placed in bulk in 20 mL scintillation vials (Kimble, Vineland, N.J.) stored at the following conditions (i) 2-8° C. refrigerated storage in a Dri-Shield 3000 foil pouch (3M, Sanford, N.C.) with desiccant (MoistureBarrierBags.com; Concord, N.C.), (ii) 25° C./60% RH, kept in a Desi-Vac container (Control Company, Friendswood, Tex.) with desiccant (Fischer Scientific, Pittsburgh, Pa.) (iii) 40° C./75% RH, kept in a Desi-Vac container with desiccant.

FPF_TD (%)<5.6 μm and 3.4 μm, as well as Dv50 (Spraytec), calcium and sodium content (HPLC) and water content (Karl Fischer) were monitored out to a 2 month timepoint for conditions (i) and (ii); and to 6 months for condition (iii). As shown in Tables 41, 42 and 43, each of Formulations I and III displayed good stability with respect to the assessed physical properties under each of these conditions.

TABLE 40

Long-term stability of Formulation I powder in bulk with dessicant.

| Condition (° C./ % RH) | Time (mo) | FPF_TD <3.4 μm | FPF_TD <5.6 μm | Dv50 (μm) | $Ca^{2+}$ content (wt %) | $Na^+$ content (wt %) | $H_20$ content (wt %) |
|---|---|---|---|---|---|---|---|
| Time zero | 0 | 57% | 68% | 2.7 | 11.8% | 13.6% | 6.2% |
| 25° C./60% | 0.5 | 57% | 67% | 2.9 | 12.0% | 13.8% | 6.1% |
| RH | 1 | 57% | 67% | 2.0 | 12.2% | 13.9% | 6.2% |
| | 2 | 52% | 64% | 2.7 | 11.5% | 13.4% | 6.3% |
| 40° C./75% | 0.5 | 57% | 69% | 2.7 | 11.8% | 13.5% | 6.3% |
| RH | 1 | 54% | 66% | 2.1 | 12.0% | 13.8% | 6.2% |
| | 2 | 52% | 64% | 2.7 | 11.8% | 13.7% | 6.4% |
| | 6 | 51% | 64% | 2.9 | 12.0% | 13.8% | 6.5% |
| 2-8° C. | 0.5 | 58% | 69% | 2.6 | 12.0% | 13.8% | 6.2% |
| | 1 | 57% | 68% | 1.8 | 12.0% | 13.9% | 6.1% |
| | 2 | 56% | 65% | 2.5 | 11.8% | 13.7% | 6.2% |

TABLE 41

Long-term stability of Formulation III powder in bulk with dessicant.

| Condition (° C./ % RH) | Time (mo) | FPF_TD <3.4 μm | FPF_TD <5.6 μm | Dv50 (μm) | $Ca^{2+}$ content (wt %) | $Na^+$ content (wt %) | $H_20$ content (wt %) |
|---|---|---|---|---|---|---|---|
| Time zero | 0 | 47% | 64% | 1.5 | 10.4% | 11.6% | 2.9% |
| 25° C./ | 0.5 | 48% | 64% | 2.1 | 10.6% | 11.7% | 2.9% |
| 60% RH | 1 | 50% | 64% | 1.1 | 10.6% | 12.1% | 2.8% |
| | 2 | 45% | 61% | 1.3 | 10.5% | 11.7% | 2.8% |
| 40° C./ | 0.5 | 50% | 64% | 1.7 | 10.2% | 11.4% | 2.7% |
| 75% RH | 1 | 50% | 65% | 1.4 | 10.5% | 12.1% | 2.8% |
| | 2 | 46% | 61% | 1.4 | 10.5% | 11.6% | 3.2% |
| | 6 | 47% | 63% | 1.6 | 10.7% | 11.9% | 3.0% |
| 2-8° C. | 0.5 | 50% | 65% | 1.8 | 10.4% | 11.6% | 2.8% |
| | 1 | 50% | 65% | 1.2 | 10.8% | 12.3% | 2.8% |
| | 2 | 47% | 61% | 1.4 | 10.6% | 11.8% | 2.9% |

The liquid feedstock was prepared as a batch by dissolving leucine in ultrapure water, then the calcium lactate, and finally the sodium chloride. All chemicals were obtained from Spectrum Chemicals (Gardena, Calif.). The solution was kept agitated throughout the process until the materials were completely dissolved in the water at room temperature. Dry powder was produced by spray drying utilizing a Niro Mobile Minor spray dryer (GEA Process Engineering Inc., Columbia, Md.) with powder collection from a product filter. Atomization of the liquid feed was performed using a Spraying Systems (Carol Stream, Ill.) two-fluid nozzle with gas cap 67147 and fluid cap 2850SS. The liquid feed was fed using gear pumps (Cole-Parmer Instrument Company, Vernon Hills, Ill.) directly into a static mixer (Charles Ross & Son Company, Hauppauge, N.Y.) immediately before introduction into the two-fluid nozzle. Nitrogen was used as the drying gas. The process gas inlet temperature was 263° C. to 267° C. and outlet temperature 98° C. to 100° C. with a liquid feedstock rate of 66 mL/min. The process gas rate was 80 kg/hr and the atomization gas rate was set to 80 g/min. The atomizing gas rate can be set to achieve a certain gas to liquid mass ratio, which directly affects the droplet size created. The pressure inside the drying drum was approximately −2 "WC. Spray dried powders were collected onto a product collection filter. The liquid feedstock was prepared using 15 g/L solids concentration dissolved in ultrapure water.

A 3 month physical stability study was conducted utilizing representative samples of Formulation II hand-filled into size 3 HPMC capsules (Capsugel, Greenwood, N.C.) placed in bulk in 20 mL HDPE bottles (Nolato, Trollhättan, Sweden) with desiccant (2.4 g silica gel) in the cap. The bottles were packaged in a heat sealed Dri-Shield 3000 foil pouch (3M, Sanford, N.C.) and stored at the following conditions (i) 2-8° C. refrigerated, (ii) 25° C./60% RH, (iii) 40° C./75% RH.

FPF_TD (%)<5.6 µm and 3.4 µm, as well as Dv50 (Spraytec), calcium and sodium content (HPLC) and water content (Karl Fischer) were monitored out to a 3 month timepoint for all conditions. As shown in Table 42 Formulation II is susceptible to a decrease in water content caused by the desiccant in the cap, but it still displayed good stability with respect to the assessed physical properties under each of these conditions.

TABLE 42

Long term stability of a Formulation III powder in HDPE bottles in foil pouch.

| Condition (° C./% RH) | Time (mo) | FPF_TD <3.4 µm | FPF_TD <5.6 µm | Dv50 (µm) | $Ca^{2+}$ content (wt %) | $Na^+$ content (wt %) | $H_2O$ content (wt %) |
|---|---|---|---|---|---|---|---|
| Time zero | 0 | 42% | 60% | 1.5 | 10% | 12% | 3.7% |
| 25° C./60% RH | 1 | 42% | 59% | 1.7 | 11% | 12% | 1.9% |
|  | 3 | 43% | 61% | 1.3 | 11% | 13% | 1.8% |
| 40° C./75% RH | 1 | 42% | 59% | 1.7 | 11% | 12% | 1.8% |
|  | 3 | 42% | 61% | 1.4 | 11% | 13% | 4.2% |
| 5° C. | 1 | 43% | 60% | 1.8 | 11% | 12% | 2.3% |
|  | 3 | 44% | 62% | 1.3 | 11% | 12% | 2.0% |

In addition, Formulation III was further tested for long term stability capped in vials with desiccant. A 6 month physical stability study was conducted utilizing representative samples of Formulation III hand-filled into size 3 HPMC capsules (Capsugel, Greenwood, N.C.) placed in 20 mL scintillation vials (Kimble, Vineland, N.J.) stored at the following conditions (i) 2-8° C. refrigerated storage in a PE Bag (Fischer Scientific, Pittsburgh, Pa.) with a desiccant sponge (Fischer Scientific, Pittsburgh, Pa.) stored as hulk powder and not encapsulated, (ii) 25° C./60% RH, kept in a Desi-Vac container (Control Company, Friendswood, Tex.) with desiccant (Fischer Scientific, Pittsburgh, Pa.) and (iii) 40° C./75% RH, kept in a Desi-Vac container with desiccant.

FPF_TD (%)<5.6 µm and 3.4 µm, as well as Dv50 (Spraytec), and water content (Karl Fischer) were monitored out to a 6 month timepoint for all conditions. As shown in Table 43 Formulation III displayed good stability with respect to the assessed physical properties under each of these conditions.

TABLE 43

Formulation III: Long term stability with dessicant.

| Condition (° C./% RH) | Time (mo) | FPF_TD <3.4 µm | FPF_TD <5.6 µm | Dv50 (µm) | $H_2O$ content (wt %) |
|---|---|---|---|---|---|
| Time zero | 0 | 42% | 61% | 1.8 | 4% |
| 25° C./60% RH | 1 | 42% | 60% | 2.0 | 4% |
|  | 3 | 42% | 61% | 1.2 | 4% |
|  | 6 | 42% | 61% | 1.5 | 3% |
| 40° C./75% RH | 0.5 | 39% | 58% | 1.8 | 6% |
|  | 1 | 40% | 58% | 3.0 | 4% |
|  | 3 | 47% | 61% | 1.5 | 4% |
|  | 6 | 39% | 59% | 1.7 | 4% |
| 2-8° C. | 3 | 43% | 63% | 1.3 | 2% |
|  | 6 | 44% | 63% | 1.6 | 2% |

Example 28

Effect of Dry Powder Dose on its Efficacy Against Ferret Influenza

Dry powders comprising calcium and sodium were previously shown to reduce the severity of flu in an in vivo model of ferret flu (see Example 11). Using this ferret flu model, the efficacy of increasing doses of Formulation III was tested (10.0% leucine, 58.6% calcium lactate, 31.4% sodium chloride; 10.8% calcium ion). Control ferrets were exposed to a powder comprised of 100% leucine under the same exposure conditions; in vitro this control powder had no effect on viral replication. Several doses of Formulation III and the leucine control powder were aerosolized with a Palas Rotating Brush Generator 1000 solid particle disperser (RBG, Palas GmbH, Karlsruhe, Germany), exposing the ferrets (n=8 per group) in a nose-only exposure system 1 hour before infection, 4 hours after infection and then twice daily (BID) for 4 days (days 1-4). The study was terminated on day 10. Nasal wash samples were collected on days 1, 2, and 4 of the study and subcutaneous body temperatures and body weights were determined twice a day beginning on day 0 of the study. Body temperatures taken on days −3, −2 and −1 were used as baseline temperatures from which to calculate the change from baseline for each animal over the course of the study. The number of inflammatory cells and the viral titer in nasal wash samples were determined. Ferrets infected with influenza typically show increases in body temperature within 2 days of infection, drop body weight over the course of the study and show clinical signs of infection such as lethargy and sneezing. These changes coincide with an increase in influenza viral titers shed from the nasal cavity and increases in nasal inflammation.

Figure 2:
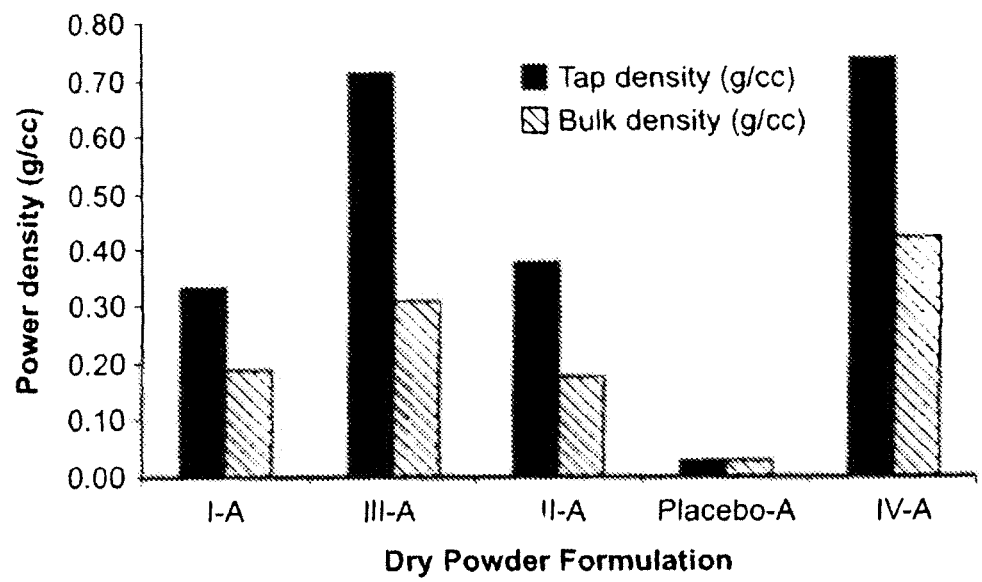
FIG. 2 is a graph that shows a comparison between the average tap and bulk densities for particles prepared from feedstock Formulations I, II and III and a placebo.
Figure 3:
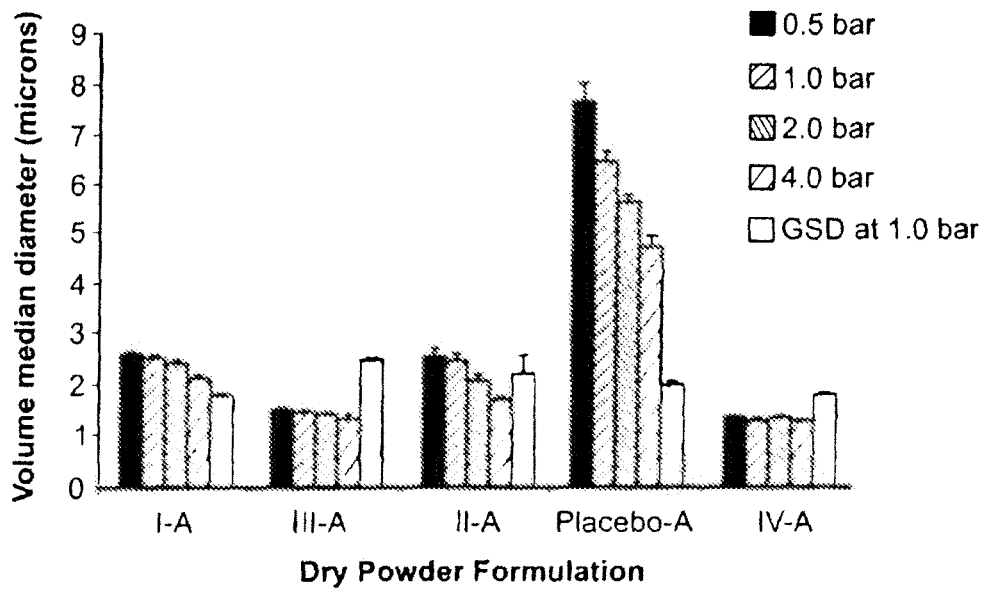
FIG. 3 is a graph that shows a comparison between the particles (prepared from feedstock Formulations I-III and a placebo) at different dispersion (regulator) pressures for measured volume median geometric diameter (x50) using a laser diffraction instrument (HELOS with RODOS).
Figure 4:
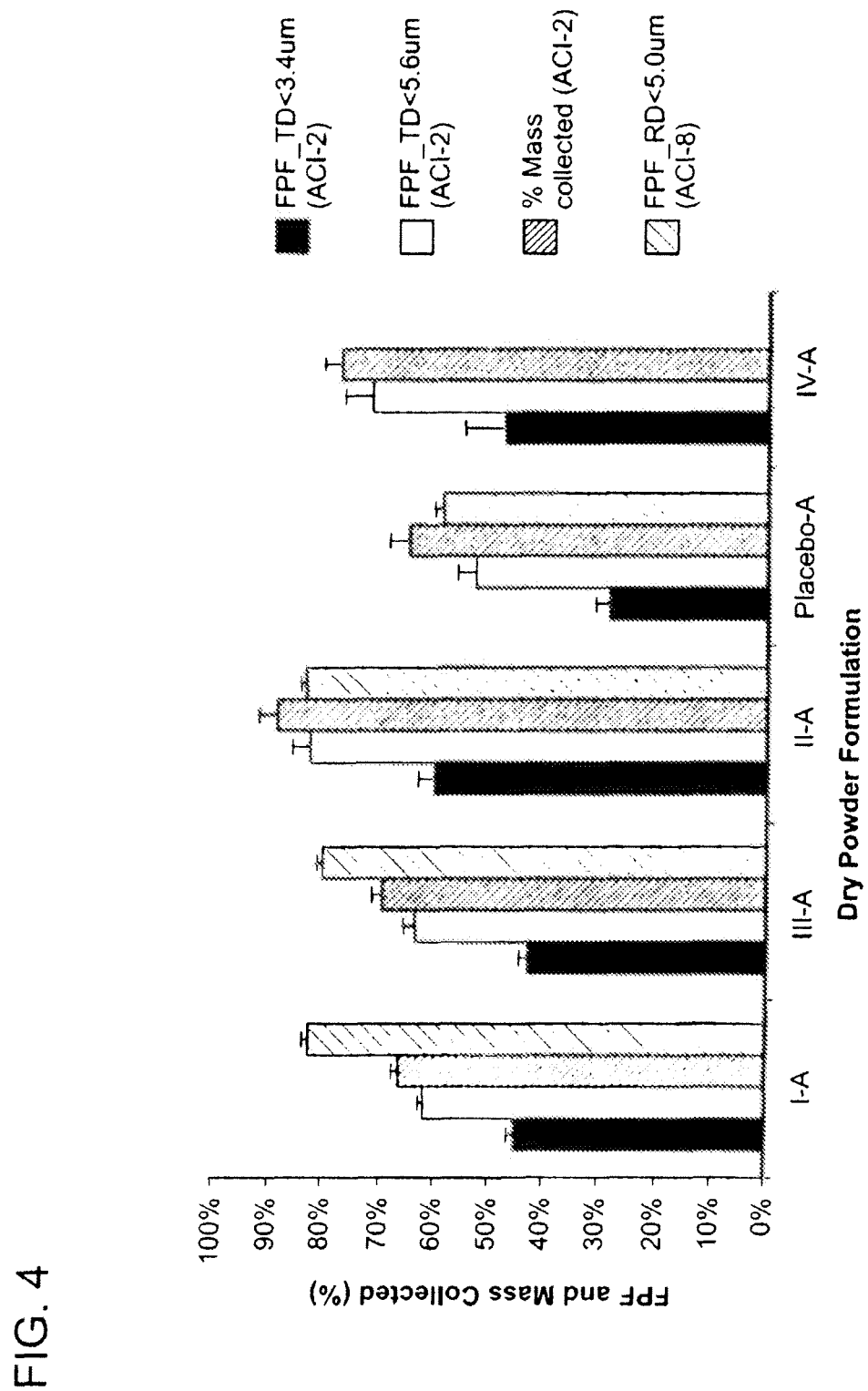
FIG. 4 is a graph that shows a comparison between the particles prepared from feedstock Formulations I (identified as PUR111 (Citrate)), II (identified as PUR112 (Sulfate)) and III (identified as PUR113 (Lactate)) and a placebo for average FPF obtained by an ACI-2 and ACI-8.
Figure 38A:
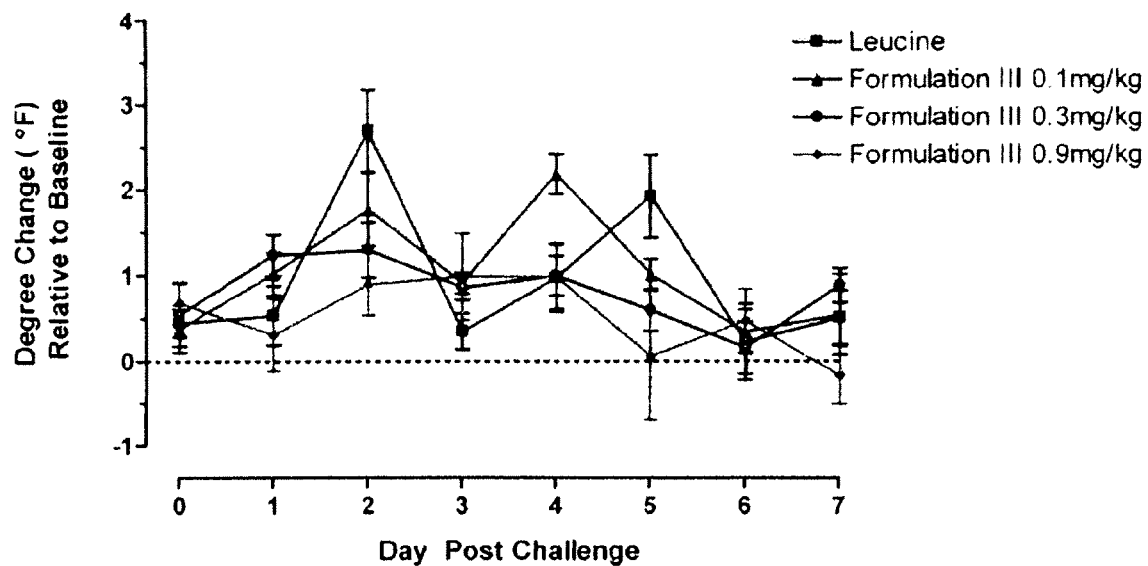
FIGS. 38A-38C are graphs showing the results of an in vivo influenza study. The graphs show the efficacy of Formulation III at three different doses (0.1 mg, 0.3 mg and 0.9 mg) on body temperature (FIGS. 38A and 38B) and body weight (FIG. 38C) ten days following infection. The data indicate that Formulation III is effective in treating ferret flu in a dose-dependent manner.
Figure 38B:
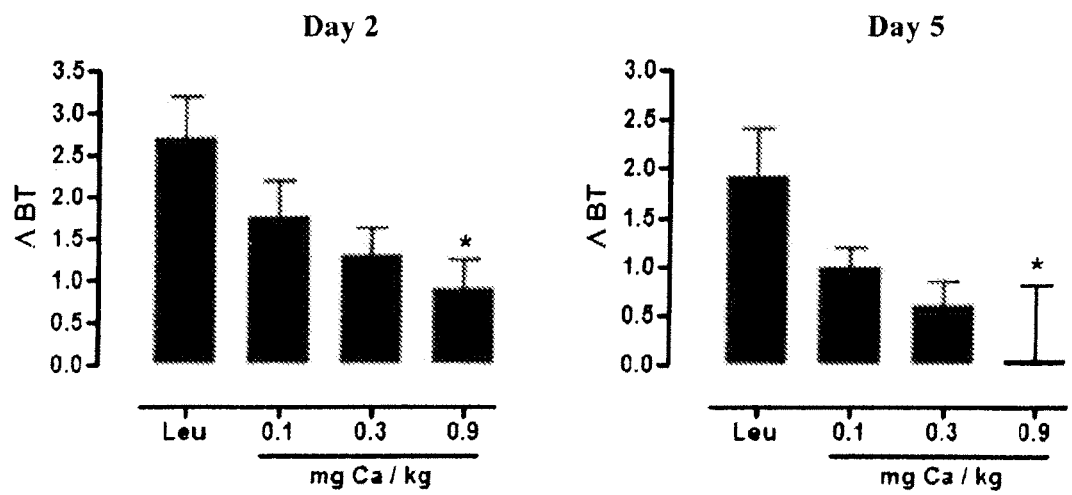
Figure 38C:
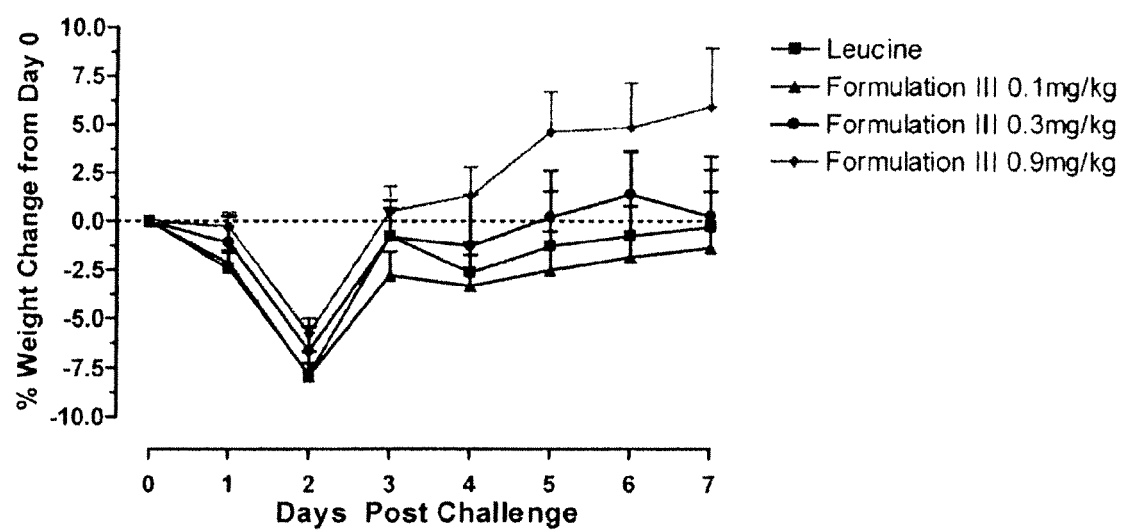
Figure 39A:
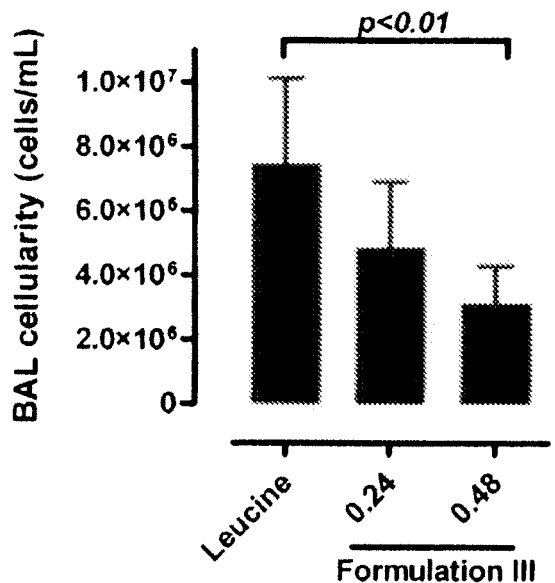
FIGS. 39A and 39B are graphs showing the efficacy of Formulation III in an OVA mouse model of allergic asthma. The data show that Formulation III decreases inflammatory cells (eosinophils) associated with asthma.
Figure 39B:
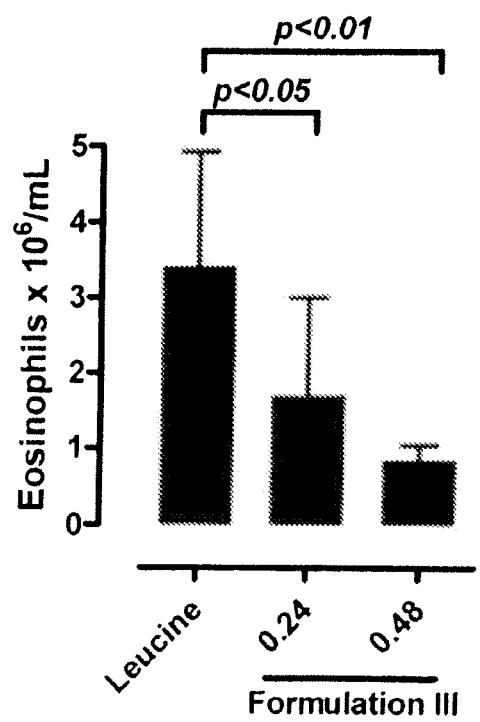

The mean±SEM of changes in body temperatures for the control group and animals given different doses of Formulation III are shown (FIG. 38A). Animals treated with Formulation III exhibited reduced body temperature increases as compared to the control-treated animal at the two peak days of fever (Days 2 and 5). As shown in FIG. 38B, 2 days and 5 days post-infection Formulation III-treated animals exhibited lower body temperatures in a dose-responsive manner. On both days, control animals exhibited the greatest increase in body temperature (Leu. FIG. 38B). In addition, the mean±SEM of changes in body temperatures of animals treated with Formulation III were less than those for the control animals. Ferrets treated with the highest dose of Formulation III exhibited less severe weight loss (kinetics and max loss) and recovered body weight more quickly than the control animals (FIG. 38C). Similar to the results with body temperature, on day 2 post-infection the body weight changes of control animals were much greater than that of ferrets treated with Formulation III; increasing calcium doses associated with less change in body temperatures (FIG. 38C).

Overall, the data indicated that Formulation III was able to decrease the severity of influenza infection in ferrets in a dose-dependent manner.

Example 29

Efficacy of Dry Powders in a Mouse Model of Asthma

Asthma is a disease characterized by recurrent attacks of breathlessness, wheezing, coughing and chest tightness, which vary in severity and frequency from person to person and can become life threatening or fatal. Asthma is due to inflammation of the air passages in the lungs and may be either a chronic respiratory impairment (chronic asthma) or an intermittent illness marked by episodic symptoms that result from a number of triggering events (intermittent asthma), like, for example environmental stimuli, allergen exposure, cold air, exercise or emotional stress.

Studies of calcium and sodium formulations in a respiratory disease model was undertaken to evaluate the effect of calcium and sodium formulations on inflammation and, specifically, to assess whether these formulations would further exacerbate changes in inflammation or could instead be safely administered therapeutically. To study the role calcium and sodium formulations, a mouse model of allergic asthma using ovalbumin (OVA) as an allergen, was employed. In this model, mice are sensitized to OVA over a period of two weeks and subsequently challenged via aerosol with OVA. The subsequent challenge with OVA induces airway inflammation and causes changes in pulmonary function. The principle change in inflammation is an increase in the number of eosinophils in the lungs. Similar changes in lung inflammation and pulmonary function are observed in humans with asthma. Mice were sensitized and challenged to OVA as shown in FIG. 55.

Sensitizations were performed by intraperotineal injection of OVA plus albumin. Challenges were performed by whole body exposure to nebulized 1% OVA solution for 20 minutes. Treatments with two different doses (Low=0.24 mg $Ca^{2+}$/kg and High=0.48 mg $Ca^{2+}$/kg) of Formulation III (10% Leucine; 58.6% calcium lactate, 31.4% sodium chloride; 10.8% calcium ion), or a 100% leucine dry powder were given 1 hour before or 4 hours after OVA challenge on days 27 to 29 and also performed twice on day 30. The dose was varied by changing the number of capsules used for each exposure. Treatments were made in a whole body exposure chamber using a capsule-based dry powder inhaler system. On the final day of the study (day 31), mice were euthanized and bronchoalveolar lavages (BAL) were performed. The total number of cells per BAL was determined. In addition, the percentage and total number of macrophages, polymorphonuclear cells (neutrophils), lymphocytes, and eosinophils were determined by differential staining. Data depict the mean±SD of 4-5 mice per group and are representative of at least two different studies.

Surprisingly, treatment of mice with 0.48 mg $Ca^{2+}$/kg reduced total BAL cell counts and the number of eosinophils in the BAL to statistically significant levels compared to the control animals (one-way ANOVA; Tukey's multiple comparison tests) (FIGS. 39A and 39B). Similarly, the lower dose of Formulation III (0.24 mg $Ca^{2+}$/kg) significantly reduced eosinophils counts, but not to the same degree as the higher dose (0.48 mg $Ca^{2+}$/kg). Thus, treatment of mice with dry powder formulations comprised of calcium lactate and sodium chloride reduced airway inflammation in a dose responsive manner.

Thus, it was discovered that the dry powder formulations of the present invention, far from exacerbating inflammation, actually reduced airway inflammation and reduced the degree of eosinophilia. This result cannot be explained simply by the biophysical mechanism of action, since it was previously observed that soluble factors, such as Der p 1 or OVA, are uninhibited in their movement across mucus-like materials following calcium exposure. Accordingly, this discovery demonstrates that the salt formulations of the present invention have an unexpected anti-inflammatory property and can either serve as a stand-alone therapy or be used in combination with other asthma medications for therapy of asthma or asthma-associated symptoms.

Example 30

Efficacy of Dry Powders in a Mouse Model of COPD

Chronic obstructive pulmonary disease (COPD) is a progressive disease associated with impaired pulmonary function and it primarily occurs as a result of cigarette smoking. COPD subjects are further susceptible to exacerbations that are often associated with an infectious agent and acute inflammation. These exacerbations lead to further declines in lung function, which in turn drives the increased frequency and severity of subsequent exacerbations.

To study both the disease and potential treatments, animal models of COPD have been developed. Animal models of tobacco smoke (TS) exposure have been established to facilitate the testing of novel therapeutics and to evaluate acute airway inflammation following TS exposure (Churg, A. et al. *Am J. Physiol Lung Cell Mol Physiol* 294(4):L612-631, 2008; Churg, A. and J. L. Wright, *Proc Am Thorac Soc* 6(6):550-552, 2009; Fox, J. C. and Fitzgerald M. R., *Curr Opin Pharmacol* 9(3):231-242, 2009).

Accordingly, a study was performed to evaluate the efficacy of a dry powder formulation comprised of calcium and sodium salts on the pulmonary inflammation induced by TS exposure. The 4-day TS exposure model shown in FIG. 55B was employed.

Mice (C57BL6/J) were exposed to TS for up to 45 minutes per day on four successive days by whole body exposure. On each day of TS exposure, mice were treated with Formulation III (10.0% leucine, 58.6% calcium lactate, 31.4% sodium chloride; 10.8% calcium ion) 1 hour before and 6 hours after Ts exposure. Formulation III dosing was performed using a whole body exposure system and a capsule based delivery system. A dry powder of 100% leucine was used as a control powder. A schematic depiction of the study design and the estimated doses delivered are shown below and in Table 44. A p38 MAP kinase inhibitor ADS110836 was used as a reference agent (WO2009/098612 Example 11) and was administered by an intranasal route.

TABLE 44

TS mouse dry powder dosing.

| Group No. | TS/Sham Exposure | Compound | n= | μg Ca/kg* (per dose) | Capsules |
|---|---|---|---|---|---|
| 1 | Sham | 100% Leucine | 10 | — | 6 |
| 2 | TS | 100% Leucine | 10 | — | 6 |

TABLE 44-continued

TS mouse dry powder dosing.

| Group No. | TS/Sham Exposure | Compound | n= | μg Ca/kg* (per dose) | Capsules |
|---|---|---|---|---|---|
| 3 | TS | Formulation III | 10 | 170 | 1 |
| 4 | TS | Formulation III | 10 | 700 | 3 |
| 5 | TS | Formulation III | 10 | 1680 | 6 |
| 6 | TS | Reference p38 inhibitor | 10 | 100** | 0 |

Different doses of calcium were delivered by increasing the number of capsules used. Doses were calculated by collecting samples from the pie cage system onto a glass fiber filter at 1LPM. The aerosol collected onto the filter was recovered and the calcium concentration was determined by HPLC. This data was used to calculate the aerosol concentration ($E_c$) of calcium ion, which was subsequently used to determine the estimated dose level. The estimated dose level ($D_L$) is given by the equation: $D_L = E_c \cdot RMV \cdot T/BW$, where RMV is the respiratory minute volume of the animal (0.21 LPM), T is the exposure time, and BW is the body weight of the animal in kg. The resulting estimated dose is then adjusted for the respirable fraction of the aerosol, which is determined based on the fine particle fraction (FPF; % mass less than 5.6 μm).

Figure 40A:
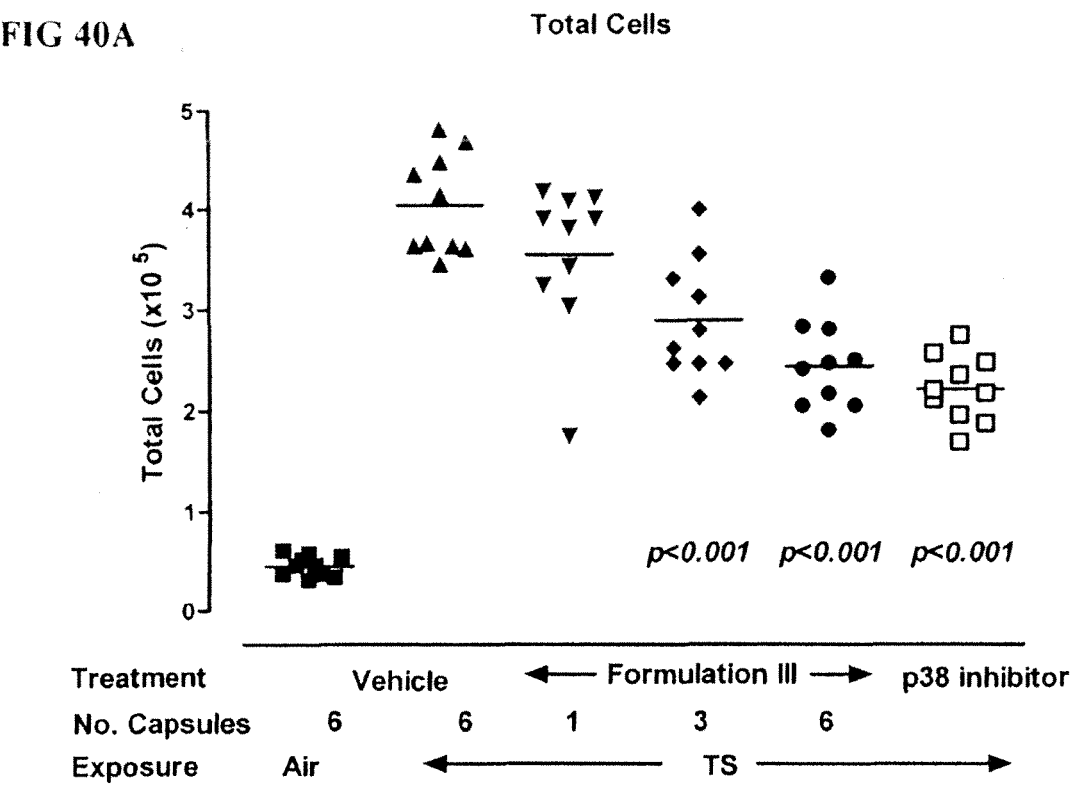
FIGS. 40A-40D are graphs showing the efficacy of Formulation III on inflammation induced in a tobacco smoke (TS) model of chronic obstructive pulmonary disease (COPD). The data indicate that Formulation III significantly decreases inflammatory cells associated with COPD.

Animals were euthanized by intra-peritoneal barbiturate anaesthetic overdose 24 hours after the final exposure to either air (sham) or TS on day 5. A bronchoalveolar lavage (BAL) was performed using 0.4 mL of phosphate buffered saline (PBS). Cells recovered from the BAL were enumerated and differential cell counts carried out using cytospin prepared slides. Inflammatory cell counts in the BAL fluid of animals exposed to TS for 4 days were determined. TS exposed animals were then exposed to Formulation III or a control dry powder of 100% leucine. The leucine treated animals exposed to TS exhibited a 9-fold increase in total cell counts compared to air treated animals that were also administered the control powder (FIG. 40A). The magnitude of this increase demonstrated the degree of inflammation observed after 4-days of TS exposure. Additional groups of animals were exposed to increasing doses of calcium-containing dry powder. Increasing doses were achieved by increasing the number of capsules used for each exposure.

Figure 40B:
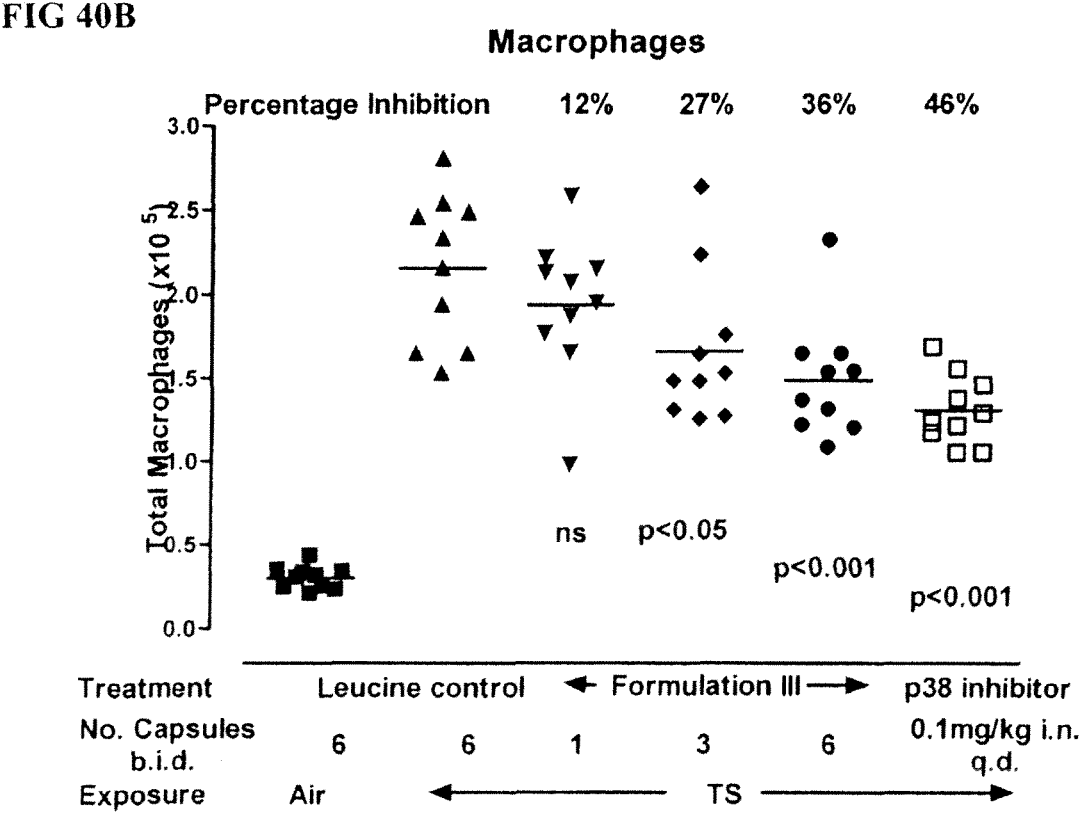
Figure 40C:
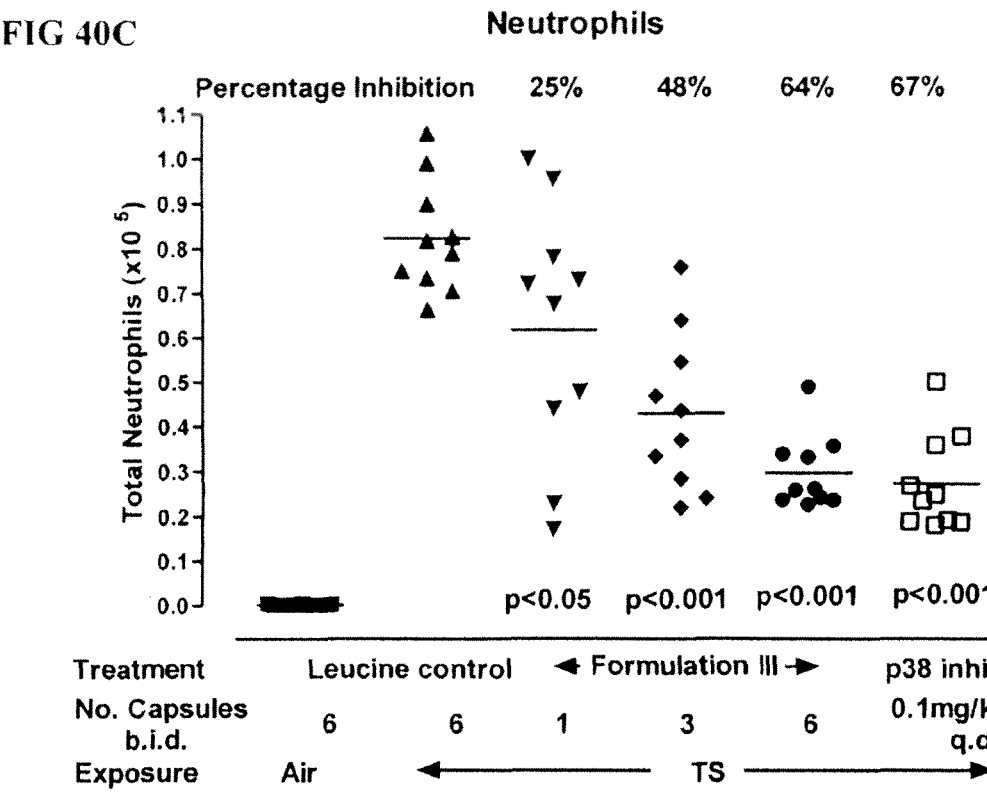
Figure 40D:
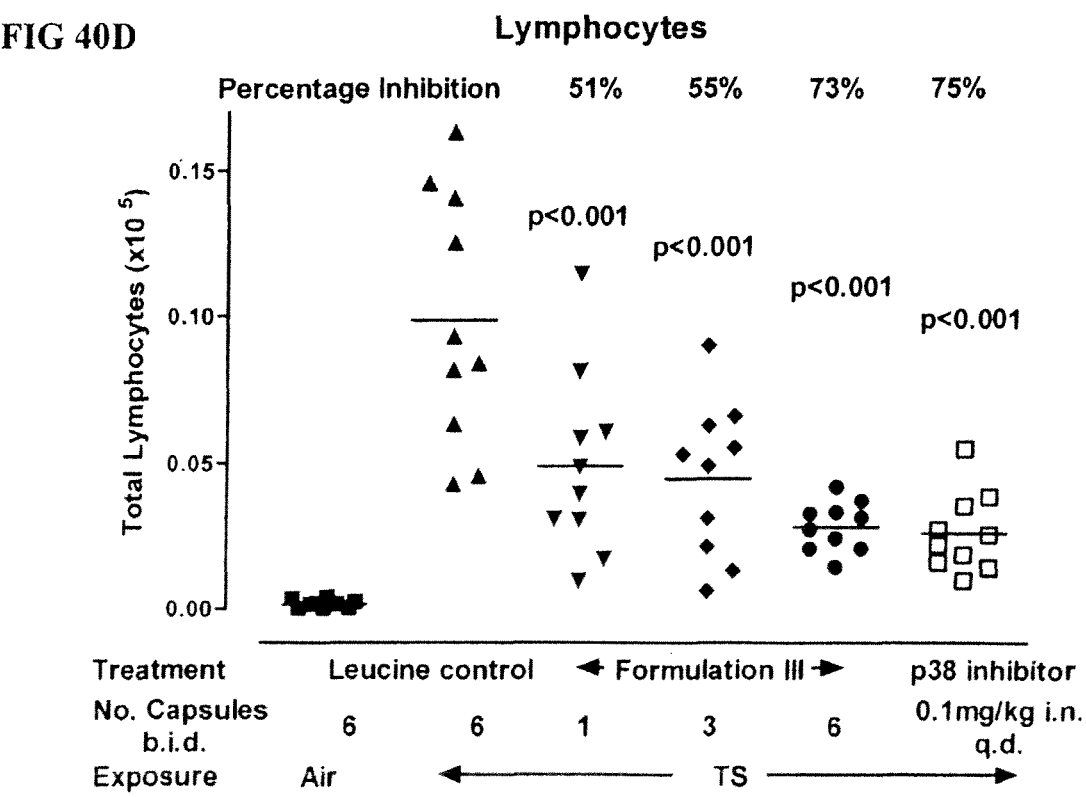

As shown in FIG. 40A, total cell counts in the BAL fluid were reduced by Formulation III treatment in a dose-responsive manner compared to the control group (14% reduction for the low dose, 32% reduction for the mid dose, and 45% reduction for the high dose). At the highest dose tested, the reduction was comparable to that of the positive control p38 MAPK inhibitor treatment (51% reduction). In addition, Formulation III significantly reduced the number of macrophages (FIG. 40B), neutrophils (FIG. 40C) and lymphocytes (FIG. 40D), in the BAL samples, with the greatest percent reduction observed for neutrophils and lymphocytes. Of note, even the low dose of calcium (1 capsule) reduced neutrophils while lymphocytes to statistically significant levels and the high dose reduced these cell types to levels that were comparable to the positive control compound (p38 inhibitor).

Together, the data indicated that aerosol delivery of dry powder formulations comprised of calcium and sodium salts can effectively limit inflammation and have a general anti-inflammatory effect. The magnitude of the effect is comparable to other drugs that are known to be effective in the model. The data suggested that dry powder formulations comprised of calcium and sodium salts could be used to treat COPD and, further, that a combination with other drugs used for the treatment of COPD (e.g., ICS, bronchodiolators (LABA/LAMA), p38 MAPK inhibitors, PDE4 inhibitors, antibody therapies, NF-κB inhibitors, and the like) would provide an enhanced benefit. To determine the specific cell types that were reduced by the treatment, differential cell counts of the same BAL samples were performed. Of note, the inflammation characteristic of the model is marked by increases in macrophages and neutrophils, with modest increases observed in lymphocytes and epithelial cells.

Example 31

Stability of Dry Powder Formulations with Various Excipients

Dry powders comprised of calcium lactate and sodium chloride and further comprising other excipients (e.g., maltodextrin and mannitol) were tested for their stability as discussed previously (Example 37). The compositions of these formulations can be found in Table 45.

TABLE 45

Dry powder calcium and sodium formulations.

| | | | Formulation Compositions | | | | | | |
|---|---|---|---|---|---|---|---|---|---|
| Form | Ca:Na molar ratio | Excipient | % Excipient (w/w) | Calcium salt | % Calcium salt (w/w) | Sodium salt | % Sodium salt (w/w) | % $Ca^{2+}$ (w/w) | % $Na^+$ (w/w) |
| III | 1:2 | Leucine | 10.0 | $CaLac_2$ | 58.6 | NaCl | 31.4 | 10.8 | 12.4 |
| IV | 1:2 | Maltodextrin | 10.0 | $CaLac_2$ | 58.6 | NaCl | 31.4 | 10.8 | 12.4 |
| V | 1:2 | Mannitol | 10.0 | $CaLac_2$ | 58.6 | NaCl | 31.4 | 10.8 | 12.4 |

The dry powders were made from liquid feedstock that was prepared as a batch by dissolving the excipient (mannitol or maltodextrin) in ultrapure water, then the calcium lactate, and finally the sodium chloride. All chemicals were obtained from Spectrum Chemicals (Gardena, Calif.). The solution was kept agitated throughout the process until the materials were completely dissolved in the water at room temperature. The solids concentration was 5 g/L in ultrapure water.

Formulation IV and V dry powders were produced by spray drying on the Büchi B-290 Mini Spray Dryer (BÜCHI Labortechnik AG, Flawil, Switzerland) with powder collection from a High Performance cyclone on a glass vessel with a plastic cover. The system used the Büchi B-296 dehumidifier. Atomization of the liquid feed utilized a Büchi two-fluid nozzle with a 1.5 mm diameter. The two-fluid atomizing gas was set at 40 mm and the aspirator rate to 90%. Room air was used as the drying gas. Inlet temperature of the process gas was 220° C. and outlet temperature at 99° C. to 104° C. with a liquid feedstock flow rate of 5 mL/min to 6 mL/min.

A 6 month physical stability study was subsequently conducted utilizing representative samples of Formulation IV and V hand-filled into size 3 HPMC capsules (Capsugel, Greenwood, N.C.) or kept in bulk, both placed in 20 mL scintillation vials (Kimble, Vineland, N.J.) stored at the following conditions (i) 2-8° C. bulk refrigerated, storage in a PE Bag (Fischer Scientific, Pittsburgh, Pa.) with a desiccant sponge (Fischer Scientific, Pittsburgh, Pa.), (ii) 25° C./60% RH, capsules kept in a Desi-Vac container (Control Company, Friendswood, Tex.) with desiccant (Fischer Scientific, Pittsburgh, Pa.) (iii) 40° C./75% RH, capsules kept in a Desi-Vac container with desiccant.

FPF_TD (%)<5.6 µm and 3.4 µm, as well as Dv50 (Spraytec), and water content (Karl Fischer) were monitored out to a 6 month timepoint for all conditions. As shown in Table 46 Formulation IV and V both displayed an increase in FPF_TD (%)<5.6 µm and 3.4 µm; however, the change was less than 20% from the values at time zero. Formulation IV showed good stability with respect to Dv50, while Formulation V showed an increase of over 20% in Dv50 for conditions (ii) and (iii). Formulation V showed good stability in water content for conditions (ii) and (iii) and a decrease of over 20% in water content for condition (i). Formulation IV also presented a decrease in water content of over 20% for conditions (i) and (ii), with stable water content for condition (iii). These results suggested that Formulation IV and V were sensitive to a decrease in water content when stored with desiccant. The decrease in water content could be the root cause for the decrease in particle size seen in the cascade impaction results.

Figure 41A:
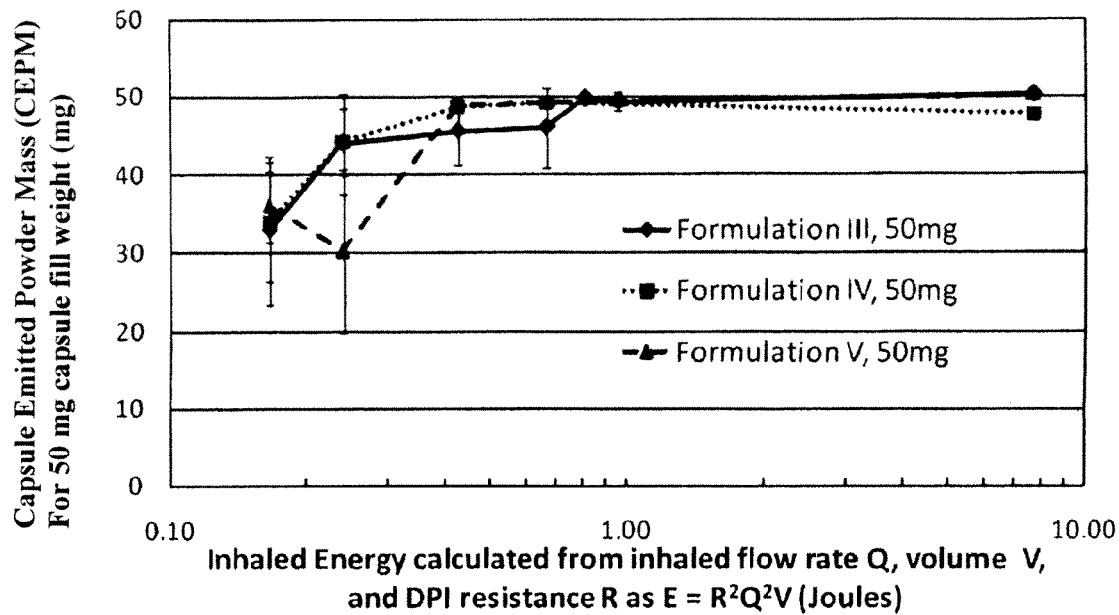
FIGS. 41A-41B are graphs showing the dispersibility of Formulations III, IV and V. The emitted dose (FIG. 41A) and volume median geometric diameter (FIG. 41B) of Formulations III, IV and V are shown as a function of inhaled energy. The data indicate that Formulation IV and Formulation V behave similarly and disperse slightly better than Formulation III.
Figure 41B:
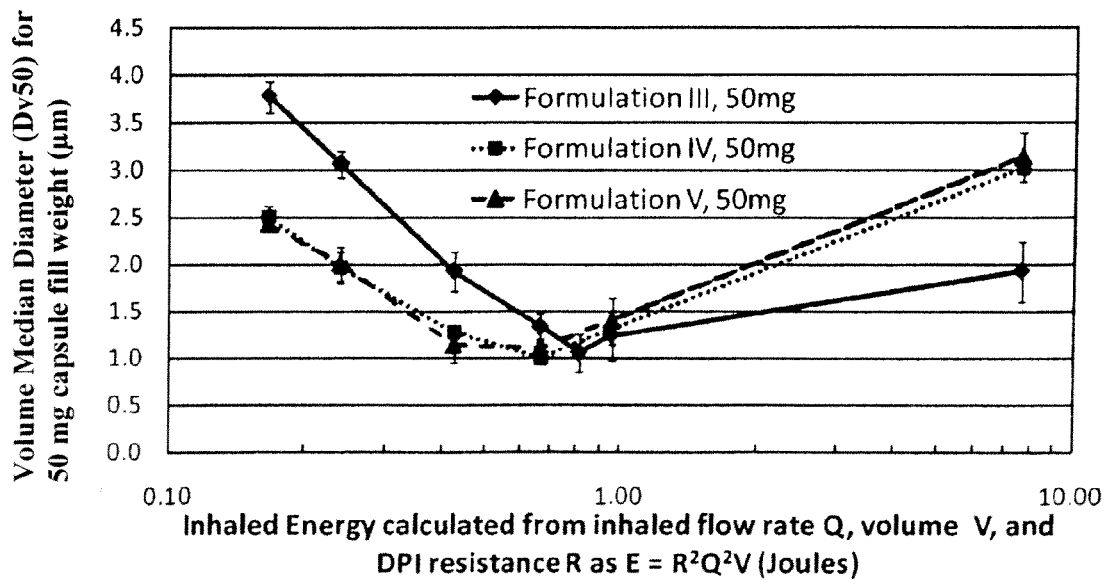

FIG. 41A shows the dose emitted from capsules containing Formulations III, IV or V at a 50 mg fill weight in a passive high resistance dry powder inhaler (RS-01 Model 7, High Resistance, Plastiape S.p.A., 0.036 $kPa^{1/2}LPM^{-1}$ resistance). As can been in FIG. 41A, all three powders emptied well from the capsules. Formulations IV and V had a similar CEPM as a function of inhalation energy, with greater than 90% of the powders emitting at 15-20 LPM, while Formulation III had about 90% CEPM at 25 LPM. FIG. 41B shows the particle size distribution of Formulations III, IV and V when emitted from the inhaler as characterized by the volume median diameter, Dv(50), plotted against the inhalation energy applied. Consistent with their CEPMs, Formulations IV and V also had similar Dv(50) characteristics while Formulation III had a higher particle size a lower flow rates (FIG. 41B). Overall, the Dv(50) values for the dry powder formulations indicated that the powders did not agglomerate and, instead, were well-dispersed.

Example 33

Efficacy of Salt Formulations Containing Leucine, Mannitol or Maltodextrin in a Mouse Model of Bacterial Pneumonia The anti-infective efficacy of calcium and sodium-containing dry powders was tested in an in vivo mouse model of bacterial pneumonia (see Example 26). Two-piece gel capsules (Capsugel Vcaps™, size 00CS) were filled to the appropriate weight with dry powders containing calcium lactate, sodium chloride and either leucine (Formulation III), maltodextrin (Formulation IV) or mannitol (Formulation V). Filled capsules were stored in laboratory desiccators until the time of treatments.

TABLE 46

Stability of dry powders containing maltodextrin and mannitol.

| Condition (° C./% RH) | Time (mo) | Formulation IV FPF$_{_TD}$ <3.4 μm | Formulation IV FPF$_{_TD}$ <5.6 μm | Formulation IV 50 (μm) | Formulation IV $H_20$ content (wt %) | Formulation V FPF$_{_TD}$ <3.4 μm | Formulation V FPF$_{_TD}$ <5.6 μm | Formulation V 50 (μm) | Formulation V $H_20$ content (wt %) |
|---|---|---|---|---|---|---|---|---|---|
| Time zero | 0 | 45% | 67% | 1.6 | 6.7% | 45% | 66% | 1.8 | 5.3% |
| 25° C./60% RH | 1 | 43% | 63% | 1.7 | 5.3% | 45% | 63% | 1.7 | 5.3% |
| (capsules/vial/ | 3 | 49% | 71% | 1.4 | 4.9% | 49% | 70% | 1.4 | 4.9% |
| dessicator) | 6 | 49% | 74% | 2.2 | 4.5% | 54% | 77% | 1.6 | 4.4% |
| 40° C./75% RH | 0.5 | 47% | 68% | 1.8 | 6.8% | 45% | 62% | 1.9 | 5.6% |
| (capsules/vial/ | 1 | 46% | 67% | 2.0 | 5.1% | 48% | 66% | 1.9 | 4.9% |
| desiccator) | 3 | 52% | 74% | 2.7 | 5.4% | 53% | 75% | 1.3 | 4.9% |
| | 6 | 50% | 71% | 1.5 | 26% | 53% | 73% | 1.6 | 5.2% |
| 2-8° C. | 3 | 50% | 71% | 1.8 | 4.7% | 50% | 73% | 1.6 | 3.8% |
| (bulk/vial) | 6 | 52% | 74% | 2.0 | 4.5% | 56% | 77% | 1.7 | 5.8% |

Example 32

Dispersibility of Dry Powder Formulations Containing Leucine, Mannitol or Maltodextrin The dispersibility of dry powder Formulations III, IV and V was assessed as described previously (see Example 15) by measuring the geometric particle size and the percentage of powder emitted from capsules with inhalation on a dry powder inhaler using flow rates representative of patient use. The particle size distribution and weight change of the filled capsules were measured as a function of flow rate, inhaled volume, and fill weight in a passive dry powder inhaler. At each flow rate, the mass of powder emitted from 5 replicate capsules was measured and the Dv(50) and CEPM results were averaged.

Serotype 3 *Streptococcus pneumoniae* bacteria were prepared by growing cultures on tryptic soy agar (TSA) blood plates overnight at 37° C. plus 5% $CO_2$. Single colonies were re-suspended in sterile PBS to an optical density at 600 nm ($OD_{600}$) of 0.3 in sterile PBS and subsequently diluted 1:2 in sterile PBS [~$4\times10^7$ Colony forming units (CFU)/mL].

C57BL6 mice were treated with either a leucine dry powder or the aforementioned dry powder (0.24 mg/kg Ca dose) formulations for 2.5 minutes/capsule in a whole-body exposure system. Dry powder aerosol was generated using a capsule based delivery system connected to a top-loading pie chamber cage that individually holds up to 11 animals. All dry powder treatments were delivered at 10 psi and 7 scfh (≈2.8 L/min). Dry powder treatments were performed 2 hours before mice were infected with 50 µL of *S. pneumoniae* suspension (~2×10⁶ CFU) by intratracheal instillation while under anesthesia. Twenty-four hours after infection, mice were euthanized by pentobarbital injection and lungs were collected and homogenized in sterile PBS. Lung homogenate samples were serially diluted in sterile PBS and plated on TSA blood agar plates. Agar plates were incubated overnight at 37° C. and CFU were enumerated the following day for quantification of bacterial burden in the lungs.

Figure 42:
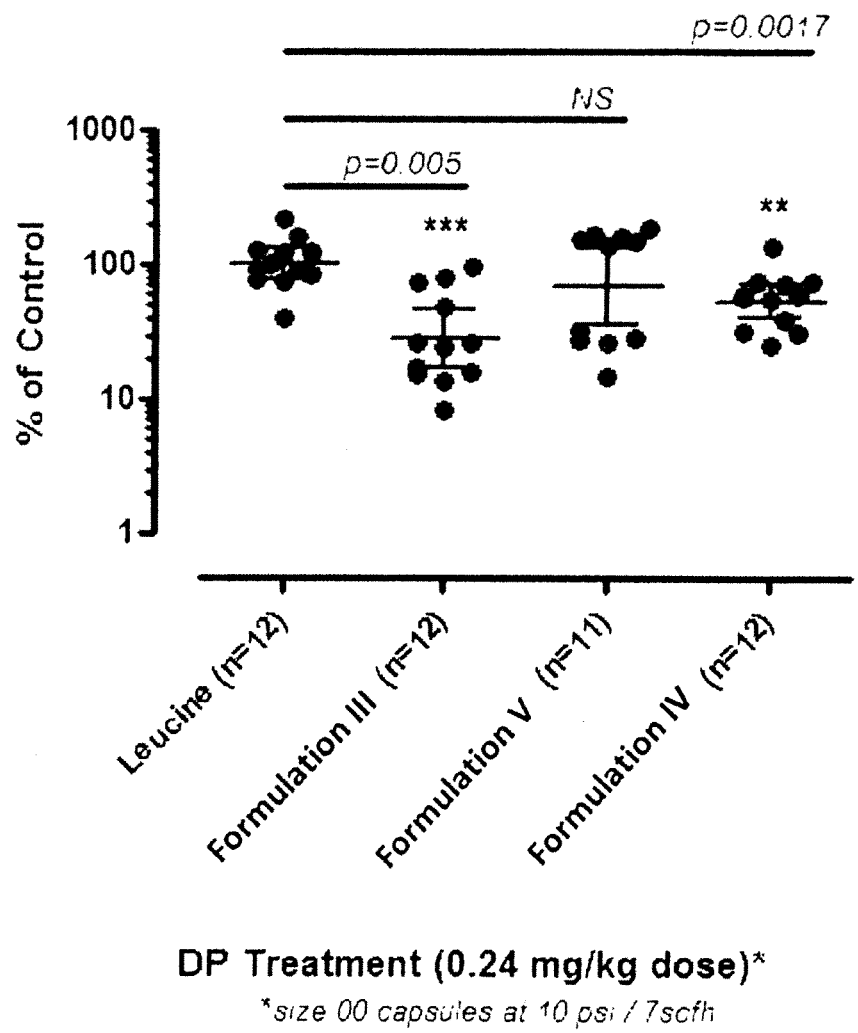

The lung bacterial burden in each animal is shown in FIG. 42. Each circle represents data from a single animal and the bar depicts the geometric mean for the group. Data were normalized to the leucine control in each respective experiment. Data are pooled from two independent experiments. The treatment groups were compared to the leucine control group by two-tailed Student 1-test. Compared to control animals, mice treated with all three dry powder formulations exhibited reduced bacterial titers 24 hours after infection. Animals treated with a formulation comprised of calcium lactate, sodium chloride and leucine (Formulation III) exhibited 5.9-fold lower bacterial titers, while those treated with mannitol- and maltodextran-containing powders exhibited approximately 2-fold lower bacterial burden. These data indicated that although calcium-sodium dry powders comprising leucine, maltodextran and mannitol were all effective, that leucine-containing powder (Formulation III) were the most effective at treating bacterial infection.

Example 34

Figure 43A:
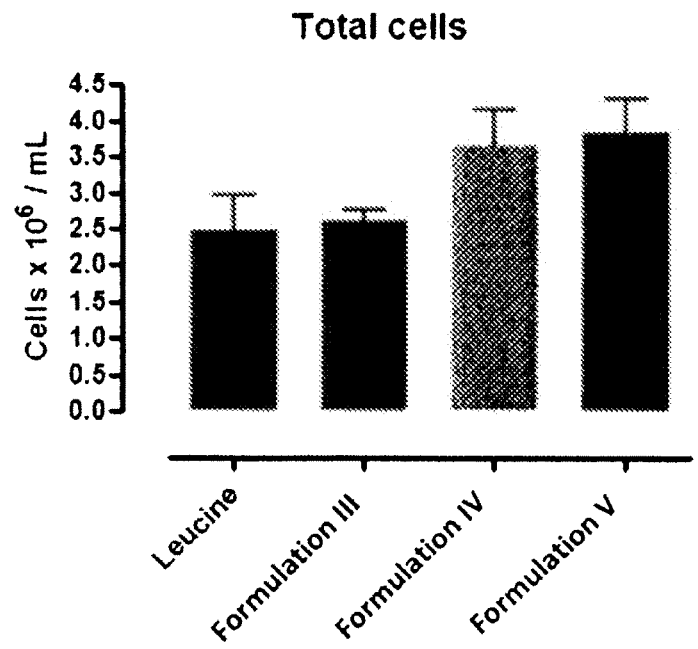
Figure 43B:
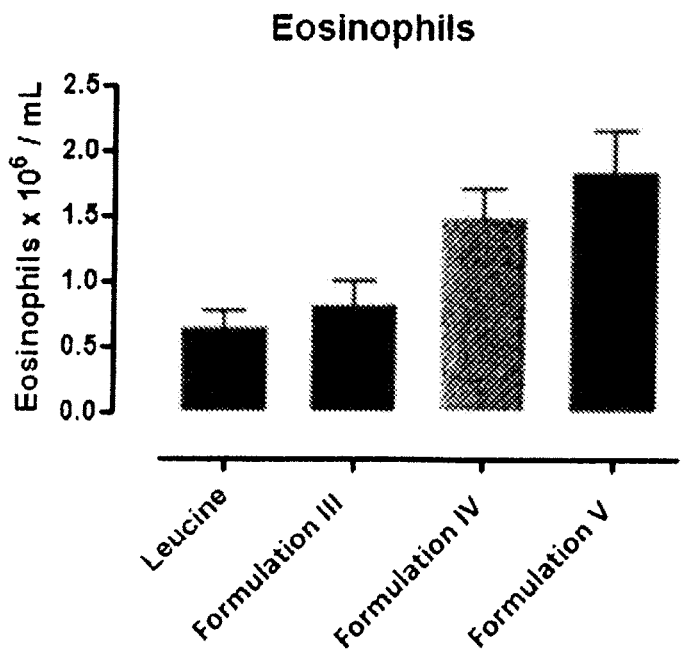

Efficacy of Dry Powders Containing Leucine, Mannitol or Maltodextrin in a Mouse OVA Model of Allergic Asthma Calcium and sodium formulations also comprising either leucine, mannitol, or maltodextrin were further evaluated for their ability to inhibit the inflammatory cell response associated with allergic asthma. The powders were tested in the OVA mouse model described previously (see Example 29). Briefly, mice were sensitized to, then challenged with OVA to induce airway inflammation similar to that seen in humans with asthma. Mice were treated with leucine alone or Formulation III, Formulation IV or Formulation V by whole body exposure 1 hour before or 4 hours after OVA challenge on days 27 through 29 and twice on day 30. On day 31, BALs were performed and total number of cells and eosinophils from them were determined by differential staining. Data depict the standard deviation of 4-5 mice per group and are representative of at least two different studies. Although cell counts in the leucine control were somewhat low, it is clear that mice treated with Formulation III had much lower total (FIG. 43A) and eosinophil (FIG. 43B) cell counts than those treated with Formulation IV or Formulation V, indicating that calcium and sodium dry powders comprising leucine were the most effective in inhibiting asthma-associated inflammation.

Example 35

Characteristics of Powders with Various Amounts of Leucine and Different Molar Ratios of Calcium to Sodium Ion Components of dry powder salt formulation can affect both their stability and their efficacy. In order to ascertain the effect of increasing levels of leucine, and that of increasing the molar ratio of calcium ion to sodium ion on the dry powders, dry powders formulations were produced.

The liquid feedstock for the powders was prepared as a batch by dissolving leucine in ultrapure water, then the calcium lactate, and finally the sodium chloride. All chemicals were obtained from Spectrum Chemicals (Gardena, Calif.). The solution was kept agitated throughout the process until the materials were completely dissolved in the water at room temperature.

Formulation III was prepared as described previously (see Example 27) and was from the same lot. All other powders were produced by spray drying on the Büchi B-290 Mini Spray Dryer (BÜCHI Labortechnik AG, Flawil, Switzerland) with powder collection from a High Performance cyclone on a 60 mL glass vessel. The system used the Büchi B-296 dehumidifier. Furthermore, when the relative humidity in the room exceeded 30% RH, an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm and the aspirator rate to 90%. Room air was used as the drying gas. Inlet temperature of the process gas was 220° C. and outlet temperature at 94° C. to 102° C. with a liquid feedstock flow rate of 4.9 mL/min to 5.3 ml/min. The solids concentration was 10 g/L in dissolved in ultrapure water.

The powders produced were characterized (e.g., for size, water content) as described previously, and the results of these characterizations are shown in Table 47.

TABLE 47

Characteristics of dry powders comprising various amounts of leucine and different molar ratios of calcium to sodium ion.

| Formulation | | | | Spraytec | | ACI-2 | | Other | | |
|---|---|---|---|---|---|---|---|---|---|---|
| Ca:Na ratio | Leu | CaLact | NaCl | Dv(50) (µm) | GSD (µm) | FPF_TD <3.4 µm | FPF_TD <5.6 µm | $H_2O$ content (wt %) | Yield % | Conc (g/L) |
| 1:2 | 10.0 | 58.6 | 31.4 | 1.5 | 2.5 | 44.6% | 62.8% | 2.7% | 88.4% | 15 |
| 8:1 | 10.0 | 87.1 | 2.9 | 4.2 | 3.5 | 26% | 57.5% | 2.3% | 78.8% | 10 |
| | 20.0 | 77.4 | 2.6 | 4.5 | 3.3 | 28.9% | 57.1% | 2.6% | 67.2% | 10 |
| | 30.0 | 67.7 | 2.3 | 5.2 | 3.9 | 32.6% | 58.6% | | 71.6% | 10 |
| | 39.4 | 58.6 | 2.0 | 5.7 | 3.6 | 36.2% | 60.8% | 2.0% | 76.3% | 10 |
| | 69.0 | 30.0 | 1.0 | 7.3 | 3.8 | 49.0% | 71.3% | 1.7% | 56.9% | 5 |
| 2:1 | 10.0 | 79.4 | 10.6 | 4.5 | 3.5 | 31.1% | 55.5% | 2.5% | 67.2% | 10 |
| | 20.0 | 70.6 | 9.4 | 1.8 | 2.8 | 43.4% | 65.0% | 3.4% | 68.6% | 5 |
| | 30.0 | 61.7 | 8.3 | 3.7 | 3.4 | 40.9% | 67.0% | 3.3% | 83.2% | 5 |

TABLE 47-continued

Characteristics of dry powders comprising various amounts of leucine and different molar ratios of calcium to sodium ion.

| Formulation | | | Spraytec | | ACI-2 | | Other | | |
|---|---|---|---|---|---|---|---|---|---|
| Ca:Na ratio | Leu | CaLact | NaCl | Dv(50) (µm) | GSD (µm) | FPF_TD <3.4 µm | FPF_TD <5.6 µm | H₂O content (wt %) | Yield % | Conc (g/L) |
| | 33.6 | 58.6 | 7.8 | 3.6 | 3.3 | 33.5% | 55.7% | 3.2% | 69.8% | 10 |
| | 66.0 | 30.0 | 4.0 | 5.3 | 3.8 | 51.3% | 73.1% | 2.1% | 63.7% | 5 |

Example 36

Stability of Dry Powders Comprising Calcium Lactate, Sodium Chloride and Leucine at Different Ratios The stability of several of the powders produced was then evaluated under conditions described previously. A 2 month physical stability study was conducted utilizing representative samples of Formulation III, VI and three more formulations encompassing a range of leucine loading and Ca:Na molar ion ratio of 2:1 and 8:1. The dry powders were hand-filled into size 3 HPMC capsules (Capsugel, Greenwood, N.C.) and placed in 20 mL scintillation vials (Kimble, Vineland, N.J.) and heat sealed in a Dri-Shield 3000 foil pouch (3M, Sanford, N.C.) stored at the following conditions (i) 2-8° C., (ii) 25° C./60% RH and (iii) 40° C./75% RH.

FPF_TD (%)<5.6 µm and 3.4 µm, as well as Dv50 (Spraytec), calcium and sodium content (HPLC) and water content (Karl Fischer) were monitored out to a 2 month timepoint for all conditions. As shown in Table 48, all formulations displayed good stability with respect to the assessed physical properties under each of these conditions.

TABLE 48

Stability of salt formulations comprising various amounts of leucine and different molar ratios of calcium to sodium ion.

| Condition (° C./% RH) | Time (mo) | FPF_TD <3.4 µm | FPF_TD <5.6 µm | Dv50 (µm) | H₂O content (wt %) | FPF_TD <3.4 µm | FPF_TD <5.6 µm | Dv50 (µm) | H₂O content (wt %) |
|---|---|---|---|---|---|---|---|---|---|
| | | Formulation III | | | | 33.6% Leucine Ca:Na 2:1 | | | |
| Time zero | 0 | 44% | 65% | 1.5 | 3.6% | 31% | 58% | 3.6 | 4.6% |
| 25° C./60% RH | 1 | 45% | 65% | 1.0 | 3.9% | 35% | 59% | 2.6 | 4.7% |
| | 2 | 45% | 63% | 1.3 | 4.1% | 31% | 56% | 4.0 | 4.7% |
| 40° C./75% RH | 1 | 45% | 64% | 1.2 | 4.1% | 26% | 52% | 3.8 | 4.6% |
| | 2 | 45% | 63% | 1.3 | 4.0% | 26% | 52% | 5.7 | 4.4% |
| 5° C. | 1 | 45% | 64% | 1.5 | 3.4% | 32% | 56% | 3.1 | 4.4% |
| | 2 | 44% | 60% | 1.7 | 3.5% | 32% | 57% | 4.6 | 4.4% |
| | | 10% Leucine Ca:Na 8:1 | | | | 20% Leucine Ca:Na 8:1 | | | |
| Time zero | 0 | 29% | 52% | 3.7 | 4.4% | 29% | 51% | 5.2 | 3.8% |
| 25° C./60% RH | 1 | 32% | 54% | 2.4 | 4.9% | 30% | 52% | 3.1 | 4.6% |
| | 2 | 35% | 58% | 3.9 | 5.0% | 31% | 52% | 4.4 | 4.5% |
| 40° C./75% RH | 1 | 33% | 55% | 0.9 | 5.1% | 32% | 54% | 3.5 | 4.9% |
| | 2 | 32% | 54% | 4.1 | 5.0% | 29% | 50% | 3.2 | 4.8% |
| 5° C. | 1 | 31% | 52% | 2.9 | 4.4% | 28% | 51% | 3.3 | 4.0% |
| | 2 | 31% | 54% | 4.0 | 4.5% | 33% | 56% | 5.1 | 4.1% |
| | | 39.4% Leucine Ca:Na 8:1 | | | | | | | |
| Time zero | 0 | 33% | 57% | 4.8 | 3.5% | | | | |
| 25° C./60% RH | 1 | 35% | 60% | 4.3 | 3.8% | | | | |
| | 2 | 35% | 59% | 4.7 | 3.8% | | | | |
| 40° C./75% RH | 1 | 31% | 55% | 4.9 | 4.0% | | | | |
| | 2 | 33% | 56% | 4.8 | 3.9% | | | | |
| 5° C. | 1 | 33% | 56% | 5.6 | 3.3% | | | | |
| | 2 | 35% | 58% | 6.1 | 3.3% | | | | |

Example 37

Aerosol Properties of Dry Powders with Different Amounts of Leucine and Various Calcium to Sodium Ion Molar Ratios Dry powders were further evaluated for their dispersibility. The dry powders tested are shown in Table 49.

TABLE 49

Dry powder calcium and sodium formulations.

Formulation Compositions

| Form | Ca:Na molar ratio | Excipient | % Excipient (w/w) | Calcium salt | % Calcium salt (w/w) | Sodium salt | % Sodium salt (w/w) | % $Ca^{2+}$ (w/w) | % $Na^+$ (w/w) |
|---|---|---|---|---|---|---|---|---|---|
| III | 1:2 | Leucine | 10.0 | $CaLac_2$ | 58.6 | NaCl | 31.4 | 10.8 | 12.4 |
| VI | 8:1 | Leucine | 39.4 | $CaLac_2$ | 58.6 | NaCl | 2.0 | 10.8 | 0.8 |
| VII | 4:1 | Leucine | 37.5 | $CaLac_2$ | 58.6 | NaCl | 3.9 | 10.8 | 1.5 |
| VIII | 4:1 | Leucine | 20.0 | $CaLac_2$ | 75.0 | NaCl | 5.0 | 13.8 | 2.0 |

The dispersibility of the above dry powder formulations were assessed when delivered from a dry powder inhaler over a range of inhalation flow rates and volumes. This dispersibility was investigated by measuring the geometric particle size and the percentage of powder emitted from capsules when inhaling on a dry powder inhaler with flow rates representative of patient use. The particle size distribution and weight change of the filled capsules were measured for multiple powder formulations as a function of flow rate, inhaled volume and fill weight in a passive dry powder inhaler.

Powder formulations were filled into size 3 HPMC capsules (Capsugel V-Caps) by hand with the fill weight measured gravimetrically using an analytical balance (Mettler Toledo XS205). Fill weights of 50 mg were filled for Formulations III, VI, VII, and VIII. A capsule-based passive dry powder inhaler (RS-01 Model 7, High Resistance, Plastiape S.p.A.) was used which had specific resistances of 0.036 $kPa^{1/2}LPM^{-1}$. Flow rate and inhaled volume were set using a timer controlled solenoid valve with flow control valve with an inline mass flow meter (TSI model 3063). Capsules were placed in the dry powder inhaler, punctured and the inhaler sealed inside a cylinder, exposing the outlet of the DPI to the laser diffraction particle sizer (Spraytec, Malvern) in its open bench configuration. The steady air flow rate through the system was initiated using the solenoid valve and the particle size distribution was measured via the Spraytec at 1 kHz for the duration of the single inhalation maneuver with a minimum of 2 seconds. Particle size distribution parameters calculated included the volume median diameter (Dv50), the geometric standard deviation (GSD), and the fine particle fraction (FPF) of particles less than 5 micrometers in diameter. At the completion of the inhalation duration, the dry powder inhaler was opened, the capsule removed and re-weighed to calculate the mass of powder that had been emitted from the capsule during the inhalation duration. At each testing condition, 5 replicate capsules were measured and the results of Dv50, FPF and capsule emitted powder mass (CEPM) were averaged.

In order to relate the dispersion of powder at different flow rates, volumes, and from inhalers of different resistances, the energy required to perform the inhalation maneuver was calculated and the particle size and dose emission data plotted against the inhalation energy. Inhalation energy was calculated as $E=R^2Q^2V$ where E is the inhalation energy in Joules, R is the inhaler resistance in $kPa^{1/2}$/LPM, Q is the steady flow rate in L/min and V is the inhaled air volume in L.

Figure 44:
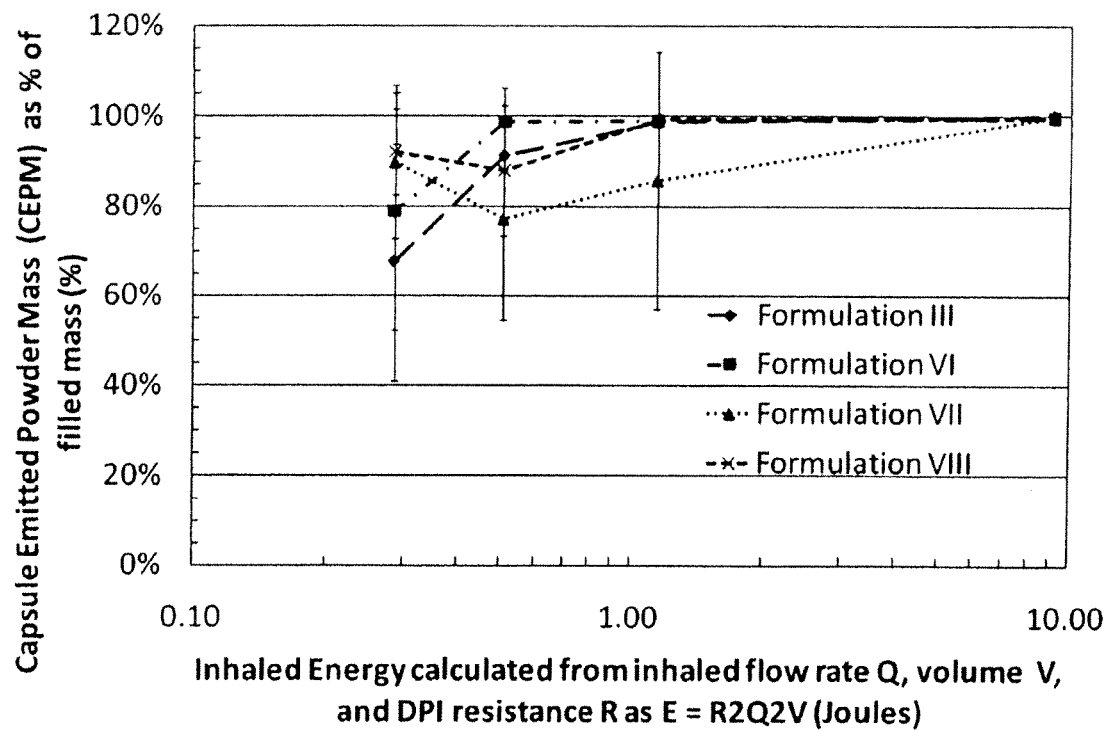

FIG. 44 shows the dose emitted from a capsule for Formulations III, VI, VII and VIII at a capsule fill weight of 50 mg using the high resistance RS-01 dry powder inhaler. For each powder, a 2 L inhalation was used at the high flow rate condition of 60 LPM, corresponding to the highest energy condition of 9.2 Joules. For the other three flow rates of 30, 20 and 15 LPM, an inhalation volume of 1 L was used. As can be seen from FIG. 44, the entire mass of powder filled into the capsule emptied out of the capsule in a single inhalation for all 4 formulations at the highest energy condition tested. For Formulation III, greater than 80% of the fill weight emptied for all tested inhalation conditions. For Formulations VI and VIII, capsule dose emission dropped below 80% of the fill weight at 0.29 Joules. For Formulation VII, capsule dose emission dropped below 80% of the fill weight at 0.51 Joules.

The particle size distributions of the emitted powder of Formulations III, VI, VII and VIII are listed in the Table 50, as characterized by the Dv50 and GSD as a function of the applied flow rate and inhalation energy. Consistent values of Dv50 at decreasing energy values indicate that the powder is well-dispersed since additional energy does not result in additional deagglomeration of the emitted powder. The Dv50 values were consistent for all 4 Formulations with the mean Dv50 increasing by less than 2 micrometers from the highest inhalation energy condition (and hence most dispersed state) down to inhalation energies of 0.29 Joules. For Formulation VIII, the mean Dv50 did not increase from baseline by 2 micrometers over the whole tested range with the maximum increase of 1.4 micrometers (from 2.1 to 3.5 micrometers) for a decrease of inhalation energy from 9.2 Joules to 0.29 Joules. In these ranges, the Dv50 was not significantly increased in size, which would be expected if the emitting powder contained a lot of agglomerates and was not well dispersed.

TABLE 50

Particle size distribution of emitted dry powders.

| | | Inhaled Energy (J), $E = R^2Q^2V$ | | | |
|---|---|---|---|---|---|
| | | 9.2 | 1.1 | 0.5 | 0.3 |
| | | Flow Rate (LPM) | | | |
| | | 60 | 30 | 20 | 15 |
| Formulation III | Dv50 (μm) | 1.0 ± 0.1 | 1.4 ± 0.1 | 2.3 ± 0.2 | 3.1 ± 0.3 |
| | GSD | 6.0 ± 0.4 | 4.4 ± 0.3 | 3.7 ± 0.6 | 3.4 ± 0.7 |
| | FPF < 5 μm | 85.2 ± 1.1 | 85.5 ± 0.7 | 78.0 ± 1.1 | 68.1 ± 1.9 |

TABLE 50-continued

Particle size distribution of emitted dry powders.

| | | Inhaled Energy (J), E = $R^2Q^2V$ | | | |
|---|---|---|---|---|---|
| | | 9.2 | 1.1 | 0.5 | 0.3 |
| | | Flow Rate (LPM) | | | |
| | | 60 | 30 | 20 | 15 |
| Formulation VI | Dv50 (μm) | 3.3 ± 0.2 | 4.0 ± 0.2 | 5.2 ± 0.2 | 6.2 ± 0.7 |
| | GSD | 5.5 ± 0.4 | 4.6 ± 0.5 | 4.4 ± 0.3 | 3.3 ± 0.2 |
| | FPF < 5 μm | 61.4 ± 1.4 | 57.1 ± 1.4 | 48.7 ± 1.2 | 41.5 ± 4.2 |
| Formulation VII | Dv50 (μm) | 2.0 ± 0.2 | 3.0 ± 0.2 | 3.6 ± 0.1 | 5.0 ± 0.3 |
| | GSD | 5.6 ± 0.2 | 4.3 ± 1.0 | 3.7 ± 0.5 | 3.6 ± 0.2 |
| | FPF < 5 μm | 69.5 ± 0.8 | 64.9 ± 2.3 | 62.0 ± 1.7 | 49.7 ± 2.3 |
| Formulation VIII | Dv50 (μm) | 2.1 ± 0.4 | 2.1 ± 0.1 | 2.8 ± 0.1 | 3.5 ± 0.1 |
| | GSD | 5.2 ± 0.3 | 4.3 ± 0.2 | 3.3 ± 0.3 | 3.3 ± 0.3 |
| | FPF < 5 μm | 73.9 ± 1.8 | 74.4 ± 0.5 | 71.0 ± 1.2 | 63.2 ± 0.8 |

Also assessed was the aerodynamic size distribution of the dry powder formulations when delivered from a dry powder inhaler in a range appropriate for deposition in the respiratory tract. The aerodynamic particle size distributions of the four powder formulations were measured by characterizing the powders with an eight stage Anderson cascade impactor (ACI). Dry powder formulations were filled into size 3 HPMC capsules (Capsugel V-Caps) by hand with the fill weight measured gravimetrically using an analytical balance (Mettler Toledo XS205). Fill weights of 50 mg were filled for Formulations III, VI, and VII, and a fill weights of 40 mg were filled for Formulation VIII. A reloadable, capsule based passive dry powder inhaler (RS-01 Model 7, High Resistance, Plastiape, Osnago, Italy) was used to disperse the powder into the cascade impactor. Two capsules were used for each measurement, with two actuations of 2 L of air at 60 LPM drawn through the dry powder inhaler (DPI) for each capsule. The flow rate and inhaled volume were set using a timer controlled solenoid valve with flow control valve (TPK2000 Copley Scientific). Three replicate ACI measurements were performed for Formulations VII and VIII and five replicates for Formulation VI and Eight replicates for Formulation III. The impactor stages, induction port (IP), entrance cone (EC) and after filter (F) were rinsed with measured volumes of water and the rinse solutions assayed by HPLC for calcium ion concentration. For Formulation III, the entrance cone was not rinsed. The size distribution, MMAD, GSD and fine particle dose <4.4 micrometers (FPD<4.4 μm) of the emitted powder was averaged across the replicates and are tabulated in Table 51. For Formulations III, VI and VII, the dose filled was two capsules of 50 mg powder fill weight which corresponded to 10.8 mg of $Ca^{2+}$ filled into the capsules. For Formulation VIII, the two capsules of 40 mg of powder filled contained the same 10.8 mg of $Ca^{2+}$ due to the formulation's higher $Ca^{2+}$ content.

All four formulations were found to have repeatable size distributions as illustrated by the low standard deviations for all the tabulated values (Table 51). All replicates of all four formulations had greater than 85% of the $Ca^{2+}$ which was filled into the two capsules recovered in the cascade impactor. This both shows that the dosing of the formulations from the DPI was consistent and had low and consistent powder retention in the capsules and DPI as well as indicating that the measured size distributions were characteristic of the full dose delivered and not just a sample of the dose. All four formulations have respirable doses as indicated in this test by the fine particle dose <4.4 micrometers that are a significant portion of the filled dose, with fine particle doses ranging from 2.0 mg to 5.4 mg of the filled 10.8 mg of calcium. With a maximum GSD of 2.1 for the four formulations, the polydispersity of the size distributions was relatively small relative to typical dry powder formulations for inhalation.

TABLE 51

| Aerodynamic particle size distribution of Formulations III, VI, VII and VIII. | | | | | |
|---|---|---|---|---|---|
| ACI Stage | | Formulation VIII | Formulation VII | Formulation VI | Formulation III |
| IP (+EC) | (mg $Ca^{2+}$) | 2.64 ± 0.06 | 1.89 ± 0.17 | 2.35 ± 0.21 | 1.76 ± 0.12 |
| −1 | (mg $Ca^{2+}$) | 1.27 ± 0.14 | 2.06 ± 0.35 | 2.70 ± 0.20 | 0.40 ± 0.04 |
| −0 | (mg $Ca^{2+}$) | 1.31 ± 0.04 | 2.01 ± 0.10 | 1.85 ± 0.07 | 0.62 ± 0.07 |
| 1 | (mg $Ca^{2+}$) | 1.31 ± 0.07 | 1.66 ± 0.08 | 1.36 ± 0.10 | 1.17 ± 0.12 |
| 2 | (mg $Ca^{2+}$) | 0.88 ± 0.08 | 0.86 ± 0.01 | 0.71 ± 0.11 | 1.34 ± 0.10 |
| 3 | (mg $Ca^{2+}$) | 1.03 ± 0.09 | 0.86 ± 0.08 | 0.67 ± 0.07 | 1.98 ± 0.15 |
| 4 | (mg $Ca^{2+}$) | 0.56 ± 0.06 | 0.52 ± 0.03 | 0.37 ± 0.06 | 1.26 ± 0.14 |
| 5 | (mg $Ca^{2+}$) | 0.22 ± 0.01 | 0.27 ± 0.03 | 0.17 ± 0.02 | 0.49 ± 0.05 |
| 6 | (mg $Ca^{2+}$) | 0.09 ± 0.01 | 0.09 ± 0.01 | 0.02 ± 0.03 | 0.14 ± 0.03 |
| F | (mg $Ca^{2+}$) | 0.10 ± 0.03 | 0.14 ± 0.01 | 0.07 ± 0.01 | 0.22 ± 0.03 |
| FPD < 4.4 μm | (mg $Ca^{2+}$) | 2.88 ± 0.10 | 2.72 ± 0.08 | 2.01 ± 0.18 | 5.43 ± 0.29 |
| MMAD | (μm) | 5.22 ± 0.21 | 6.29 ± 0.32 | 7.17 ± 0.23 | 3.12 ± 0.11 |
| GSD | | 2.05 ± 0.01 | 1.93 ± 0.03 | 1.79 ± 0.02 | 2.13 ± 0.01 |

Example 38

Solid State Properties of Powders Formulations VII and VIII

Figure 45A:
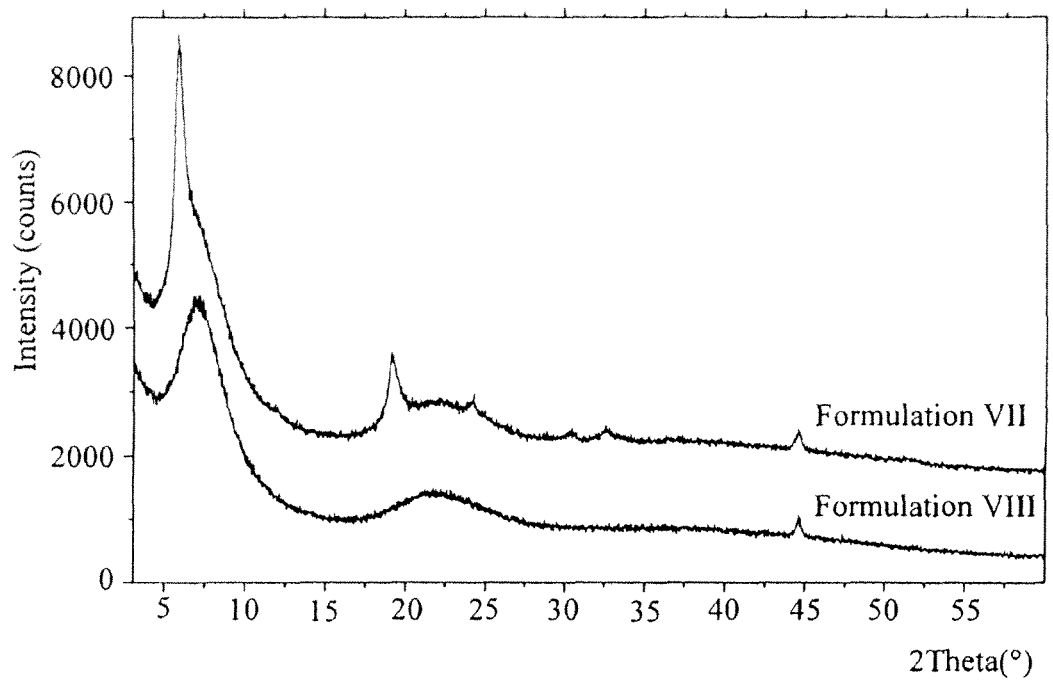

Formulations VII and VIII were also analyzed for amorphous/crystalline content and polymorphic form using high resolution X-ray powder diffraction (XRPD). For XRPD, phase identification was performed to identify any crystalline phases observed in each XRPD pattern. XRPD patterns were collected using a PANalytical X'Pert Pro diffractometer (Almelo, The Netherlands). The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop was used to minimize the background generated by air scattering. Soller slits were used for the incident and diffracted beams to minimize axial divergence. Diffraction patterns were collected using a scanning position-sensitive detector (X'Celerator) located 240 mm from the specimen. Scans were obtained over 3-60° with a step size of 0.017° and a step time of 70 s. As shown in FIG. 45A, peaks at approximately 6, 19, 24, 31 and 33° characteristic of leucine (leucine scan not shown) can be seen in the diffractogram for Formulation VII, indicating the presence of crystalline leucine in this powder (the peak at approximately 44° in each scan is due to the sample holder). No crystallinity peaks characteristic of either calcium lactate pentahydrate or sodium chloride were observed in the diffractograms for either Formulations VIII and VII, indicating that these components were likely present in an amorphous form in these powders.

Figure 45B:
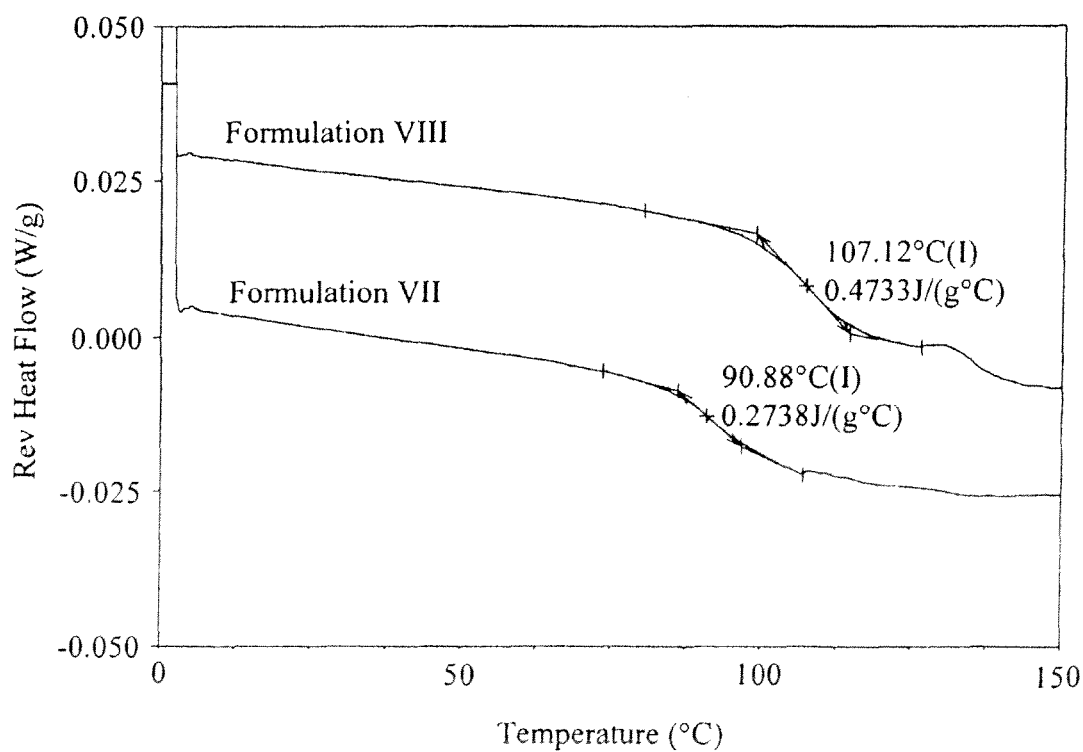

Modulated Differential Scanning calorimetry (mDSC) experiments were performed utilizing a DSCQ200 System from TA Instruments Inc. Approximately 10 mg of samples were placed inside hermetically sealed pans. mDSC conditions were: equilibration at 0° C. and modulation with a heating rate of 2° C./min, amplitude of 0.32° C. and period of 60 s until 250° C. Glass transition temperatures were determined by the inflection point of the step change in the reversible heat flow versus temperature curve. Using this method, the glass transition temperature ($T_g$) of Formulation VIII was determined to be approximately 107° C. and that of Formulation VII approximately 91° C. (FIG. 45B).

Example 39

Figure 46A:
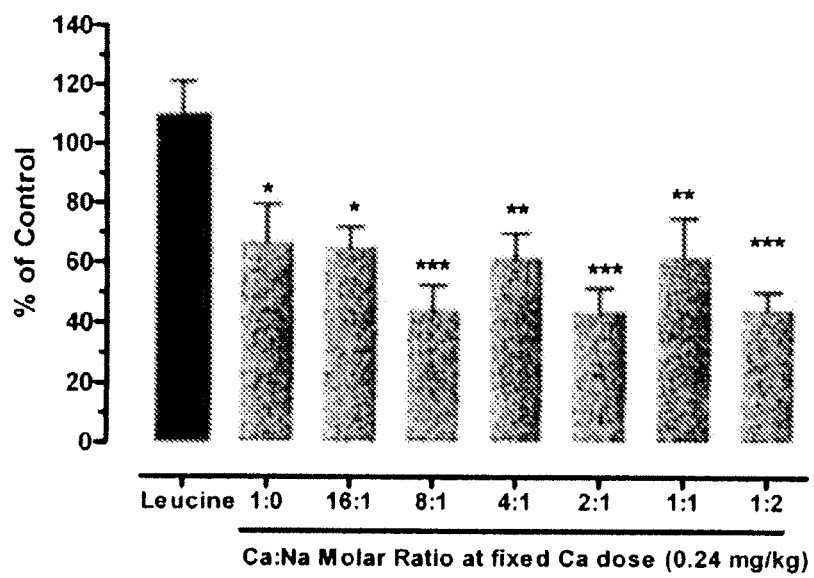

Effect of Calcium to Sodium Ion Molar Ratio in Dry Powder Efficacy in a Mouse Model of Bacterial Pneumonia Dry powders with various molar ratios of calcium to sodium were also tested for their ability to reduce bacterial infection in a mouse model of pneumonia. In a whole-body exposure system (see Example 33), C57BL6 mice were treated with either a leucine powder or dry powders having a fixed calcium dose of 0.24 mg/kg, but various molar ratios of calcium to sodium: 1:0, 16:1, 8:1, 4:1, 2:1, 1:1 and 1:2. Two hours after treatment, mice were infected with Serotype 3 *Streptococcus pneumonia* and, 24 hours after infection, euthanized and the bacterial burden of their lungs assessed as described previously (see Examples 26 and 34). The lung bacterial burden of mice in each group was determined and is shown as a percent of the bacterial burden in control mice. As shown in FIG. 46A, calcium and sodium-containing dry powders at all calcium:sodium molar ratios (1:1-16:1) significantly reduced the bacterial burden in *S. pneumonia* infected mice.

Figure 46B:
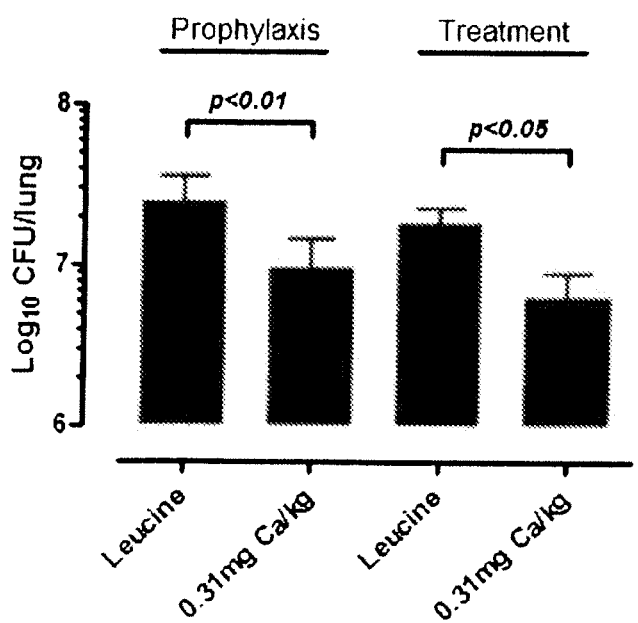

Further, the ability of dry powders of the invention to treat mice already infected with bacteria was assessed. Thus, either leucine, or a dry powder (0.31 Ca mg/kg) having a calcium to sodium molar ratio of 4:1 (Formulation VIII) was administered to mice either 2 hours before *S. pneumonia* infection (prophylaxis, FIG. 46B) or 4 hours after *S. pneumonia* infection (treatment, FIG. 46B). Compared to leucine-treated mice, Formulation VIII was able to not only reduce bacterial burden in mice when administered before bacterial infection, but was also able do so when given after mice were already infected by bacteria. Accordingly, the data indicated that calcium and sodium dry powders could be used to treat not only infections acquired after salt formulation treatment, but to also treat pre-existing and/or established bacterial and viral infections.

Example 40

Effect of Leucine Load and Calcium:Sodium Molar Ion Ratio in Treating Ferret Influenza Dry powders with calcium and sodium molar ion ratios of 1:2 (Formulation III) and 8:1 (Formulation VI) were also tested for efficacy in reducing the severity of influenza in a ferret flu model (see Example 28). In a nose-only exposure system, ferrets (n=8) were exposed to a control powder of 100% leucine, Formulation III (10.0% leucine, 58.6% calcium lactate, 31.4% sodium chloride; 10.8% calcium ion) at 0.1 mg/kg, 0.3 mg/kg or 0.9 mg/kg or to Formulation VI (39.4% leucine, 58.6% calcium lactate, 2.0% sodium chloride; 10.8% calcium ion) at 0.3 mg/kg. The ferrets were exposed to the powders 1 hour before infection, 4 hours after infection, then twice daily (BID). The body weights and subcutaneous body temperatures of the animals were taken twice a day starting at day 0, where the body temperatures taken 1 through 3 days before the study were used as a baseline from which body temperature changes were calculated.

Figure 47A:
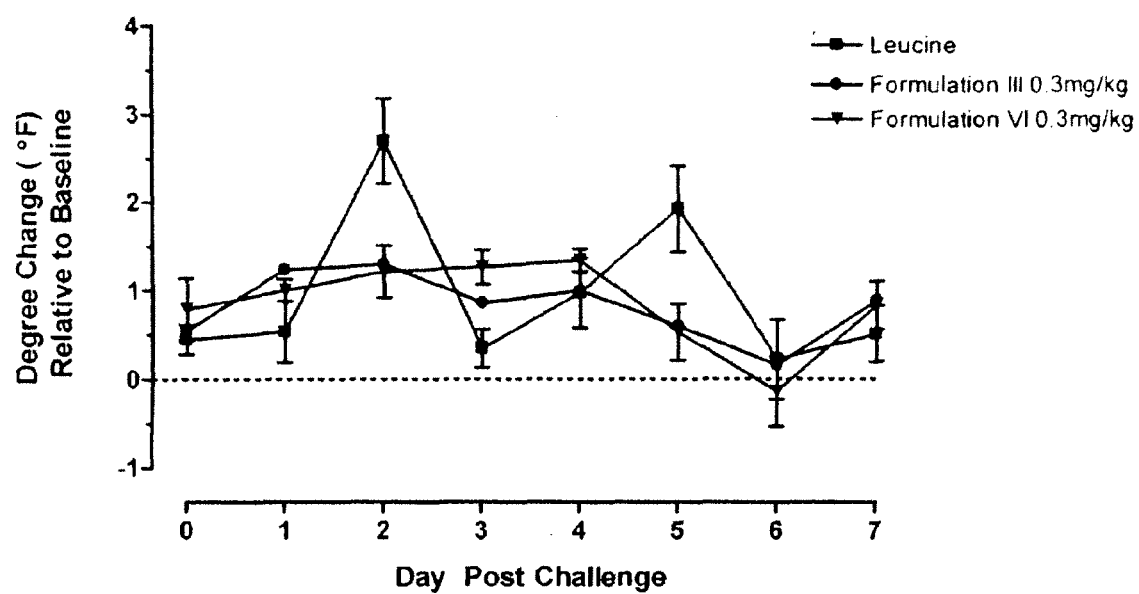
Figure 47B:
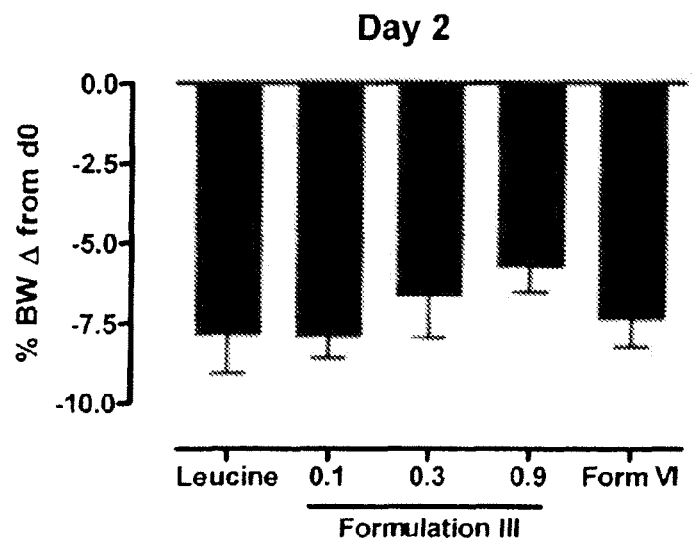

Ferrets treated with control leucine powders showed the typical increase in body temperatures at day 2 and day 5 post-influenza infection. Compared to control animals, however, both Formulation III and Formulation VI suppressed this increase in body temperature (FIG. 47A). Further, Formulation VI reduced the severe loss in body weight typically seen in influenza-infected ferrets, while Formulation III did so in a dose-responsive manner. Thus, both powders were able to decrease the severity of ferret influenza and could be used to treat viral infections.

Example 41

Figure 48A:
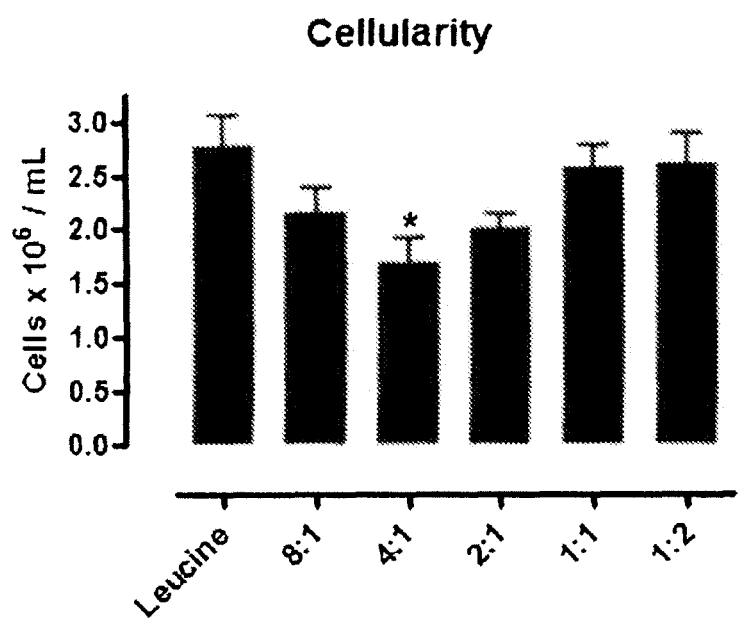
Figure 48B:
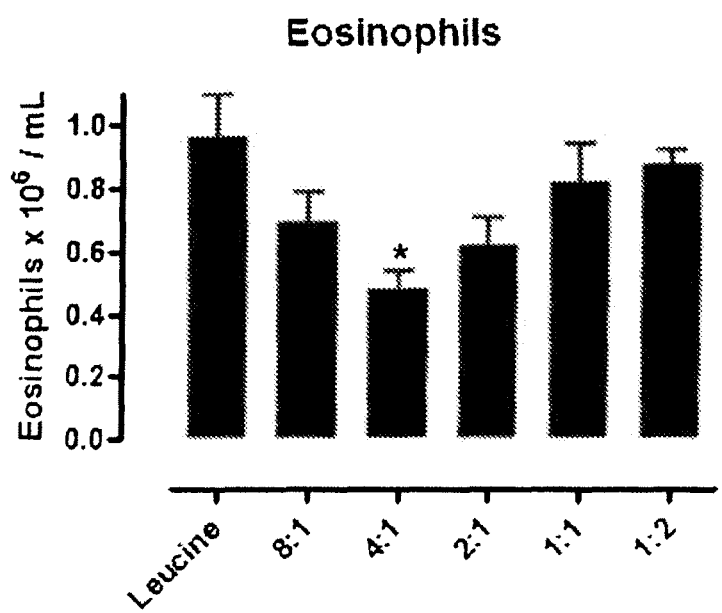

Efficacy of Salt Formulations with Various Calcium:Sodium Molar Ion Ratios on Mouse Allergic Asthma Dry powder formulations having various calcium and sodium ion molar ratios but a fixed dose of calcium (0.24 mg/kg) were tested in the OVA mouse model of allergic asthma (Example 29). After sensitization to ovalbumin, mice were treated with a leucine powder or dry powders at 8:1, 4:1, 2:1, 1:1 or 1:2 Ca:Na molar ion ratios by whole-body exposure 1 hour before and 4 hours after challenge of the sensitized mice with OVA on days 27 through 29 and twice on day 30. Bronchoaveolar lavages were performed on day 31 and the total number of cells and eosinophils determined by differential staining. The data depicted are the standard deviation of 4-5 mice per group and representative of at least two different studies. Dry powders with a higher ratio of calcium ion to sodium ion, that is those with Ca:Na molar ratio of 8:1, 4:1 and 2:1, had the greatest effect in reducing both total cell numbers (FIG. 48A) and eosinophils (FIG. 48B). These data suggested that the molar ratio of calcium to sodium ion could play a role in the broad anti-inflammatory effect of the dry powder formulations.

Example 42

Effect of Dry Powders with Different Molar Ratios of Calcium to Sodium Ion in TS Mouse-Associated Inflammation To determine the efficacy of other calcium-sodium powders and of a once-daily dosing regimen (QD), a similar study was performed using the 4 day tobacco smoke (TS) mouse model described previously (see Example 30). Formulation III (10.0% leucine, 58.6% calcium lactate, 31.4% sodium chloride; 10.8% calcium ion; Ca:Na molar ratio 1:2) and Formulation VII (37.6% leucine, 58.6% calcium lactate, 4% sodium chloride; 10.8% calcium ion; Ca:Na molar ratio 4:1) were tested in the COPD model. Two different doses of calcium were delivered using Formulation VII by increasing the number of capsules used. Doses were calculated as described previously (See Example 30). Six groups of mice were exposed to TS daily for 4 days. Each group received one of the following treatments: Formulation III, Formulation VII or a leucine control vehicle administered twice daily (BID) 1 hour prior to and 6 hours after TS-exposure by whole-body dry-powder inhalation. Formulation III was also administered on a once-daily regimen (QD) 1 hour prior to TS-exposure and a just leucine control powder administered 6 hours after TS-exposure. The p38 inhibitor ADS 110836 was administered by the intra-nasal route (i.n.) 1 hour prior to TS-exposure. One further group (sham) was exposed to air instead of TS for a similar period and received a leucine control powder administered BID 1 hour prior to and 6 hours after air exposure. Animals were euthanized by intra-peritoneal barbiturate anaesthetic overdose 24 hours after the final exposure to either air (sham) or TS on day 5, and a bronchoalveolar lavage (BAL) was performed using 0.4 mL of phosphate buffered saline (PBS). Cells recovered from the BAL were enumerated and differential cell counts carried out using cytospin prepared slides.

Figure 49A:
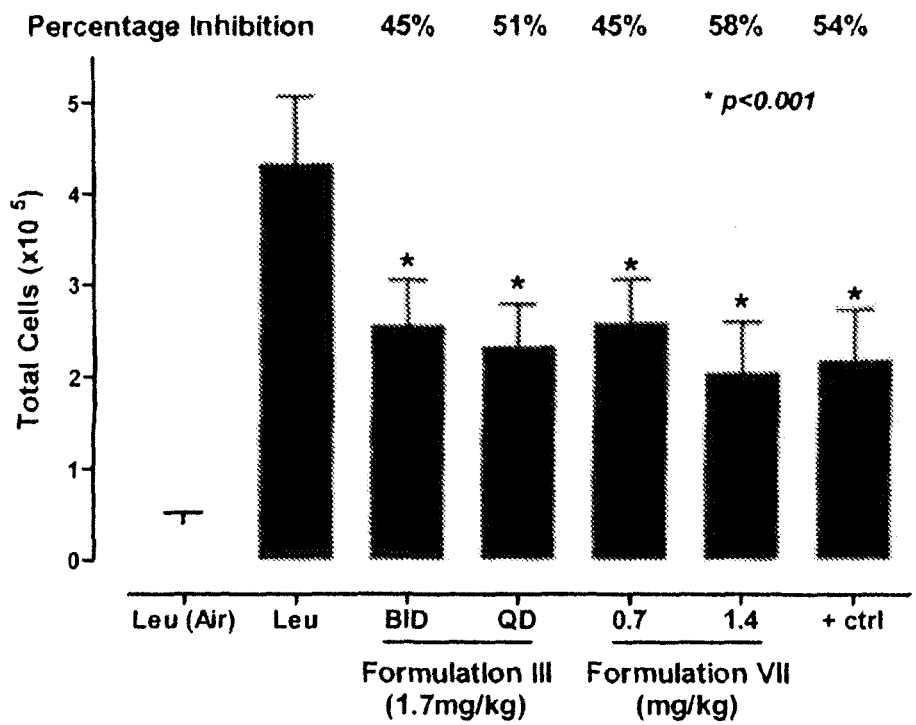
Figure 49B:
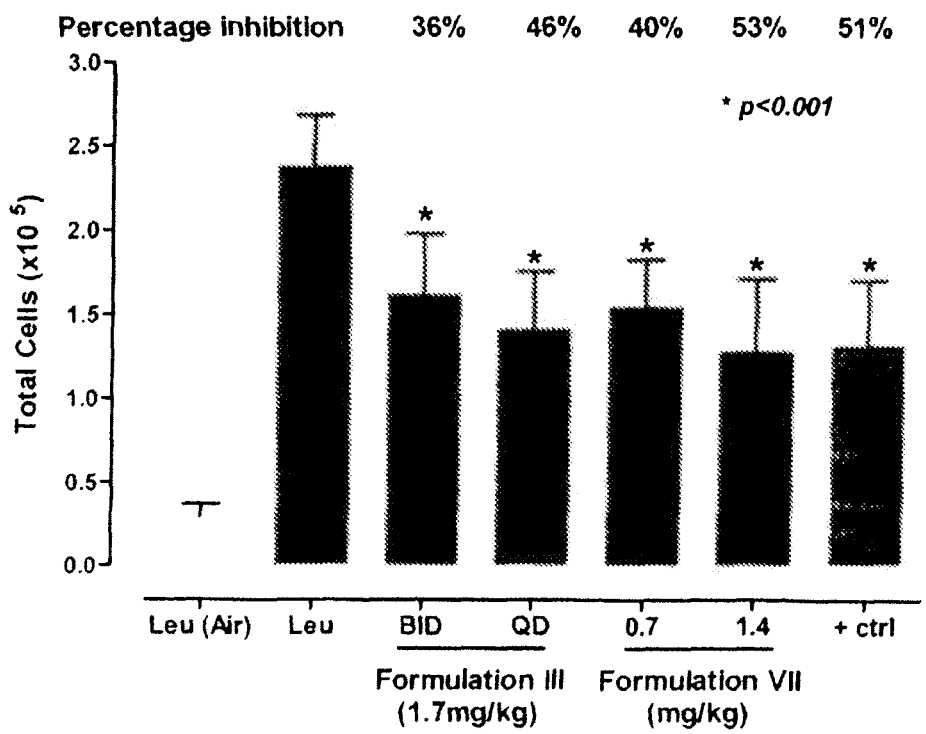
Figure 49C:
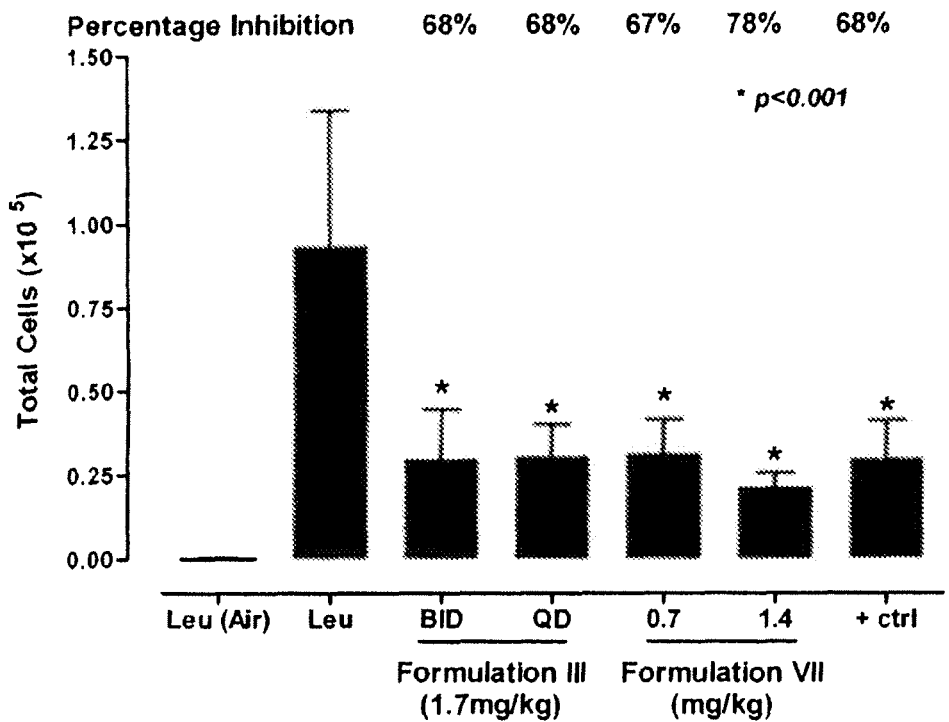
Figure 49D:
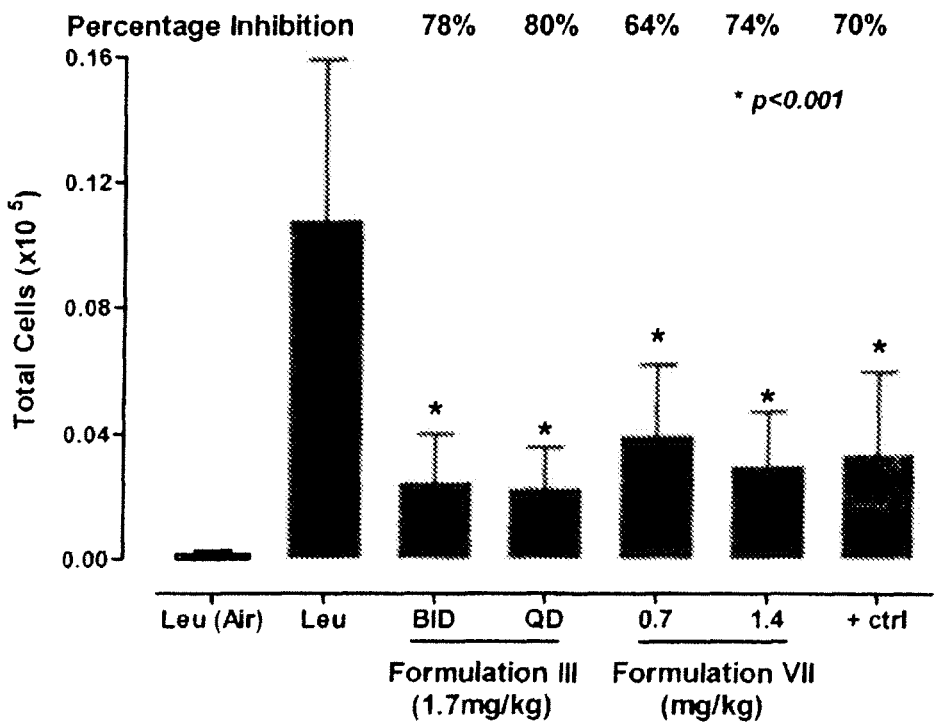

The leucine treated animals exposed to TS exhibited a 10-fold increase in total cell counts compared to air treated animals who were also administered the control powder. In contrast, the p38 MAPK positive control reference compound inhibited inflammation (FIG. 49A). As before, treatment twice daily (BID) with approximately 1.68 mg Ca ion/kg with Formulation III significantly reduced total cell counts to 45% of that of the control animals. Treatment with the same dose of calcium only once, 1 hour before TS exposure (QD) resulted in a similar reduction in total cell counts (51%) (FIG. 49A). Formulation VII also reduced total cell counts in the BAL fluid in a dose responsive manner compared to the control group (45% reduction for the 0.68 mg Ca/kg dose and 58% reduction for the 1.41 mg Ca/kg dose). In addition, both Formulation III and Formulation VII significantly reduced the number of inflammatory cells, including macrophages (FIG. 49B), neutrophils (FIG. 49C) and lymphocytes (FIG. 49D), with the greatest effect occurring on macrophages and neutrophil. In fact, Formulation VII reduced neutrophil and macrophage cell counts to a greater degree than the positive control reference compound, the p38 MAPK inhibitor ADS110836. Surprisingly, the lower of the two doses of Formulation VII reduced inflammatory cell counts to the same level as the high dose of Formulation III, despite the delivery of approximately 3-times less calcium ion. Likewise, the high dose of Formulation VII exhibited the greatest reduction in neutrophils of all the treatments.

Collectively, the data suggested that calcium-sodium dry powders have a significant impact in reducing airway inflammation and are suitable therapies for treating/preventing inflammation, particularly that associated with respiratory diseases like asthma, COPD and CF. Further, the fact that the once-daily and twice-daily dosing treatments had comparable effects suggested that a once-daily dosing treatment regimen could be used therapeutically.

Example 43

Dry Powders Reduce the Expression of Inflammatory Chemokines/Cytokines

Figure 50A:
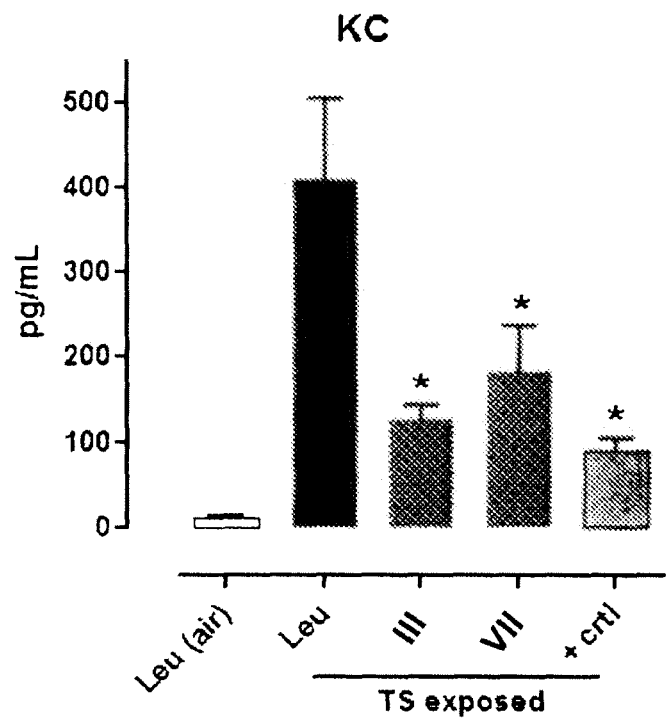
Figure 50B:
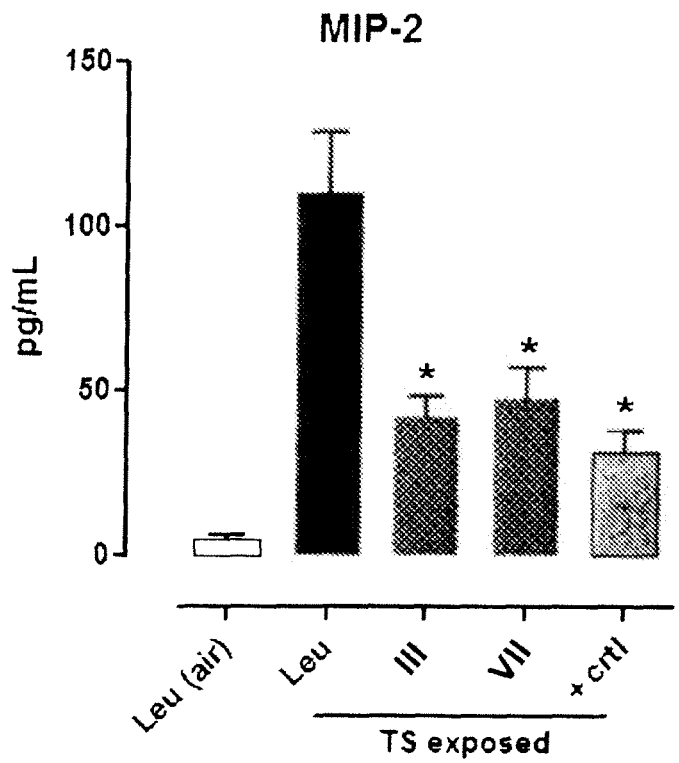

In diseases like allergic asthma and COPD, the influx of inflammatory cells like eosinophils, macrophages and neutrophils into the airway lumen in response to environmental insult is due to cellular release of cytokines and/or chemokines. These cytokines/chemokines signal to induce the chemotaxis of inflammatory cells to the airway lumen. Using the previously described tobacco smoke (TS) mouse model of COPD, studies were undertaken to determine if the calcium-containing dry powders both reduced inflammation and modulated inflammatory cytokine/chemokine expression. Mice were exposed to TS for 4 consecutive days and treated with Formulation III or Formulation VII once daily 1 hour before TS exposure. Control animals were exposed to a dry powder formulation of 100% leucine and a second control group was treated with leucine, but not exposed to TS. At euthanasia, bronchoalveolar lavages (BAL) were performed and BAL samples were assayed for a panel of 13 different cytokines and chemokines that have a role in the inflammation. Protein levels were assessed in a multiplex assay using Luminex technology and concentrations of each protein were determined from standard curves. Data were analyzed by one-way ANOVA and the p values are shown below each group relative to the vehicle group * p<0.05. KC and MIP2 represent two key neutrophil chemokines and perform a function analogous to IL-8 in humans. KC and MIP2 expression was upregulated by exposure to TS (see FIGS. 50A-B, Leu Air versus Leu bars). Treatment with either Formulation III or VII reduced the BAL levels of KC (FIG. 50A) and MIP2 (FIG. 50B) compared to leucine treated animals. The data were similar to the effects of these same formulations on neutrophil chemotaxis to the lung in the same animals and suggested that one mechanism by which the dry powder formulations reduced neutrophilic inflammation is through the reduction of chemokine levels that recruit these cells to the lung. These data further suggested that treatment with calcium-containing formulations modulates the biochemical and biological response of the airway epithelium and airway macrophages.

Example 44

Dry Powders Treat a Pathogen-Induced Acute Exacerbation of Mouse Allergic Asthma Acute exacerbations in asthmatics and COPD patients are a significant cause of lung function decline, morbidity and mortality. Rhinovirus infection is associated with a significant number of acute exacerbations in both patient populations. Calcium-containing dry powder formulations reduced rhinovirus infection in cultured epithelial cells (see Example 13 and FIG. 13C). Preclinical models of rhinovirus in mice have been hampered by the fact that major strains of rhinovirus do not bind to mouse ICAM-1 and therefore do not infect mouse cells. Recently, a mouse model of rhinovirus infection using a minor strain (RV1B) has been described (Bartlett N W et al. Nat Med. 2008 February; 14(2):199-204). Bartlett et al. describes both rhinovirus infection of naïve mice and rhinovirus infection of ovalbumin-challenged mice as a model of acute exacerbations. Using these models, the efficacy of a calcium-sodium dry powder against rhinovirus infection and inflammation was evaluated. The rhinovirus exacerbation model is shown in FIG. 55c.

Figure 51A:
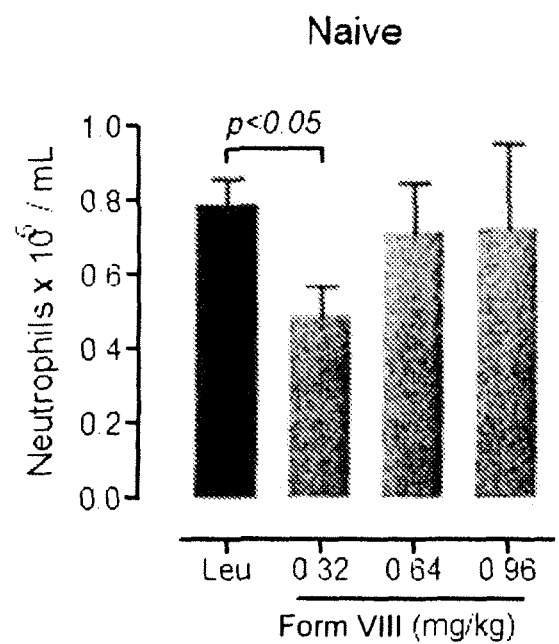
Figure 51B:
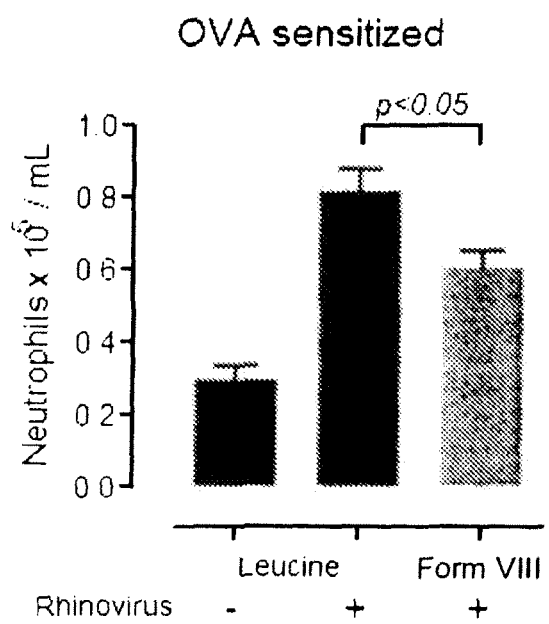

BALB/c mice (n=5) were treated with different doses of Formulation VIII BID for three days before intranasal infection with RV1B. On the day of infection, mice were treated 1 hour before and 4 hours after infection. Twenty-four hours after infection, lung inflammation was assessed by total and differential cell counts in bronchoalveolar lavage samples. At the lowest dose tested, Formulation VIII significantly reduced the number of total inflammatory cells and neutrophils compared to leucine control treated animals (FIG. 51A). To extend these findings to an exacerbation like model, mice were sensitized to OVA by standard protocol (see Example 29) and dosed BID on each day of OVA challenge. One hour after the final OVA challenge, mice were infected with RV1B. Twenty-four hours after infection, lung inflammation was assessed by total and differential cell counts in bronchoalveolar lavage samples. Rhinovirus infection was associated with increased neutrophilic inflammation compared to uninfected control animals (FIG. 51B). Formulation VIII reduced that neutrophilic inflammation compared to leucine control treated animals (one-way ANOVA; Tukey's multiple comparison test) (FIG. 51B). Together, these data suggested that an inhaled calcium dry powder could reduce the frequency and severity of acute exacerbations in patients with respiratory disease, in part, by diminishing the inflammation associated with the infection.

Example 45

Calcium-Containing Dry Powders do not Cause Airway Hyperreactivity

In respiratory diseases and conditions, the inhalation of foreign particles can often have adverse effects on the small airway of the lung. This can result in airway constriction leading to increased airway resistance, work of breathing and, in extreme cases, a considerable risk to the health of a patient. Thus, it is vital that inhaled therapies, particularly in the setting of inflamed or hyper reactive airways, do not result in any unintended consequences such as bronchoconstriction. Accordingly, a study was undertaken to determine whether a calcium-sodium formulation (Formulation VIII) would have an adverse effect on airway bronchoconstriction. Airway resistance was assessed utilizing dual chamber plethysmography. Briefly, mice were constrained in a conical restrainer and placed in a device that consists of two sealed chambers; one encompassing the head and the other encompassing the body with an airtight seal between the two. Pneumotachs measured airflow in each individual chamber and specific airway resistance (sRaw), a direct measure of airway caliber, was calculated as a function of the time delay between flow signals. In order to precisely determine the influence of Formulation VIII on sRaw, 5 minutes of baseline sRaw measurements were obtained and the mice were subsequently exposed to a high dose of Formulation VIII (0.90 mg $Ca^{2+}$/kg). Exposure of the mice to the dry powder was accomplished through the use of a whole body exposure chamber using a capsule-based dry powder inhaler system. Following treatment, 5 minutes of post-treatment sRaw measurements were obtained. Mice were then exposed to escalating doses of methacholine chloride (MCh) in 0.9% sodium chloride for inhalation via nebulization into the head chamber for 10 seconds. The experimental procedure is shown in FIG. 55D.

After each subsequent dose of MCh (0, 6.25, 12.5 25, and 50 mg/ml) the head chamber was cleared and an additional 5 minutes of sRaw was taken. The average sRaw for each 5 minute period was calculated for each animal and normalized to baseline sRaw. This was repeated for two additional groups of mice, whereby the first group was treated with 100% leucine dry power in place of Formulation VIII, and the second group received a sham treatment consisting of dry air only.

Figure 52:
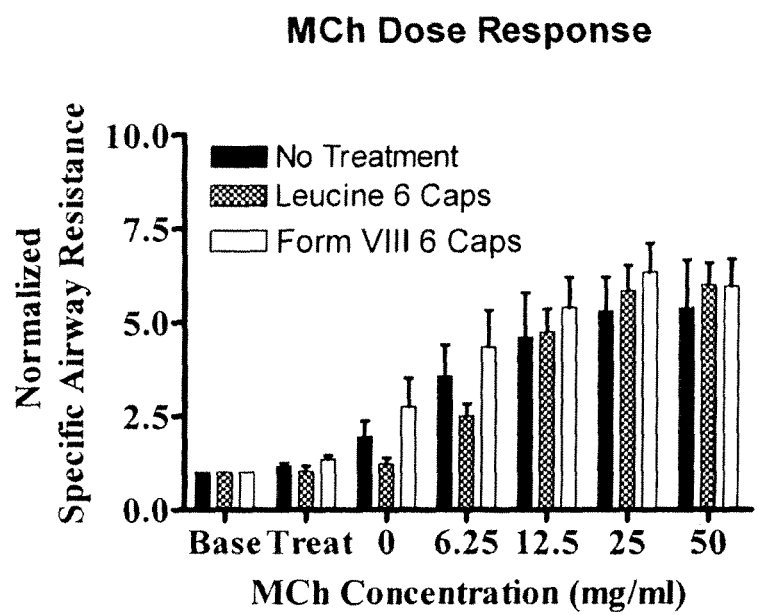

Surprisingly, treatment with Formulation VIII (and leucine) resulted in little change in sRaw and, instead, was statistically indistinguishable from the sham treatment (FIG. 52). In fact, when the animals were exposed to nebulized saline for inhalation (0 mg/ml MCh), the magnitude increase in sRaw was higher than that which was seen during dry powder treatment. In each group, sRaw increased with escalating MCh dose; however, at no point was there a significant difference in sRaw between treatment groups.

Overall, the data demonstrated that calcium dry powder treatment had little influence on sRaw in healthy non-challenged airways and that a calcium dry powder does not adversely influence airway response during periods of bronchoconstriction. Unexpectedly, 0.9% sodium chloride solution for inhalation, a widely utilized diluent for inhaled drug therapies, resulted in a larger magnitude increase in sRaw than did Formulation VIII. These results clearly demonstrated that calcium-containing dry powders are not likely to inadvertently constrict small airways like some currently accepted therapies (e.g., mannitol inhalation therapy for cystic fibrosis) and could serve as a safe and effective therapy for conditions like COPD, asthma and CF.

Example 46

In Vivo Sheep Mucociliary Clearance Studies Using Formulation VIII

A liquid and a dry powder formulation were evaluated in an established sheep mucociliary clearance (MCC) model. MCC was evaluated in four healthy sheep by measurement of the clearance of pulmonary Tc99m-labeled sulfur colloid aerosols that were delivered by inhalation. Immediately following the treatment aerosol exposures, the radio-labeled sulfur colloid aerosol was delivered to each of the sheep via the same aerosol delivery system and MCC determined via the collection of serial images.

A Pari LC jet nebulizer operating with a single sheep exposure system was used to deliver Formulation 46-A (which is 9.4% $CaCl_2$ (w/v), 0.62% NaCl (w/v) in water, at a concentration resulting in a tonicity factor of 8 times isotonic). The nebulizer was connected to a dosimeter system consisting of a solenoid valve and a source of compressed air (20 psi). The output of the nebulizer is connected to a T-piece, with one end attached to a respirator (Harvard Apparatus Inc., Holliston, Mass.). The system was activated for 1 second at the onset of the inspiratory cycle of the respirator, which was set at an inspiratory/expiratory ratio of 1:1 and a rate of 20 breaths/minute. A tidal volume of 300 ml was used to deliver the nebulized formulation. The nebulizer was filled with 4 mL of Formulation 46-A and run to dryness. A dry powder, Formulation VIII, was delivered with a similar exposure system but with a rotating brush generator (RBG1000, Palas) used to generate the dry powder aerosol instead of the nebulizer. A 15 minute dose of the dry powder Formulation VIII was delivered with the aerosol continuously generated by the RBG.

The same aerosol exposure system as the liquid treatment was used to deliver aerosolized technetium labeled sulfur colloid (99mTC-SC) immediately after treatment. Animals were conscious, supported in a mobile restraint, intubated with a cuffed endotracheal tube and maintained conscious for the duration of the study.

After 99mTC-SC nebulization, the animals were immediately extubated and positioned in their natural upright position underneath a gamma camera (Dyna Cam, Picker Corp., Nothford, Conn.) so that the field of image was perpendicular to the animals' spinal cord. After acquisition of a baseline image, serial images were obtained at 5 min intervals for the first hour. All images were obtained and stored in the computer for analysis. An area of interest was traced over the image corresponding to the right lung of the animals, and counts were recorded. The left lung was excluded from analysis because its corresponding image was superimposed over the stomach and counts could be affected by swallowed radiolabeled mucus. The counts were corrected for decay and clearance expressed as the percentage reduction of radioactivity present from the baseline image.

The dose delivered for both formulations was measured in-vitro with a breathing simulator system drawing the inspiratory flow through filter samples collected at the distal end of a tracheal tube. For the Formulation VIII dry powder, 10 filter samples of 1.5 minutes each were assayed for deposited calcium by HPLC and the average rate of calcium deposition was determined. From this the dose delivered in 15 minutes to a 50 kg sheep was calculated to be 0.5 mg $Ca^{2+}$/kg. For the liquid Formulation 46-A, 1.5 minute filter samples were again assayed for calcium content by HPLC and the dose delivered when running the 4 mL solution to dryness was calculated for a 50 kg sheep to be 0.5 mg $Ca^{2+}$/kg. These measured doses correspond to the dose delivered from the distal end of the tracheal tube to the sheep during treatment.

Each formulation was tested on 4 different sheep. The sheep mucociliary clearance model is a well established model with vehicle clearance typically measuring approximately 5-10% at 60 minutes after delivery of the radioactive aerosol (see for example Coote et al, 2009, JEPT 329:769-774). It is known in the art that average clearance measurements greater than about 10% at 60 minutes post baseline indicate enhanced clearance in the model. Both the dry powder Formulation VIII and the liquid Formulation 46-A show enhanced mucociliary clearance in the sheep model, with average clearances±standard error at 60 minutes post baseline of 16.7%±2.7% and 18.9%±1.2% of baseline radioactivity respectively.

The mucociliary clearance was found to increase over the 60 minute period post dosing. For example, the clearance at 10 minutes was 2.9±2.3% of baseline and 4.5±1.4% of baseline, the clearance at 20 minutes was 4.6±2.8% of baseline and 9.4±1.8% of baseline, the clearance at 30 minutes was 7.7±4.0% of baseline and 10.6±1.7% of baseline, the clearance at 40 minutes was 12.1±2.5% of baseline and 13.6±0.1% of baseline, the clearance at 50 minutes was 13.1±2.6% of baseline and 14.5±1.2% of baseline, the clearance at 60 minutes was 16.7±2.7% of baseline and 18.9±1.2% of baseline for Formulations VIII and 46-A, respectively.

The data presented herein show that calcium salt based dry powder and hypertonic liquid formulations can be used to increase mucociliary clearance.

Example 47

In Vivo Canine Mucociliary Clearance Studies

The purpose of this study was to evaluate a liquid and a dry powder formulation in a canine mucociliary clearance (MCC) model. MCC was evaluated in six healthy male Beagle dogs by serial image measurement of the removal of pulmonary Tc99m-labeled sulfur colloid aerosols that were delivered by inhalation immediately following the treatment or control aerosol exposures in a cross-over study.

A Pari LC Plus jet nebulizer operating with a single dog exposure system utilizing a two-way valve and a dual phase respirator (Harvard Apparatus; Holliston, Mass.) was used to deliver Formulation 47-A (which is 9.4% CaCl2 (w/v), 0.62% NaCl (w/v) in water, at a concentration resulting in a tonicity factor of 8 times isotonic). A dry powder—calcium based formulation (Formulation III) was delivered with a similar exposure system but with a rotating brush generator (RBG1000, Palas) or with dry powder insufflators for the lowest dose. Untreated and isotonic sodium chloride (0.9% w/v) were used as negative controls, while hypertonic saline (7% w/v) was used as a positive control in the model. All doses were delivered for 15 minute durations with the exception of Formulation 47-A which was delivered for a duration of 7.5 minutes and the low dose of Formulation III which was delivered by 4 bolus deliveries from dry powder insufflators. Animals were anesthetized with propofol during the exposure and imaging periods and mechanically ventilated during exposure. Immediately following the radiolabeled exposures, serial planar images were collected every two minutes until 11 minutes and then every 5 minutes out to ~33 minutes. Region of interest analysis was conducted on the lungs to determine the amount of activity remaining as a function of time and a fitted linear regression parameter of the rate of radioactivity clearance calculated.

Treatment aerosols were collected from the end of the intubation tube while the Harvard pump was running prior to intubating the dogs to determine the aerosol concentration (gravimetrically or chemically by HPLC) and size distribution (APS, TSI, Model 3321). To calculate the inhaled deposited dose, the respiratory minute volume (RMV) was calculated allometrically (Bide et al. 2000, J. Appl. Toxicol. 20:273-290). The estimated dose was then calculated using the following formula: Dose=(C×RMV×T×DF)/BW, where C is the concentration of the test article in the exposure atmosphere, T is exposure time, BW is body weight and the deposition fraction (DF=30%) (Guyton AC. 1974, American Journal of Physiology 150:70-77). The aerosol concentrations, calculated delivered doses and resulting rate of MCC are shown in Table 52.

TABLE 52

Aerosol treatment delivered doses and effect on MCC.

| Treatment Group | Aerosol Concentration (mg dry solids/L) | Deposited Dose (mg dry solids/kg) | Deposited Dose (mg $Ca^{2}$/kg) | Rate of radioactivity clearance (%/minute) |
|---|---|---|---|---|
| Untreated Baseline | NA | NA | NA | −0.233 |
| Isotonic Saline | 0.05 | 0.08 | NA | −0.243 |
| Hypertonic Saline | 0.4 | 0.58 | NA | −0.281 |
| Formulation 47-A | 0.46 | 0.33 | 0.11 | −0.285 |
| Formulation III—low dose | 0.56 | 0.81 | 0.08 | −0.275 |
| Formulation III—mid dose | 1.9 | 2.75 | 0.3 | −0.291 |
| Formulation III—high dose | 3.5 | 5.06 | 0.55 | −0.326 |

The high dose of Formulation III was found to have a slope of −0.326%/min which was significantly different from untreated baseline (p<0.05) over the 32 minute imaging interval. The mid dose of Formulation III (slope=−0.291%/min) as well as Formulation 47-A (slope=−0.285%/min) treatment and the 7% hypertonic saline (slope=−0.281%/min) treatments were all found to be significantly different from untreated baseline at a significance level of p<0.10, demonstrating an enhanced rate of mucociliary clearance in the dogs compared to untreated. The mid and high dose of Formualtion III enhanced clearance at least equivalent to 7% hypertonic saline. The 7.5 minute dose of Formulation 47-A provided an increase in mucociliary clearance equivalent to the 15 minute dose of 7% hypertonic saline with only half the dosing duration at similar tonicities.

Example 48

Calcium-Containing Dry Powders Combined with Other Active Agents

A. Powder Preparation.

Feedstock solutions were prepared and used to manufacture dry powders comprised of neat, dry particles containing calcium lactate, sodium chloride, optionally leucine, and other pharmaceutically active agents. Table 53 lists the components of the feedstock formulations used in preparation of the dry powders comprised of dry particles. Weight percentages are given on a dry basis.

TABLE 53

Feedstock compositions of calcium-salt with other pharmaceutically active agents

| Formulation | Feedstock Composition (w/w) |
|---|---|
| X | 75.0% calcium lactate, 5.0% sodium chloride, 18.96% leucine, 0.91% fluticasone propionate (FP), 0.13% salmeterol xinafoate (SX) |
| XI | 75.0% calcium lactate, 5.0% sodium chloride, 15.42% leucine, 4.0% fluticasone propionate, 0.58% salmeterol xinafoate |
| XII | 75.0% calcium lactate, 5.0% sodium chloride, 15.31% leucine, 4.0% fluticasone propionate, 0.58% salmeterol xinafoate, 0.113% tiotropium bromide (TioB) |
| XIII | 75.0% calcium lactate, 5.0% sodium chloride, 18.85% leucine, 0.91% fluticasone propionate, 0.13% salmeterol xinafoate, 0.113% tiotropium bromide |
| XIV | 75.0% calcium lactate, 5.0% sodium chloride, 19.89% leucine, 0.113% tiotropium bromide |
| XV | 75.0% calcium lactate, 5.0% sodium chloride, 16.0% leucine, 4.0% fluticasone propionate |
| XVI | 75.0% calcium lactate, 5.0% sodium chloride, 15.89% leucine, 4.0% fluticasone propionate, 0.113% tiotropium bromide |
| XVII | 75.0% calcium lactate, 5.0% sodium chloride, 20% levofloxacin (Levo) |
| XVIII | 75.0% calcium lactate, 5.0% sodium chloride, 17.5% leucine, 2.5% Immunoglobulin G (IgG) |
| XIX | 75.0% calcium lactate, 5.0% sodium chloride, 19.9% leucine, 0.1% formoterol fumarate (FF) |
| XX | 75.0% calcium lactate, 5.0% sodium chloride, 18.92% leucine, 1.08% albuterol sulfate (AS) |

The feedstock solutions were made according to the parameters in Table 54.

TABLE 54

Formulation Conditions

| | Formulation: | | | | | |
|---|---|---|---|---|---|---|
| | X | XI | XII | XIII | XIV | XV |
| Total solids (g) | 4 | 5 | 4 | 4 | 3 | 4 |
| Total volume water (L) | 0.4 | 0.5 | 0.4 | 0.4 | 0.3 | 0.4 |
| Amount leucine in 1 L (g) | 1.9 | 1.541 | 1.53 | 1.89 | 1.99 | 1.6 |
| Amount FP in 1 L (g) | 0.091 | 0.4 | 0.4 | 0 | 0 | 0.4 |
| Amount SX in 1 L (g) | 0.013 | 0.058 | 0.058 | 0 | 0 | 0 |
| Amount TioB in 1 L (g) | 0 | 0 | 0.0113 | 0.0113 | 0.0113 | 0 |
| Amount Levo in 1 L (g) | 0 | 0 | 0 | 0 | 0 | 0 |
| Amount IgG in 1 L (g) | 0 | 0 | 0 | 0 | 0 | 0 |
| Amount FF in 1 L (g) | 0 | 0 | 0 | 0 | 0 | 0 |
| Amount AS in 1 L (g) | 0 | 0 | 0 | 0 | 0 | 0 |

| | Formulation: | | | | |
|---|---|---|---|---|---|
| | XVI | XVII | XVIII | XIX | XX |
| Total solids (g) | 4 | 5 | 5 | 4 | 4 |
| Total volume water (L) | 0.4 | 0.5 | 0.5 | 0.4 | 0.4 |
| Amount leucine in 1 L (g) | 1.59 | 0 | 1.75 | 1.99 | 1.892 |

TABLE 54-continued

| Formulation Conditions | | | | | |
|---|---|---|---|---|---|
| Amount FP in 1 L (g) | 0.091 | 0 | 0 | 0 | 0 |
| Amount SX in 1 L (g) | 0 | 0 | 0 | 0 | 0 |
| Amount TioB in 1 L (g) | 0.0113 | 0 | 0 | 0 | 0 |
| Amount Levo in 1 L (g) | 0 | 2 | 0 | 0 | 0 |
| Amount IgG in 1 L (g) | 0 | 0 | 0.25 | 0 | 0 |
| Amount FF in 1 L (g) | 0 | 0 | 0 | 0.01 | 0 |
| Amount AS in 1 L (g) | 0 | 0 | 0 | 0 | 0.108 |

For all formulations, the liquid feedstock was batch mixed, the total solids concentration was 10 g/L, the amount of sodium chloride in 1 liter was 0.5 g, and the amount of calcium lactate pentahydrate in 1 liter was 10.6 g.

Formulation X through XX dry powders were produced by spray drying on the Büchi B-290 Mini Spray Dryer (BÜCHI Labortechnik AG, Flawil, Switzerland) with powder collection on a 60 mL glass vessel from a High Performance cyclone. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm and the aspirator rate to 90%. Air was used as the drying gas and the atomization gas. Table 55 below includes details about the spray drying conditions.

TABLE 55

Spray Drying Process Conditions

| Process Parameters | X | XI | XII | XIII | XIV | XV | XVI | XVII | XVIII | XIX | XX |
|---|---|---|---|---|---|---|---|---|---|---|---|
| Liquid feedstock solids concentration (g/L) | 10 g/L | 10 g/L | 10 g/L | 10 g/L | 10 g/L | 10 g/L | 10 g/L | 10 g/L | 10 g/L | 10 g/L | 10 g/L |
| Process gas inlet temperature (° C.) | 180 | 180 | 180 | 180 | 180 | 180 | 180 | 179-180 | 100 | 180 | 180 |
| Process gas outlet temperature (° C.) | 87-90 | 73-75 | 73-75 | 74-75 | 84-93 | 76-79 | 76-80 | 91-95 | 55-57 | 80 | 74-78 |
| Process gas flowrate (liter/hr, LPH) | 667 | 667 | 667 | 667 | 667 | 667 | 667 | 667 | 667 | 667 | 667 |
| Atomization gas flowrate (meters³/hr) | 35 | 28 | 28 | 28 | 28 | 28 | 28 | 35 | 32 | 28 | 28 |
| Liquid feedstock flowrate (mL/min) | 9.5 | 10 | 10 | 10 | 5.2 | 10 | 9.8 | 5.7 | 2.7 | 5.7 | 5.7 |

B. Powder Characterization.

Powder physical and aerosol properties are summarized in Tables 57, 58, 59 and 60 below. Values with ±indicates standard deviation of the value reported. Table 56 shows that all formulations had an $FPF_{TD}$<3.4 μm greater than 18%. Formulations X, XI, XIV, XV, XVI, XVII, XVIII and XIX each had an $FPF_{TD}$<3.4 μm greater than 25%. Formulations X, XI, XV, and XVI each had $FPF_{TD}$<3.4 μm greater than 30%. All formulations had an $FPF_{TD}$<5.6 μm greater than 40%. Formulations X, XI, XIV, XV, XVI, XVII, XVIII, and XIX had an $FPF_{TD}$<5.6 μm greater than 50%. Formulation XV had an $FPF_{TD}$<5.6 μm greater than 60%. All formulations had a tapped density greater than 0.45 g/cc. Formulations X, XII, XIII, XIV, XV, XVII, XVIII, XIX and XX each had tapped densities greater than 0.5 g/cc. Formulations X, XIII, XIV, XVII, XVIII, XIX and XX each had tapped densities greater than 0.65 g/cc. All formulations had a Hausner Ratio greater than 1.8. Formulations XII, XIV, XV, XVI, XVIII, and XIX each had a Hausner Ratio greater than 2.0. Formulations XV, XVI, and XIX each had a Hausner Ratio equal to or greater than 2.4.

TABLE 56

Aerodynamic and density properties

| | ACI-2 | | | | Density | | | | |
| --- | --- | --- | --- | --- | --- | --- | --- | --- | --- |
| Form. | FPF$_{TD}$ < 3.4 μm % | | FPF$_{TD}$ < 5.6 μm % | | Bulk g/cc | | Tapped g/cc | | H.R. |
| X | 30.48% | ± 0.66% | 56.85% | ± 0.17% | 0.34 | ± 0.01 | 0.66 | ± 0.03 | 1.93 |
| XI | 30.77% | ± 0.54% | 56.37% | ± 0.24% | N/A | ± N/A | N/A | ± N/A | N/A |
| XII | 18.64% | ± 0.79% | 45.30% | ± 0.29% | 0.25 | ± 0.09 | 0.51 | ± 0.02 | 2.05 |
| XIII | 18.37% | ± 0.65% | 41.29% | ± 1.14% | 0.36 | ± 0.01 | 0.69 | ± 0.01 | 1.93 |
| XIV | 28.25% | ± 1.01% | 53.19% | ± 0.23% | 0.36 | ± 0.01 | 0.86 | ± 0.03 | 2.38 |
| XV | 36.15% | ± 0.55% | 62.62% | ± 1.83% | 0.23 | ± 0.02 | 0.58 | ± 0.04 | 2.46 |
| XVI | 31.34% | ± 0.37% | 59.34% | ± 0.21% | 0.18 | ± 0.01 | 0.48 | ± 0.03 | 2.65 |
| XVII | 25.16% | ± 1.02% | 52.17% | ± 1.14% | 0.34 | ± 0.08 | 0.68 | ± 0.02 | 1.98 |
| XVIII | 27.18% | ± 1.31% | 52.38% | ± 1.47% | 0.36 | ± 0.01 | 0.77 | ± 0.02 | 2.15 |
| XIX | 27.84% | ± 9.09% | 52.59% | ± 8.34% | 0.37 | ± 0.00 | 0.90 | ± 0.09 | 2.40 |
| XX | 23.78% | ± 0.92% | 47.71% | ± 0.60% | 0.40 | ± 0.07 | 0.79 | ± 0.02 | 1.99 |

Form = Formulation; H.R. = Hausner Ratio

Table 57 shows that all formulations had geometric diameters (Dv50) of less than 3.5 μm at a dry powder inhaler flowrate of 60 LPM. Formulations X, XIII, XIV, XV, XVI, XVII, XVIII, XIX and XX had Dv50 of less than 2.5 um at 60 LPM. All formulations had a Dv50 of less than 6.0 μm at 15 LPM. Formulations X, XIII, XIV, XV, XVII, XVIII, XIX, and XX had a Dv50 of less than 4.6 μm at 15 LPM. Formulations XIV, XV, XVII, XVIII, XIX and XX had a Dv50 of less than 4.0 μm at 15 LPM.

TABLE 57

Dispersibility properties (Spraytec geometric diameters)

| | Dispersibility—Spraytec | | | | | | | |
| --- | --- | --- | --- | --- | --- | --- | --- | --- |
| | @ 60 LPM | | | | @ 15 LPM | | | |
| Formulation | Dv50 (μm) | | GSD | | Dv50 (μm) | | GSD | |
| X | 2.10 | ± 0.08 | 4.15 | ± 0.45 | 4.38 | ± 0.15 | 3.88 | ± 0.24 |
| XI | 2.76 | ± 0.11 | 4.18 | ± 0.50 | 4.93 | ± 0.14 | 2.49 | ± 0.50 |
| XII | 3.09 | ± 0.32 | 4.68 | ± 0.16 | 5.95 | ± 0.31 | 3.39 | ± 0.15 |
| XIII | 2.23 | ± 0.11 | 4.15 | ± 0.40 | 4.58 | ± 0.12 | 4.19 | ± 0.18 |
| XIV | 1.92 | ± 0.17 | 6.04 | ± 0.42 | 2.51 | ± 0.11 | 3.07 | ± 0.40 |
| XV | 1.95 | ± 0.06 | 5.47 | ± 0.24 | 3.78 | ± 0.08 | 3.25 | ± 0.16 |
| XVI | 2.18 | ± 0.08 | 5.24 | ± 0.47 | 4.72 | ± 0.14 | 3.00 | ± 0.19 |
| XVII | 2.01 | ± 0.13 | 6.12 | ± 0.45 | 2.83 | ± 0.24 | 2.61 | ± 0.42 |
| XVIII | 1.80 | ± 0.11 | 6.07 | ± 0.22 | 2.23 | ± 0.21 | 3.16 | ± 0.55 |
| XIX | 2.11 | ± 0.12 | 5.38 | ± 0.67 | 2.60 | ± 0.05 | 3.04 | ± 0.19 |
| XX | 2.13 | ± 0.08 | 5.83 | ± 0.20 | 2.56 | ± 0.04 | 3.22 | ± 0.20 |

Table 58 shows that all formulations had a capsule emitted particle mass (CEPM) of greater than 94% at 60 LPM. Formulations X, XI, XII, XIV, XV, XVI, XVII, XVIII, XIX and XX each had a CEPM of greater than 97% at 60 LPM. All formulations had a CEPM of greater than 80% at 15 LPM, except XI. Formulations XII, XIV, XV, XVI, XVIII, XIX and XX each had a CEPM of greater than 90% at 15 LPM.

TABLE 58

Dispersitibilty properties (CEPM)

| | Dispersibility—CEPM | | | | |
| --- | --- | --- | --- | --- | --- |
| | @ 60 LPM | | | @ 15 LPM | |
| Formulation | CEPM | | | CEPM | |
| X | 97.48% | ± 0.49% | | 80.33% | ± 4.27% |
| XI | 99.09% | ± 0.24% | | 59.92% | ± 27.96% |
| XII | 97.19% | ± 0.25% | | 93.15% | ± 3.90% |
| XIII | 94.80% | ± 1.53% | | 82.46% | ± 4.61% |
| XIV | 97.83% | ± 0.45% | | 95.99% | ± 0.32% |
| XV | 98.05% | ± 0.39% | | 92.22% | ± 3.48% |
| XVI | 103.32% | ± 2.01% | | 101.23% | ± 2.07% |
| XVII | 99.57% | ± 0.00% | | 80.41% | ± 0.32% |
| XVIII | 99.71% | ± 0.16% | | 98.08% | ± 0.57% |
| XIX | 100.22% | ± 0.22% | | 98.06% | ± 0.47% |
| XX | 99.87% | ± 0.22% | | 98.10% | ± 0.21% |

Table 59 shows that all measured formulations had a Dv50 using the RODOS at its 1.0 bar setting of less than 2.5 μm.

Formulations X, XIII, XIV, XV, XVI, XVII, and XVIII each had a Dv50 of less than 2.2 μm. Formulations X, XIII, XV, XVI, and XVII each had a Dv50 of less than 2.0 μm. All measured formulations had a RODOS Ratio for 0.5/4 bar of less than 1.2. All measured formulations had a RODOS Ratio for 1/4 bar of less than 1.1.

TABLE 59

Dispersitibilty properties (Geometric diameter using RODOS)

| | RODOS | | | | | | | |
|---|---|---|---|---|---|---|---|---|
| | 0.5 bar | | 1.0 bar | | 4.0 bar | | 0.5/4 | 1/4 |
| Formulation | Dv50 (μm) | GSD | Dv50 (μm) | GSD | Dv50 (μm) | GSD | bar | bar |
| X | 1.92 | 2.15 | 1.78 | 2.12 | 1.67 | 2.04 | 1.15 | 1.07 |
| XI | N/A | N/A | N/A | N/A | N/A | N/A | N/A | N/A |
| XII | 2.64 | 2.21 | 2.40 | 2.15 | 2.24 | 2.17 | 1.18 | 1.07 |
| XIII | 1.87 | 2.12 | 1.95 | 2.17 | 2.36 | 2.13 | 0.79 | 0.83 |
| XIV | 2.01 | 2.16 | 2.12 | 2.22 | 1.99 | 2.19 | 1.01 | 1.07 |
| XV | 2.12 | 2.16 | 1.84 | 2.15 | 1.92 | 2.16 | 1.10 | 0.96 |
| XVI | 2.13 | 2.15 | 1.83 | 2.14 | 1.87 | 2.18 | 1.14 | 0.98 |
| XVII | 1.93 | 2.23 | 1.83 | 2.24 | 1.69 | 2.17 | 1.14 | 1.08 |
| XVIII | 2.08 | 2.12 | 2.03 | 2.09 | 1.95 | 2.15 | 1.07 | 1.04 |
| XIX | 2.13 | 2.14 | 2.26 | 2.20 | 2.15 | 2.25 | 0.99 | 1.05 |
| XX | 2.24 | 2.14 | 2.22 | 2.19 | 2.23 | 2.22 | 1.00 | 1.00 |

C. Anti-Inflammatory Efficacy of a Co-Formulation of a Calcium Salt with Fluticasone Propionate and Salmeterol Xinafoate (Formulation XI) in an OVA Mouse Model of Allergic Asthma Formulation XI was evaluated in a mouse model of allergic asthma using ovalbumin (OVA) as an allergen. The model has been described and shown pictorally in Example 29.

In this model, mice were sensitized to OVA over a period of two weeks and subsequently challenged, via a liquid aerosol, with OVA (Example 29). This challenge induced lung inflammation and increased airway hyperreactivity in response to an airway challenge. The principle change in inflammation was an increase in the number of eosinophils in the lungs. Similar changes in lung inflammation and pulmonary function have been observed in humans with asthma.

Balb/c mice were sensitized and challenged to OVA, as per the sensitization protocol described in Example 29. Mice were treated with Placebo-B dry powder (98% leucine, 2% NaCl, w/w on a dry basis), Formulation 48-A (30% leucine, 65.4% NaCl, 4.0% fluticasone propionate and 0.13% salmeterol xinafoate, w/w on a dry basis), and Formulation XI (75.0% calcium lactate, 15.31% leucine, 5.0% NaCl, 4.0% fluticasone propionate and 0.58% salmeterol xinafoate, w/w on a dry basis). Treatments were made in a whole body exposure chamber using a capsule based dry powder inhaler system. On the final day of the study (day 31), mice were euthanized and bronchoalveolar lavages (BAL) were performed. The total number of cells per BAL was determined. In addition, the percentage and total number of eosinophils, neutrophils, macrophages, and lymphocytes were determined by differential staining.

The effect of Formulation XI on inflammation was assessed. Based on the literature, such as, (Ohta, S. et al. (2010), "Effect of tiotropium bromide on airway inflammation and remodeling in a mouse model of asthma", Clinical and Experimental Allergy 40:1266-1275), and (Riesenfeld, E. P. (2010), "Inhaled salmeterol and/or fluticasone alters structure/function in a murine model of allergic airways disease", Respiratory Research, 11:22), fluticasone propionate (FP) is known to reduce eosinophilic cells and total cellularity in the mouse OVA model.

What was unknown in the art was the effect of co-formulating FP with a calcium salt formulation. Therefore, Formulation XI was tested. The results in Table 60 show that for a similar dose (mg FP/kg mouse body weight), Formulation XI was equally as efficacious in reducing eosinophilic cells and total cellularity as when the FP was formulated without the calcium salt (Formulation 48-A).

TABLE 60

Formulation XI reduces eosinophilic and total cellular inflammation in a murine model of allergic asthma

| | Placebo-B | | Formulation 48-A | | Formulation XI | |
|---|---|---|---|---|---|---|
| | cells * $10^6$/ml | Std Dev | cells * $10^6$/ml | Std Dev | cells * $10^6$/ml | Std Dev |
| Eosinophils | 0.55 | 0.27 | 0.11 | 0.10 | 0.11 | 0.09 |
| Total cells (Cellularity) | 1.38 | 0.50 | 0.49 | 0.20 | 0.71 | 0.91 |

D. Effect of Co-Formulations of a Calcium Salt and Salmeterol Xinafoate and Tiotropium Bromide (Formulations XI and XVII, Respectively) on Specific Airway Resistance in a Mouse OVA Model The sensitization of mice with OVA and subsequent challenging of mice with OVA was achieved, as described in Example 29. In addition to changes in inflammation, mice sensitized and challenged with OVA exhibit increased airway hyperreactivity, which can be measured as changes in airway resistance following bronchoprovocation. Pulmonary function testing was conducted one hour following treatment on day 30. This involved measuring the specific airway resistance (sRaw) in the mice. Baseline sRaw measurements were taken for 5 minutes. The mice subsequently underwent a methacholine (MCh) challenge for assessing pulmonary function with escalating concentrations of MCh delivered via nebulization in a head chamber using doses of MCh of 0 mg/ml, 50 ing/ml or 100 mg/ml.

The mice were challenged to test their pulmonary function according to the methods described in Example 45. It was known from the literature, for example, (Schutz, N. (2004), "Prevention of bronchoconstriction in sensitized guinea pigs: efficacy of common prophylactic drugs", Respir Physiol Neurobiol 141(2): 167-178), and (Ohta, S. et al. (2010), "Effect of tiotropium bromide on airway inflammation and remodeling in a mouse model of asthma", Clinical and Experimental Allergy 40:1266-1275), that both salmeterol xinafoate (SX) and tiotropium bromide (TioB) enhanced pulmonary function, resulting in lower sRaw values, for animals and human beings challenged with methacholine chloride (MCh) in 0.9% sodium chloride for inhalation.

While the effects of SX and TioB on sRaw were known from the literature, the effect of co-formulating SX and TioB formulations with a calcium salt were unknown. Formulations XI (75.0% calcium lactate, 15.31% leucine, 5.0% NaCl, 4.0% fluticasone propionate and 0.58% salmeterol xinafoate, w/w on a dry basis), XIV (75.0% calcium lactate, 19.89% leucine, 5.0% NaCl, and 0.113% tiotropium bromide, w/w on a dry basis), 48-A (30% leucine, 65.4% NaCl 4.0% fluticasone propionate and 0.13% salmeterol xinafoate, w/w on a dry basis), and 48-B (34.47% leucine, 65.42% NaCl and 0.113% tiotropium bromide, w/w on a dry basis) were tested.

changes in lung inflammation and pulmonary function were observed in humans suffering from acute lung injury.

Mice were exposed to whole body exposure with nebulized LPS, 1.12 mg/ml, for 30 minutes. Treatment with dry powder Formulations XI (75.0% calcium lactate, 15.31% leucine, 5.0% NaCl, 4.0% fluticasone propionate and 0.58% salmeterol xinafoate, w/w on a dry basis) was performed 1 hour following LPS exposure using a whole body exposure chamber using a capsule based dry powder inhaler system. Animals were treated with 2, 90 mg capsules corresponding to approximately 0.32 mg $Ca^{2+}$/kg delivered to the lung. To compare the influence of formulations with and without calcium salt, an additional group of animals was exposed to an equivalent amount (i.e. mg of fluticasone/kg of body mass) of an additional powder consisting of Formulation 48-A (30% leucine, 65.4% NaCl, 4.0% fluticasone propionate and 0.13% salmeterol xinafoate). A separate group of animals was treated with 2, 30 mg capsules of Placebo-B control powder (98% leucine, 2% NaCl). Three hours following dry powder treatment, all mice were euthanized and underwent whole lung lavage for determination of total and differential cell counts.

As shown in Table 61, treatment of mice with Formulation XI significantly reduced total cell counts and neutrophils in the BAL fluid when compared with animals exposed to Placebo-B and reduced inflammatory cells to a greater extent than the calcium-free Formulation 48-A. Thus, treatment of mice with Formulation XI significantly reduced lung inflammation in an LPS model of acute lung injury.

TABLE 61

Formulation XI reduces inflammation in a rodent model of acute lung injury.

| | Placebo-B | | Formulation 48-A | | Formulation XI | |
|---|---|---|---|---|---|---|
| | cells * $10^6$/ml | Std Dev | cells * $10^6$/ml | Std Dev | cells * $10^6$/ml | Std Dev |
| Neutrophils | 1.80 | 0.69 | 1.27 | 0.47 | 1.01 | 0.46 |
| Total cells (Cellularity) | 1.94 | 0.71 | 1.37 | 0.52 | 1.12 | 0.47 |

Figure 53:
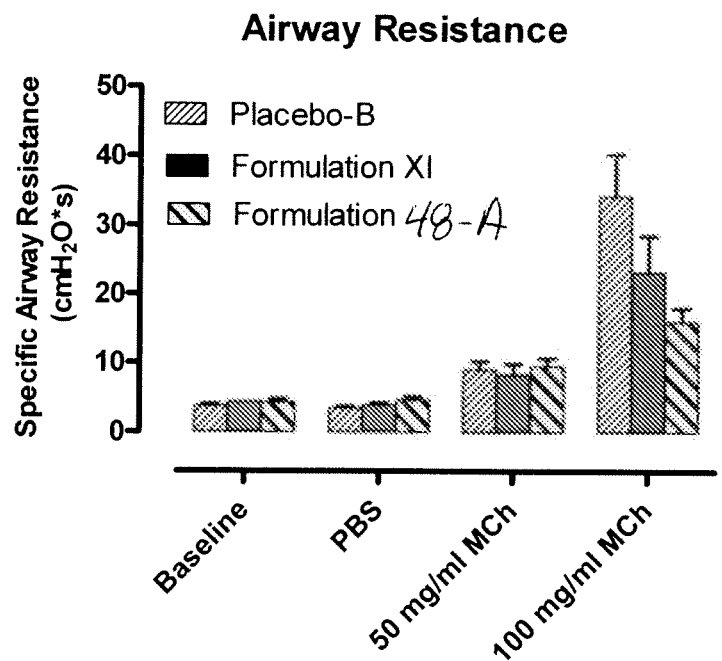
Figure 54:
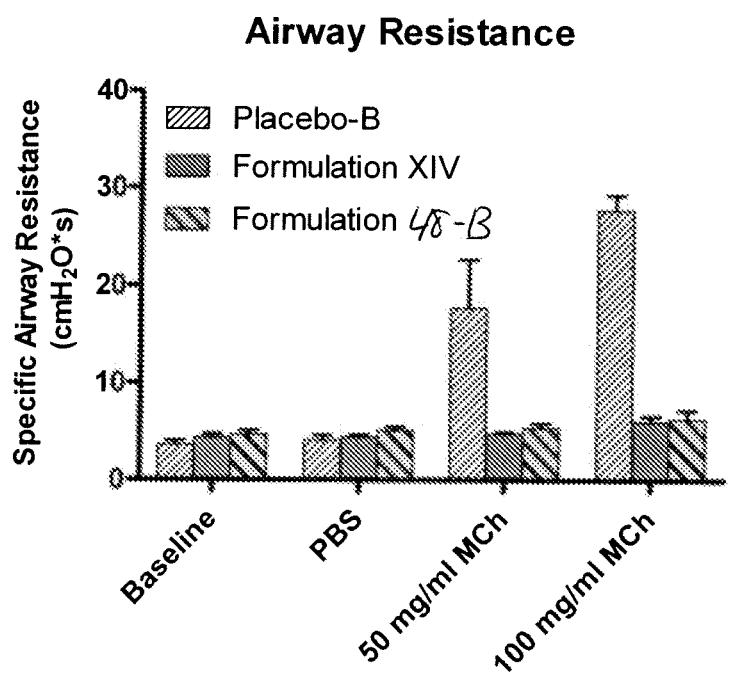

Non-calcium containing Formulations 48-A and 48-B were tested in order to contrast the efficacies of the calcium-containing Formulations XI and XIV, respectively. Results from pulmonary function testing are shown in FIG. 53 and FIG. 54 for Formulations XI and XIV, respectively. These data show that calcium-containing Formulation XIV matched the positive control, Formulation 48-B, and completely eliminates airway hyperreactivity in response to methacholine challenge in an OVA model of allergic asthma. Treatment with Formulation XI did not match the reduction in sRaw that Formulation 48-A achieved, however, the variability within the group treated with Formulation XI overlapped that of Formulation 48-A and the mean reduction was lower than that observed with Placebo-B.

E. Efficacy of Co-Formulations of a Calcium Salt with Fluticasone Propionate and Salmeterol Xinafoate in an LPS Mouse Model of Acute Lung Injury In this study, a mouse model of acute lung injury was used to study the effects of calcium and sodium formulations combined with other therapeutics on pulmonary inflammation. Mice were exposed to aerosolized lipopolysaccharide (LPS) isolated from *Pseudomonas aeruginosa*. This challenge resulted in lung inflammation and caused changes in pulmonary function. The principle change in inflammation was an increase in the number of neutrophils in the lungs. Similar F. Anti-Bacterial Efficacy of Co-Formulations of a Calcium Salt and Levofloxacin on in a *Pseudomonas aeruginosa* Mouse Model A mouse model of bacterial infection was used to evaluate the efficacy of Formulation XVII in vivo. Neutropenia was induced by injection of cyclophosphamide (100 mg/Kg) on days −4 and −1. Bacteria (*Pseudomonas aeruginosa*) were grown overnight in 2 ml of Luria Bertani broth at 37° C. and approximately 5000 CFU were delivered per mouse via intranasal administration in 50 µl of PBS. Four hours following infection the animals were treated with Placebo-B powder (98% leucine, 2% NaCl), Formulation 48-C (27% leucine, 52% NaCl and 20% levofloxacin), and Formulation XVII (75.0% calcium lactate, 5.0% NaCl, 20% levofloxacin) using a whole body exposure chamber using a capsule based dry powder inhaler system. The next day, animals were euthanized and the lungs and the spleen were harvested and homogenized to determine lung bacterial load and systemic bacterial load, respectively. Homogenates were serially diluted on tryptin-soyagar plates and allowed to incubate overnight at 37° C. The following day, colony forming units were counted and CFU/ml for each the lung and the spleen was calculated.

The results are shown in Table 62. It was seen that Formulations XVII and 48-C significantly reduced bacterial burden in the lung by more than 5 $\log_{10}$ CFU and in the spleen by almost 100-fold compared to the Placebo-B treated animals. Thus, treatment of mice with Formulation XVII significantly reduced lung and systemic bacterial burden during *Pseudomonas aeruginosa* infection. It was observed from these data that the presence of calcium in levofloxacin dry powder formulations did not have a deleterious effect on the efficacy of levofloxacin. This is a surprising result given the literature which says that magnesium and calcium based antacids deleteriously affect the bioavailability of levofloxacin taken through the gastrointestinal tract. (Flor, S. et al. (1990), "Effects of Magnesium-Aluminum Hydroxide and Calcium Carbonate Antacids on Bioavailability of Ofloxacin", Antimicrobial Agents and Chemotherapy 34(12): 2436-2438), and (Pai, M P. et al. (2006), "Altered steady state pharmacokinteics of levofloxacin in adult cystic fibrosis patients receiving calcium carbonate", J. Cyst. Fibros., August; 5(3):153-7). (Ofloxacin is a racemic mixture, which consists of 50% levofloxacin, which is known to be biologically active, and 50% of its enantiomer.)

TABLE 62

Formulation XII reduces bacterial burden during *Pseudomonas aeruginosa* infection

|  | Placebo | | Formulation 48-C | | Formulation XVII | |
| --- | --- | --- | --- | --- | --- | --- |
|  | CFU/ml | Std Dev | CFU/ml | Std Dev | CFU/ml | Std Dev |
| Lung | $2.85 \times 10^8$ | $2.88 \times 10^8$ | $2.08 \times 10^4$ | $3.87 \times 10^4$ | $9.22 \times 10^3$ | $1.78 \times 10^3$ |
| Spleen | $1.57 \times 10^5$ | $1.78 \times 10^5$ | $2.16 \times 10^3$ | $6.81 \times 10^2$ | $2.53 \times 10^3$ | $2.41 \times 10^3$ |

G. Co-Formulation of a Calcium Salt and a Protein (Formulation XVIII) Provides for Delivery of the Protein Both Locally in the Lungs and Systemically In this study, Formulation XVIII (75.0% calcium lactate, 17.5% leucine, 5.0% sodium chloride, 2.5% bovine immunoglobulin G (IgG), w/w on a dry basis) was used to determine if calcium containing dry powder formulations can be used to deliver proteins to the lung and if this dry powder can be used to deliver proteins systemically.

In this study, mice were treated with Formulation XVIII using a whole body exposure chamber using a capsule based dry powder inhaler system. Animals were then treated with 2, 4 or 6 capsules of Formulation XVIII with another group of animals were treated with 6 capsules of Placebo-B control powder (98% leucine, 2% NaCl). The placebo controls were run to ensure that there was no cross reactivity with the bovine IgG assay and native mouse proteins in either the serum or the broncho-alveolar lavage (BAL). Immediately following DP treatment the animals were euthanized, underwent BAL and serum was collected. lavage fluid and serum were then assayed for bovine IgG using a commercially available ELISA kit. The results are shown in Table 63. Placebo-B (n=3 animals, data not reported in table) was below the detectable range of the assay, which was indicative that there was no cross reactivity between the bovine IgG and the native mouse protein in either the serum or the BAL. It can be seen that IgG delivered to the lung increases stepwise with increasing number of capsules delivered to the animals. Furthermore, while treatment with 2 or 4 capsules of Formulation XVIII resulted in slight increases in serum IgG content that were in the range of the detection limit of the ELISA kit, treatment with 6 capsules IgG resulted in an increase to approximately 100 ng/ml IgG. Assuming an approximate serum volume of 2 ml, this would suggest that, on average, 200 ng of IgG was delivered systemically with 6 capsules of Formulation XVII treatment. This demonstrated that calcium-containing dry powders can be utilized to deliver proteins systemically.

TABLE 63

Calcium containing, inhaled dry powders can be utilized to deliver proteins to the lungs and systemically

|  | Lung IgG | | Serum IgG | |
| --- | --- | --- | --- | --- |
|  | IgG (ng) | Std Dev | IgG (ng/ml) | Std Dev |
| Form. XVIII (2 capsules) | 100.61 | 39.45 | 3.68 | 6.05 |
| Form. XVIII (4 capsules) | 148.32 | 28.90 | 6.63 | 10.58 |
| Form. XVIII (6 capsules) | 274.73 | 72.52 | 107.41 | 49.41 | n = 6 animals each for the 2, 4, and 6 capsule groups

Example 49

Magnesium-Containing Dry Powders Combined with Active Pharmaceutical Agents

A. Powder Preparation.

Feedstock solutions were prepared in order to manufacture dry powders comprised of neat, dry particles containing a magnesium salt, optionally a non-salt excipient, and at least one pharmaceutical active agent. Table 64 lists the components of the feedstock formulations used in preparation of the dry powders comprised of dry particles. Weight percentages are given on a dry basis.

TABLE 64

Feedstock compositions of calcium-salt with other pharmaceutically active agents

| Formulation | Feedstock Composition (w/w) |
| --- | --- |
| XXI | 89.89% magnesium lactate, 10.0% maltodextrin, 0.113% tiotropium bromide (TioB) |
| XXII | 65.42% magnesium sulfate, 34.47% leucine, 0.113% tiotropium bromide (TioB) |
| XXIII | 65.42% magnesium sulfate, 34.0% leucine, 0.58% salmeterol xinafoate |
| XXIV | 65.42% magnesium sulfate, 29.89% leucine, 4.0% fluticasone propionate, 0.58% salmeterol xinafoate, 0.113% tiotropium bromide |

The feedstocks solutions were made according to the conditions in Table 65.

TABLE 65

Formulation Conditions

| Formulation: | XXI | XXII | XXIII | XXIV |
|---|---|---|---|---|
| Total solids (g) | 2 | 3 | 3 | 4 |
| Total volume water (L) | 0.25 | 0.3 | 0.3 | 1.45 |
| Amount magnesium lactate (ML) or magnesium sulfate (MS) in 1 L (g) | 7.19 | 6.54 | 6.54 | 2.35 |
| Amount of maltodextrin (Malto) or leueine (Leu) (g) | 0.8 | 3.45 | 3.4 | 0.275 |
| Amount FP in 1 L (g) | 0 | 0 | 0 | 0.11 |
| Amount SX in 1 L (g) | 0 | 0 | 0.058 | 0.016 |
| Amount TioB in 1 L (g) | 0.009 | 0.0113 | 0 | 0.0036 |

Formulation XXI through XXIV dry powders were produced by spray drying on the Büchi B-290 Mini Spray Dryer (BÜCHI Labortechnik AG, Flawil, Switzerland) with powder collection on a 60 mL glass vessel from a High Performance cyclone. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm and the aspirator rate to 90%. Air was used as the drying gas and the atomization gas. Table 66 below includes details about the spray drying conditions.

TABLE 66

Spray Drying Process Conditions

| | Formulation | | | |
|---|---|---|---|---|
| Process Parameters | XXI | XXII | XIII | XXIV |
| Liquid feedstock solids concentration (g/L) | 8 | 10 | 10 | 2.75 |
| Process gas inlet temperature (° C.) | 115 | 115 | 115 | 180 |
| Process gas outlet temperature (° C.) | 63 | 65-67 | 65 | 68-73 |
| Process gas flowrate (liter/hr, LPH) | 667 LPH | 667 LPH | 667 LPH | 667 LPH |
| Atomization gas flowrate (meters$^3$/hr) | 35 m$^3$/h | 35 m$^3$/h | 35 m$^3$/h | 35 m$^3$/h |
| Liquid feedstock flowrate (mL/min) | 2.5 | 2.5 | 2.5 | 12.1 |

B. Powder Characterization.

Powder physical and aerosol properties are summarized in Tables 68, 69, and 70 below. Values with ±indicates standard deviation of the value reported. Table 67 shows that all formulations had an FPF$_{TD}$<3.4 µm greater than 25%. Formulations XXI, XXII, and XXIII each had an FPF$_{TD}$<3.4 µm greater than 35%. Formulations XXII and XXIII each had FPF$_{TD}$<3.4 µm greater than 39%. All formulations had an FPF$_{TD}$<5.6 µm greater than 50%. Formulations XXI, XXII, and XXIII had an FPF$_{TD}$<5.6 µm greater than 60%. Formulation XXIII had an FPF$_{TD}$<5.6 µm greater than 68%. All formulations had a tapped density greater than 0.70 g/cc. Formulations XXII and XXIII each had tapped densities greater than 0.90 g/cc. All formulations had a Hausner Ratio greater than 1.7. Formulations XXII and XXIII had Hausner Ratios greater than 2.0.

TABLE 67

Aerodynamic and density properties

| | ACI-2 | | | | Density | | | | |
|---|---|---|---|---|---|---|---|---|---|
| Form. | FPF$_{TD}$ < 3.4 µm % | | FPF$_{TD}$ < 5.6 µm % | | Bulk g/cc | | Tapped g/cc | | H.R. |
| XXI | 35.50% ± | 1.22% | 63.47% ± | 0.33% | 0.40 ± | 0.01 | 0.71 ± | 0.00 | 1.77 |
| XXII | 39.87% ± | 0.71% | 61.27% ± | 2.10% | 0.53 ± | 0.02 | 1.09 ± | 0.04 | 2.08 |
| XXIII | 47.74% ± | 1.48% | 68.41% ± | 1.02% | 0.39 ± | 0.01 | 0.94 ± | 0.07 | 2.44 |
| XXIV | 27.73% ± | 2.59% | 51.51% ± | 0.74% | 0.40 ± | 0.00 | 0.72 ± | 0.02 | 1.77 |

Form. = Formulation; H.R. = Hausner Ratio

TABLE 68

Geometric Diameters

| | Dispersibility—Spraytec | | | | | | | |
|---|---|---|---|---|---|---|---|---|
| | @ 60 LPM | | | | @ 15 LPM | | | |
| Formulation | Dv50 (µm) | | GSD | | Dv50 (µm) | | GSD | |
| XXI | 1.77 ± 0.12 | | 5.96 ± 0.11 | | 2.37 ± 0.09 | | 2.74 ± 0.37 | |
| XXII | 1.99 ± 0.13 | | 6.40 ± 0.54 | | 2.27 ± 0.08 | | 3.16 ± 0.26 | |
| XXIII | 1.32 ± 0.08 | | 6.72 ± 0.40 | | 2.23 ± 0.09 | | 3.26 ± 0.21 | |
| XXIV | 2.12 ± 0.07 | | 4.92 ± 0.36 | | 6.21 ± 0.60 | | 4.94 ± 0.32 | |

Table 68 shows that all formulations had geometric diameters (Dv50) of less than 2.2 um at a dry powder inhaler flowrate of 60 LPM. Formulations XXI, XXII, and XXIII had Dv50 of less than 2.0 um at 60 LPM. Formulations XXI, XXII, and XXIII had a Dv50 of less than 2.5 um at 15 LPM.

Table 69 shows that all formulations had a capsule emitted particle mass (CEPM) of greater than 97% at 60 LPM. All formulations had a CEPM of greater than 80% at 15 LPM. Formulations XXI, XXII, and XXIII each had a CEPM of greater than 92% at 15 LPM. Formulations XXII and XXIII each had a CEPM of greater than 97% at 15 LPM.

TABLE 69

Dispersitibilty properties

| Formulation | Dispersibility—CEPM @ 60 LPM CEPM | | | @ 15 LPM CEPM | | |
|---|---|---|---|---|---|---|
| XXI | 97.06% | ± | 0.40% | 92.57% | ± | 1.36% |
| XXII | 99.43% | ± | 0.33% | 97.14% | ± | 0.35% |
| XXIII | 98.56% | ± | 0.23% | 97.32% | ± | 0.99% |
| XXIV | 98.41% | ± | 0.28% | 80.79% | ± | 16.16% |

Table 70 shows that all formulations had a Dv50 using the RODOS at its 1.0 bar setting of less than 2.2 μm. Formulations XXI, XXIII, and XXIV each had a Dv50 of less than 1.9 μm. Formulation XXIV had a Dv50 of 1.57 μm. All measured formulations had a RODOS Ratio for 0.5/4 bar of less than 1.2. All measured formulations had a RODOS Ratio for 1/4 bar of less than 1.1.

TABLE 70

Dispersitibilty properties (Geometric diameter using RODOS)

| | RODOS | | | | | | | |
|---|---|---|---|---|---|---|---|---|
| | 0.5 bar | | 1.0 bar | | 4.0 bar | | 0.5/4 | 1/4 |
| Formulation | Dv50 (μm) | GSD | Dv50 (μm) | GSD | Dv50 (μm) | GSD | bar | bar |
| XXI | 1.93 | 2.14 | 1.83 | 2.11 | 1.90 | 2.16 | 1.02 | 0.96 |
| XXII | 2.06 | 2.25 | 2.19 | 2.17 | 2.09 | 2.23 | 0.99 | 1.05 |
| XXIII | 1.90 | 2.12 | 1.85 | 2.16 | 1.78 | 2.13 | 1.07 | 1.04 |
| XXIV | 1.76 | 2.08 | 1.57 | 2.03 | 1.53 | 2.01 | 1.15 | 1.03 |

Example 50

Effect of a Magnesium-Containing Formulation on Airway Eosinophilic Inflammation and Pulmonary Function in a Model of Allergic Inflammation Asthma A. Inflammation Dry powder Formulation XXV comprising leucine (37.5%), magnesium lactate (58.3%) and sodium chloride (4.2%) was evaluated in a mouse model of allergic asthma using ovalbumin (OVA) as an allergen. The model has been described and the dosing protocol shown pictorially in Example 29.

In this model, Balb/c mice were sensitized to OVA over a period of two weeks and subsequently challenged, via a liquid aerosol of OVA (graphic in Example 29). This challenge induced lung inflammation and increased airway hyperreactivity in response to an airway challenge. The principle change in inflammation was an increase in the number of eosinophils in the lungs. Similar changes in lung inflammation and pulmonary function have been observed in humans with asthma.

Mice were treated with Placebo-B dry powder (98% leucine, 2% NaCl, w/w on a dry basis) or Formulation XXV. Treatments were administered by a whole body exposure chamber using a capsule based dry powder inhaler system. On the final day of the study (day 31), mice were euthanized and bronchoalveolar lavages (BAL) were performed. The total number of cells per BAL was determined. In addition, the percentage and total number of eosinophils, neutrophils, macrophages, and lymphocytes were determined by differential staining.

The effect of Formulation XXV on inflammation was assessed. Based on the literature, magnesium was not known to reduce eosinophilic cells and total cellularity in the mouse OVA model. This knowledge was confirmed in this experiment. The eosinophilic and total cell count was not significantly different between Formulation XXV and Placebo-B, as reported in Table 71.

TABLE 71

Formulation XXV does not reduces eosinophilic and total cellular inflammation in a murine model of allergic asthma

| | Placebo-B | | Formulation XXV | |
|---|---|---|---|---|
| | cells*10$^6$/ml | Std Dev | cells*10$^6$/ml | Std Dev |
| Eosinophils | 0.35 | 0.20 | 0.31 | 0.10 |
| Total cells (Cellutarity) | 1.55 | 0.53 | 1.31 | 0.26 |

B. Pulmonary Function

The sensitization of mice with OVA and subsequent challenging of mice with OVA was described above. Beside acquiring elevated eosinophilic inflammation, these OVA sensitized mice also developed increased airway hyperreactivity, which can be measured as changes in airway resistance following bronchoprovocation. Based on the literature (Okayama, H. et al. (1987), "Bronchodilating effect of intravenous magnesium sulfate in bronchial asthma", JAMA, February 27; 257(8):1076-8), magnesium sulfate is known to reduce bronchoconstriction following intravenous administration. What was unknown is whether inhaled delivery of magnesium salts to the airway would have a similar impact on bronchoconstriction in a preclinical model. To test the efficacy of Formulation XXV in reducing the mice's susesptibility to airway hyperreactivity, pulmonary function testing was conducted one hour following treatment on day 30. This involved measuring the specific airway resistance (sRaw) in the mice. Baseline sRaw measurements were taken for 5 minutes. The mice subsequently underwent a methacholine (MCh) challenge for assessing pulmonary function with escalating concentrations of MCh delivered via nebulization in a head chamber using doses of MCh of 0 mg/ml, 25 mg/ml or 50 mg/ml.

The mice were challenged to test their pulmonary function according to the methods described in Example 45. From a survey of the literature, it was possible that Formulation XXV would have efficacy in reducing air hyperreactivity, and thereby result in lower sRaw values, for animals and human beings challenged with methacholine chloride (MCh) in 0.9% sodium chloride for inhalation.

Results from pulmonary function testing are shown in Table 72 for Formulations XXV and Placebo-B. These data show that magnesium-containing Formulation XXV matched the placebo, a negative control, and that Formulation XXV did not mimic the literature result where intravenous administration of magnesium sulfate reduced bronchoconstriction.

TABLE 72

Magnesium-containing Formulation XXV was not observed to have a significant effect on pulmonary function as measured in the MCh challenge test.

| | Specific Airway Resistance | | | |
|---|---|---|---|---|
| | Placebo-B | | Formulation XXV | |
| | $cmH_2O*s$ | Std Dev | $cmH_2O*s$ | Std Dev |
| Baseline | 3.70 | 0.82 | 3.33 | 1.31 |
| PBS | 4.97 | 2.54 | 3.90 | 0.60 |
| 25 mg/ml MCh | 21.36 | 15.21 | 22.97 | 6.54 |
| 50 mg/ml MCh | 25.53 | 11.91 | 24.61 | 8.08 |

Formulation XXV was tested in a mouse model of allergic inflammation, the OVA model. Formulation XXV was found not to cause a significant decrease in eosinophilic or total inflammation cell counts vs. Placebo-B. Likewise, Formulation XXV was tested to ascertain its role in pulmonary function. Formulation XXV was found not to cause a significant decrease in sensitivity to MCh challenge vs. Placebo-B.

Example 51

Effect of Dry Powders with Magnesium in TS Mouse-Associated Inflammation

To determine the efficacy of a magnesium formulation in a COPD-like model of lung inflammation, a study was performed using the 4 day tobacco smoke (TS) mouse model. This model has been previously described in Example 30. Formulation XXVI (19.6% leucine, 75.0% magnesium lactate, 5.4% sodium chloride) and Formulation VIII (20.0% leucine, 75.0% calcium lactate, 5.0% sodium chloride) were tested in the COPD-like model. The doses of calcium and magnesium administered to the mice were matched on a µmol of salt/kg basis and doses were achieved by the delivery of Formulations XXVI and VIII in 6 capsules of each formulation in the experiment. Doses were calculated as described previously (See Example 30). Six groups of mice were exposed to TS daily for 4 days. Each group received one of the following treatments: Formulation XXVI, Formulation VIII or a leucine control vehicle administered once daily (QD) 1 hour prior to TS-exposure by whole-body dry-powder inhalation. The p38 inhibitor ADS 110836 was administered by the intra-nasal route (i.n.) 1 hour prior to TS-exposure. One further group (sham) was exposed to air instead of TS for a similar period and received a leucine control powder administered BID 1 hour prior to air exposure. Animals were euthanized by intra-peritoneal barbiturate anaesthetic overdose 24 hours after the final exposure to either air (sham) or TS on day 5, and a bronchoalveolar lavage (BAL) was performed using 0.4 ml, of phosphate buffered saline (PBS). Cells recovered from the BAL, were enumerated and differential cell counts carried out using cytospin prepared slides.

The leucine treated animals exposed to TS exhibited an 8.4-fold increase in total cell counts compared to air treated animals who were also administered the control powder. As before, QD treatment with approximately 1.68 mg Ca ion/kg with Formulation VIII significantly reduced total cell counts to 53% of that of the control animals. Treatment with the same dose of Mg ion/kg did not result in a statistically significant reduction in total cell counts (Table 73). A similar result was seen in in the inflammatory cell counts for macrophages (Table 73), neutrophils (Table 73) and lymphocytes (Table 73), i.e. Formulation VIII reduced the cell counts for each category by a statistically significant amount. In contrast, Formulation XXVI did not reduce the total cell counts, neutrophils or lymphocytes to statistically significant levels, and only slightly reduced the number of macrophages (21%) to a level that was far less than the 65% reduction observed following treatment with Formulation VIII at a similar dosing of moles of salt. The p38 MAPK inhibitor ADS110836 reduced cell counts in for each cell type by a statistically significant amount, as was expect (Table 73).

TABLE 73

Efficacy of Formulation XXVI and VIII in the TS mouse model

| | Compound | | | | | | | | | |
|---|---|---|---|---|---|---|---|---|---|---|
| | Formulation VIII | | NaCl | | Form. XXVI | | ADS115398 | | | |
| | | | Dose | | | | | | | |
| | 6 capsules | | 3 capsules | | 6 capsules | | 6 capsules | | 0.1 mg/kg | |
| | Inflammatory markers in BAL | | | | | | | | | |
| | Inhibition | | Inhibition | | Inhibition | | Inhibition | | Inhibition | |
| | % | p | % | p | % | p | % | p | % | p |
| Total cells | 53 | <0.001 | 44 | <0.001 | 4 | ns | 15 | ns | 48 | <0.001 |
| Macrophages | 52 | <0.001 | 41 | <0.001 | 8 | ns | 21 | <0.05 | 43 | <0.001 |
| Epithelial cells | 37 | <0.50 | 34 | ns | −3 | ns | −4 | ns | 47 | <0.01 |
| Neutrophils | 62 | <0.001 | 54 | <0.001 | 0 | ns | 13 | ns | 61 | <0.001 |
| Eosinophils | 84 | ns | 44 | ns | −35 | ns | 52 | ns | 73 | ns |
| Lymphocytes | 65 | <0.001 | 54 | <0.01 | −4 | ns | 20 | ns | 53 | <0.05 | ns = not statistically significant

Collectively, the data suggested that calcium-based dry powders had a significant impact in reducing airway inflammation and are suitable therapies for treating/preventing neutrophilic inflammation, which is particularly associated with respiratory diseases like asthma, COPD and CF. Further, that magnesium-based dry powders did not have a significant impact in reducing airway inflammation and are not suitable therapies for treating/preventing neutrophilic inflammation which is particularly associated with respiratory diseases like asthma, COPD and CF.

Example 52

Comparison of Calcium and Magnesium Containing Dry Powders to Treat Acute Lipopolysaccharide Inflammation In this study, a mouse model of acute lung injury was used to study the effects of calcium and magnesium dry powder formulations on pulmonary inflammation. Mice were exposed to aerosolized lipopolysaccharide (LPS) isolated from *Pseudomonas Aeruginosa*. This challenge resulted in lung inflammation and caused changes in pulmonary function. The principle change in inflammation was an increase in the number of neutrophils in the lungs and similar changes in lung inflammation and pulmonary function were observed in humans suffering from acute lung injury.

The goal of these studies was to evaluate the efficacy of calcium lactate and magnesium lactate dry powders on pulmonary inflammation. In the course of this work it was discovered that both calcium and magnesium lactate powders significantly reduced pulmonary lung inflammation.

Mice were exposed to whole body exposure with nebulized LPS, 1.12 mg/ml, for 30 minutes. One hour following LPS exposure animals were treated with a Placebo-B (98% leucine, 2% NaCl) dry powder, Formulation VIII (20% leucine, 75% calcium lactate, 5% NaCl), or Formulation XXVII (20% leucine, 75% magnesium lactate, 5% NaCl) using a whole body exposure chamber and a capsule based dry powder inhaler system. Animals were treated with two, 90 mg capsules that would correspond to approximately 0.32 mg $Ca^{2+}$/kg delivered to the lung with the calcium lactate containing dry powder. Three hours following dry powder treatment all mice were euthanized and underwent whole lung lavage for determination of total and differential cell counts.

As shown in Table 74, treatment of mice with both Formulations VIII and XXVII significantly reduced total cell counts and neutrophils in the BAL fluid when compared with animals exposed to a placebo powder. This indicates that both calcium lactate and magnesium lactate dry powders may serve as an effective therapy for the treatment of pulmonary inflammation.

The content of each of the patents, patent applications, patent publications and published articles cited in this specification are herein incorporated by reference in their entirety.

The invention claimed is:

1. A respirable dry powder comprising respirable dry particles comprising magnesium lactate in an amount that provides magnesium ion in an amount of at least about 5%, leucine in an amount of about 5% to about 45%, and one or more therapeutic agents in an amount of about 0.01% to about 20%,
wherein all percentages are weight percentages and the magnesium lactate, leucine and one or more therapeutic agents amount to 100 weight %, wherein the respirable dry particles have a volume median geometric diameter (VMGD) at 1 bar as measured using a HELOS/RODOS system of about 5 microns or less, a dispersibility ratio (1/4 bar) of 1.5 or less, and a tap density of greater than about 0.4 g/cc.

2. The respirable dry powder of claim 1, wherein the respirable dry particles have a tap density of about 0.5 g/cc to about 1.2 g/cc.

3. The respirable dry powder of claim 1, wherein said magnesium salt does not have a biological activity selected from the group consisting of anti-bacterial activity, anti-viral activity, anti-inflammatory activity and combinations thereof.

4. The respirable dry powder of claim 1, wherein the one or more additional-therapeutic agents are independently selected from the group consisting of LABAs, short-acting beta agonists, corticosteroids, LAMAs, antibiotics, dornase alpha, sodium channel blockers, and combinations thereof.

5. The respirable dry powder of claim 1, wherein the respirable dry powder has a Fine Particle Fraction (FPF) of less than 5.6 microns of at least 45%.

6. A method of treating a respiratory disease comprising administering to the respiratory tract of a patient in need thereof an effective amount of a respirable dry powder of claim 1.

7. A method of treating or preventing an infectious disease of the respiratory ac comprising administering to the respiratory tract of a patient in need thereof an effective amount of a respirable dry powder of claim 1.

8. A method of reducing inflammation comprising administering to the respiratory tract of a patient in need thereof an effective amount of a respirable dry powder of claim 1.

* * * * *

Formulations VIII and XXVII reduce inflammation in a rodent model of acute lung injury.

| | Placebo-B | | Formulation VIII | | Formulation XXVII | |
|---|---|---|---|---|---|---|
| | cells * 10⁶/ml | Std Dev | cells * 10⁶/ml | Std Dev | cells * 10⁶/ml | Std Dev |
| Neutrophils | 3.39 | 1.00 | 1.60 | 0.52 | 1.36 | 0.22 |
| Total cells (Cellularity) | 3.54 | 1.05 | 1.72 | 0.49 | 1.55 | 0.32 |